(12) United States Patent
Takahashi et al.

(10) Patent No.: US 7,781,479 B2
(45) Date of Patent: Aug. 24, 2010

(54) HETEROARYL DERIVATIVES

(75) Inventors: Yoko Takahashi, Osaka (JP); Ryu Nagata, Osaka (JP); Kantaro Ushiroda, Osaka (JP)

(73) Assignee: Dainippon Sumitomo Pharma Co., Ltd., Osaka (JP)

( * ) Notice: Subject to any disclaimer, the term of this patent is extended or adjusted under 35 U.S.C. 154(b) by 3 days.

(21) Appl. No.: 11/795,147

(22) PCT Filed: Jan. 12, 2006

(86) PCT No.: PCT/JP2006/300248

§ 371 (c)(1),
(2), (4) Date: Jul. 12, 2007

(87) PCT Pub. No.: WO2006/075638

PCT Pub. Date: Jul. 20, 2006

(65) Prior Publication Data

US 2008/0167306 A1 Jul. 10, 2008

(30) Foreign Application Priority Data

Jan. 14, 2005 (JP) ............................. 2005-006950

(51) Int. Cl.
*A61K 31/405* (2006.01)
*A61K 31/404* (2006.01)
*A61K 31/192* (2006.01)
*C07D 209/04* (2006.01)
*C07D 209/12* (2006.01)

(52) U.S. Cl. ........................ 514/415; 514/419; 514/569; 514/570; 548/492; 548/493; 562/405

(58) Field of Classification Search ................. 514/415, 514/419; 548/469, 493, 511
See application file for complete search history.

(56) References Cited

U.S. PATENT DOCUMENTS

| | | | |
|---|---|---|---|
| 6,635,655 B1 | 10/2003 | Jayyosi et al. | |
| 6,911,468 B2 | 6/2005 | Matsumoto et al. | |
| 7,179,823 B1 | 2/2007 | Momose et al. | |
| 7,186,764 B2 * | 3/2007 | Maekawa | 523/209 |
| 7,345,085 B2 * | 3/2008 | Acton et al. | 514/419 |
| 2003/0144338 A1 | 7/2003 | Matsumoto et al. | |
| 2004/0162331 A1 | 8/2004 | Nagata et al. | |
| 2008/0306275 A1 * | 12/2008 | Watanabe et al. | 546/256 |

FOREIGN PATENT DOCUMENTS

| | | |
|---|---|---|
| WO | WO-00/64888 A1 | 11/2000 |
| WO | WO-02/085851 A1 | 10/2002 |
| WO | WO-03-091211 A1 | 11/2003 |
| WO | WO 2004020409 A1 * | 3/2004 |
| WO | WO-2004/048341 A1 | 6/2004 |

OTHER PUBLICATIONS

Wu and Farrelly, Toxicology 236:1-6, 2007.*
Guerre-Millo et al., "Preoxisome Proliferator-activated Receptor α Activators Improve Insulin Sensitivity and Reduce Adiposity," Journal of Biological Chemistry, vol. 275, No. 22, 2000, pp. 16638-16642.
Willson et al., "The PPARs: From Orphan Receptors to Drug Discovery," Journal of Medicinal Chemistry, vol. 43, No. 4, 2000, pp. 527-550.
Acton et al., "Benzoyl 2-methyl indoles as selective PPARγ modulators," Bioorganic & Medicinal Chemistry Letters, vol. 15, 2005, pp. 357-362.
Minoura et al, "Pharmacological characteristics of a novel nonthiazolidinedione insulin sensitizer, FK614," European Journal of Pharmacology, vol. 494, 2004, pp. 273-281.

* cited by examiner

*Primary Examiner*—Yong Chu
(74) *Attorney, Agent, or Firm*—Birch, Stewart, Kolasch & Birch, LLP

(57) ABSTRACT

A compound of the following formula (1), or its prodrug or pharmaceutically acceptable salt thereof, being useful as a diabetic medicine or preventive, or blood sugar regulator, or therapeutic agent for hyperlipemia, etc.

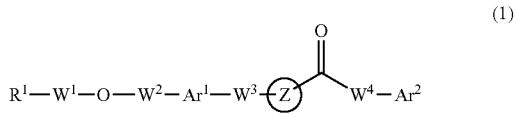

(1)

wherein the ring Z is an optionally substituted heteroaryl, $W^4$ is a single bond, lower alkylene, etc., $Ar^2$ is an optionally substituted aryl, etc., $W^3$ is a single bond, lower alkylene, etc., $Ar^1$ is an optionally substituted arylene, etc., each of $W^1$ and $W^2$ is an optionally substituted lower alkylene, etc., and $R^1$ is carboxyl, an alkoxycarbonyl.

10 Claims, No Drawings

HETEROARYL DERIVATIVES

RELATED APPLICATIONS

The present application is the national stage under 35 USC §371 of International Application PCT/JP2006/300248, filed Jan. 12, 2006, which in turn claims priority under 35 USC §119 (a)-(d) of Japanese application 2005-006950, filed on Jan. 14, 2005.

TECHNICAL FIELD

The present invention relates to a novel heteroaryl compound having anti-diabetic activity or a salt thereof. More particularly, the present invention relates to a novel heteroaryl compound having an anti-diabetic activity, which improves insulin resistance and control the blood glucose level more safely, and/or being useful for treating or preventing metabolic diseases such as hyperlipemia, arteriosclerosis or metabolic syndrome. Further particularly, the present invention relates to a novel heteroaryl compound that regulates activity of peroxisome proliferator-activated receptor (PPAR) α, PPARγ, or PPAR α/γ.

BACKGROUND ART

The number of patients with diabetes mellitus has been increasing steadily owing to the recent change in the lifestyle. According to the research done in 1997 in Japan, it has been speculated that the number of people strongly-speculated as having diabetic mellitus is 6.9 million, and the number of people who can not be deniable the possibility of diabetes mellitus is 6.8 million. Most of the patients with diabetes mellitus in Japan are classified into type 2 diabetes mellitus, wherein the basal pathological conditions thereof are the reduced output of insulin and the insulin resistance, and medicaments against to each condition have been developed.

Although sulfonylurea (SU) agents, which is known from of old, have widely been used for improving the reduced output of insulin, the agents are known to have a risk of hypoglycemia as a serious side effect, and further to be apt to cause obesity.

On the other hand, thiazolidinedione agents are known as an insulin resistance improving agent.

Troglitazone was first put on market as a thiazolidinedione agent, but its sale was discontinued due to a serious hepatic damage. In Japan, pioglitazone has been clinically used at the present, but the heart failure due to the increase in circulating plasma volume was reported as a serious side effect thereof, and hence, Urgent Safety Information on pioglitazone was issued on October, 2000, which announced that pioglitazone needs careful attention to heart failure and edema. As to rosiglitazone, which has been widely used in Europe and the U.S., there are reported side effects such as infection of upper respiratory tract, anemia, edema, weight gain, etc. Thus, any thiazolidinedione agent having no concern regarding hepatic damage or side effects on the cardiovascular system has not been put on the market yet.

Thiazolidinedione agents are thought to exhibit anti-diabetic activity by activating PPARγ. It is known that PPAR has subtypes such as α, γ, δ (β), etc. Fibrate agents (e.g., clofibrate, fenofibrate, etc.), which are used as an agent for treating hyperlipemia, are considered to exhibit their pharmacological activities by activating PPARα. It has recently been reported that the insulin resistance is improved by administering a PPARα activator to animal models (cf., Journal of Biological Chemistry, vol. 275, p 16638, 2000), and there is a growing possibility where PPARα activators may show an effectiveness against diabetes mellitus as well as hyperlipidemia.

Many of compounds activating PPARγ or both PPARα and PPARγ such as isoxazolidindiones are reported other than thiazolidinedione agents (cf., Journal of Medicinal Chemistry, 43, p. 527, 2000), but the efficacy and safety thereof in the clinical field are not confirmed yet. At the present, PPARα agonists, PPARγ agonists, PPARα/γ agonists or PPARα/γ activation regulators having a good antidiabetic activity, are useful for treating or preventing metabolic diseases such as hyperlipemia, arteriosclerosis or metabolic syndrome and having high safety have been desired.

Many diabetic agents called PPARγ activation regulators (modulators, partial agonists) have been recently reported (c.f., Bioorganic & Medicinal Chemistry Letters, Vol. 15, p357-362 (2005), and European Journal of Pharmacology, p273-281 (2004)). There is suggested a possibility that these agents do not show side effects such as weight gain, edema or increase in heart weight observed in PPARγ full agonist such as pioglitazone or rosiglitazone, and have a good antidiabetic activity. The medicament having partial activity of PPARγ has been greatly expected to become a diabetic agent with high safety.

In addition, diabetic medicines having a pyrrole group in its structure have are known (cf, JP-A-2002-121186, WO 02/085851, WO 2004/048341), but the efficacy and safety thereof in the clinical field are not reported yet.

DISCLOSURE OF INVENTION

An object of the present invention is to provide an agent for preventing or treating diabetes mellitus, which shows PPARα regulating activity, PPARγ regulating activity, or PPARα/γ regulating activity, and improves insulin resistance and further shows a high safety.

The present inventors have intensively studied, and have found that a novel heteroaryl derivative improves diabetes mellitus.insulin resistance and/or are useful for treating or preventing metabolic diseases such as hyperlipemia, arterioscrelosis or metabolic syndrome by partially activating PPARα, PPARγ, or PPARα/γ, and further shows a good safety without showing side effects such as weight gain, edema or increase in heart weight observed in known PPARγ full agonists, and have a possibility to become useful for treating and preventing diabetes mellitus, and finally they have accomplished the present invention.

Namely, the present invention provides the following.

[1] A compound of the formula (1):

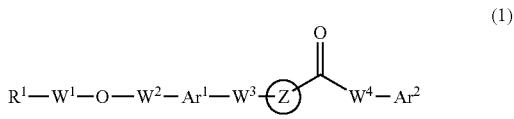

wherein Ring Z is an optionally substituted heteroaryl;

$W^4$ is a single bond, —$NR^{10}$—, —$NR^{10}$—$W^6$— (in which $R^{10}$ is a hydrogen atom, or an optionally substituted lower alkyl, and $W^6$ is a lower alkylene), a lower alkylene, or a lower alkenylene;

$Ar^2$ is an optionally substituted aryl or an optionally substituted heteroaryl;

W³ is a single bond, a lower alkylene, a lower alkenylene, or —Y¹—W⁵-(in which Y¹ is an oxygen atom, a sulfur atom, —S(O)— or —S(O)₂—, and W⁵ is a lower alkylene or a lower alkenylene);

Ar¹ is an optionally substituted arylene or an optionally substituted heteroarylene;

W¹ and W² are independently an optionally substituted lower alkylene or an optionally substituted lower alkenylene;

R¹ is a carboxyl group, an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, or a tetrazolyl group, or a prodrug thereof, or a pharmaceutically acceptable salt thereof.

[2] The compound according to the above [1], wherein Ring Z is an optionally substituted pyrrole ring, an optionally substituted pyrazole ring, an optionally substituted indole ring, or an optionally substituted indazole ring, Ar² is an optionally substituted aryl group, W³ is a single bond, a C₁-C₃ alkylene, a C₂-C₃ alkenylene, Ar¹ is an optionally substituted arylene, and W¹ is an optionally substituted lower alkylene; or Ring Z is a group represented by following formula (2);

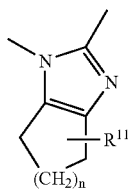

(2)

wherein the number of R¹¹ is zero or one or more, and R¹¹ is a halogen atom, an optionally substituted lower alkyl group, an optionally substituted alkoxy group, hydroxy group, an optionally substituted amino group, or oxo group, n is 1, 2 or 3; or W³ is a lower alkenylene and a double bond of it is cis configuration; or W¹ or W² is a lower alkynylene, or a prodrug thereof, or a pharmaceutically acceptable salt thereof.

[3] The compound according to the above [1], wherein Ring Z is an optionally substituted pyrrole ring, an optionally substituted pyrazole ring, an optionally substituted indole ring, or an optionally substituted indazole ring, Ar² is an optionally substituted aryl group, W³ is a single bond, a C₁-C₃ alkylene, a C₂-C₃ alkenylene, Ar¹ is an optionally substituted arylene, and W¹ is an optionally substituted lower alkylene; or W³ is a lower alkenylene and a double bond of it is cis configuration; or W¹ or W² is a lower alkynylene, or a prodrug thereof, or a pharmaceutically acceptable salt thereof.

[4] The compound according to the above [1], wherein Ring Z is selected from the following formulae (3), (4) and (5):

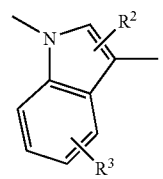

(3)

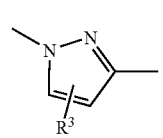

(4)

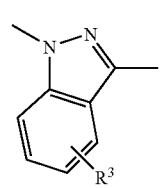

(5)

wherein the number of R² may be zero or one, and R² is a halogen atom, an optionally substituted alkyl, an optionally substituted aryl, an optionally substituted heteroaryl, or an optionally substituted thiol, the number of R³ may be zero, one or more, and R³ is independently, a halogen atom, an optionally substituted alkyl, an optionally substituted thiol, an optionally substituted alkoxy group, an optionally substituted amino, hydroxy group, cyano group, nitro group, carboxyl group, an optionally substituted acyl group, an optionally substituted saturated heterocyclic group, or an optionally substituted carbamoyl group, and W⁴ is a single bond, W³ is a single bond, methylene, ethylene, vinylene, or propenylene, W¹ is methylene optionally substituted by a C₁-C₃ alkyl group, W² is methylene or propenylene, Ar¹ is phenylene, Ar² is an optionally substituted phenyl group; or W³ is a lower alkenylene and a double bond of it is cis configuration;

W¹ or W² is a lower alkynylene, or a prodrug thereof, or a pharmaceutically acceptable salt thereof.

[5] The compound according to the above [1], wherein Ring Z is an optionally substituted pyrrole ring, an optionally substituted pyrazole ring, an optionally substituted indole, or an optionally substituted indazole ring, Ar² is an optionally substituted aryl group, W³ is a single bond, C₁-C₃ alkylene or C₂-C₃ alkenylene, Ar¹ is an optionally substituted arylene, and W¹ is an optionally substituted lower alkylene, or a prodrug thereof, or a pharmaceutically acceptable salt thereof.

[6] The compound according to the above [1], wherein Ring Z is selected from the following formulae (3), (4) and (5):

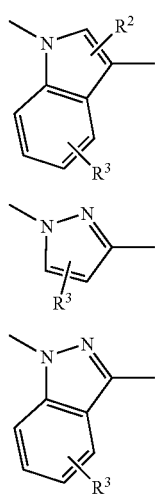

wherein the number of $R^2$ may be zero or one, and $R^2$ is a halogen atom, an optionally substituted alkyl, an optionally substituted aryl, an optionally substituted heteroaryl, or an optionally substituted thiol, the number of $R^3$ may be zero, one or more, and $R^3$ is independently, a halogen atom, an optionally substituted alkyl, an optionally substituted thiol, an optionally substituted alkoxy group, an optionally substituted amino, hydroxy group, cyano group, nitro group, carboxy group, an optionally substituted acyl group, an optionally substituted saturated heterocyclic group, or an optionally substituted carbamoyl group, $W^4$ is a single bond, $W^3$ is a single bond, methylene, ethylene, vinylene, or propenylene, $W^1$ is methylene optionally substituted by a $C_1$-$C_3$ alkyl group, $W^2$ is methylene or propenylene, $Ar^1$ is phenylene, and $Ar^2$ is an optionally substituted phenyl group, or a prodrug thereof, or a pharmaceutically acceptable salt thereof.

[7] The compound according to above [6], wherein $W^2$ is methylene, $W^3$ is methylene or propenylene, $Ar^2$ is phenyl group optionally substituted by a lower alkyl group or alkoxy group, and $R^1$ is carboxy group, or a prodrug thereof, or a pharmaceutically acceptable salt thereof.

[8] The heteroaryl compound according to above [1], wherein Ring Z is a group represented by following formula (2);

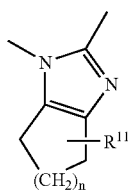

wherein the number of $R^{11}$ is zero or one or more, and $R^{11}$ is independently a halogen atom, an optionally substituted lower alkyl group, an optionally substituted alkoxy group, hydroxy group, an optionally substituted amino group, or oxo group, n is 1, 2 or 3, or a prodrug thereof or a pharmaceutically acceptable salt thereof.

[9] The compound according to above [8], wherein Ring Z is a group represented by following formula (6);

(6)

wherein n is 1, 2 or 3, $W^4$ is a single bond, $W^3$ is a single bond, $C_1$-$C_3$ alkylene, or $C_2$-$C_3$ alkenylene, $W^1$ is optionally substituted $C_1$-$C_3$ alkylene, $W^2$ is $C_1$-$C_3$ alkylene or $C_2$-$C_3$ alkenylene, $Ar^1$ is arylene, and $Ar^2$ is an optionally substituted aryl group, or a prodrug thereof or a pharmaceutically acceptable salt thereof.

[10] The compound according to above [9], wherein $W^3$ is a single bond, methylene, ethylene, vinylene, or propenylene, $W^1$ is methylene optionally substituted by a $C_1$-$C_3$ alkyl group, $W^2$ is methylene or propenylene, $Ar^1$ is phenylene, and $Ar^2$ is a phenyl group optionally substituted by lower alkyl or alkoxy;

or a prodrug thereof or a pharmaceutically acceptable salt thereof.

[11] The compound according to above [10], wherein $W^2$ is methylene, $W^3$ is methylene or propenylene, and $R^1$ is carboxy group; or a prodrug thereof or a pharmaceutically acceptable-salt thereof.

[12] The compound according to above [1], wherein $W^3$ is a lower alkenylene and a double bond of it is cis configuration, or a prodrug thereof, or a pharmaceutically acceptable salt thereof.

[13] The derivative according to the above [12], wherein Ring Z is an optionally substituted pyrrole ring, an optionally substituted pyrazole ring, an optionally substituted imidazole ring, an optionally substituted triazole ring, an optionally substituted indole ring, an optionally substituted indazole ring, or an optionally substituted benzimidazole ring, $W^4$ is a single bond, —$NR^{10}$— (wherein $R^{10}$ is hydrogen atom or an optionally substituted $C_1$-$C_8$ alkyl group), a $C_1$-$C_4$ alkylene, a $C_2$-$C_4$ alkenylene, and $W^1$ and $W^2$ is an optionally substituted lower alkylene, or a prodrug thereof, or a pharmaceutically acceptable salt thereof.

[14] The compound according to above [13], wherein Ring Z is a group selected from the group represented by following formula (A);

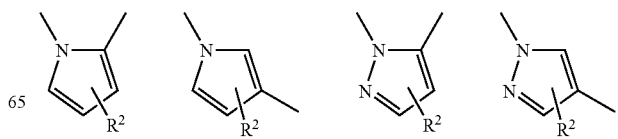

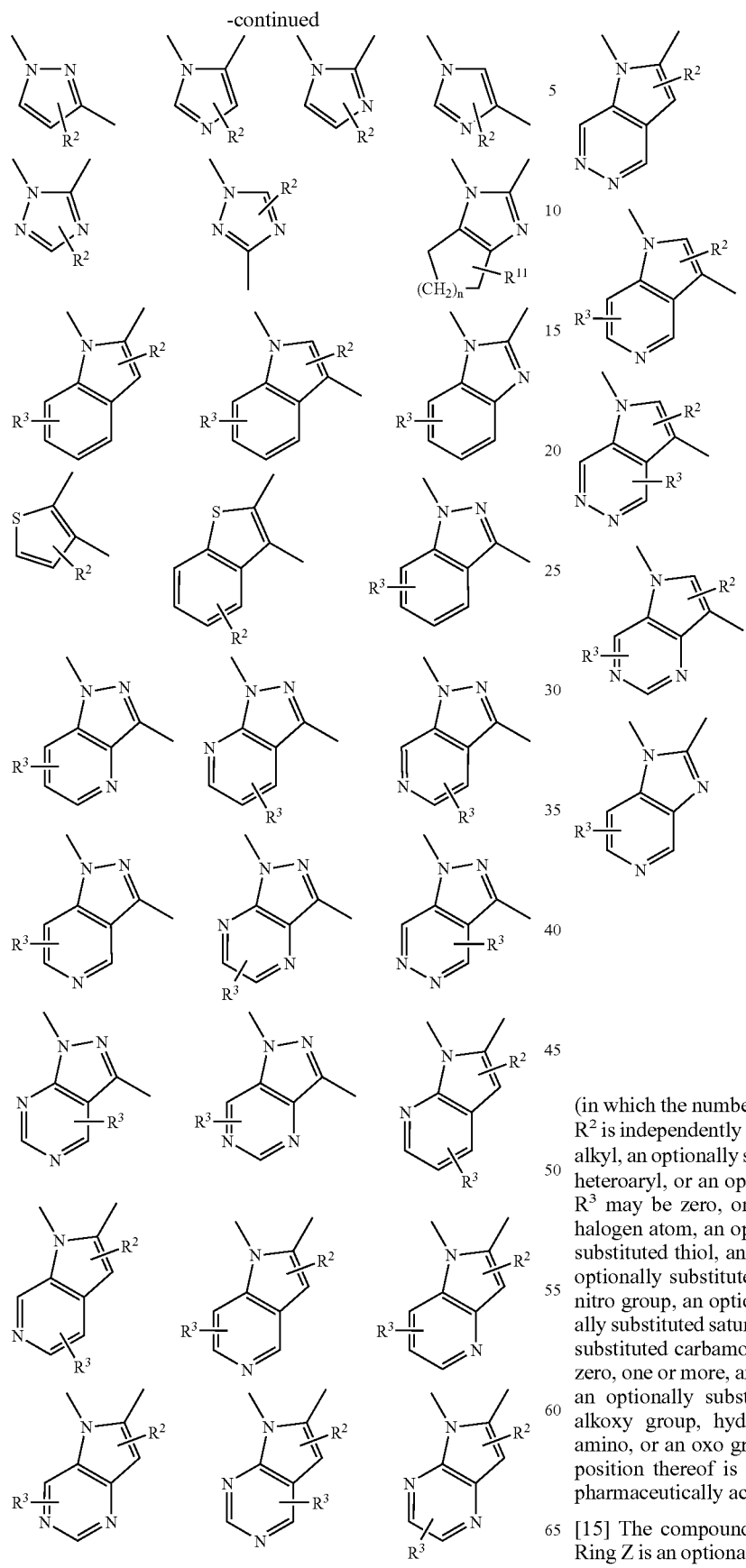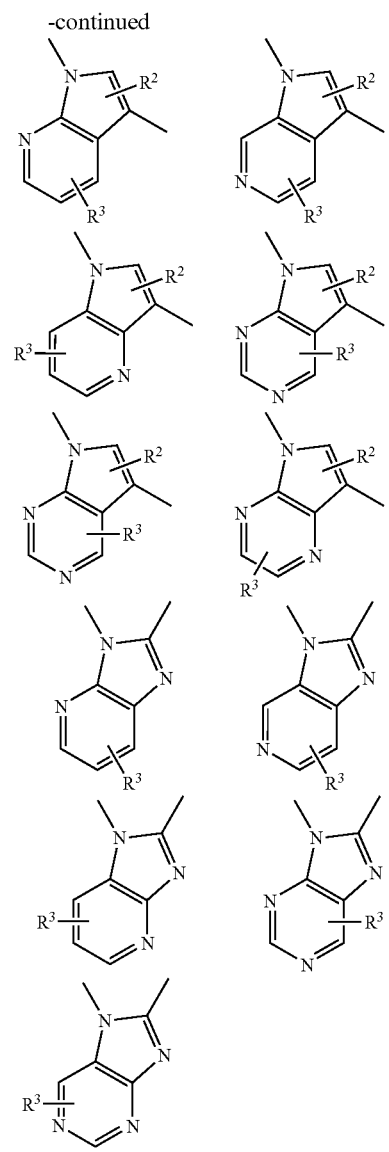

(in which the number of $R^2$ may be zero, or one or more, and $R^2$ is independently a halogen atom, an optionally substituted alkyl, an optionally substituted aryl, an optionally substituted heteroaryl, or an optionally substituted thiol, the number of $R^3$ may be zero, one or more, and $R^3$ is independently, a halogen atom, an optionally substituted alkyl, an optionally substituted thiol, an optionally substituted alkoxy group, an optionally substituted amino, hydroxy group, cyano group, nitro group, an optionally substituted acyl group, an optionally substituted saturated heterocyclic group, or an optionally substituted carbamoyl group, and the number of $R^{11}$ may be zero, one or more, and $R^{11}$ is independently, a halogen atom, an optionally substituted alkyl, an optionally substituted alkoxy group, hydroxy group, an optionally substituted amino, or an oxo group, and n is 1, 2 or 3) and the binding position thereof is not limited, or a prodrug thereof, or a pharmaceutically acceptable salt thereof.

[15] The compound according to the above [14], wherein Ring Z is an optionally substituted pyrrole ring, an optionally substituted imidazole ring, or an optionally substituted benzimidazole ring, W⁴ is a single bond, W¹ is an optionally substituted $C_1$-$C_3$ alkylene, and W² is a $C_1$-$C_3$ alkylene, or a $C_2$-$C_3$ alkenylene, Ar¹ is arylene and Ar² is an optionally substituted aryl, or a prodrug thereof, or a pharmaceutically acceptable salt thereof.

[16] The compound according to above [15], wherein W³ is vinylene, or propenylene and a double bond of said alkenylene is a cis configuration, W¹ is methylene optionally substituted by a $C_1$-$C_3$ alkyl group, W² is methylene or propenylene, Ar¹ is phenylene, and Ar² is a phenyl group optionally substituted by a lower alkyl group, a halogen atom or an alkoxy group, or a prodrug thereof or a pharmaceutically acceptable salt thereof.

[17] The compound according to above [16], wherein W² is a methylene, and R¹ is a carboxyl group, or a prodrug thereof or a pharmaceutically acceptable salt thereof.

[18] The compound according to above [1], wherein W¹ or W² is a lower alkenylene, or a prodrug thereof or a pharmaceutically acceptable salt thereof.

[19] The compound according to the above [18], wherein Ring Z is an optionally substituted pyrrole ring, an optionally substituted pyrazole ring, an optionally substituted imidazole ring, an optionally substituted triazole ring, an optionally substituted indole ring, an optionally substituted indazole ring, or an optionally substituted benzimidazole ring, and W⁴ is a single bond, —NR¹⁰— (wherein R¹⁰ is hydrogen atom or an optionally substituted $C_1$-$C_8$ alkyl group), a $C_1$-$C_4$ alkylene, or a $C_2$-$C_4$ alkenylene), or a prodrug thereof, or a pharmaceutically acceptable salt thereof.

[20] The compound according to above [19], wherein Ring Z is a group selected from the group represented by following formula (A);

(A)

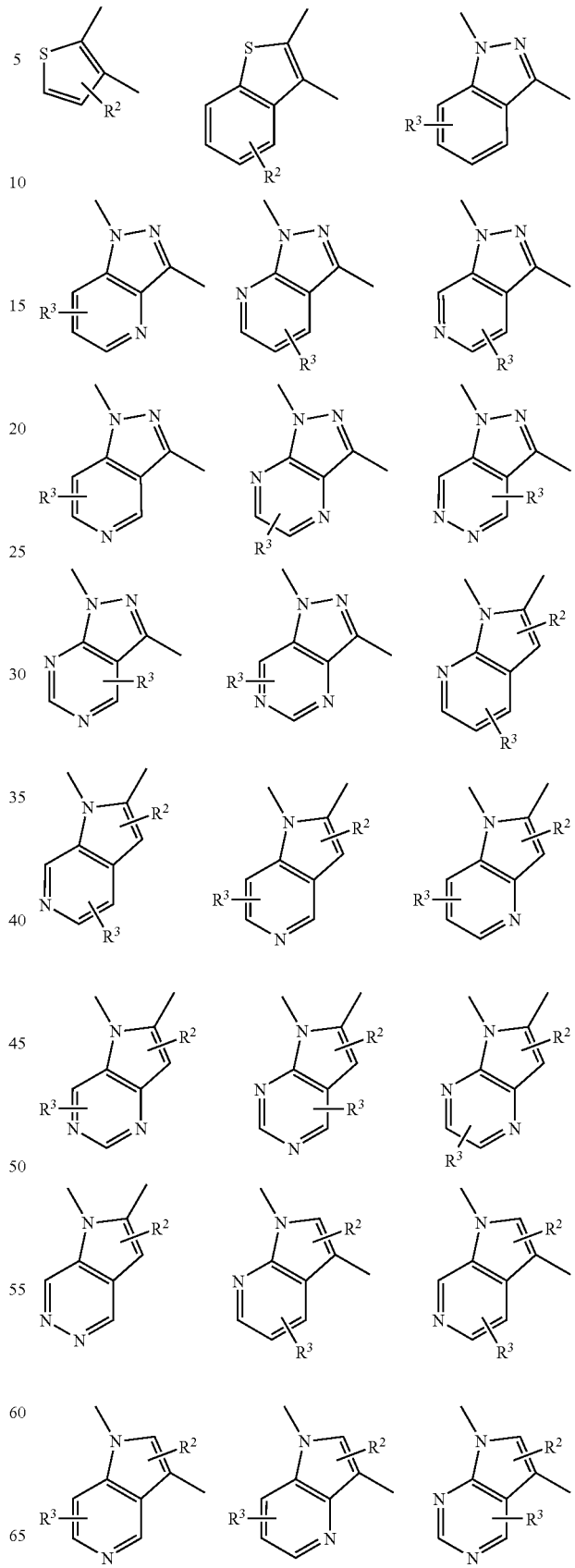

-continued

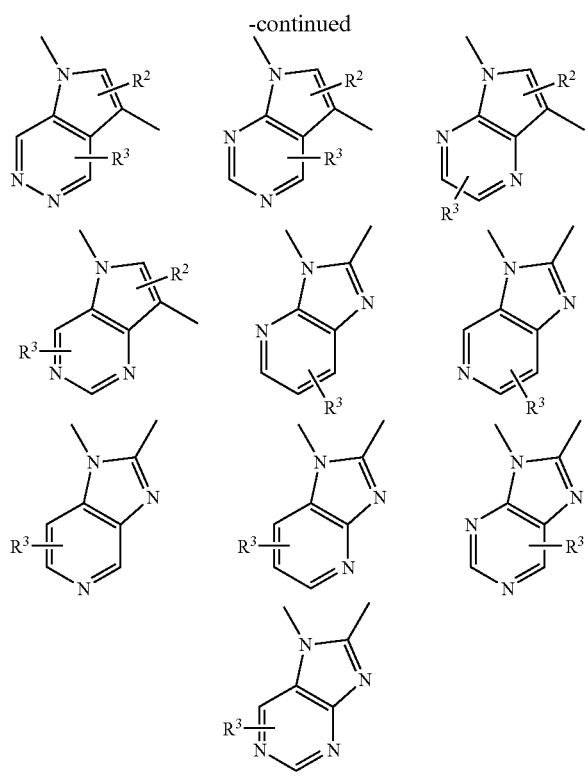

(in which the number of $R^2$ may be zero, or one or more, and $R^2$ is independently a halogen atom, an optionally substituted alkyl, an optionally substituted aryl, an optionally substituted heteroaryl, or an optionally substituted thiol, the number of $R^3$ may be zero, one or more, and $R^3$ is independently, a halogen atom, an optionally substituted alkyl, an optionally substituted thiol, an optionally substituted alkoxy group, an optionally substituted amino, hydroxy group, cyano group, nitro group, an optionally substituted acyl group, an optionally substituted saturated heterocyclic group, or an optionally substituted carbamoyl group, and the number of $R^{11}$ may be zero, one or more, and $R^{11}$ is independently, a halogen atom, an optionally substituted alkyl, an optionally substituted alkoxy group, hydroxy group, an optionally substituted amino, or an oxo group, and n is 1, 2 or 3) and the binding position thereof is not limited, or a prodrug thereof, or a pharmaceutically acceptable salt thereof.

[21] The compound according to the above [20], wherein Ring Z is an optionally substituted pyrrole ring, an optionally substituted imidazole ring, or an optionally substituted benzimidazole ring, $W^4$ is a single bond, $W^3$ is a single bond, $C_1$-$C_3$ alkylene, or a $C_2$-$C_3$ alkenylene, $Ar^1$ is arylene, and $Ar^2$ is an optionally substituted aryl, or a prodrug thereof, or a pharmaceutically acceptable salt thereof.

[22] The compound according to above [21], wherein $W^1$ or $W^2$ are propenylene, $W^3$ is a single bond, methylene, ethylene, vinylene, or propenylene, $Ar^1$ is phenylene, and $Ar^2$ is a phenyl group optionally substituted by a lower alkyl group or an alkoxy group, or a prodrug thereof or a pharmaceutically acceptable salt thereof.

[23] The compound according to above [22], wherein $W^3$ is methylene or propenylene, and $R^1$ is a carboxyl group, or a prodrug thereof or a pharmaceutically acceptable salt thereof.

[24] A pharmaceutical composition comprising the compound according to any one of above [1] to [23], a prodrug thereof or a pharmaceutically acceptable salt thereof as an active ingredient.

[25] A PPARα, PPARγ, or PPARα/γ activity regulating agent comprising the compound according to any one of above [1] to [23], a prodrug thereof or a pharmaceutically acceptable salt thereof as an active ingredient.

[26] An agent for treating diabetes mellitus or hyperlipidemia comprising the compound according to any one of above [1] to [23], a prodrug thereof or a pharmaceutically acceptable salt thereof as an active ingredient.

[27] A method for treating diabetes mellitus or hyperlipidemia by administering to a patient who needs for treatment of it an effective amount of the compound according to any one of above [1] to [23], a prodrug thereof or a pharmaceutically acceptable salt thereof.

[28] Use of the compound according to any one of above [1] to [23], a prodrug thereof or a pharmaceutically acceptable salt thereof in the manufacture of a medicament for treating diabetes mellitus or hyperlipidemia.

The compound represented by a formula (1), a prodrug thereof or a pharmaceutically acceptable salt thereof is if necessary, abbreviated as "the compound of the present invention" hereinafter.

By the present invention, it has become possible to provide a novel heteroaryl derivative or a salt thereof, which improves insulin resistance and shows a good safety without showing side effects observed in known PPARγ full agonists, and is useful as an agent for prophylaxis or treatment of diabetic mellitus.

BEST MODE FOR CARRYING OUT THE INVENTION

With respect to the heteroaryl derivative of the formula (1) of the present invention, the definitions in said formula are explained in more detail below. The number substituted by the group defined by the term, "optionally substituted" or "substituted" is not limited as long as the number is possible and not indicated, and is one or more. The explanation of each group corresponds to the group that is moiety of other group or substituents of the group, provided the definition is specified.

The heteroaryl for Ring Z includes, for example, a pyrrole ring, a pyrazole ring, an imidazole ring, a triazole ring, an indole ring, an indazole ring, a benzimidazole ring, and a group of the following formulae (11):

(11)

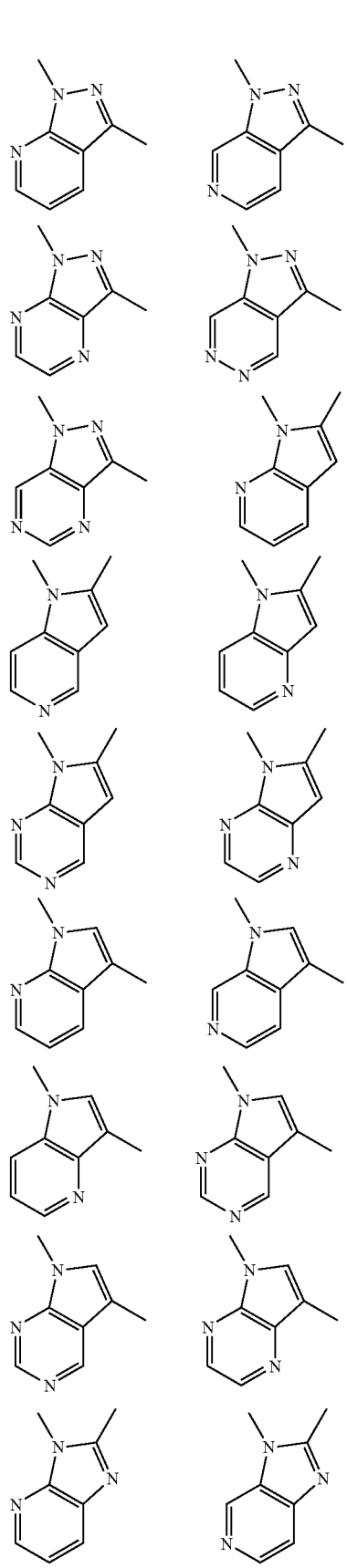
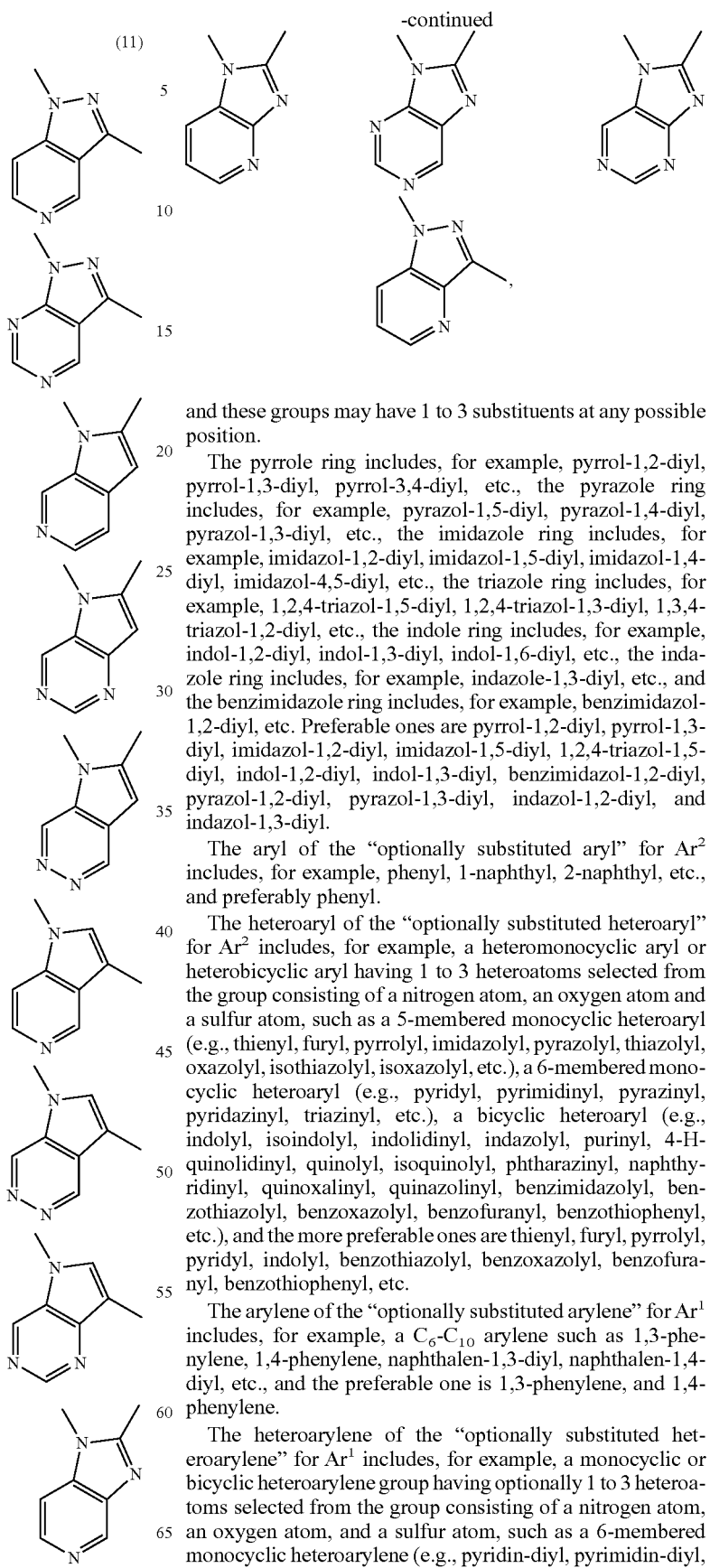

and these groups may have 1 to 3 substituents at any possible position.

The pyrrole ring includes, for example, pyrrol-1,2-diyl, pyrrol-1,3-diyl, pyrrol-3,4-diyl, etc., the pyrazole ring includes, for example, pyrazol-1,5-diyl, pyrazol-1,4-diyl, pyrazol-1,3-diyl, etc., the imidazole ring includes, for example, imidazol-1,2-diyl, imidazol-1,5-diyl, imidazol-1,4-diyl, imidazol-4,5-diyl, etc., the triazole ring includes, for example, 1,2,4-triazol-1,5-diyl, 1,2,4-triazol-1,3-diyl, 1,3,4-triazol-1,2-diyl, etc., the indole ring includes, for example, indol-1,2-diyl, indol-1,3-diyl, indol-1,6-diyl, etc., the indazole ring includes, for example, indazole-1,3-diyl, etc., and the benzimidazole ring includes, for example, benzimidazol-1,2-diyl, etc. Preferable ones are pyrrol-1,2-diyl, pyrrol-1,3-diyl, imidazol-1,2-diyl, imidazol-1,5-diyl, 1,2,4-triazol-1,5-diyl, indol-1,2-diyl, indol-1,3-diyl, benzimidazol-1,2-diyl, pyrazol-1,2-diyl, pyrazol-1,3-diyl, indazol-1,2-diyl, and indazol-1,3-diyl.

The aryl of the "optionally substituted aryl" for $Ar^2$ includes, for example, phenyl, 1-naphthyl, 2-naphthyl, etc., and preferably phenyl.

The heteroaryl of the "optionally substituted heteroaryl" for $Ar^2$ includes, for example, a heteromonocyclic aryl or heterobicyclic aryl having 1 to 3 heteroatoms selected from the group consisting of a nitrogen atom, an oxygen atom and a sulfur atom, such as a 5-membered monocyclic heteroaryl (e.g., thienyl, furyl, pyrrolyl, imidazolyl, pyrazolyl, thiazolyl, oxazolyl, isothiazolyl, isoxazolyl, etc.), a 6-membered monocyclic heteroaryl (e.g., pyridyl, pyrimidinyl, pyrazinyl, pyridazinyl, triazinyl, etc.), a bicyclic heteroaryl (e.g., indolyl, isoindolyl, indolidinyl, indazolyl, purinyl, 4-H-quinolidinyl, quinolyl, isoquinolyl, phtharazinyl, naphthyridinyl, quinoxalinyl, quinazolinyl, benzimidazolyl, benzothiazolyl, benzoxazolyl, benzofuranyl, benzothiophenyl, etc.), and the more preferable ones are thienyl, furyl, pyrrolyl, pyridyl, indolyl, benzothiazolyl, benzoxazolyl, benzofuranyl, benzothiophenyl, etc.

The arylene of the "optionally substituted arylene" for $Ar^1$ includes, for example, a $C_6$-$C_{10}$ arylene such as 1,3-phenylene, 1,4-phenylene, naphthalen-1,3-diyl, naphthalen-1,4-diyl, etc., and the preferable one is 1,3-phenylene, and 1,4-phenylene.

The heteroarylene of the "optionally substituted heteroarylene" for $Ar^1$ includes, for example, a monocyclic or bicyclic heteroarylene group having optionally 1 to 3 heteroatoms selected from the group consisting of a nitrogen atom, an oxygen atom, and a sulfur atom, such as a 6-membered monocyclic heteroarylene (e.g., pyridin-diyl, pyrimidin-diyl, pyrazin-diyl, pyridazin-diyl, triazin-diyl, etc.), a 5-membered monocyclic heteroarylene (e.g., thiophen-diyl, furan-diyl, pyrrol-diyl, imidazol-diyl, pyrazol-diyl, thiazol-diyl, oxazol-diyl, isothiazol-diyl, isoxazol-diyl, etc.), a bicyclic heteroarylene (e.g., indol-diyl, isoindol-diyl, indolidin-diyl, indazol-diyl, purin-diyl, 4-H-quinolidin-diyl, quinolin-diyl, isoquinolin-diyl, phthalazin-diyl, naphthyridin-diyl, quinoxalin-diyl, quinazolin-diyl, benzimidazol-diyl, benzothiazol-diyl, benzoxazol-diyl, benzofuran-diyl, benzothiophen-diyl, etc.), and more preferable ones are pyridin-diyl, thiophen-diyl, pyrrol-diyl, furan-diyl, and indol-diyl.

The "optionally substituted aryl" and the "optionally substituted heteroaryl" for $Ar^2$, and the "optionally substituted arylene" and the "optionally substituted heteroarylene" for $Ar^1$ may have 1 to 5 substituents, preferably 1 to 3 substituents, at any substitutable position. Said substituent includes, for example, an optionally substituted lower alkyl, a lower alkenyl, an aryl, a substituted aryl, a heteroaryl, a substituted heteroaryl, an optionally substituted saturated heterocyclic group, a halogen atom, an optionally substituted amino, an optionally substituted acyl, an optionally substituted hydroxy, an optionally substituted thiol, an alkylsulfonyl, cyano, nitro, a carbamoyl group optionally substituted by an alkyl.

The lower alkyl of the "optionally substituted lower alkyl" includes, for example, a straight chain or a branched chain $C_1$-$C_8$ alkyl, such as methyl, ethyl, 1-propyl, 2-propyl, 1-butyl, 2-butyl, t-butyl, or a $C_1$-$C_8$ alkyl having a cyclic structure, such as cyclopropyl, cyclopropylmethyl, cyclobutyl, cyclobutylmethyl, cyclopentyl, cyclopentylmethyl, cyclohexyl, cyclohexylmethyl, cyclohexylethyl, etc., and preferably methyl, ethyl, 2-propyl, and cyclopropyl.

The "lower alkenyl" includes a straight chain or a branched chain $C_2$-$C_8$ alkenyl or a $C_2$-$C_8$ alkenyl having a cyclic structure, for example, vinyl, 1-propenyl, 2-propenyl, 2-methyl-1-propenyl, etc., and preferably vinyl and 2-propenyl.

The substituent of said "optionally substituted lower alkyl or lower alkenyl" includes, for example, hydroxy group, oxo, amino, a $C_1$-$C_8$ monoalkylamino (e.g., methylamino, ethylamino, propylamino, etc.), a $C_2$-$C_{12}$ dialkylamino (e.g., dimethylamino, ethylmethylamino, diethylamino, etc.), a $C_1$-$C_8$ alkoxy (e.g., methoxy, ethoxy, 1-propyloxy, 2-propyloxy, etc.), a halogen atom (e.g., fluorine atom, chlorine atom, bromine atom, etc.), a $C_1$-$C_8$ haloalkoxy (e.g., trifluoromethoxy, etc.), a saturated heterocyclic group (e.g., morpholino, piperidino, pyrrolidino, 4-methyl-1-piperazino, etc.), an aryl (e.g., phenyl, 1-naphthyl, etc.), or a heteroaryl (e.g., pyridyl, thienyl, furanyl, etc.), and preferably methylamino, ethylamino, dimethylamino, diethylamino, methoxy, ethoxy, 2-propyloxy, fluorine atom, chlorine atom, trifluoromethoxy, morpholino, piperidino, pyrrolidino, phenyl, and pyridyl.

The aryl of the "aryl or substituted aryl" includes, for example, phenyl, 1-naphthyl, 2-naphthyl, etc., and preferably phenyl.

The heteroaryl of "heteroaryl or substituted heteroaryl" is the same as those for the heteroaryl for $Ar^2$, and preferable ones are thiophene, furan, pyrrole and pyridine, etc.

The saturated heterocyclic group of the "optionally substituted saturated heterocyclic group" includes one having 2 to 6 carbon atoms, and as a ring-forming member, having 1 to 3 heteroatoms selected from an oxygen atom, a sulfur atom and a nitrogen atom in addition to the carbon atoms, for example, morpholino, thiomorpholino, piperidino, pyrrolidino, 4-methyl-1-piperazino, etc. The preferable ones are morpholino, piperidino and pyrrolidino.

The substituents of said "substituted aryl, substituted heteroaryl, optionally substituted saturated heterocyclic group" includes, for example, a $C_1$-$C_8$ alkyl (e.g., methyl, ethyl, 1-propyl, 2-propyl, 1-butyl, 2-butyl, t-butyl, etc.), a $C_1$-$C_8$ alkoxy (e.g., methoxy, ethoxy, 1-propyloxy, 2-propyloxy, etc.), a halogen atom (e.g., fluorine atom, chlorine atom, bromine atom, etc.), a $C_1$-$C_8$ haloalkoxy (e.g., trifluoromethoxy, etc.), a $C_1$-$C_8$ haloalkyl (e.g., trifluoromethyl, etc.), and the preferable ones are methyl, ethyl, 2-propyl, methoxy, ethoxy, fluorine atom, chlorine atom, trifluoromethoxy, trifluoromethyl.

The halogen atom is fluorine atom, chlorine atom, bromine atom, iodine atom, and preferable one is fluorine atom and chlorine atom.

The "optionally substituted amino" includes, for example, amino, and an amino optionally mono or di-substituted by a $C_1$-$C_8$ alkyl (e.g., methyl, ethyl, propyl, etc.), a $C_1$-$C_8$ acyl (e.g., acetyl, propionyl, etc.), an aryl (e.g., phenyl, etc.), and a heteroaryl, and preferable ones are methylamino, dimethylamino, ethylamino, diethylamino, cyclohexylamino, acetylamino, benzoylamino, phenylamino, etc.

The acyl of the "optionally substituted acyl" includes, in addition to formyl group, a group consisted by combining a carbonyl group with a $C_1$-$C_8$ alkyl (e.g., methyl, ethyl, 1-propyl, 2-propyl, 1-butyl, 2-butyl, t-butyl, etc.), an aryl (e.g., phenyl, etc.), or a heteroaryl (e.g., thienyl, pyridyl, etc.), and preferable ones are acetyl, propionyl, cyclobutanecarbonyl, cyclohexanecarbonyl, benzoyl, etc.

Said acyl group may have 1 to 3 substituents at any substitutable position, and said substituent includes a $C_1$-$C_3$ straight chain or branched chain alkyl (preferably methyl, ethyl, 2-propyl, etc.), a $C_1$-$C_3$ straight chain or branched chain alkoxy (preferably methoxy, ethoxy, 2-propoxy, etc.), a halogen atom (preferably fluorine atom and chlorine atom), hydroxy, amino, etc.

The "optionally substituted hydroxy group" includes a hydroxy, an optionally substituted alkoxy, an optionally substituted aralkyloxy, an optionally substituted aryloxy, and an optionally substituted acyloxy, etc.

The alkoxy of the "optionally substituted alkoxy" includes a $C_1$-$C_8$ alkoxy (e.g., methoxy, ethoxy, 2-propoxy, cyclopentyloxy, etc.), and preferable ones are methoxy, ethoxy and 2-propyloxy. When an alkyl or an alkoxy exists adjacently, said groups may combine together to form a ring having a substituent, for example, methylenedioxy, ethylenedioxy, 2-methyl-methylenedioxy, 2-methyl-ethylenedioxy, 1-oxy-2-ethylene, 1-oxy-2-propylene, etc., and preferable ones are methylenedioxy, and ethylenedioxy.

The aralkyloxy of the "optionally substituted aralkyloxy" includes, for example, a phenyl-($C_1$-$C_4$ alkyl)oxy, and preferably benzyloxy and phenethyloxy.

The aryloxy of the "optionally substituted aryloxy" includes, for example, phenyloxy, 1-naphthyloxy, etc., and preferably phenyloxy.

The acyloxy of the "optionally substituted acyloxy" includes, for example, acetyloxy, propionyloxy, etc.

The substituent of the above-mentioned "optionally substituted alkoxy, optionally substituted aralkyloxy, optionally substituted aryloxy, or optionally substituted acyloxy" includes, for example, a halogen (preferably fluorine and chlorine), a $C_1$-$C_3$ straight chain or branched chain alkoxy (preferably methoxy, ethoxy and 2-propoxy), a $C_1$-$C_3$ straight chain or branched chain alkyl (preferably methyl, ethyl, 2-propyl, etc.), trifluoromethyl, trifluoromethoxy, etc.

The "optionally substituted thiol" includes thiol, an alkylthio, an aralkylthio, an arylthio, a heteroarylthio, etc.

The "alkylthio" includes, for example, methylthio, ethylthio, 2-propylthio, cyclopentylthio, etc., and preferable ones are methylthio and ethylthio.

The "aralkylthio" includes, for example, a phenyl-($C_1$-$C_8$ alkyl)thio, and preferable ones are benzylthio and phenethylthio.

The "arylthio" includes, for example, phenylthio, 1-naphthylthio, etc., and preferable one is phenylthio.

The "heteroarylthio" is preferably pyridylthio, imidazolylthio, etc.

The "alkylsulfonyl" includes a straight chain or branched chain $C_1$-$C_8$ alkylsulfonyl, and preferable ones are methanesulfonyl, ethanesulfonyl, 2-propylsulfonyl, etc.

The "carbamoyl group optionally substituted by an alkyl" includes, for example, carbamoyl, a straight chain or branched chain $C_1$-$C_6$ monoalkylaminocarbonyl, or a straight chain or branched chain $C_2$-$C_{12}$ dialkylaminocarbonyl. The straight chain or branched chain $C_1$-$C_6$ alkylaminocarbonyl is preferably methylaminocarbonyl, ethylaminocarbonyl, propylaminocarbonyl and 2-propylaminocarbonyl. The straight chain or branched chain $C_2$-$C_{12}$ dialkylaminocarbonyl includes, for example, a carbamoyl substituted by the same or different alkyl groups, and preferable one is dimethylaminocarbonyl, diethylaminocarbonyl, ethylmethylaminocarbonyl, methylpropylaminocarbonyl, and dicyclohexylaminocarbonyl.

The lower alkylene for $W^4$ and $W^6$ includes, for example, a straight chain or branched chain $C_1$-$C_{10}$ alkylene and a $C_3$-$C_{10}$ alkylene having a cyclic structure, and preferable one is a straight chain or branched chain $C_1$-$C_4$ alkylene or a $C_3$-$C_4$ alkylene having a cyclic structure. The straight chain or branched chain $C_1$-$C_4$ alkylene includes, for example, methylene, ethylene, trimethylene, 1-methylmethylene, 1-ethylmethylene, 1-propylmethylene, 1-methylethylene, 2-methylethylene, 1-ethylethylene, etc., and preferable one is methylene and ethylene. The $C_3$-$C_4$ alkylene having a cyclic structure is an alkylene selected from the following formulae (12):

(12)

The lower alkenylene for $W^4$ includes, for example, a $C_2$-$C_8$ alkenylene, and preferable one is a $C_2$-$C_4$ alkenylene. The $C_2$-$C_4$ alkenylene includes, for example, a straight chain or branched chain $C_2$-$C_4$ alkenylene, such as cis- or trans-vinylene, cis- or trans-1-propenylene, cis- or trans-2-propenylene, cis- or trans-1-butenylene, cis- or trans-2-butenylene, trans-1-methyl-vinylene, trans-1-ethyl-vinylene, trans-1-methyl-1-propenylene, trans-2-methyl-1-propenylene, etc., and preferably cis- or trans-vinylene.

The lower alkylene for $W^3$ and $W^5$ includes, for example, a straight chain or branched chain $C_1$-$C_{10}$ alkylene, or a $C_3$-$C_{10}$ alkylene having a cyclic structure, and preferable one is a straight chain or branched chain $C_1$-$C_5$ alkylene or a $C_3$-$C_5$ alkylene having a cyclic structure. The straight chain or branched chain $C_1$-$C_5$ alkylene is, for example, methylene, ethylene, trimethylene, tetramethylene, 1-methyl-ethylene, 1,1-dimethyl-ethylene, 1-methyl-propylene, 1,1-dimethyl-propylene, etc., and the $C_3$-$C_5$ alkylene having a cyclic structure is an alkylene selected from the following formulae (13):

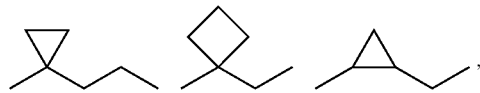

(13)

and preferable one is ethylene, trimethylene and tetramethylene.

The lower alkenylene for $W^3$ and $W^5$ includes, for example, a $C_2$-$C_8$ alkenylene, and preferable one is a $C_2$-$C_5$ alkenylene. The $C_2$-$C_5$ alkenylene includes, for example, a straight chain or branched chain $C_2$-$C_5$ alkenylene, such as cis- or trans-vinylene, cis- or trans-1-propenylene, cis- or trans-2-propenylene, cis- or trans-1-butenylene, cis- or trans-2-butenylene, cis- or trans-3-butenylene, cis- or trans-1-methyl-2-propenylene, cis- or trans-3-methyl-2-propenylene, cis- or trans-2-methyl-2-propenylene, cis- or trans-1-methyl-2-propenylene, etc., and more preferable one is trans-1-propenylene, cis-1-propenylene and trans-vinylene.

In case that $W^3$ is a lower alkenylene and a double bond(s) therein is cis configuration, at least one double bond is Z-formation, for example, an alkylene selected from the following formulae (B):

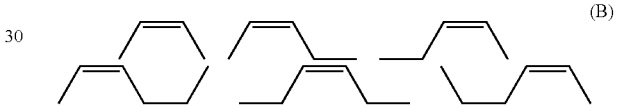

(B)

and so on.

The lower alkylene of the "optionally substituted lower alkylene" for $W^1$ and $W^2$ includes, for example, a straight chain $C_1$-$C_{10}$ alkylene or a $C_3$-$C_{10}$ alkylene having a cyclic structure, and preferable one is a straight chain $C_1$-$C_4$ alkylene or a $C_3$-$C_8$ alkylene having a cyclic structure. The straight chain $C_1$-$C_4$ alkylene is methylene, ethylene, trimethylene, etc., and more preferable one is methylene and ethylene. The $C_3$-$C_8$ alkylene containing a cyclic structure includes an alkylene of the following formulae (14):

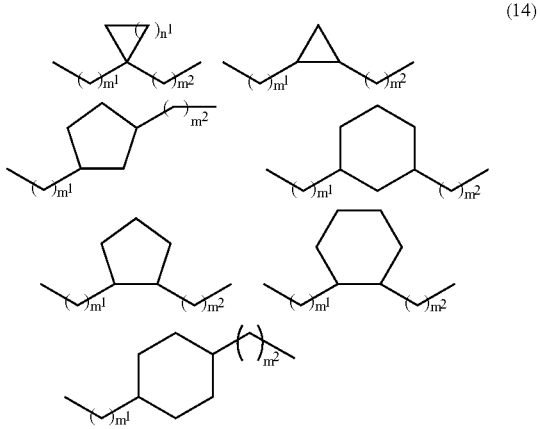

(14)

(wherein $m^1$ and $m^2$ are integer of 0 to 2, and $n^1$ is an integer of 1 to 4), etc. The lower alkenylene includes, for example, a $C_2$-$C_8$ alkenylene, and preferable one is a $C_2$-$C_4$ alkenylene. The $C_2$-$C_4$ alkenylene includes, for example, a straight chain or branched chain $C_2$-$C_4$ alkenylene, such as cis- or trans-vinylene, cis- or trans-1-propenylene, cis- or trans-2-propenylene, cis- or trans-1-butenylene, cis- or trans-2-butenylene, trans-1-methyl-vinylene, trans-1-ethyl-vinylene, trans-1-methyl-1-propenylene, trans-2-methyl-1-propenylene, etc., and more preferable one is trans-1-propenylene and trans-1-butenylene.

The substituent of the "optionally substituted lower alkylene or lower alkenylene" for $W^1$ and $W^2$ includes, for example, an optionally substituted alkyl, an optionally substituted aryl, an optionally substituted heteroaryl, a halogen atom, an optionally substituted amino, an optionally substituted acyl, an optionally substituted thiol, and an optionally substituted hydroxy, etc., and further an oxo, etc. may be exemplified, provided that when the substituent is an oxo, then a benzoic acid ester is not included. The number of said substituent may be 1 to 5, preferably 1 to 2, at any substitutable position.

The substituents of said "optionally substituted lower alkyl", "optionally substituted aryl", "optionally substituted heteroaryl", a halogen atom, an optionally substituted amino, an optionally substituted acyl, "optionally substituted hydroxy group" and "optionally substituted thiol" are the same as those as defined in the "optionally substituted aryl", and the "optionally substituted heteroaryl" for $Ar^2$, and the "optionally substituted arylene" and the "optionally substituted heteroarylene" for $Ar^1$.

The substituent of the "optionally substituted lower alkylene" for $W^1$ and $W^2$ is preferably methyl, ethyl, 1-propyl, 2-propyl, cyclopropyl, cyclobutyl, cyclopentyl, benzyl, phenethyl, pyridylmethyl, trifluoromethyl, phenyl, pyrrole, thiophene, pyridine, fluorine atom, methylamino, dimethylamino, acethylamino, acetyl, benzoyl, methylthio, ethylthio, methoxy, ethoxy, 1-propyloxy, 2-propyloxy, oxo, etc.

The alkoxycarbonyl for $R^1$ includes, for example, a carbonyl having a straight chain or branched chain $C_1$-$C_8$ alkoxy such as methoxy, ethoxy, propoxy, 2-propoxy, 2-methylpropoxy, butoxy, 2-methyl-2-propoxy, etc., and preferable one is methoxycarbonyl, ethoxycarbonyl, propoxycarbonyl and 2-propoxycarbonyl.

The optionally substituted carbamoyl for $R^1$ includes, for example, a straight chain or branched chain $C_1$-$C_8$ alkylaminocarbonyl or a straight chain or branched chain $C_2$-$C_{12}$ dialkylaminocarbonyl. The straight chain or branched chain $C_1$-$C_8$ alkylaminocarbonyl includes, for example, methylaminocarbonyl, ethylaminocarbonyl, propylaminocarbonyl, 2-propylaminocarbonyl, butylaminocarbonyl, etc., and preferable one is a straight chain or branched chain $C_1$-$C_4$ alkylaminocarbonyl. The straight chain or branched chain $C_2$-$C_{12}$ dialkylaminocarbonyl includes, for example, a carbamoyl substituted by the same or different alkyl groups, such as dimethylaminocarbonyl, diethylaminocarbonyl, dipropylaminocarbonyl, diisopropylaminocarbonyl, dibutylaminocarbonyl, ethylmethylaminocarbonyl, methylpropylaminocarbonyl, butylmethylaminocarbonyl, ethylbutylaminocarbonyl, dicyclohexylaminocarbonyl, etc., and preferable one is a straight chain or branched chain $C_2$-$C_8$ dialkylaminocarbonyl.

The cyclic amino of the optionally substituted cyclic aminocarbonyl for $R^1$ includes, for example, a 5- to 7-membered cyclic amino group optionally containing an oxygen atom, a sulfur atom, or a nitrogen atom as a ring-forming atom, which may be further optionally substituted by a $C_1$-$C_8$ alkyl, a hydroxy group, etc., such as pyrrolidino, piperidino, piperazinyl, 4-methylpiperazinyl, morpholino, thiomorpholino, 4-hydroxypiperidino, etc., and preferable one is pyrrolidino, morpholino, 4-hydroxypiperidino and 4-methylpiperazinyl.

The alkylsulfonyl of the optionally substituted alkylsulfonylcarbamoyl for $R^1$ includes, for example, an optionally substituted straight chain or branched chain $C_1$-$C_8$ alkylsulfonyl, etc., such as methanesulfony, ethanesulfonyl, 1-propanesulfonyl, 2-propanesulfonyl, butanesulfonyl, trifluoromethanesulfonyl, phenylmethylsulfonyl, pyridylmethylsulfonyl, etc., and preferable one is methanesulfonyl, ethanesulfonyl and 2-propanesulfonyl.

The arylsulfonyl of the optionally substituted arylsulfonylcarbamoyl for $R^1$ includes, for example, benzenesulfonyl, 4-methylbenzenesulfonyl, 4-chlorobenzenesulfonyl, 4-trifluoromethylbenzenesulfonyl, 3-methylbenzenesulfonyl, 1-naphthylsulfonyl, 2-naphthylsulfonyl, etc., and preferable one is benzenesulfonyl.

The lower alkyl of the "optionally substituted lower alkyl" for $R^{10}$ includes, for example, a straight chain $C_1$-$C_{10}$ alkyl or a $C_3$-$C_{10}$ alkyl having a cyclic structure, and preferable one is a straight chain $C_1$-$C_5$ alkyl or a $C_3$-$C_5$ alkyl containing a cyclic structure, such as methyl, ethyl, 2-propyl, etc.

The substituent of said "optionally substituted $C_1$-$C_8$ alkyl for $R^{10}$" includes, for example, a halogen atom, a $C_1$-$C_3$ straight chain or branched chain alkoxy, a $C_1$-$C_3$ straight chain or branched chain alkyl, trifluoromethyl, trifluoromethoxy, phenyl, pyridyl, etc., and preferable one is fluorine atom, chlorine atom, methoxy, ethoxy, 2-propoxy, methyl, ethyl, 2-propyl, trifluoromethyl, trifluoromethoxy, phenyl and pyridyl.

The lower alkyl of the "optionally substituted lower alkyl" for $R^{11}$ includes, for example, a straight chain $C_1$-$C_{10}$ alkyl or a $C_3$-$C_{10}$ alkyl having a cyclic structure, and preferable one is a straight chain $C_1$-$C_5$ alkyl or a $C_3$-$C_5$ alkyl containing a cyclic structure, such as methyl, ethyl, 2-propyl, etc.

The alkoxy of the "optionally substituted alkoxy" for $R^{11}$ includes a $C_1$-$C_8$ alkoxy (e.g., methoxy, ethoxy, 2-propoxy, cyclopentyloxy, etc.), and preferable ones are methoxy, ethoxy and 2-propyloxy. When an alkyl or an alkoxy exists adjacently, said groups may combine together to form a ring having a substituent, for example, methylenedioxy, ethylenedioxy, 2-methyl-methylenedioxy, 2-methyl-ethylenedioxy, 1-oxy-2-ethylene, 1-oxy-2-propylene, etc., and preferable ones are methylenedioxy and ethylenedioxy.

The substituent of said "optionally substituted lower alkyl for $R^{11}$" and said "optionally substituted alkoxy for $R^{1}$" includes, for example, a halogen atom, a $C_1$-$C_3$ straight chain or branched chain alkoxy, a $C_1$-$C_3$ straight chain or branched chain alkyl, trifluoromethyl, trifluoromethoxy, phenyl, pyridyl, etc., and preferable one is fluorine atom, chlorine atom, methoxy, ethoxy, 2-propoxy, methyl, ethyl, 2-propyl, trifluoromethyl, trifluoromethoxy, phenyl and pyridyl.

The "optionally substituted amino" for $R^{11}$ includes, for example, amino, and an amino optionally mono or di-substituted by a $C_1$-$C_8$ alkyl (e.g., methyl, ethyl, propyl, etc.), a $C_1$-$C_8$ acyl (e.g., acetyl, propionyl, etc.), an aryl (e.g., phenyl, etc.), and a heteroaryl, and preferable ones are methylamino, dimethylamino, ethylamino, diethylamino, cyclohexylamino, acetylamino, benzoylamino, phenylamino, etc.

The halogen atom for $R^2$ is, for example, fluorine atom, chlorine atom, bromine atom, iodine atom, and preferable ones are fluorine atom and chlorine atom.

The lower alkyl of the "optionally substituted lower alkyl" for $R^2$ is, for example, a $C_1$-$C_8$ straight chain, branched chain or an alkyl having a cyclic structure, and preferable one is methyl, ethyl, 2-propyl, cyclopropyl, cyclopropylmethyl, etc.

The aryl of the "optionally substituted aryl" for $R^2$ is, for example, phenyl, 1-naphthyl, 2-naphthyl, etc., and preferable one is phenyl.

The heteroaryl of the "optionally substituted heteroaryl" for $R^2$ is the same ones as defined above for the "heteroaryl of the optionally substituted heteroaryl for $Ar^2$", and preferable one is thiophene, furan, pyrrole, pyridine, etc.

The optionally substituted thiol for $R^2$ is the same as those as defined above for the "substituent of the aryl or heteroaryl for $Ar^2$", and preferable one is methylthio, ethylthio, 2-propylthio, benzylthio, phenylthio, pyridylthio, imidazolylthio, etc.

The substituent of the "optionally substituted alkyl, optionally substituted aryl, optionally substituted heteroaryl" for $R^2$ includes, for example, a halogen atom, a $C_1$-$C_3$ straight chain or branched chain alkoxy, a $C_1$-$C_3$ straight chain or branched chain alkyl, trifluoromethyl, trifluoromethoxy, etc., and preferable one is fluorine atom, chlorine atom, methoxy, ethoxy, 2-propoxy, methyl, ethyl, 2-propyl, trifluoromethyl, trifluoromethoxy, etc.

The halogen atom, the "optionally substituted alkyl" and the "optionally substituted thiol" for $R^3$ are the same as those as defined for $R^2$.

The "optionally substituted alkoxy, optionally substituted amino, optionally substituted acyl, optionally substituted saturated heterocyclic group, or optionally substituted carbamoyl" for $R^3$ are the same as those defined above for the "substituents of the aryl or heteroaryl for $Ar^2$", and preferable one is methoxy, ethoxy, 2-propoxy, trifluoromethoxy, fluorine atom, etc.

The "prodrug" means a compound, which can be hydrolyzed chemically or biochemically in the living body and converted into the compound of the present invention. For example, when the heteroaryl compound of the present invention has a carboxyl group, then a compound wherein said carboxyl group is converted into a suitable ester group is a prodrug thereof. Preferable examples of the ester are methyl ester, ethyl ester, 1-propyl ester, 2-propyl ester, pivaloyloxymethyl ester, acetyloxymethyl ester, cyclohexylacetyloxymethyl ester, 1-methylcylohexylcarbonyloxymethyl ester, ethyloxycarbonyloxy-1-ethyl ester, cyclohexyloxycarbonyloxy-1-ethyl ester, etc.

The "pharmaceutically acceptable salt" includes, for example, an alkali metal salt such as sodium salt, potassium salt, etc., an alkaline earth metal salt such as calcium salt, magnesium salt, etc., an inorganic metal salt such as zinc salt, a salt with an organic base such as triethylamine, triethanolamine, trihydroxymethylaminomethane, amino acid, etc., when the heteroaryl compound of the present invention or a pharmaceutically acceptable salt thereof has an acidic group. When the heteroaryl compound of the present invention or a pharmaceutically acceptable salt thereof has a basic group, the pharmaceutically acceptable salt includes, for example, a salt with an inorganic acid such as hydrochloride, hydrobromide, sulfate, phosphate, nitrate, etc., a salt with an organic acid such as acetate, propionate, succinate, lactate, malate, tartrate, citrate, maleate, fumarate, methanesulfonate, p-toluenesulfonate, benzenesulfonate, ascorbate, etc.

The present invention includes a prodrug of the heteroaryl compound of the formula (1). Besides, the present invention also includes hydrates and solvates such as ethanolates of the heteroaryl compounds of the formula (1), a prodrug thereof, and a pharmaceutically acceptable salt thereof.

The heteroaryl compound of the present invention may be prepared, for example, by the methods disclosed hereinafter in detail, or a modified method of those methods.

The compounds to be used as a starting compound may be used in the form of a salt thereof.

The heteroaryl moiety of the heteroaryl compound of the present invention may be prepared by a conventional method, for example, methods disclosed in The Chemistry of Heterocyclic Compounds (cf., pyrrole derivatives: vol. 48 part 1, part 2; pyrazole derivatives: vol. 22; imidazole derivatives: vol. 6 part 1; triazole derivatives: vol. 6 part 1; indole derivatives: vol. 25 part II, part III, part 4; indazole derivatives: vol. 22; benzimidazole derivatives: vol. 40 part 1, part 2, etc.), Methoden der Organischen Chemie (Houben-Weyl) (cf., pyrrole derivatives: Hetarene I, TEIL 1, E6a, p 556-798; pyrazole derivatives: Hetarene III, TEIL 2, E8b, p 399-710; imidazole derivatives: Hetarene III, TEIL 3, E8c, p 1-215; triazole derivatives: Hetarene II, TEIL 2, E7b, p 286-686; indole derivatives: Hetarene I, TEIL 2a, E6b1, p 546-848, E6b2, p 849-1336; indazole derivatives: Hetarene III, TEIL 2, E8b, p764-856; benzimidazole derivatives: Hetarene III, TEIL 3, E8c, p 216-391, etc.), Comprehensive Heterocyclic Chemistry (cf., pyrrole derivatives, indole derivatives: vol. 4; pyrazole derivatives, indazole derivatives: vol. 5; imidazole derivatives, benzimidazole derivatives: vol. 5; triazole derivatives: vol. 5; thiophene derivatives: vol. 5; benzthiophene derivatives: vol. 6, etc.), Comprehensive Heterocyclic Chemistry II (cf., pyrrole derivatives, indole derivatives: vol. 2; pyrazole derivatives, indazole derivatives: vol. 3; imidazole derivatives, benzimidazole derivatives: vol. 3; triazole derivatives: vol. 4, etc.), Chemistry of heterocyclic compounds (Kodansha, published in 1988), Shin-Jikken-Kagaku Koza, vol. 14 [IV] (Maruzen, published in 1977), WO 02/085851, WO 02/10131-A1, WO 03/91211-A1, WO 04/048341, etc., or a modified method thereof.

The reactions as disclosed in the above are merely exemplified for illustrative purpose, and the present compounds can be suitably prepared by methods other than the above, based on the knowledge of persons who may well know the organic chemistry.

In each reaction as mentioned below, a functional group can be protected if necessary. The protecting groups to be employed and the techniques for protection or deprotection thereof are disclosed in detail in the literature of T. W. Greene and P. G. M. Wuts, "Protecting Groups in Organic Synthesis", the 3rd edition, JOHN WILEY & SONS, INC., New York (1999).

Process (1)

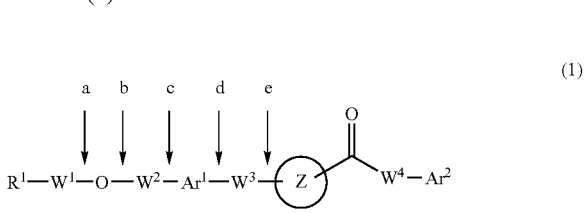

The heteroaryl derivative of the formula (1) may be prepared by forming the bond at the parts of a-e. The method for forming a bond at the parts of a-e can be illustrated as shown in Process (1-1)-(1-3). The order of the forming a bond at the parts of a-e may be appropriately changed. The starting compounds in each Process may be prepared from conventional starting materials by combining the methods for bond-forming at the parts of a-e.

Process (1-1): Synthesis of the Parts of a and b

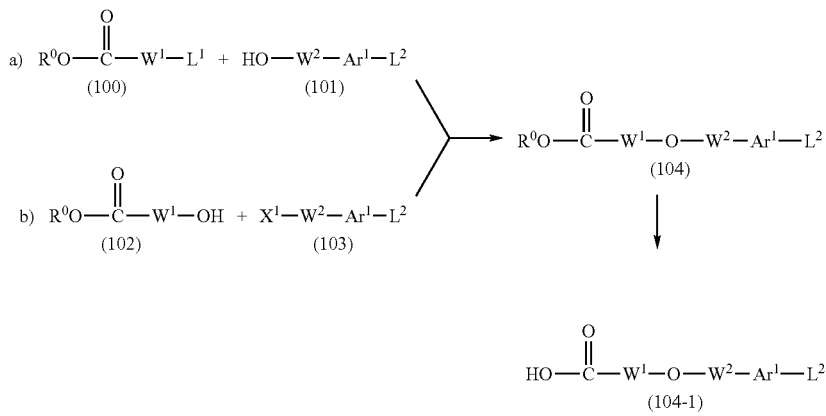

(wherein $R^0$ is an alkyl such as methyl, ethyl, t-butyl, etc.; $L^1$ and $L^2$ are independently chlorine atom, bromine atom or iodine atom; $X^1$ is a leaving group such as chlorine atom, bromine atom, iodine atom, triflate, etc., and the other symbols are as defined above.)

Compound (100), Compound (101), Compound (102), and Compound (103) may be prepared, for example by the methods disclosed in Shin-Jikken-Kagaku Koza, vol. 14 (Maruzen, published in 1977), Jikken-Kagaku Koza vol. 19 to 26 (Maruzen, published in 1992), Fine Organic Synthesis (Nankodo, published in 1983), Fundamentals and Experiments of Peptide synthesis (Maruzen, published in 1985), Compendium of Organic Synthetic Methods, Vol. 1-9 (John Wiley & Sons), Comprehensive Organic Synthesis, Vol. 1-9 (1991, Pergamon Press), Comprehensive Organic Transformations (1989, VCH Publishers), etc., or a modified method thereof.

Compound (104) may be prepared by reacting Compound (100) and Compound (101), or Compound (102) and Compound (103), in an inert solvent in the presence of a base. Namely, Compound (104) may be prepared by O-alkylation reaction disclosed in Jikken Kagaku Koza, vol. 20 (Maruzen, published in 1992), J. Org. Chem., 56, 1321 (1991), Heterocycles, 31, 1745 (1990), etc., or a modified method thereof.

The inert solvent includes, for example, ethers (e.g., ether, tetrahydrofuran (THF), dioxane, etc.), hydrocarbons (e.g., toluene, benzene, xylene, etc.), halogenated hydrocarbons (e.g., dichloromethane, chloroform, dichloroethane, carbon tetrachloride, etc.), aprotic solvents (e.g., dimethyl sulfoxide, N,N-dimethylformamide, acetonitrile, etc.). These solvents may be used by mixing two or more thereof at an appropriate ratio.

The base includes, for example, alkali metal hydrides (e.g., sodium hydride, potassium hydride, etc.), alkali metal carbonates (e.g., potassium carbonate, sodium carbonate, sodium hydrogen carbonate, cesium carbonate, etc.), alkylamines (e.g., triethylamine, ethyldiisopropylamine, etc.), metal alkoxides (e.g., sodium methoxide, potassium t-butoxide, etc.).

The reaction temperature may be selected from a range of about –20° C. to a boiling point of the solvent, and preferably from a range of about 0° C. to a boiling point of the solvent.

Compound (104-1) may be prepared by de-protecting Compound (104) by a conventional method. For example, Compound (104-1) may be prepared by subjecting Compound (104) to hydrolysis in the presence of an acid or a base.

The acid includes, for example, hydrochloric acid, sulfuric acid, acetic acid, hydrobromic acid, trifluoroacetic acid, methanesulfonic acid, etc.

The solvent includes, for example, ethers (e.g., ether, THF, dioxane, etc.), aprotic solvents (e.g., acetone, dimethyl sulfoxide, N,N-dimethylformamide, acetonitrile, etc.), alcohols (e.g., methanol, ethanol, etc.), and these solvents may be used by mixing one or more thereof with water at an appropriate ratio. The reaction can be carried out without a solvent.

The reaction temperature is selected from a range of about –20° C. to a boiling point of the solvent, and preferably from a range of about –10° C. to a boiling point of the solvent.

The base includes, for example, an alkali metal hydroxide (e.g., sodium hydroxide, potassium hydroxide, lithium hydroxide, etc.), an alkali metal carbonate (e.g., potassium carbonate, sodium carbonate, potassium hydrogen carbonate, sodium hydrogen carbonate, etc.), and the reaction is carried out in an aqueous solvent.

The aqueous solvent is a mixed solvent of water and one or more solvents selected from ethers (e.g., ether, THF, dioxane, etc.), aprotic solvents (e.g., acetone, dimethyl sulfoxide, N,N-dimethylformamide, acetonitrile, etc.), alcohols (e.g., methanol, ethanol, etc.) at an appropriate ratio.

The reaction temperature is selected from a range of about –20° C. to a boiling point of the solvent, and preferably from a range of about –10° C. to a boiling point of the solvent.

Process (1-2): Synthesis of the Parts of c, d and e

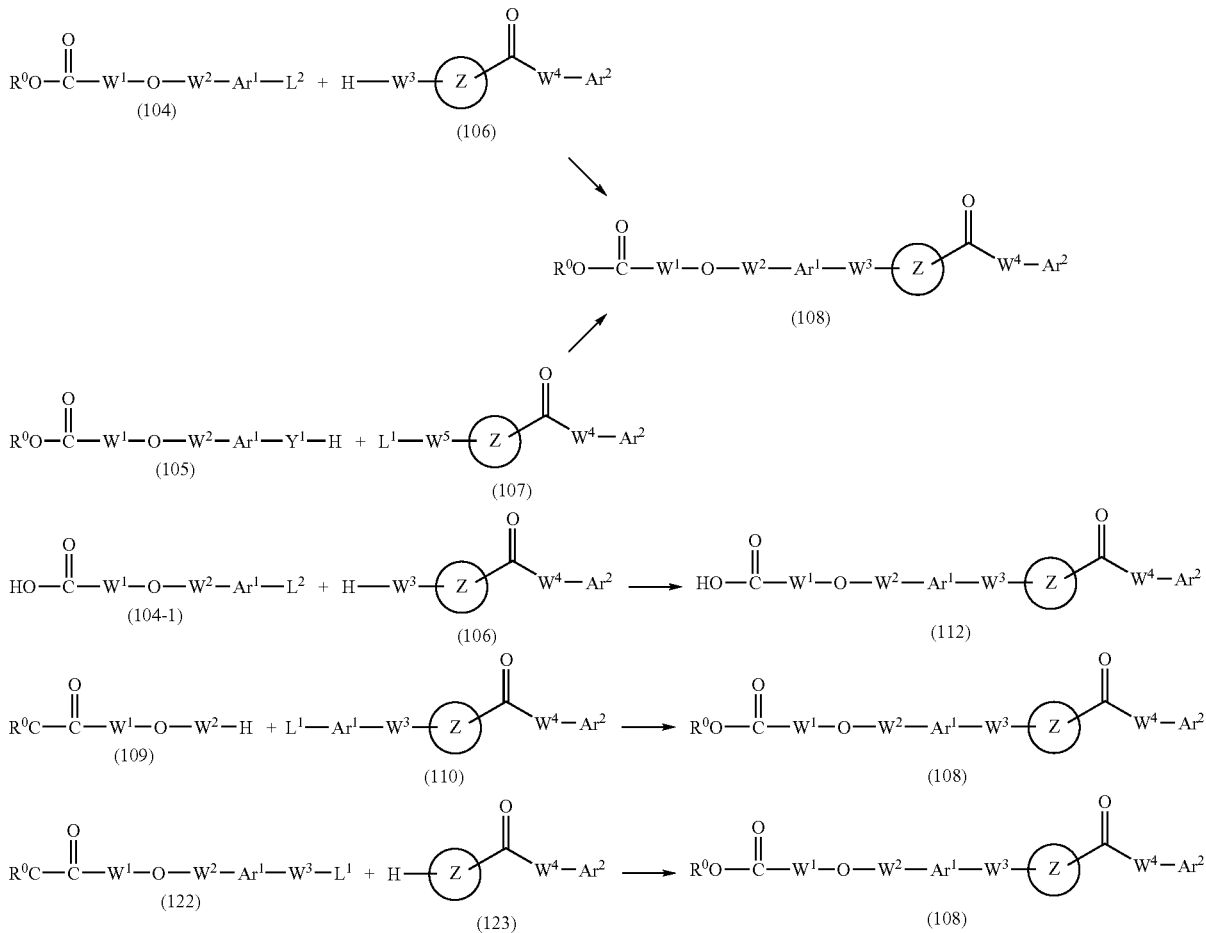

(wherein all of the symbols are as defined above)

The method for bond-forming at the part c, the method for bond-forming at the part d, the method for bond-forming at the part e, and the process for preparing Compounds (106), (107), (109), (110), (122), and (123) are carried out by the methods disclosed in WO 02/085851, WO 02/10131-A1, WO 03/91211-A1, WO 04/048341, Organic Letters, 4, 973 (2002), Tetrahedron Letters, 40, 2657 (1997), Chemical Communications, 188 (2004), Tetrahedron Letters, 35, 4133 (1994), Bull. Korean Chem. Soc., 21, 618 (2000), Synlett, 10, 1591 (1999), Tetrahedron Letters, 46, 2405 (2005), J. Am. Chem. Soc, 124, 11684 (2002), or a modified method thereof.

$$X^1-W^2-Ar^1-Y^1-Pg \quad (113)$$

$$HO-W^2-Ar^1-Y^1-Pg \quad (114)$$

$$R^0O-\overset{O}{\underset{\|}{C}}-W^1-O-W^2-Ar^1-Y^1-Pg \quad (111)$$

(wherein Pg is a protecting group, and the other symbols are as defined above)

Compound (105) can be prepared by deprotecting compound (111) according to the methods of T. W. Greene and P. G. M. Wuts, "Protective Groups in Organic Synthesis", 3rd Ed., John Wiley and Sons, inc., New York (1999). Compound (111) is prepared by O-alkylating compound (113) or (114) according to Jikken Kagaku Kouza Vo. 20 (Maruzenn, published in 1992), J. Org. Chem., 56, 1321 (1991), Heterocycles, 31, 1745 (1990), etc., or a modified method thereof.

Compound (113) and Compound (114) are prepared, for example, by the method disclosed in Shin-Jikken Kagaku Koza, vol. 14 (Maruzen, published in 1977), Jikken Kagaku Koza, vol. 19-26 (Maruzen, published in 1992), Fine Organic Synthesis (Nankodo, published in 1983), Compendium of Organic Synthetic Methods, Vol. 1-9 (John Wiley & Sons), etc., or a modified method thereof.

Process (1-3)

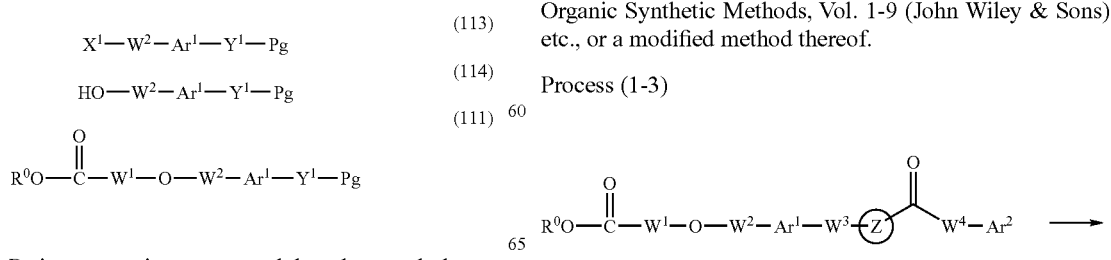

-continued

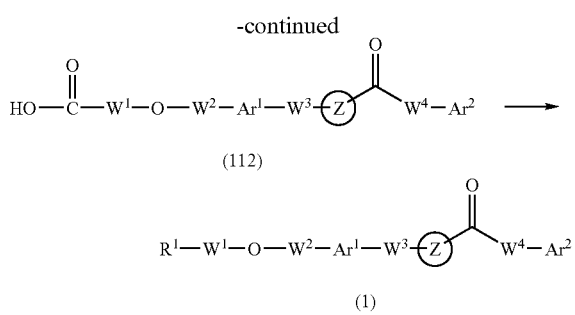

(wherein $R^1$ is an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, or a tetrazolyl group among the definitions as defined above, and the other symbols are as defined above)

Compound (112) may be prepared from Compound (108) by using a conventional deprotection technique, for example, by hydrolysis in the presence of an acid or a base. The acid includes, for example, hydrochloric acid, sulfuric acid, acetic acid, hydrobromic acid, trifluoroacetic acid, methansulfonic acid, etc.

The solvent includes, for example, ethers (e.g., ether, THF, dioxane, etc.), aprotic solvents (e.g., acetone, dimethyl sulfoxide, N,N-dimethylformamide, acetonitrile, etc.), alcohols (e.g., methanol, ethanol, etc.), and these solvents may be used by mixing one or more thereof with water at an appropriate ratio. The reaction may also be carried out without a solvent.

The reaction temperature is selected from a range of about −20° C. to a boiling point of the solvent, preferably from a range of about −10° C. to a boiling point of the solvent.

The base includes, for example, an alkali metal hydroxide (e.g., sodium hydroxide, potassium hydroxide, lithium hydroxide., etc.), an alkali metal carbonate (e.g., potassium carbonate, sodium carbonate, potassium hydrogen carbonate, sodium hydrogen carbonate, etc.), and the reaction is carried out in an aqueous solvent.

The aqueous solvent is a mixed solvent of water and one or more solvents selected from ethers (e.g., ether, THF, dioxane, etc.), aprotic solvents (e.g., acetone, dimethyl sulfoxide, N,N-dimethylformamide, acetonitrile, etc.), alcohols (e.g., methanol, ethanol, etc.) at an appropriate ratio.

The reaction temperature is selected from a range of about −20° C. to a boiling point of the solvent, and preferably from a range of about −10° C. to a boiling point of the solvent.

Compound (1) may be prepared from Compound (112) by a conventional method such as the methods disclosed in Shin-Jikken Kagaku Koza, vol. 14 (Maruzen, published in 1977), Jikken Kagaku Koza, vol. 19 to 26 (Maruzen, published in 1992), Fine Organic Synthesis (Nankodo, published in 1983), Fundamentals and Experiments of Peptide Synthesis (Maruzen, published in 1985), Compendium of Organic Synthetic Methods, Vol. 1-9 (John Wiley & Sons), Comprehensive Organic Synthesis, Vol. 1-9 (1991, Pergamon Press), Comprehensive Organic Transformations (1989, VCH Publishers), J. Org. Chem., 56, 2395 (1991), Org. Synth. 3, 646 (1955), Org. Synth. 29, 75 (1949), Org. Synth. 50, 18 (1970), Org. Synth. 50, 52 (1970), J. Org. Chem., 64, 2322 (1999), Tetrahedron Lett., 41, 6981 (2000), Org. Lett., 2, 2789 (2000), Org. Lett., 3, 193 (2001), J. Org. Chem., 57, 5285 (1992), J. Org. Chem., 66, 7945 (2001), etc. or a modified method thereof.

This reaction shows a conversion reaction from —$CO_2H$ to an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, a tetrazolyl group, or a conversion reaction from —$CO_2H$ to a cyano group and a conversion reaction from a cyano group to a tetrazolyl group.

Process (2): Method for Construction of Ring Z

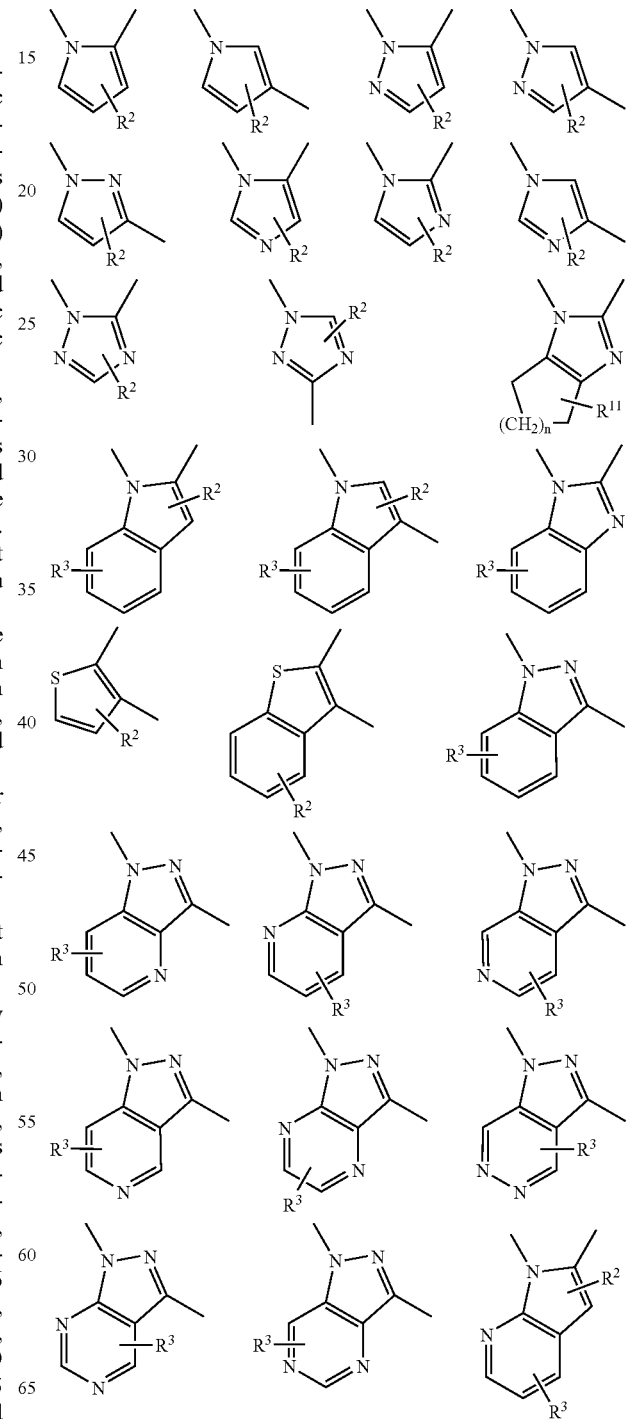

-continued

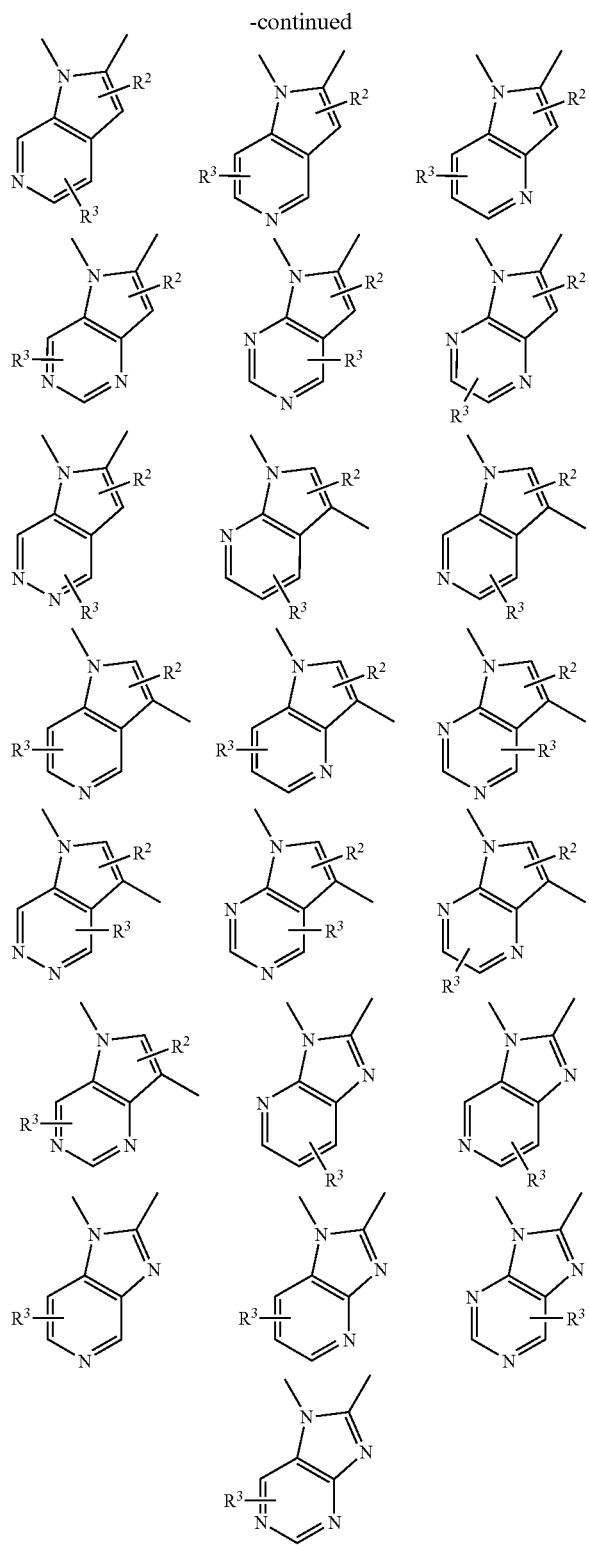

When Ring Z is prepared, or a substituent R² or R³ is introduced in Ring Z, it is prepared, for example, by the method disclosed in the above-mentioned Comprehensive Heterocyclic Chemistry (cf., pyrrole derivatives, indole derivatives: vol. 4; pyrazole derivatives, indazole derivatives: vol. 5; imidazole derivatives, benzimidazole derivatives: vol.

5; triazole derivatives: vol. 5; thiophene derivatives: vol. 5; benzothiophene derivatives: vol. 6, etc.), Comprehensive Heterocyclic Chemistry II (cf., pyrrole derivatives, indole derivatives: vol. 2; pyrazole derivatives, indazole derivatives: vol. 3; imidazole derivatives, benzimidazole derivatives: vol. 3; triazole derivatives: vol. 4, etc.), Tetrahedron, 53, 3637 (1997), Tetrahedron Lett., 39, 5159 (1998), Tetrahedron, 49, 2885 (1993), Synthesis, 877 (1996), J. Heterocycl. Chem., 6, 775 (1969), Heterocycles, 34, 2379 (1992), Bioorg. Med. Chem. Lett., 10, 2171 (2000), Bioorg. Med. Chem. Lett., 10, 2167 (2000), Angew. Chem. Int. Ed., 39, 2488 (2000), Tetrahedron, 54, 2931 (1998), J. Org. Chem., 48, 1060 (1983), J. Org. Chem., 30, 1528 (1965), J. Org. Chem., 65, 7825 (2000), J. Med. Chem., 16, 1296 (1973), Tetrahedron, 48, 10549 (1992), Heterocycles, 41, 161 (1995), Synthetic Communications, 27 (7), 1199-1207 (1997), Synthesis, 1166-1169 (2000), J. Am. Chem. Soc, 124, 15168 (2002), WO 02/08188-A1, WO 2004/020408-A1, etc., or a modified method thereof.

For example, when Ring Z is an imidazole, Compound (117) can be prepared, for example, by heating Compound (115) or Compound (116) with formamide at a temperature of 150 to 200° C.

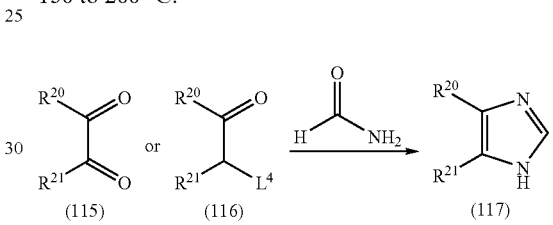

(wherein $R^{20}$ and $R^{21}$ are independently a hydrogen atom, a halogen atom, an optionally substituted alkyl, an optionally substituted aryl, an optionally substituted heteroaryl, or an optionally substituted thiol, and $R^{20}$ and $R^{21}$ may be taken together to form a ring with the adjacent carbon atoms, and $L^4$ is a hydroxy group, an amino, bromine atom, chlorine atom, etc.)

For example, when the ring Z is indole, Compound (121) can be prepared by heating Compound (118) and Compound (119) or compound (120) in acetic acid.

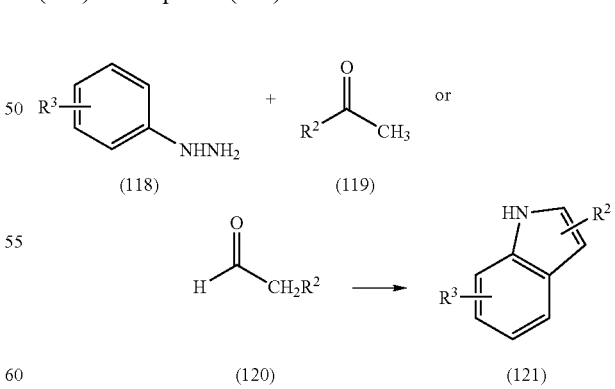

Compound (121) can be prepared, for example, by coupling Compound (122) and Compound (123) under palladium to give Compound (124) and then one electron reducing the compound under a reducing agent such as titanium chloride, etc.

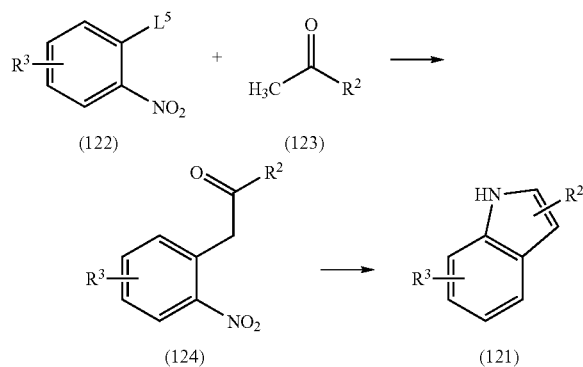

For example, the ring Z is indazole and $W^4$ is a single bond, Compound (126) can be prepared by reacting Compound (125) with sodium nitrite in the presence of an acid.

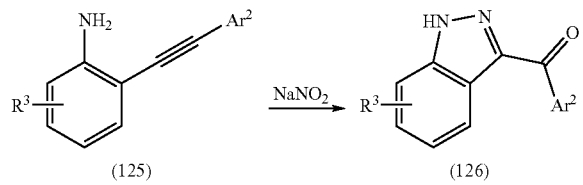

The acid includes, for example, hydrochloric acid, sulfuric acid, actetic acid, hydrobromic acid, trifluoroacetic acid, methanesulfonic acid, etc.

The solvent includes, for example, ethers such as ether, THF, dioxane, etc., aprotic solvent, such as acetone, dimethyl sulfoxide, N,N-dimethylformamide, acetonitrile, etc. These solvents may be used by mixing one or more thereof with water at an appropriate ratio. The reaction may also be carried out without a solvent.

The reaction temperature is selected from the range of about −20° C. to around of a boiling point of the solvent, preferably about −10° C. to around of a boiling point of the solvent.

In addition, when bromine or iodine exists for $R^2$ and $R^3$ as a substituent on Ring Z, an aryl or a heteroaryl can be introduced into $R^2$ or $R^3$ by Suzuki Coupling Reaction with an aryl borate or a heteroaryl borate (by the method disclosed in J. Organomet. Chem., 576, 147 (1999), J. Am. Chem. Soc, 122, 4020 (2000), J. Am. Chem. Soc, 124, 6343 (2002), or a modified method thereof), Stille Coupling Reaction with an aryl-tin compound or a heteroaryl-tin compound (by the method disclosed in Angew. Chem. Int. Ed. Engl, 25, 508 (1986) or a modified method thereof), etc.

The compound of the present invention may exist in an asymmetric form or may have a substituent having an asymmetric carbon atom, and in those cases, the compound of the present invention may exist in the form of an optical isomer. The compound of the present invention also includes a mixture of these isomers or each isolated isomer. Such optical isomers may be purely isolated, for example, by optical resolution.

The optical resolution may be carried out, for example, by forming a salt with the compound of the present invention or its intermediate and an optically active acid (e.g., monocarboxylic acids such as mandelic acid, N-benzyloxyalanine, lactic acid, etc., dicarboxylic acids such as tartaric acid, o-di- isopropyridentartaric acid, malic acid, etc., sulfonic acids such as camphorsulfonic acid, bromocamphorsulfonic acid, etc.) in an inert solvent (e.g., alcohols such as methanol, ethanol, 2-propanol, etc., ethers such as diethyl ether, etc., ester solvents such as ethyl acetate, etc., aromatic hydrocarbons such as toluene, etc., acetonitrile, or a mixture of these solvents).

When the compound of the present invention or an intermediate thereof has an acidic substituent such as carboxyl group, then it can be made to form a salt with an optically active amine (e.g., organic amines such as α-phenethylamine, 1,2-diphenyl-ethanolamine, (1R,2R)-(−)-2-amino-1,2-diphenylethanol, (1S,2R)-(+)-2-amino-1,2-diphenylethanol, quinine, quinidine, cinchonidine, cinchonine, strychnine, etc.).

The temperature for forming the salt may be in the range of room temperature to a boiling point of the solvent. In order to increase the optical purity, it is preferable to raise the reaction temperature to a temperature around the boiling point once. The precipitated salt is cooled, if necessary, prior to collection by filtration, and the yield thereof can be improved. The amount of the optically active acid or amine is in the range of about 0.5 to about 2.0 equivalents, preferably about 1 equivalent to the substrate. If necessary, the precipitated crystals are recrystallized in an inert solvent (e.g., alcohols such as methanol, ethanol, 2-propanol, etc., ethers such as diethyl ether, ester solvents such as ethyl acetate, etc., aromatic hydrocarbons such as toluene, etc., acetonitrile, etc., or a mixture thereof) to give an optically active salt in high purity. If necessary, the obtained salt is treated with an acid or a base by a conventional method to give a free compound.

The compound of the present invention or a salt thereof can be administered either orally or parenterally. When administered orally, it can be administered in a conventional dosage form. When administered parenterally, it can be administered in the form of topical administration formulations, injections, transdermal preparations, intranasal formulations, etc. The preparations for oral administration or rectal administration are, for example, capsules, tablets, pills, powders, cachets, suppositories, liquids, etc. The injection preparations are, for example, aseptic solutions or suspensions. The preparations for topical administration are, for example, creams, ointments, lotions, transdermal preparations such as conventional patches, matrixes, etc.

The above formulations are prepared by a conventional method with pharmaceutically acceptable excipients and additives. The pharmaceutically acceptable excipients or additives are, for example, carriers, binders, flavors, buffering agents, thickening agents, coloring agents, stabilizers, emulsifiers, dispersing agents, suspending agents, antiseptic agents, etc.

The pharmaceutically acceptable carriers are, for example, magnesium carbonate, magnesium stearate, talc, sugar, lactose, pectin, dextrin, starch, gelatin, tragacanth, methyl cellulose, sodium carboxymethyl cellulose, wax of low melting point, cacao butter, etc. Capsules can be prepared by putting the compound of the present invention together with a pharmaceutically acceptable carrier into capsules. The compound of the present invention can be put into capsules without any excipient or by mixing with a pharmaceutically acceptable carrier. The cache formulations may also be prepared likewise.

The liquid preparations for injection are, for example, solutions, suspensions, emulsions, etc. For example, aqueous solutions, a solution of water and propylene glycol solution are exemplified. The liquid preparation may be prepared in the form of a solution of polyethyleneglycol or/and propyleneglycol which may contain water. The liquid preparation suitable for oral administration may be prepared by adding the compound of the present invention into water, and further, if necessary, adding thereto a coloring agent, a flavor, a stabilizer, a sweetening agent, a solubilizer, a thickening agent, etc. Further the liquid preparation suitable for oral administration may also be prepared by adding the compound of the present invention together with a dispersing agent into water and thickening the solution. The thickening agent is, for example, pharmaceutically acceptable naturally occurring or synthetic gum, resin, methyl cellulose, sodium carboxymethyl cellulose, or a conventional suspending agent.

The formulation for topical administration includes, for example, the above-mentioned liquid preparations, creams, aerosol, sprays, powders, lotions, ointments, etc. The above-mentioned formulations for topical administration may be prepared by mixing the compound of the present invention with a conventional pharmaceutically acceptable diluent or carrier. The ointment and cream preparations are prepared by adding a thickening agent and/or gelatinizing agent into an aqueous or oily base, and formulating the resultant. The base includes, for example, water, liquid paraffin, vegetable oils (e.g., peanut oil, castor oil, etc.), etc. The thickening agent includes, for example, soft paraffin, aluminum stearate, cetostearyl alcohol, propylene glycol, polyethylene glycol, lanoline, hydrogenated lanoline, bee wax, etc.

The lotion preparations may be prepared, for example, by adding one or more kinds of pharmaceutically acceptable stabilizers, suspending agents, emulsifiers, diffusing agents, thickening agents, coloring agents, flavors, etc. into an aqueous or oily base.

The powder preparations may be prepared by formulating together with a pharmaceutically acceptable base. The base includes, for example, talc, lactose, starch, etc. The drop preparations may be prepared by formulating together with an aqueous or non-aqueous base and one, or more kinds of pharmaceutically acceptable diffusing agents, suspending agents, solubilizers, etc.

The formulations for topical administration may optionally contain, if necessary, antiseptic agents and bacterial growth inhibitors such as methyl hydroxybenzoate, propyl hydroxybenzoate, chlorocresol, benzalkonium chloride, etc.

The compound of the present invention or a salt thereof may be administered to a patient with diabetic mellitus, especially to a patient with type 2 diabetic mellitus or insulin-independent diabetes mellitus. Besides, the compound of the present invention can control the blood glucose level of a patient with diabetic mellitus. On such occasions, the dose, administration frequency may vary according to the conditions, ages, body weights of patients, or administration form, etc. When administered orally, then the dose of the compound of the present invention is in the range of about 1 to about 500 mg per day in adult, preferably in the range of about 5 to about 100 mg per day in adult, which is administered once a day or divided into several dosage units. When administered in the form of an injection, the dosage of the compound of the present invention is in the range of about 0.1 to about 300 mg per day in adult, preferably in the range of about 1 to about 100 mg per day in adult, which is administered once a day or divided into several dosage units.

The compound of the present invention can be used in order to promote its effect, in combination of a drug such as antidiabetes, a treating agent for antidiabetic complication, antihyperlipidemia, hypotensive agent, antiobesity, diuretics and so on (abbreviated as a coadministration drug hereinafter). Administration times of the compound of the present invention and the coadministration drug are not limited, and they may be administered at same time or at different times. Furthermore, the compound of the present invention can be used in combination of the coadministration drug. The amount of the coadministration drug is determined based on the standard of clinically administered dosage. Ratio of the compound of the present invention and the coadministration drug is appropriately determined according to clients, administration route, diseases, conditions of the diseases, the combination of drugs, etc. For example, when the subject is human being, ratio of the compound of the present invention and the coadministration drug is preferably 1:0.01~100 per weight.

Antidiabetes include insulin preparations (e.g., animal insulin preparations derived from bovine or porcine pancreas; insulin preparations prepared by gene manipulation using *E. coli* or yeast), insulin resistance improving agent (e.g., pioglitazone or its hydrochloride, troglitazone, rosiglitazone or its maleate, GI-262570, JTT-501, MCC-555, YM-440, KRP-297, CS-011, etc.), α-glucosidase inhibitor (e.g., voglibose, acarbose, miglitol, emiglitate, etc.), biguanides (e.g., metoformin, etc.), insulin secretion promoter (e.g., sulfonyl urea, such as tolubutamide, glibenclamide, gliclazide, chlorpropamide, tolazamide, acetohexamide, glyclopyramide, glimepiride, etc.; repaglinide, senaglinide, nateglinide, mitiglinide, etc.), GLP-1, GLP-1 analogue (exenatide, liraglutide, SUN-E7001, AVE010, BIM-51077, CJC1131, etc.), protein thirocin phosphatase inhibitor (e.g., vanadic acid, etc.), β3 agonist (e.g., GW-427353B, N-5984, etc.).

Agents for treating diabetic complication include aldose reductase inhibitor (e.g., tolrestat, epalrestat, zenarestat, zopolrestat, minarestat, fidarestat, SK-860, CT-112, etc.), neurotorophy factor (e.g., NGF, NT-3, BDNF, etc.), PKC inhibitor (e.g., LY-333531, etc.), AGE inhibitor (e.g., ALT946, pimagedine, pyratoxathine, N-phenacylthiazolium bromide (ALT766), etc.), active oxigen removing agent (e.g., thioctic acid, etc.), cerebrovasodilator (e.g., tiapride, mexiletine, etc.). Antihyperlipidemia includes HMG-CoA reductase inhibitor (e.g., pravastatin, simvastatin, lovastin, atorvastatin, fluvastatin, itavastatin or its sodium salt, etc.), squalene synthetase inhibitor, ACAT inhibitor and so on. Antihypotensives include angiotensin-converting enzyme inhibitors (e.g., captopril, enalapril, alacepril, delapril, lisinopril, imidapril, benazepril, cilazapril, temocapril, trandolapril, etc.), angiotensin II antagonist (e.g., olmesartan, medoxomil, candesartan, cilexetil, losartan, eprosartan, valsartan, telmisartan, irbesartan, tasosartan, etc.), calcium antagonist (e.g., nicardipine hydrochloride, manidipine hydrochloride, nisoldipine, nitrendipine, nilvadipine, amlodipine, etc.), and so on.

Antiobesity includes central antiobesity (e.g., fentermine, sibutramine, amfepramone, dexamphetamine, mazindol, SR-141716A, etc.), pancreatic lipase inhibitor (e.g., orlistat, etc.), peptide anorexiant (e.g., leptin, CNTF (ciliary neurotorophy factor), etc.), cholecystokinin agonist (e.g., lintitript, FPL-15849, etc.), etc. Diuretics include xanthine derivative (e.g., sodium salicylate theobromine, calcium salicylate theobromine, etc.), thiazide preparation (e.g., ethiazide, cyclopenthiazide, trichloromethiazide, hydrochlorothiazide, hydroflumethiazide, benzylhydrochlorothiazide, penflutizide, polythiazide, methyclothiazide, etc.), antialdosterone preparation (e.g., spironolactone, triamterene, etc.), carbonate dehydratase (e.g., acetazolamide, etc.), chlorbenzenesulfonamide preparation (e.g., chlortalidone, mefruside, indapamide, etc.), azosemide, isosorbide, ethacrynic acid, piretanide, bumetanide, flosemide, etc.

The coadministration drug preferably includes GLP-1, GLP-1 analogues, α-glucosidase inhibitor, biguanides, insulin secretion promoter, insulin resistance improving agent, etc. The above coadministration drug may be used in combination of other coadministration drugs.

When the compound of the present invention is used in combination of the coadministration drug, the amount of those drugs can be reduced in the range of safety considering the side effects of the drugs. Especially the amount of biguanides can be reduced comparing with ordinary dosage. Therefore, the side effects which would be caused by these drugs can be safely protected. In addition, the dosages of diabetic complication, antihyperlipidemia, hypotensive agent, etc., can be reduced. As a result, the side effects which would be caused by these drugs can be effectively protected.

The concrete examples of the compound of the formula (1) which is obtained by the present invention are compounds as listed in the following Table.

| Compound No. | Structure |
| --- | --- |
| 1 | 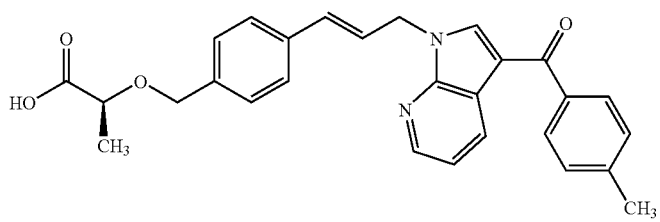 |
| 2 | 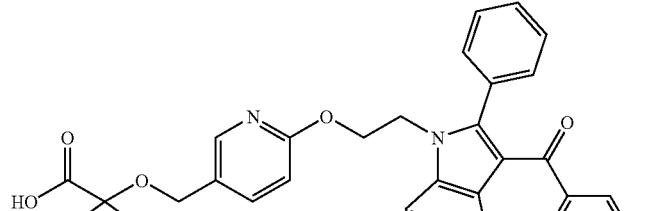 |
| 3 | 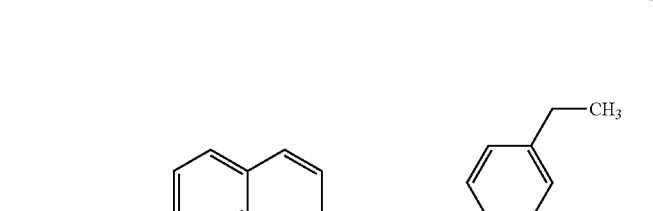 |
| 4 | 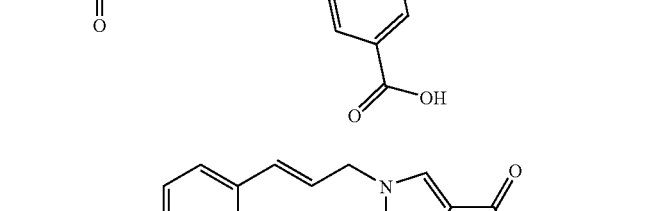 |

-continued
| Compound No. | Structure |
|---|---|
| 5 | 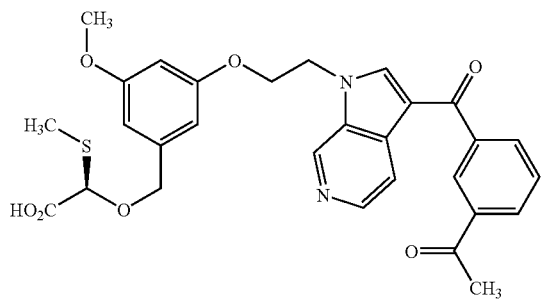 |
| 6 | 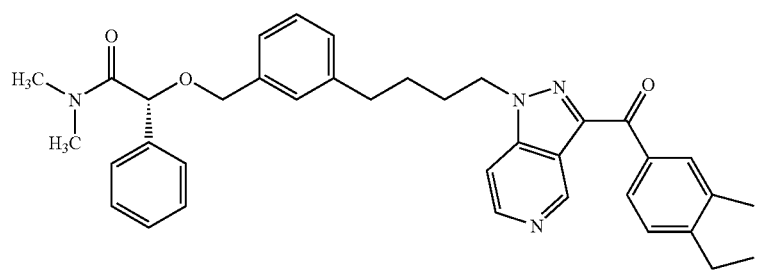 |
| 7 | 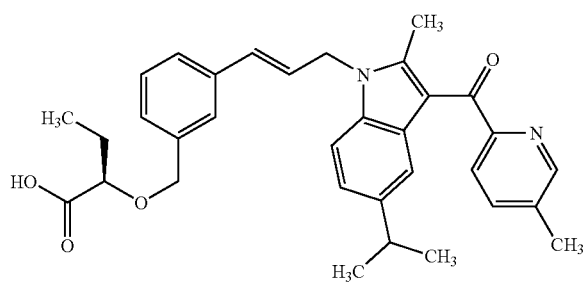 |
| 8 | 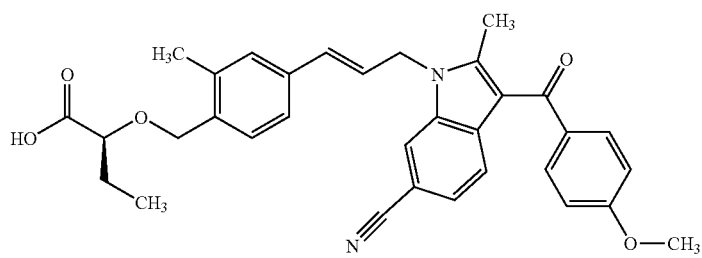 |
| 9 | 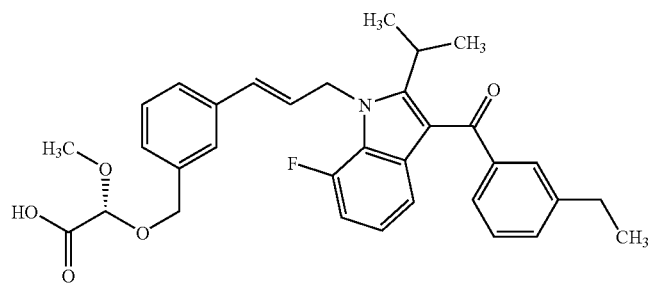 |

-continued
| Compound No. | Structure |
|---|---|
| 10 | 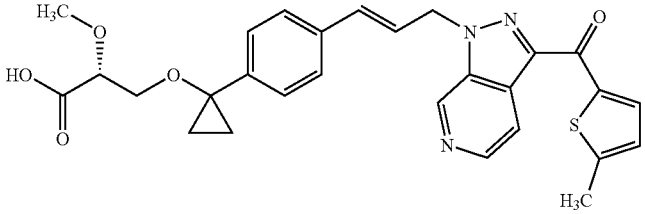 |
| 11 | 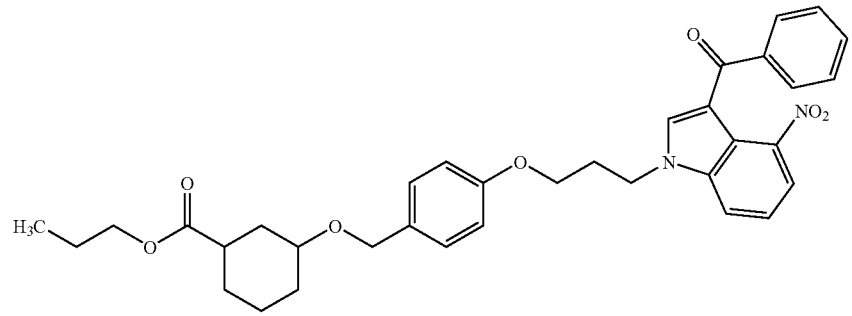 |
| 12 | 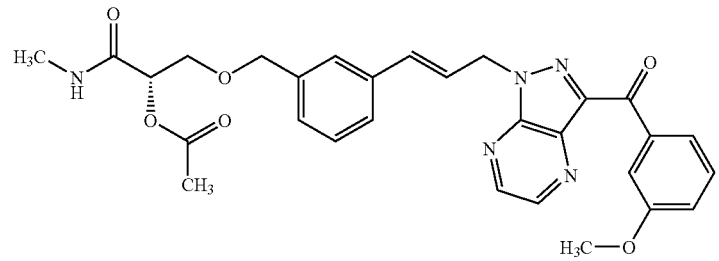 |
| 13 | 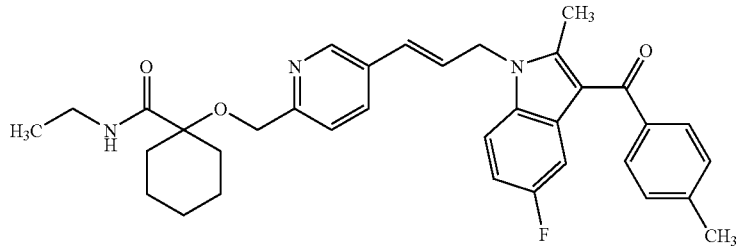 |
| 14 | 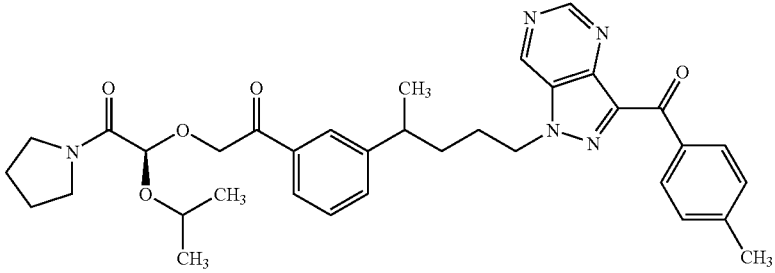 |
| 15 | 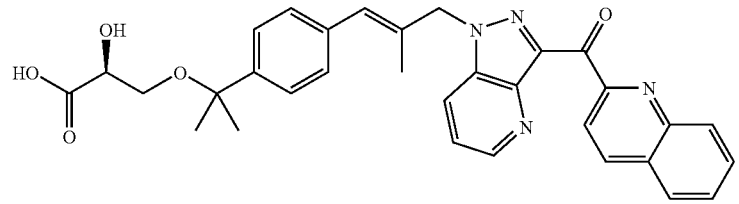 |

| Compound No. | Structure |
|---|---|
| 16 | 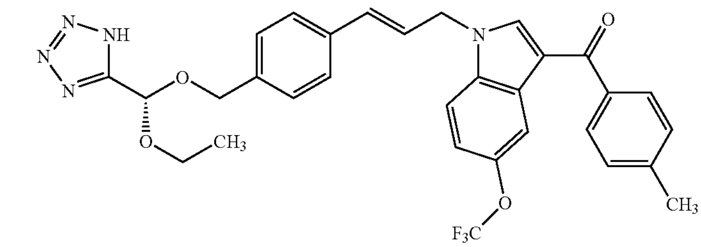 |
| 17 | 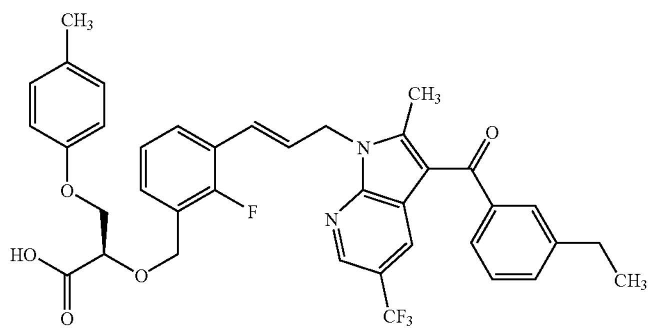 |
| 18 | 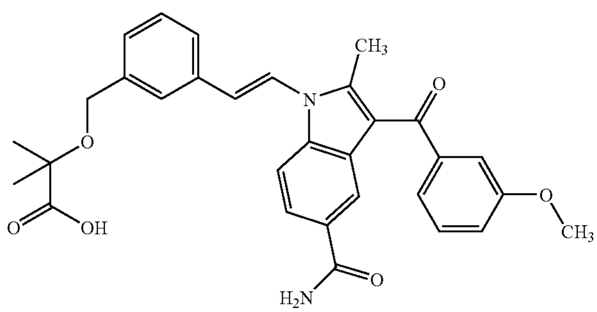 |
| 19 | 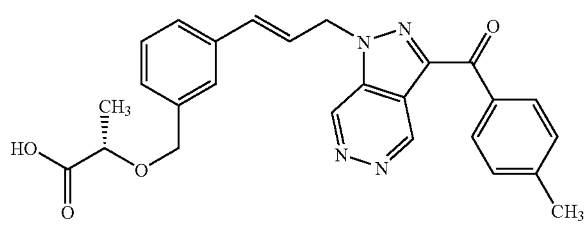 |
| 20 | 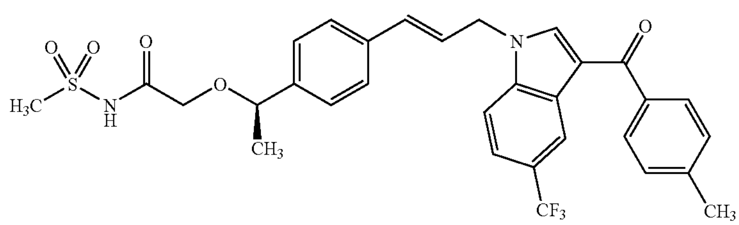 |

-continued
| Compound No. | Structure |
|---|---|
| 21 | 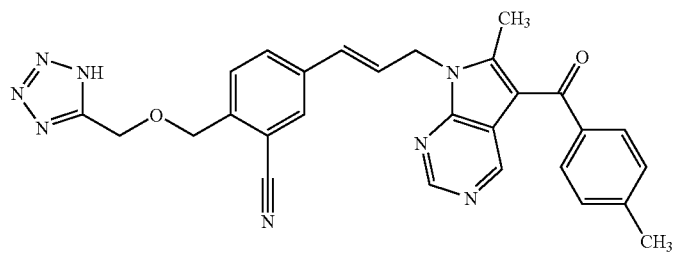 |
| 22 | 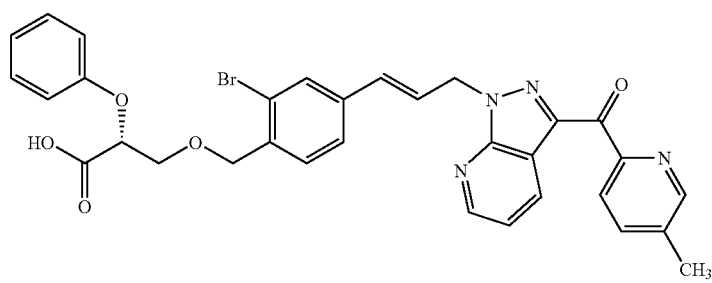 |
| 23 | 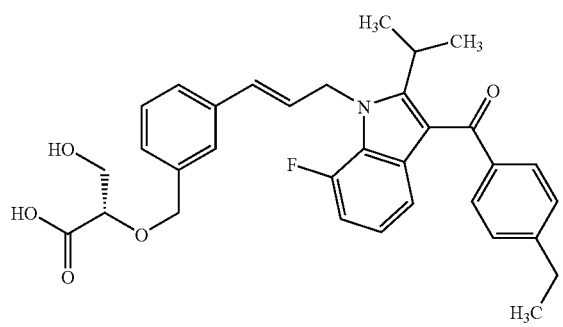 |
| 24 | 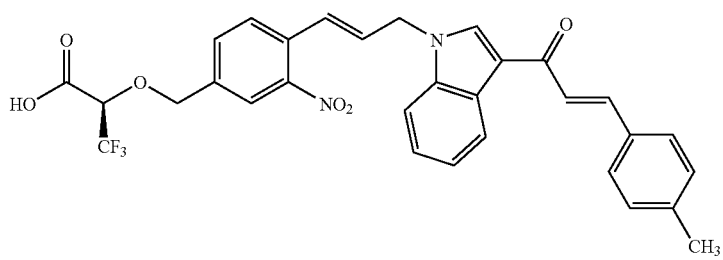 |
| 25 | 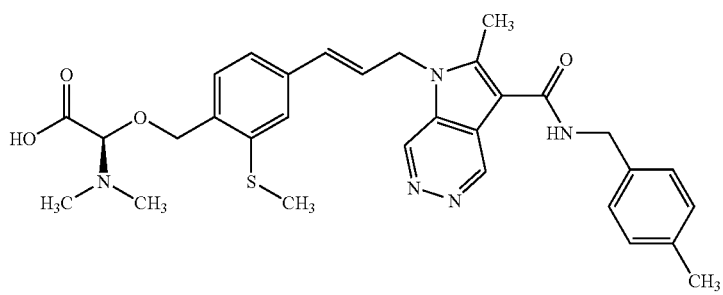 |

| Compound No. | Structure |
|---|---|
| 26 | *(chemical structure)* |
| 27 | *(chemical structure)* |
| 28 | *(chemical structure)* |
| 29 | *(chemical structure)* |
| 30 | *(chemical structure)* |
| 31 | *(chemical structure)* |

-continued
| Compound No. | Structure |
| --- | --- |
| 32 | 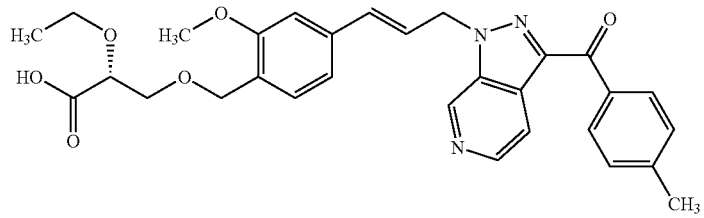 |
| 33 | 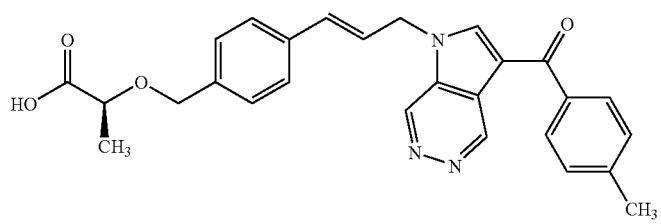 |
| 34 | 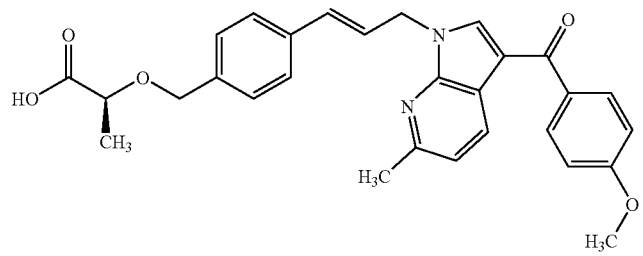 |
| 35 | 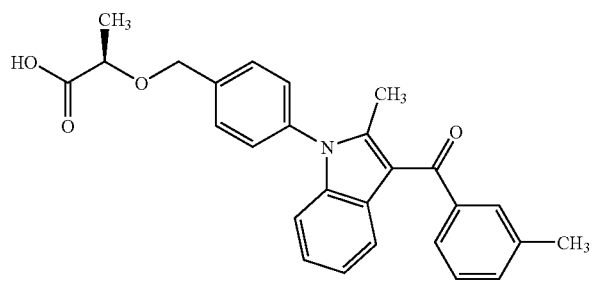 |
| 36 | 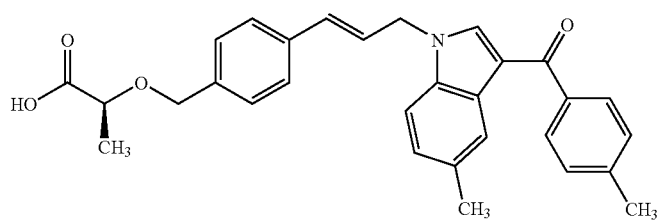 |
| 37 | 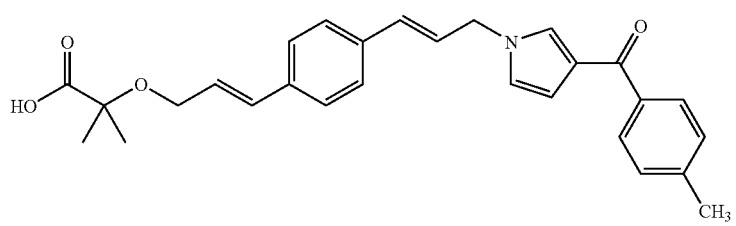 |

-continued
| Compound No. | Structure |
|---|---|
| 38 | 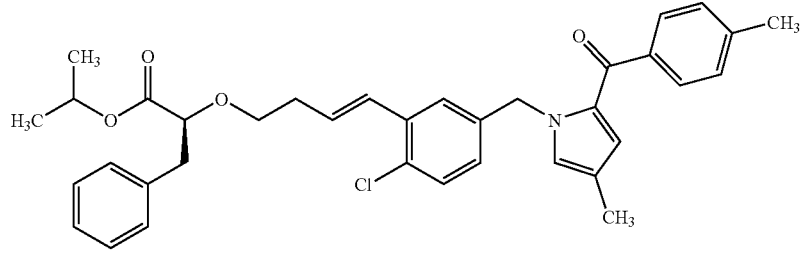 |
| 39 | 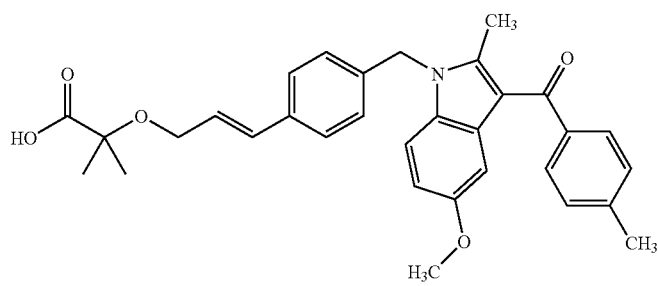 |
| 40 | 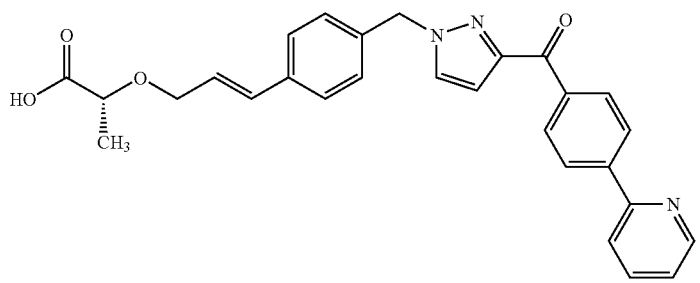 |
| 41 | 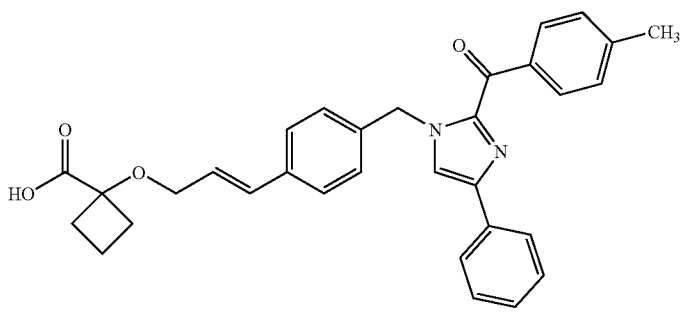 |
| 42 | 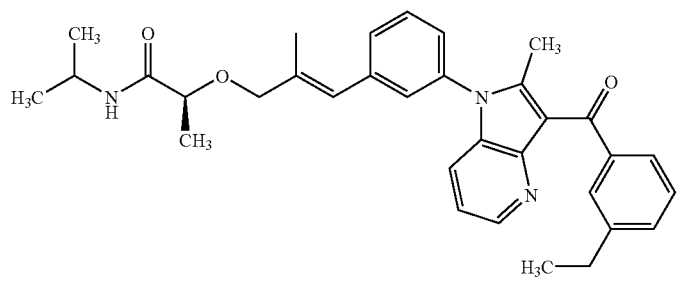 |

| Compound No. | Structure |
|---|---|
| 43 | 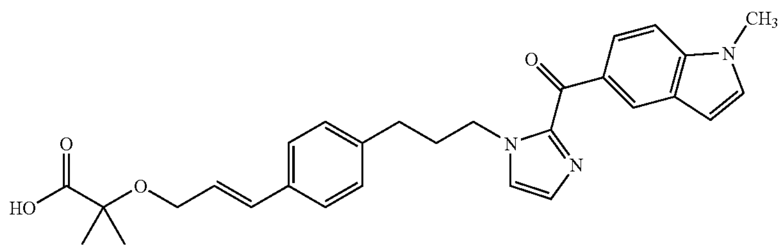 |
| 44 | 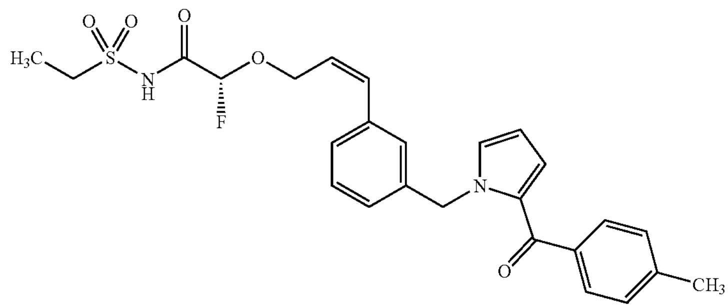 |
| 45 | 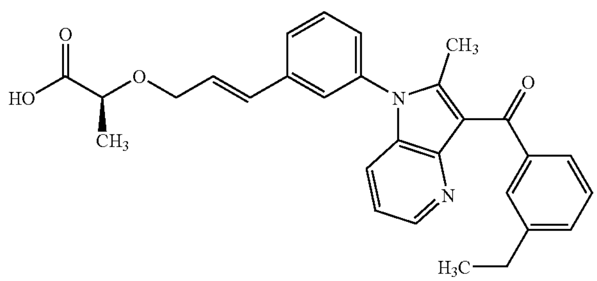 |
| 46 | 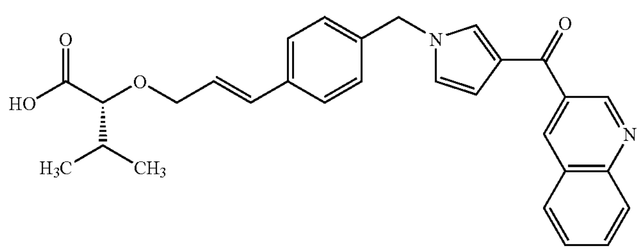 |
| 47 | 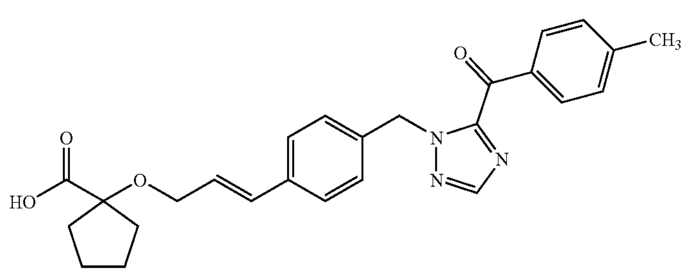 |

-continued
| Compound No. | Structure |
|---|---|
| 48 | 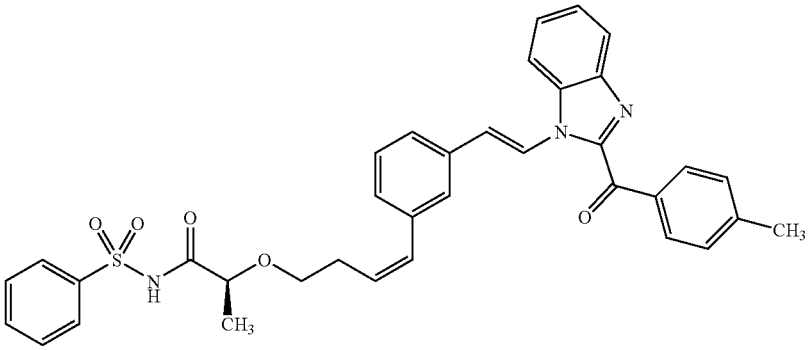 |
| 49 | 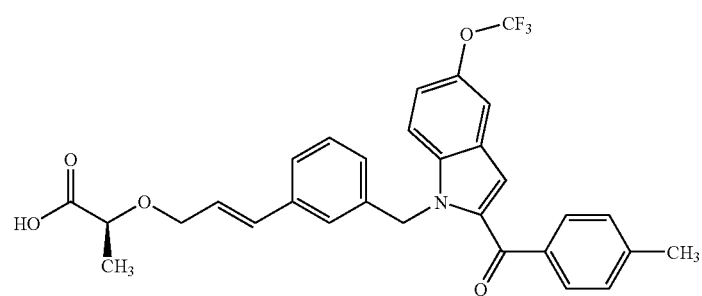 |
| 50 | 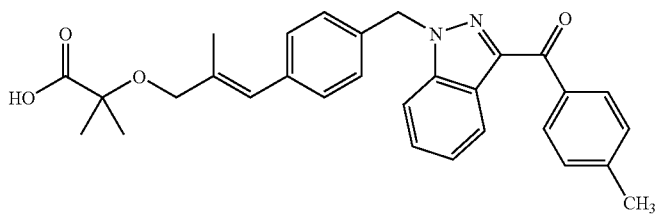 |
| 51 | 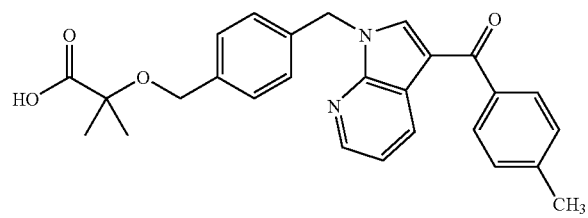 |
| 52 | 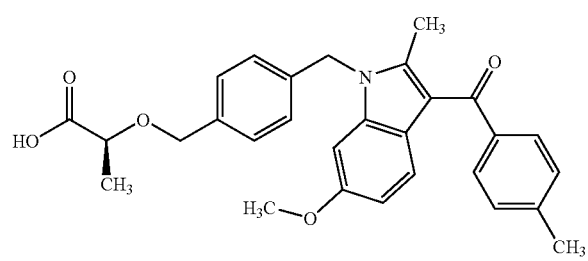 |
| 53 | 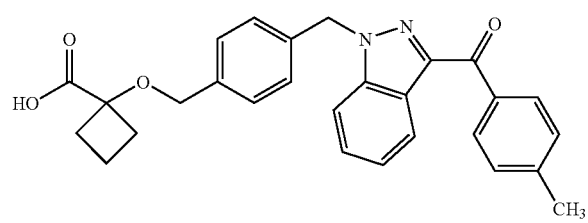 |

-continued
| Compound No. | Structure |
|---|---|
| 54 | 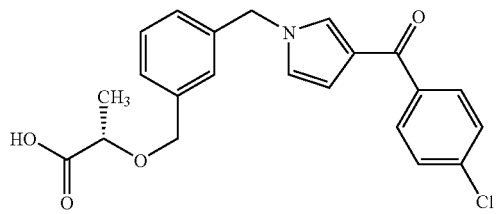 |
| 55 | 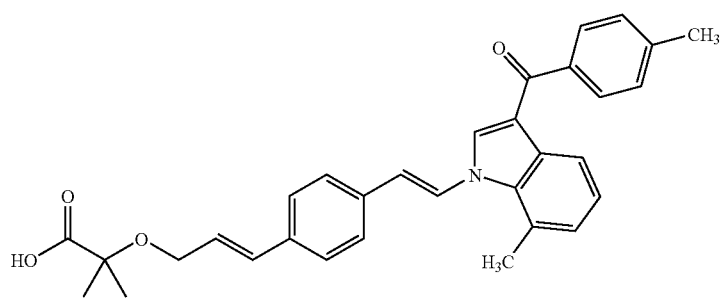 |
| 56 | 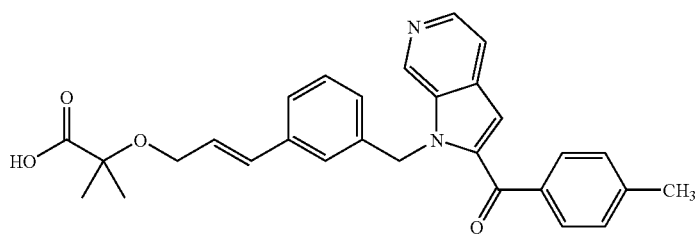 |
| 57 | 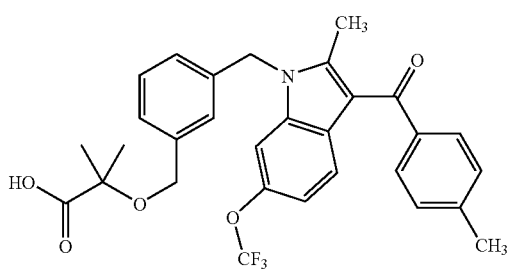 |
| 58 | 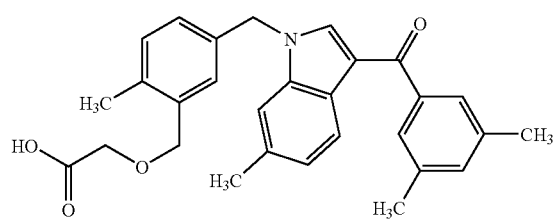 |
| 59 | 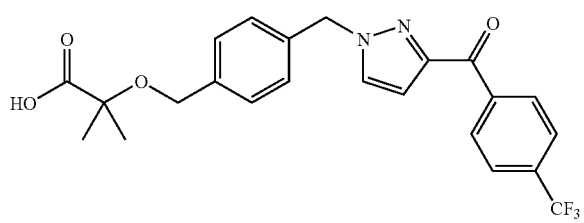 |

| Compound No. | Structure |
|---|---|
| 60 | (structure) |
| 61 | (structure) |
| 62 | (structure) |
| 63 | (structure) |
| 64 | (structure) |

-continued
| Compound No. | Structure |
|---|---|
| 65 | 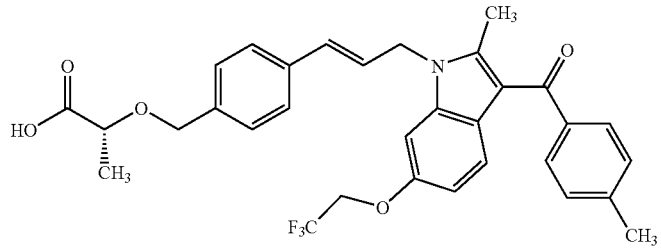 |
| 66 | 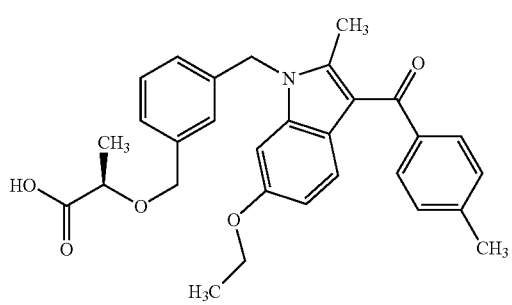 |
| 67 | 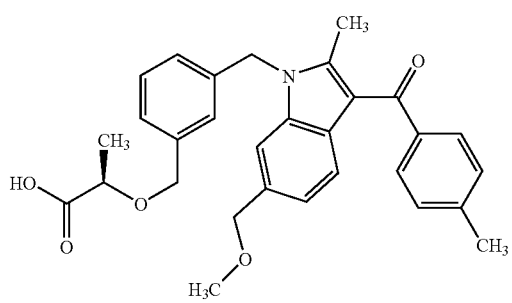 |
| 68 | 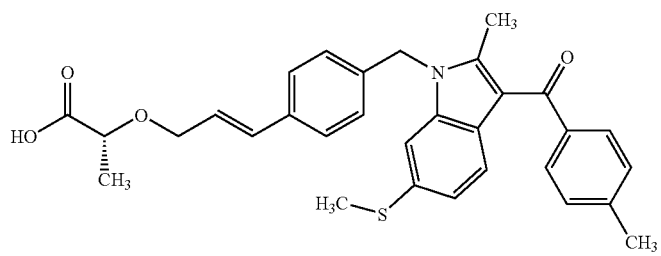 |
| 69 | 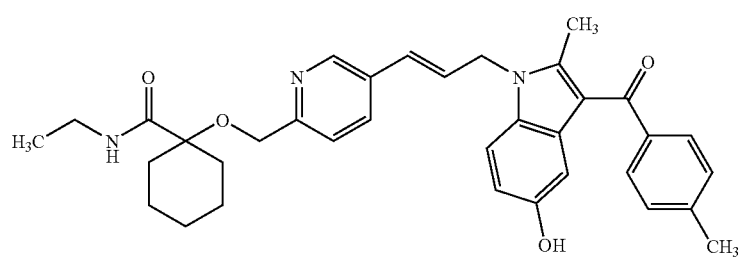 |

-continued
| Compound No. | Structure |
|---|---|
| 70 | 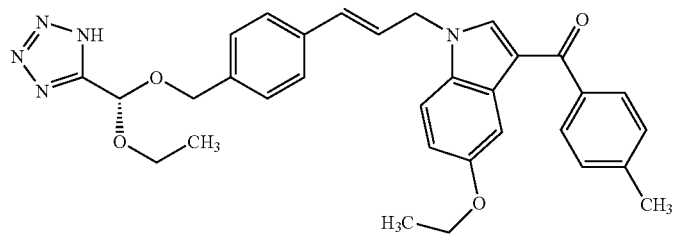 |
| 71 | 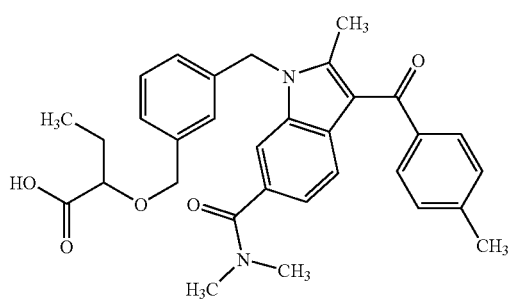 |
| 72 | 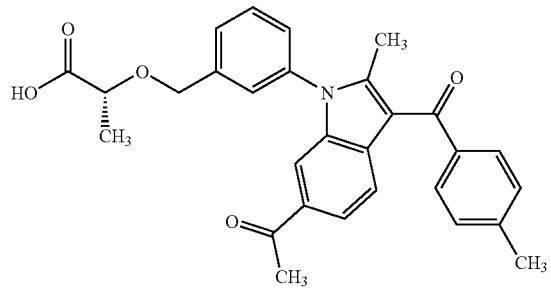 |
| 73 | 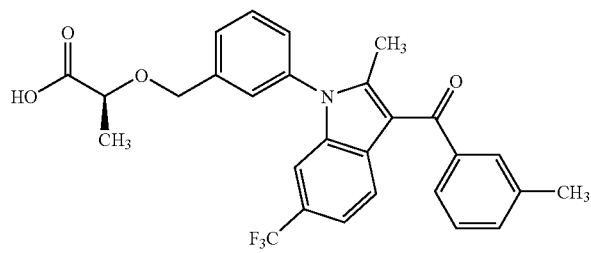 |
| 74 | 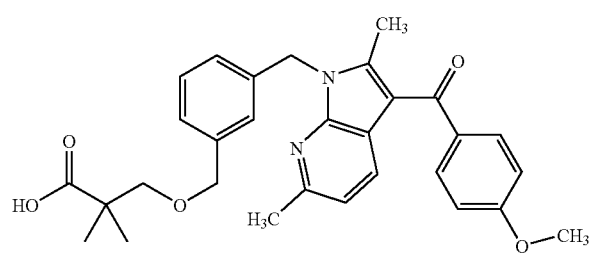 |

-continued
| Compound No. | Structure |
|---|---|
| 75 | 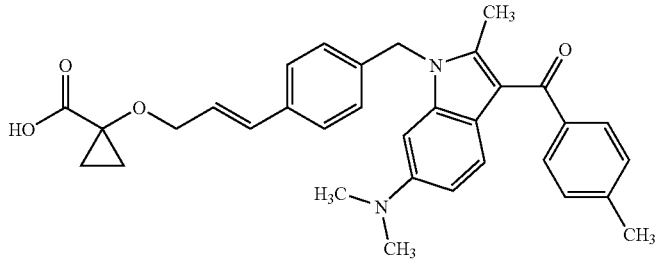 |
| 76 | 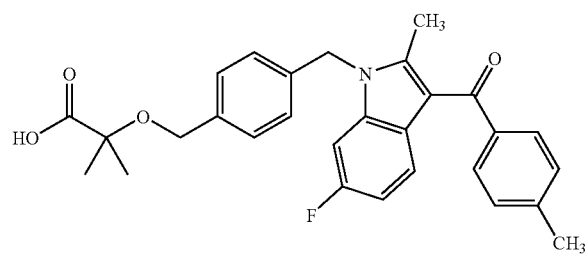 |
| 77 | 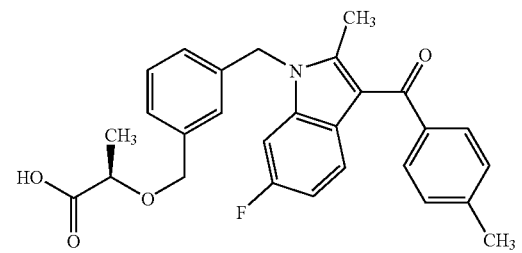 |
| 78 | 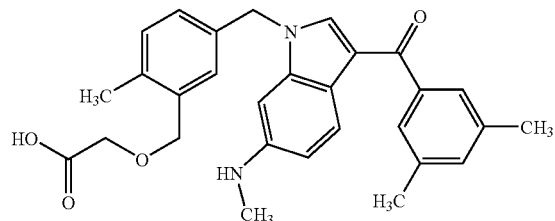 |
| 79 | 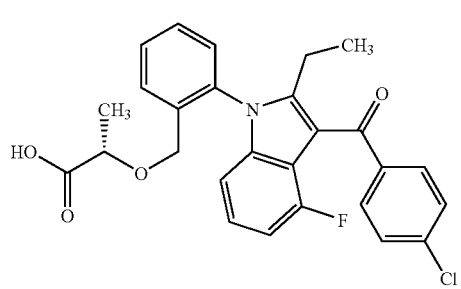 |
| 80 | 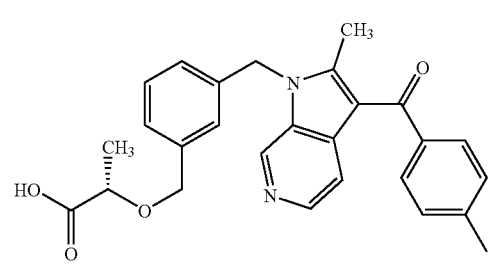 |

| Compound No. | Structure |
|---|---|
| 81 | 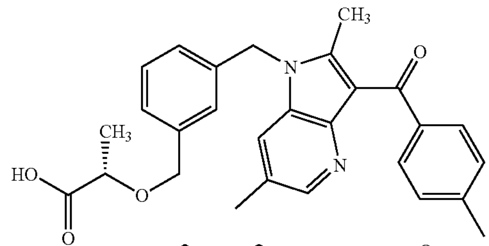 |
| 82 | 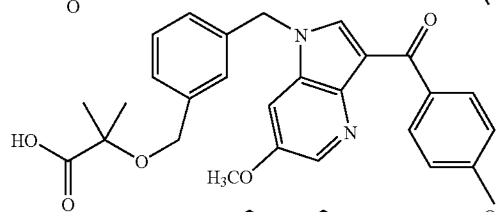 |
| 83 | 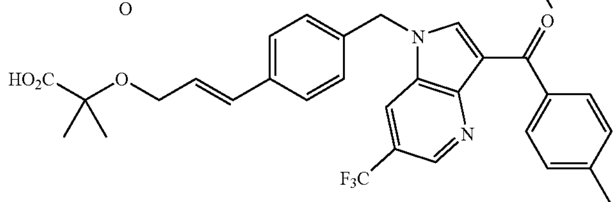 |
| 84 | 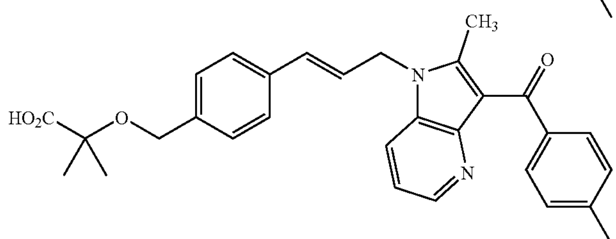 |

EXAMPLES

The present invention is illustrated in more detail by Reference Examples, Examples and Tests, but the present invention should not be construed to be limited thereto. In addition, the nomenclature of compounds as indicated in the following Reference Examples and Examples was done according to ACD Labs 7.0 Name.

Conditions for LC-MS Analysis:
Machine body: API 150EX (PE SCIE Inc.), ionization method: ESI
Column: CombiScreen Hydroshere C 18 S-5 μm (4.0×50 mm) (YMC Inc.)
Solution A: 0.05% Aqueous trifluoroacetic acid
Solution B: Acetonitrile containing 0.035% trifluoroacetic acid
Flow rate: 3.5 ml/min Conditions for Analysis:
0.0 min→0.5 min: Solution A 90% constant (Solution B 10%)
0.5 min→4.2 min: Solution A 90%→10% (Solution B 10%→90%)
4.2 min→4.4 min: Solution A 10% constant (Solution B 90%)
r.t.=retention time In the present specification, the following abbreviations may be used if necessary.

THF: Tetrahydrofuran
DMF: N,N-Dimethylformamide
DMSO: Dimethyl sulfoxide
DBU: 1,8-Diazabicyclo[5.4.0]-7-undecene
Ph: Phenyl Reference Example 1

(4-Methylphenyl) (1H-pyrrol-2-yl)methanone

Reference Example 1-1

(4-Methylphenyl) [1-(phenylsulfonyl)-1H-pyrrol-2-yl]methanone

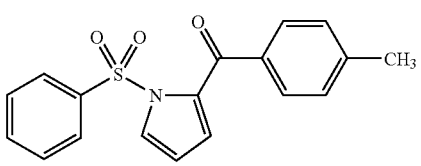

To a solution of 1-benzenesulfonyl-1H-pyrrole (284 g, 1.37 mol) in dichloromethane (1.0 L) were added p-toluoyl chloride (318 g, 2.06 mol) and boron trifluoride ether complex (350 g, 2.47 mol) in a stream of nitrogen and the mixture was allowed to stand for 7 hours at room temperature. The reaction mixture was washed with 1N aqueous hydrochloric acid solution (750 mL) twice, 1N aqueous sodium hydroxide solution (750 mL) and saturated brine (100 mL) successively, dried over magnesium sulfate and filtered. The filtrate was concentrated under reduced pressure so that the volume became about 500 ml and thereto was added hexane (500 mL). Further the mixture was concentrated so that the volume became about 500 ml, and cooled to 10° C. and resulting crystals were collected by filtration. The crystals were washed with hexane and then toluene and dried to give the subject compound (315 g, 71%).

$^1$H NMR (CDCl$_3$, 300 MHz) δ 8.12 (d, 2H, J=8.3 Hz), 7.78-7.75 (m, 1H), 7.72 (brd, 2H, J=7.9 Hz), 7.65 (brt, 1H, J=7.9 Hz), 7.58 (brt, 2H, J=7.9 Hz), 7.25 (d, 2H, J=8.3 Hz), 6.72-6.69 (m, 1H), 6.35 (dd, 1H, J=3.1, 0.5 Hz), 2.42 (s, 3H).

Reference Example 1-2

(4-Methylphenyl)(1H-pyrrol-2-yl)methanone

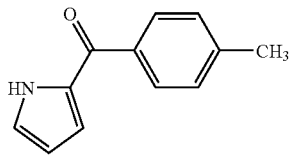

The compound (145 g, 446 mmol) of Reference example 1-1 was suspended in methanol (1.0 L) and thereto was added 5N aqueous sodium hydroxide solution (1.1 kg), followed by heating under reflux for 30 minutes. The solution was cooled to 0° C., and resulting crystals were filtered and dried to give the subject compound (80 g, 97%).

$^1$H NMR (CDCl$_3$, 300 MHz) δ 9.52 (brs, 1H), 8.25 (d, 2H, J=8.3 Hz), 7.29 (d, 2H, J=8.3 Hz), 7.12 (brs, 1H), 6.91-6.88 (m, 1H), 6.36-6.32 (m, 1H), 2.44 (s, 3H).

Reference Example 2

Methyl 4-(1H-pyrrol-2-yl-carbonyl)benzoate

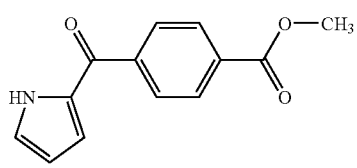

The subject compound was prepared in the same method as Reference example 1.

$^1$H NMR (CDCl$_3$, 400 MHz) δ 9.73 (brs, 1H), 8.16 (d, 2H, J=8.1 Hz), 7.94 (d, 2H, J=8.1 Hz), 7.19 (brs, 1H), 6.89-6.86 (m, 1H), 6.39-6.35 (m, 1H), 3.97 (s, 3H).

Reference Example 3

Methy 2-({4-[(1Z)-3-bromoprop-1-en-1-yl]benzyl}oxy)-2-methylpropionate

Reference Example 3-1

Methyl 2-[(4-iodobenzyl)oxy]-2-methylpropionate

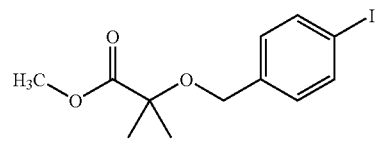

To a suspension of sodium hydride (55% in liquid paraffin) (315 mg, 7.3 mmol) in THF (2 ml) was dropped a solution of methyl 2-hydroxyisobutyrate (0.84 g, 7.1 mmol) in THF (2 ml). The reaction mixture was stirred for 30 minutes at 60° C. Thereto was dropped a solution of 4-iodobenzyl bromide (2.0 g, 6.7 mmol) in THF (4 ml) at 60° C. The mixture was stirred for 5 hours at 60° C. Therein were added ethyl acetate and a saturated ammonium chloride solution. After stirring for 5 minutes the mixture was separated by a separating funnel. The organic layer was washed with saturated brine, dried over anhydrous sodium sulfate and filtered. The solvent was removed in vacuo and the residue was purified by silica gel column chromatography to give the subject compound (1.93 g, 86%).

$^1$H NMR (CDCl$_3$, 400 MHz) δ 7.66 (d, 2H, J=8.3 Hz), 7.14 (d, 2H, J=8.3 Hz), 4.40 (s, 2H), 3.75 (s, 3H), 1.50 (s, 6H).

Reference Example 3-2

Methyl 2-{[4-(3-hydroxyprop-1-yl-1-yl)benzyl]oxy}-2-methylpropionate

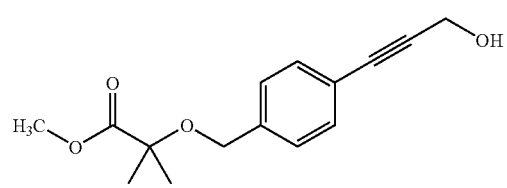

The compound of Reference example 3-1 (1.93 g, 5.78 mmol) was dissolved in THF (13 ml). To the solution were added propargyl alcohol (470 mg, 8.38 mmol), triethylamine (13 ml), bis(triphenylphosphine) palladium(II) chloride (243 mg, 0.35 mmol), and copper iodide (52 mg, 0.27 mmol) and the mixture was stirred for 4.5 hours at 60° C. After the mixture was cooled to room temperature and then filtered, the solvent was removed in vacuo and the residue was purified by silica gel column chromatography to give the subject compound (1.32 g, 87%).

$^1$H NMR (CDCl$_3$, 400 MHz) δ 7.41 (d, 2H, J=8.2 Hz), 7.34 (d, 2H, J=8.2 Hz), 4.50 (d, 2H, J=6.1 Hz), 4.45 (s, 2H), 3.76 (s, 3H), 1.72 (brs, 1H), 1.52 (s, 6H).

Reference Example 3-3

Methyl 2-({4-[(1Z)-3-hydroxyprop-1-en-1-yl]benzyl}oxy)-2-methylpropionate

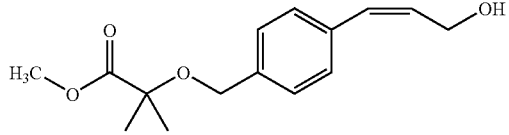

To a solution of the compound of Reference example 3-2 (1.22 g, 4.65 mmol) in ethyl acetate (23 ml) were added quinoline (2.44 g) and Lindlar catalyst (2.44 g) and the mixture was stirred under a hydrogen atmosphere at room temperature for 3.5 hours. After removal the catalyst over Cellite, the solvent was removed in vacuo. The residue was dissolved in ethyl acetate and the organic layer was washed with 1N diluted hydrochloric acid twice, a saturated sodium hydrogen carbonate solution and saturated brine and dried over anhydrous sodium sulfate. After filtration, the solvent was removed in vacuo and the residue was purified by silica gel column chromatography to give the subject compound (1.13 g, 92%).

$^1$H NMR (CDCl$_3$, 400 MHz) δ 7.37 (d, 2H, J=8.1 Hz), 7.18 (d, 2H, J=8.1 Hz), 6.56 (brd, 1H, J=11.7 Hz), 5.86 (dt, 1H, J=11.7, 6.4 Hz), 4.46 (s, 2H), 4.46-4.41 (m, 2H), 3.77 (s, 3H), 1.52 (s, 6H).

Reference Example 3-4

Methyl 2-({4-[(1Z)-3-bromoprop-1-en-1-yl]benzyl}oxy)-2-methylpropionate

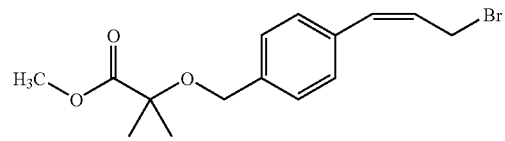

To a solution of the compound of Reference example 3-3 (532 mg, 2.01 mmol) in dichloromethane (10 ml) were added N-bromosuccinimide (448 mg, 2.52 mmol) and triphenylphosphine (623 mg, 2.38 mmol), and the mixture was stirred for 1.5 hours at room temperature. The solvent was removed in vacuo and the residue was purified by silica gel column chromatography to give the subject compound (464 mg, 70%).

$^1$H NMR (CDCl$_3$, 400 MHz) δ 7.42 (d, 2H, J=8.1 Hz), 7.32 (d, 2H, J=8.1 Hz), 6.59 (d, 1H, J=11.3 Hz), 5.97 (dt, 1H, J=11.3, 8.6 Hz), 4.47 (s, 2H), 4.16 (d, 2H, J=8.6 Hz), 3.77 (s, 3H), 1.53 (s, 6H).

Reference Example 4

Ethyl 2-({4-[(1Z)-3-bromoprop-1-en-1-yl]benzyl}oxy)propionate

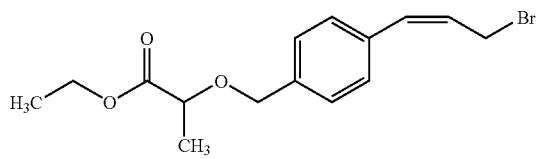

The compound of Reference example 4 was prepared in the same method as Reference example 3.

$^1$H NMR (CDCl$_3$, 400 MHz) δ 7.40 (d, 2H, J=8.1 Hz), 7.33 (d, 2H, J=8.1 Hz), 6.59 (d, 1H, J=11.3 Hz), 5.98 (dt, 1H, J=11.3, 8.7 Hz), 4.70 (d, 1H, J=11.7 Hz), 4.46 (d, 1H, J=11.7 Hz), 4.26 (dq, 1H, J=10.7, 7.1 Hz), 4.21 (dq, 1H, J=10.7, 7.1 Hz), 4.16 (d, 2H, J=8.7 Hz), 4.07 (q, 1H, J=6.8 Hz), 1.45 (d, 3H, J=6.8 Hz), 1.31 (t, 3H, J=7.1 Hz).

Reference Example 5

2-Methyl-5-(trifluoromethoxy)-1H-indole

Reference Example 5-1

2-[(2-Oxopropyl)thio]benzoic acid

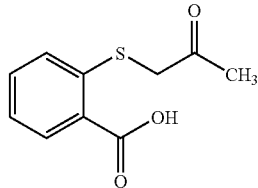

To a solution of chloroacetone (5.18 g, 55.99 mmol) in DMF (25 ml) were added thiosalicylic acid (8.63 g, 55.99 mmol) and potassium carbonate (7.74 g, 55.99 mmol), and the mixture was stirred at room temperature for 19 hours. To the reaction solution was added water and ethyl acetate and the mixture was separated by a separating funnel. The aqueous layer was acidified with 1N diluted hydrochloric acid (about pH 4) and extracted with ethyl acetate. Further the organic layer was washed with water and saturated brine and dried over anhydrous sodium sulfate. After filtration the solvent was removed in vacuo to give the subject compound (7.44 g, 63%).

$^1$H NMR (DMSO-d$_6$, 400 MHz) δ 7.89 (dd, 1H, J=7.8, 1.5 Hz), 7.49 (ddd, 1H, J=7.8, 7.8, 1.5 Hz), 7.25 (d, 1H, J=7.8 Hz), 7.22 (dd, 1H, J=7.8, 7.8 Hz), 4.02 (s, 2H), 2.24 (s, 3H).

Reference Example 5-2

2-{[2-Methyl-5-(trifluoromethoxy)-1H-indol-3-yl]thio}benzoic acid

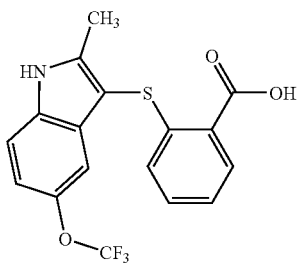

To the compound of Reference example 5-1 (920 mg, 4.37 mmol) were added acetic acid (20 ml) and 4-(trifluoromethoxy)phenylhydrazine hydrochloride (1 g, 4.37 mmol), and the mixture was stirred for 4 hours at 100° C. After being cooled to room temperature, the solvent was removed in vacuo. The residue was diluted with ethyl acetate, washed with water and saturated brine, dried over anhydrous sodium sulfate and filtered. The solvent was removed in vacuo and the residue was purified by silica gel column chromatography to give the subject compound (931 mg, 58%).

$^1$H NMR (CDCl$_3$, 400 MHz) δ 8.48 (brs, 1H), 8.17 (dd, 1H, J=8.0, 1.6 Hz), 7.35 (d, 1H, J=8.0 Hz), 7.35 (brs, 1H), 7.20 (ddd, 1H, J=8.0, 7.4, 1.6 Hz), 7.12 (ddd, 1H, J=7.4, 7.4, 1.1 Hz), 7.08 (brd, 1H, J=8.8 Hz), 6.71 (dd, 1H, J=8.1, 1.1 Hz), 2.51 (s, 3H).

Reference Example 5-3

2-Methyl-5-(trifluoromethoxy)-1H-indole

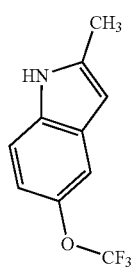

To the compound of Reference example 5-2 (2.09 g, 5.69 mmol) were added trifluoroacetic acid (22 ml) and thiosalicylic acid (878 mg, 5.69 mmol), and the mixture was stirred for 3 hours at 50° C. The reaction mixture was diluted with ethyl acetate and neutralized with 1N aqueous sodium hydroxide solution and the mixture was separated by a separating funnel. The organic layer was washed with 1N aqueous sodium hydroxide solution and saturated brine, dried over anhydrous sodium sulfate and filtered. The solvent was removed in vacuo and the residue was purified by silica gel column chromatography to give the subject compound (727 mg, 59%).

$^1$H NMR (CDCl$_3$, 400 MHz) δ 7.95 (brs, 1H), 7.35 (brs, 1H), 7.24 (d, 1H, J=8.7 Hz), 6.97 (brd, 1H, J=8.7 Hz), 6.24-6.22 (m, 1H), 2.45 (s, 3H).

Reference Example 6

6-Methoxy-2-methyl-1H-indole

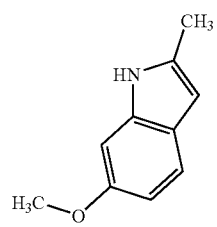

The subject compound was prepared in the same method as Reference example 5 using 3-methoxyphenylhydrazine hydrochloride.

$^1$H NMR (CDCl$_3$, 400 MHz) δ 7.74 (brs, 1H), 7.37 (d, 1H, J=8.6 Hz), 6.80 (d, 1H, J=2.3 Hz), 6.74 (dd, 1H, J=8.8, 2.3 Hz), 6.13 (brs, 1H), 3.83 (s, 3H), 2.41 (s, 3H).

Reference Example 7

4-Methoxy-2-methyl-1H-indole

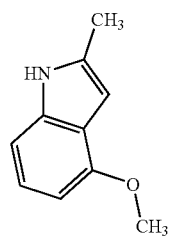

The subject compound was prepared in the same method as Reference example 5 using 3-methoxyphenylhydrazine hydrochloride.

$^1$H NMR (CDCl$_3$, 400 MHz) δ 7.86 (brs, 1H), 7.03 (dd, 1H, J=7.9, 7.9 Hz), 6.93 (d, 1H, J=7.9 Hz), 6.50 (d, 1H, J=7.9 Hz), 6.31 (brs, 1H), 3.94 (s, 3H), 2.43 (s, 3H).

Reference Example 8

2-Methyl-6-(trifluoromethyl)-1H-indole

Reference Example 8-1

1'-[2-Nitro-4-(trifluoromethyl)phenyl]acetone

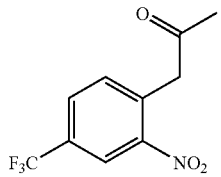

To a solution of 1-chloro-2-nitro-4-trifluoromethylbenzene (5.38 g, 23.41 mmol) in toluene (46 ml) were added acetone (10.3 ml, 140.46 mmol), phenol (441 mg, 4.68 mmol), calcium phosphate (12.42 g, 58.52 mmol), 2-dicyclohexylphosphino-2'-(N,N-dimethylamino)biphenyl (369 mg, 0.94 mmol) and tris(dibenzylideneacetone)dipalladium(0) (214 mg, 0.23 mmol) successively and the mixture was stirred for 9 hours at 50° C. After being cooled to room temperature, the reaction mixture was filtered by silica gel with ethyl acetate and the solvent was removed in vacuo. The residue was purified by silica gel column chromatography to give the subject compound (4.59 g, 79%).

$^1$H NMR (CDCl$_3$, 400 MHz) δ 8.40 (d, 1H, J=1.2 Hz), 7.85 (dd, 1H, J=8.0, 1.2 Hz), 7.44 (d, 1H, J=8.0 Hz), 4.22 (s, 2H), 2.37 (s, 3H).

Reference Example 8-2

2-Methyl-6-(trifluoromethyl)-1H-indole

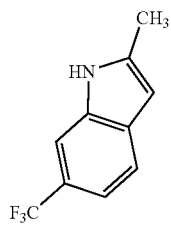

To titanium chloride (20% aqueous solution, 114.6 g, 148.56 mmol) were added 6.6M aqueous ammonium acetate solution (135 ml, 891.36 mmol) and ethanol (70 ml). Thereto was dropped a solution of the compound of Reference example 8-1 (4.59 g, 18.57 mmol) in ethanol (50 ml) and the mixture was stirred for 2.5 hours at room temperature. The reaction solution was extracted with diethyl ether three times, and the organic layer was washed with a saturated sodium hydrogen carbonate solution and saturated brine, dried over anhydrous sodium sulfate and filtered. The solvent was removed in vacuo and the residue was purified with silica gel column chromatography to give the subject compound (2.99 g, 81%).

$^1$H NMR (CDCl$_3$, 400 MHz) δ 8.08 (brs, 1H), 7.57 (d, 1H, J=8.0 Hz), 7.55 (d, 1H, J=1.3 Hz), 7.30 (dd, 1H, J=8.0, 1.3 Hz), 6.28 (brs, 1H), 2.48 (s, 3H).

Reference Example 9

3-Methyl-6-(trifluoro methyl)-1H-indole

Reference Example 9-1

N-[2-Bromo-5-(trifluoromethyl)phenyl]methanesulfonamide

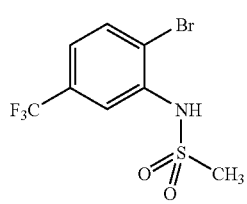

To a solution of 2-bromo-5-trifluoromethylaniline (3.18 g, 13.25 mmol) in pyridine (18 ml) was added methanesulfonyl chloride (1.03 ml, 13.25 mmol) and the mixture was stirred for 6 hours at room temperature. The solvent was removed in vacuo and the residue was diluted with chloroform. The organic layer was washed with water, 1N hydrochloric acid, a saturated sodium hydrogen carbonate solution and saturated brine and dried over anhydrous sodium sulfate. The solvent was removed in vacuo and the residue was purified by recrystallization to give the subject compound (2.18 g, 52%).

$^1$H NMR (CDCl$_3$, 400 MHz) δ 7.93 (d, 1H, J=1.9 Hz), 7.74 (d, 1H, J=8.4 Hz), 7.33 (dd, 1H, J=8.4, 1.9 Hz), 6.94 (brs, 1H), 3.07 (s, 3H).

Reference Example 9-2

3-Methyl-1-(methylsulfonyl)-6-(trifluoromethyl)-1H-indole

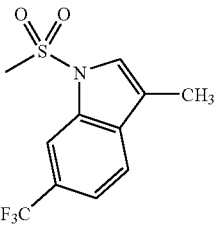

To a solution of the compound of Reference example 9-1 (1.84 g, 5.78 mmol) in DMF (29 ml) were added allyl acetate (1.16 g, 11.57 mmol), potassium carbonate (2.40 g, 17.35 mmol), lithium chloride (245 mg, 5.78 mmol) and palladium acetate (65 mg, 0.29 mmol) successively, and the mixture was stirred for 16 hours at 120° C. After being cooled to room temperature, thereto was added a saturated aqueous ammonium chloride solution and the mixture was extracted with ethyl acetate. The organic layer was washed with water and saturated brine, dried over anhydrous magnesium sulfate and filtered. The solvent was removed in vacuo and the residue was purified by silica gel column chromatography to give the subject compound (0.82 g, 51%).

$^1$H NMR (CDCl$_3$, 400 MHz) δ 8.19 (d, 1H, J=1.0 Hz), 7.66 (d, 1H, J=8.3 Hz), 7.57 (dd, 1H, J=8.3, 1.0 Hz), 7.35 (q, 1H, J=1.2 Hz), 3.10 (s, 3H), 2.33 (d, 3H, J=1.2 Hz).

Reference Example 9-3

3-Methyl-6-(trifluoromethyl)-1H-indole

To a solution of the compound of Reference example 9-2 (0.82 g, 2.98 mmol) in THF (16 ml) was added tetrabutylammonium fluoride (1.0M THF solution, 6.1 ml, 6.14 mmol), and the mixture was stirred under reflux for 5.5 hours. After being cooled to room temperature, thereto was added water and the mixture was extracted with ethyl acetate. The organic layer was washed with saturated brine, dried over anhydrous sodium sulfate and filtered. The solvent was removed in vacuo and the residue was purified by silica gel column chromatography to give the subject compound (0.54 g, 99%).

$^1$H NMR (CDCl$_3$, 400 MHz) δ 8.13 (brs, 1H), 7.65 (d, 1H, J=8.3 Hz), 7.63 (d, 1H, J=1.1 Hz), 7.35 (dd, 1H, J=8.3, 1.1 Hz), 7.12 (q, 1H, J=1.1 Hz), 2.35 (d, 3H, J=1.1 Hz).

Reference Example 10

2-Methyl-1H-pyrrolo[2,3-b]pyridine

Reference Example 10-1 tert-Butyl (3-methylpyridin-2-yl)carbamate

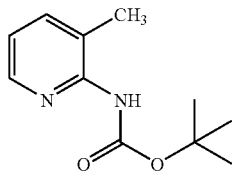

To di t-butylcarbonate (32.29 g, 147.95 mmol) was added hexane (35 ml) and the solution was refluxed under heating at 80° C. Under refluxing, 2-amino-3-methylpyridine (10.00 g, 92.47 mmol) in ethyl acetate (10 ml) was dropped in a period of 15 minutes. After the mixture was refluxed for 2 hours and cooled to room temperature, thereto was added hexane (20 ml). The resulting crystals were filtered and dried in vacuo to give the subject compound (12.39 g, 64%).

$^1$H NMR (CDCl$_3$, 400 MHz) δ 8.27 (dd, 1H, J=4.8, 1.4 Hz), 7.51 (dd, 1H, J=7.5, 1.4 Hz), 7.03 (dd, 1H, J=7.5, 4.8 Hz), 6.95 (brs, 1H), 2.29 (s, 3H), 1.51 (s, 9H).

Reference Example 10-2

2-Methyl-1H-pyrrolo[2,3-b]pyridine

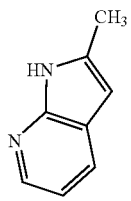

To a solution of the compound of Reference example 10-1 (3.47 g, 16.66 mmol) in THF (67 ml) was dropped at −1° C. n-butyllithium (2.67M hexane solution, 44.6 ml, 118.99 mmol) in a period of 23 minutes, and the mixture was stirred for 1 hour. Thereto was dropped dimethylacetamide (1.58 ml, 16.99 mmol) in a period of 10 minutes, the mixture was warmed to 18° C. and stirred for 1 hour. To separately prepared 5.5N hydrochloric acid (16.7 ml) was added the above reaction mixture at 0° C. and the mixture was warmed to 48° C. and stirred for 5 hours. After being cooled to room temperature, the organic layer and the aqueous layer were separated, and the aqueous layer was neutralized to pH 7 with 5N aqueous sodium hydroxide solution. Then the aqueous layer was combined to the organic layer and the mixture was extracted with ethyl acetate. The organic layer was washed with saturated brine, dried over anhydrous sodium sulfate and filtered. The solvent was removed in vacuo and the residue was purified by silica gel column chromatography to give the subject compound (1.07 g, 49%).

$^1$H NMR (CDCl$_3$, 400 MHz) δ 11.36 (brs, 1H), 8.21 (dd, 1H, J=4.8, 1.4 Hz), 7.82 (dd, 1H, J=7.7, 1.4 Hz), 7.03 (dd, 1H, J=7.7, 4.8 Hz), 6.18 (s, 1H), 2.55 (s, 3H).

Reference Example 11

(5-Methoxy-2-methyl-1H-indol-3-yl)(4-methylphenyl)methanone

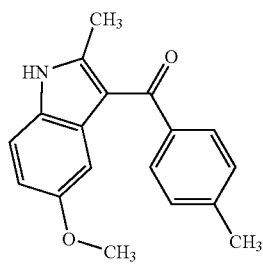

To a solution of 5-methoxy-2-methylindole (816 mg, 5.06 mmol) in dichloromethane (15 ml) were added zinc chloride (1.52 g, 11.14 mmol) and ethyl magnesium bromide diethy ether (3.0 mol/l, 2.02 ml, 6.07 mmol) and the mixture was stirred for 1 hour at room temperature. Thereto was added p-toluoyl chloride (1.25 g, 8.10 mmol). After stirring for 1 hour, thereto was added alminium chloride (337 mg, 2.53 mmol) and the mixture was stirred at room temperature for 20 hours. To the reaction mixture was added an aqueous saturated ammonium chloride solution and the mixture was extracted with chloroform. The organic layer was washed with a saturated sodium hydrogen carbonate solution and saturated brine, dried over anhydrous sodium sulfate and filtered. The solvent was removed in vacuo and the residue was purified by silica gel column chromatography and by recrystallization to give the subject compound (833 mg, 59%).

$^1$H NMR (CDCl$_3$, 400 MHz) δ 8.55 (brs, 1H), 7.66 (d, 2H, J=8.1 Hz), 7.26 (d, 2H, J=8.1 Hz), 7.19 (d, 1H, J=8.8 Hz), 7.05 (d, 1H, J=2.4 Hz), 6.81 (dd, 1H, J=8.8, 2.4 Hz), 3.71 (s, 3H), 2.46 (s, 3H), 2.43 (s, 3H).

Reference Example 12

(6-Methoxy-2-methyl-1H-indol-3-yl)(4-methylphenyl)methanone

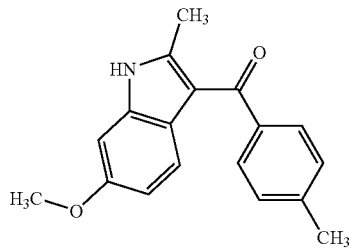

The subject compound was prepared in the same method as Reference example 11 by using the compound of Reference example 6.

$^1$H NMR (DMSO-d$_6$, 400 MHz) δ 11.70 (brs, 1H), 7.51 (d, 2H, J=8.0 Hz), 7.30 (d, 2H, J=8.0 Hz), 7.22 (d, 1H, J=8.7 Hz), 6.86 (d, 1H, J=2.3 Hz), 6.67 (dd, 1H, J=8.7, 2.3 Hz), 3.76 (s, 3H), 2.39 (s, 3H), 2.34 (s, 3H).

Reference Example 13

(6-Methoxy-2-methyl-1H-indol-3,5-diyl)bis[(4-methylphenyl)methanone]

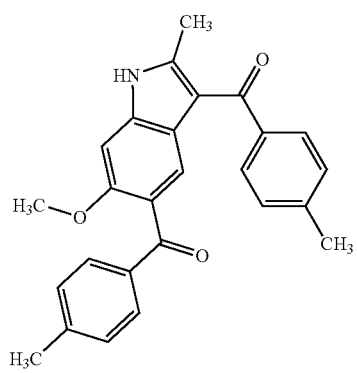

The subject compound was prepared in the same method as Reference example 11 by using the compound of Reference example 6.

LC-MS: R.T. 4.10 min., m/z 398 (M+1)

Reference Example 14

(4-Methoxy-2-methyl-1H-indol-3-yl)(4-methylphenyl)methanone

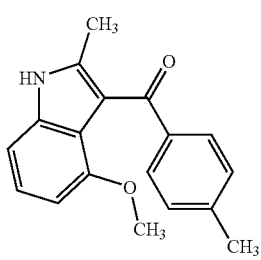

The subject compound was prepared in the same method as Reference example 11 by using the compound of Reference example 7.

$^1$H NMR (CDCl$_3$, 400 MHz) δ 8.36 (brs, 1H), 7.70 (d, 2H, J=8.0 Hz), 7.17 (d, 2H, J=8.0 Hz), 7.11 (dd, 1H, J=8.0, 8.0 Hz), 6.97 (d, 1H, J=8.0 Hz), 6.49 (d, 1H, J=8.0 Hz), 3.40 (s, 3H), 2.49 (s, 3H), 2.40 (s, 3H).

Reference Example 15

(2,5-Dimethyl-1H-indol-3-yl)(4-methylphenyl)methanone

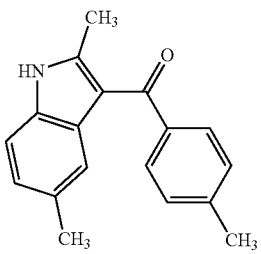

The subject compound was prepared in the same method as Reference example 11 by using 2,5-dimethylindole.

$^1$H NMR (DMSO-d$_6$, 400 MHz) δ 11.78 (brs, 1H), 7.53 (d, 2H, J=8.0 Hz), 7.31 (d, 2H, J=8.0 Hz), 7.26 (d, 1H, J=8.3 Hz), 7.24 (d, 1H, J=1.5 Hz), 6.94 (dd, 1H, J=8.3, 1.5 Hz), 2.41 (s, 3H), 2.33 (s, 3H), 2.29 (s, 3H).

Reference Example 16

(5-Chloro-1H-indol-3-yl)(4-methylphenyl)methanone

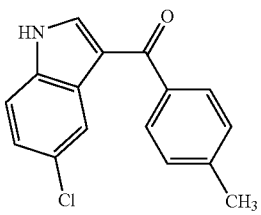

The subject compound was prepared in the same method as Reference example 11 by using 5-chloroindole.

LC-MS: R.T. 3.74 min., m/z 270 (M+1)

Reference Example 17

(5-Fluoro-1H-indol-3-yl)(4-methylphenyl)methanone

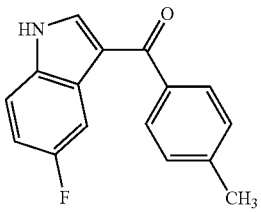

The subject compound was prepared in the same method as Reference example 11 by using 5-fluoroindole.

LC-MS: R.T. 3.53 min., m/z 254 (M+1)

Reference Example 18

(4-Methylphenyl) [3-methyl-6-(trifluoromethyl)-1H-indol-2-yl]methanone

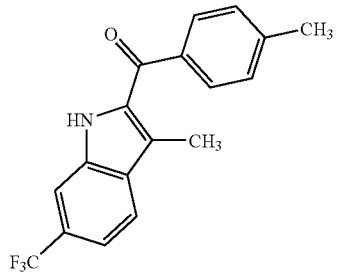

The subject compound was prepared in the same method as Reference example 11 by using the compound of Reference example 9-3.

$^1$H NMR (CDCl$_3$, 400 MHz) δ 9.07 (brs, 1H), 7.77 (d, 1H, J=8.5 Hz), 7.71 (d, 2H, J=8.2 Hz), 7.70 (d, 1H, J=1.1 Hz), 7.38 (dd, 1H, J=8.5, 1.1 Hz), 7.33 (d, 2H, J=8.2 Hz), 2.47 (s, 3H), 2.33 (s, 3H).

Reference Example 19

(4-Methylphenyl)(1H-pyrrolo[2,3-b]pyridin-3-yl)methanone

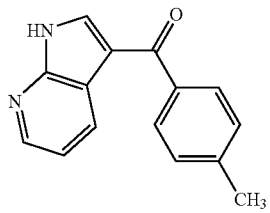

The subject compound was prepared in the same method as Reference example 11 by using 7-azaindole.

$^1$H NMR (CDCl$_3$, 400 MHz) δ 12.79 (brs, 1H), 9.30 (d, 1H, J=7.8 Hz), 8.54 (d, 1H, J=5.0 Hz), 8.20 (s, 1H), 7.79 (d, 2H, J=8.0 Hz), 7.66 (dd, 1H, J=7.8, 5.0 Hz), 7.35 (d, 2H, J=8.0 Hz), 2.48 (s, 3H).

Reference Example 20

(4-Methylphenyl)(2-methyl-1H-pyrrolo[2,3-b]pyridin-3-yl)methanone

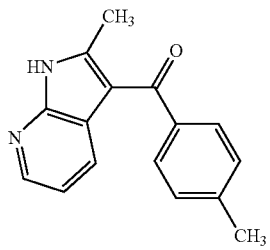

The subject compound was prepared in the same method as Reference example 11 by using the compound of Reference example 10-2.

$^1$H NMR (CDCl$_3$, 400 MHz) δ 12.71 (brs, 1H), 8.29 (dd, 1H, J=4.8, 1.5 Hz), 7.80 (dd, 1H, J=8.0, 1.5 Hz), 7.68 (d, 2H, J=8.0 Hz), 7.29 (d, 2H, J=8.0 Hz), 7.12 (dd, 1H, J=8.0, 4.8 Hz), 2.72 (s, 3H), 2.46 (s, 3H).

Reference Example 21

(6-Bromo-1H-indol-3-yl)(4-methylphenyl)methanone

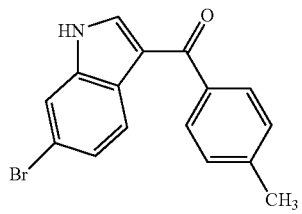

The subject compound was prepared in the same method as Reference example 11 by using 6-bromoindole.

LC-MS: R.T. 3.93 min., m/z 314 (M+1), 316 (M+3)

Reference Example 22

1H-Indol-3-yl(4-methylphenyl)methanone

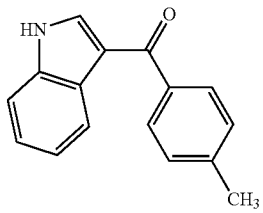

The subject compound was prepared in the same method as Reference example 11 by using indole.

$^1$H NMR (DMSO-d$_6$, 400 MHz) δ 12.05 (brs, 1H), 8.24 (dd, 1H, J=7.1, 1.5 Hz), 7.94 (s, 1H), 7.71 (d, 2H, J=8.1 Hz), 7.52 (dd, 1H, J=7.1, 1.4 Hz), 7.35 (d, 2H, J=8.1 Hz), 7.26 (ddd, 1H, J=7.1, 7.1, 1.5 Hz), 7.23 (ddd, 1H, J=7.1, 7.1, 1.4 Hz), 2.42 (s, 3H).

Reference Example 23

(2-Methyl-1H-indol-3-yl)(4-methylphenyl)methanone

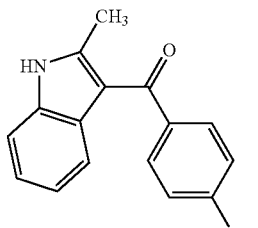

The subject compound was prepared in the same method as Reference example 11 by using 2-methylindole.

$^1$H NMR (DMSO-d$_6$, 400 MHz) δ 7.53 (d, 2H, J=8.0 Hz), 7.38 (d, 1H, J=7.1 Hz), 7.33 (d, 1H, J=7.1 Hz), 7.31 (d, 2H, J=8.0 Hz), 7.11 (dd, 1H, J=7.1, 7.1 Hz), 7.01 (dd, 1H, J=7.1, 7.1 Hz), 2.41 (s, 3H), 2.40 (s, 3H).

Reference Example 24

(4-Methylphenyl) [2-methyl-5-(trifluoromethoxy)-1H-indol-3-yl]methanone

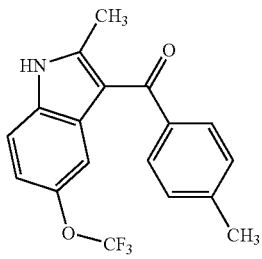

The subject compound was prepared in the same method as Reference example 11 by using the compound of Reference example 5-3.

$^1$H NMR (DMSO-d$_6$, 400 MHz) δ 12.21 (s, 1H), 7.54 (d, 2H, J=8.1 Hz), 7.49 (d, 1H, J=8.7 Hz), 7.33 (d, 1H, J=1.7 Hz), 7.33 (d, 2H, J=8.1 Hz), 7.12 (dd, 1H, J=8.7, 1.7 Hz), 2.41 (s, 3H), 2.36 (s, 3H).

Reference Example 25

(5-Methoxy-2-methyl-1H-indol-3,6-diyl)bis[(4-methylphenyl)methanone]

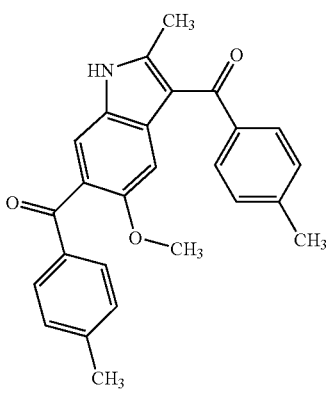

The subject compound was prepared in the same method as Reference example 11 by using 2-methyl-5-methoxyindole.

LC-MS: R.T. 4.18 min., m/z 398 (M+1)

Reference Example 26

(4-Methylphenyl) [2-methyl-6-(trifluoromethyl)-1H-indol-3-yl]methanone

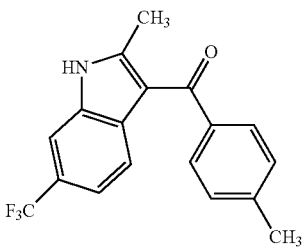

The subject compound was prepared in the same method as Reference example 11 by using the compound of Reference example 8-2.

$^1$H NMR (CDCl$_3$, 400 MHz) δ 8.84 (brs, 1H), 7.68 (d, 2H, J=8.1 Hz), 7.58 (d, 1H, J=1.0 Hz), 7.48 (d, 1H, J=8.4 Hz), 7.31 (dd, 1H, J=8.4, 1.0 Hz), 7.27 (d, 2H, J=8.1 Hz), 2.61 (s, 3H), 2.45 (s, 3H).

Reference Example 27

(1-Allyl-5-methoxy-2-methyl-1H-indol-3-yl)(4-methylphenyl)methanone

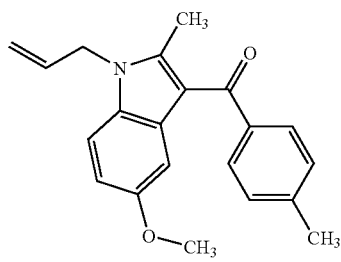

To a solution of the compound of Reference example 11 (261 mg, 0.93 mmol) in DMF (5 ml) was added potassium carbonate (258 mg, 1.87 mmol) and the mixture was stirred for 30 minutes at room temperature. Thereto was added allyl bromide (169 mg, 1.40 mmol) and the mixture was stirred for 9 hours at 60° C., followed by stirring for 4.5 hours at 80° C. The mixture was cooled to room temperature. Thereto was added 5% aqueous potassium hydrogen sulfate solution and the mixture was extracted with ethyl acetate. The organic layer was washed with saturated brine, dried over anhydrous sodium sulfate and filtered. The solvent was removed in vacuo and purified by silica gel column chromatography to give the subject compound (186 mg, 62%).

$^1$H NMR (CDCl$_3$, 400 MHz) δ 7.67 (d, 2H, J=8.1 Hz), 7.25 (d, 2H, J=8.1 Hz), 7.17 (d, 1H, J=8.9 Hz), 6.98 (d, 1H, J=2.4 Hz), 6.83 (dd, 1H, J=8.9, 2.4 Hz), 5.95 (ddt, 1H, J=17.1, 10.3, 4.6 Hz), 5.19 (brd, 1H, J=10.3 Hz), 4.89 (brd, 1H, J=17.1 Hz), 4.72 (ddd, 2H, J=4.6, 1.8, 1.8 Hz), 3.69 (s, 3H), 2.47 (s, 3H), 2.43 (s, 3H).

Reference Example 28

[1-Allyl-2-methyl-5-(trifluoromethoxy-)-1H-indol-3-yl](4-methylphenyl)methanone

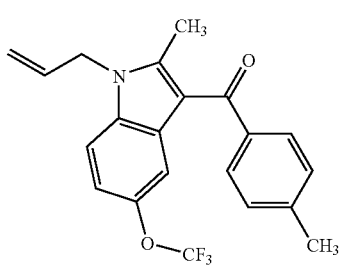

The subject compound was prepared in the same method as Reference example 27 by using the compound of Reference example 24.

$^1$H NMR (CDCl$_3$, 400 MHz) δ 7.66 (d, 2H, J=8.1 Hz), 7.28-7.23 (m, 4H), 7.06 (ddd, 1H, J=8.9, 2.1, 0.8 Hz), 5.96 (ddt, 1H, J=17.1, 10.4, 4.7 Hz), 5.23 (brd, 1H, J=10.4 Hz), 4.91 (ddd, 1H, J=17.1, 1.8, 1.2 Hz), 4.77 (ddd, 2H, J=4.7, 1.8, 1.8 Hz), 2.54 (s, 3H), 2.45 (s, 3H).

Reference Example 29

(1-Allyl-5-chloro-2-methyl-1H-indol-3-yl)(4-methylphenyl)methanone

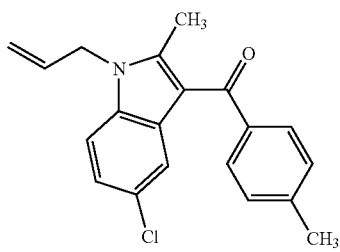

The subject compound was prepared in the same method as Reference examples 11 and 27 by using 5-chloro-2-methylindole.

$^1$H NMR (CDCl$_3$, 400 MHz) δ 7.67 (d, 2H, J=8.1 Hz), 7.40 (d, 1H, J=1.9 Hz), 7.27 (d, 2H, J=8.1 Hz), 7.19 (d, 1H, J=8.6 Hz), 7.14 (dd, 1H, J=8.6, 1.9 Hz), 5.95 (ddt, 1H, J=17.1, 10.3, 4.6 Hz), 5.21 (brd, 1H, J=10.3 Hz), 4.87 (brd, 1H, J=17.1 Hz), 4.75 (ddd, 2H, J=4.6, 1.8, 1.8 Hz), 2.51 (s, 3H), 2.45 (s, 3H).

Reference Example 30

(1-Allyl-2-methyl-1H-indol-3-yl)(4-methylphenyl)methanone

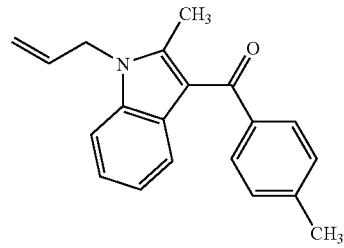

The subject compound was prepared in the same method as Reference example 27 by using the compound of Reference example 23.

$^1$H NMR (CDCl$_3$, 400 MHz) δ 7.69 (d, 2H, J=8.1 Hz), 7.36 (brd, 1H, J=8.0 Hz), 7.29 (brd, 1H, J=8.2 Hz), 7.25 (d, 2H, J=8.1 Hz), 7.19 (ddd, 1H, J=8.2, 7.1, 1.0 Hz), 7.07 (ddd, 1H, J=8.0, 7.1, 1.0 Hz), 5.97 (ddt, 1H, J=17.1, 10.3, 4.7 Hz), 5.20 (brd, 1H, J=10.3 Hz), 4.91 (brd, 1H, J=17.1 Hz), 4.78 (ddd, 2H, J=4.7, 1.8, 1.8 Hz), 2.56 (s, 3H), 2.44 (s, 3H).

Reference Example 31

(1-Allyl-1H-indol-3-yl)(4-methylphenyl)methanone

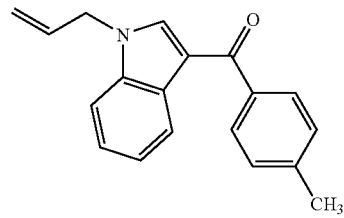

The subject compound was prepared in the same method as Reference example 27 by using the compound of Reference example 22.

$^1$H NMR (CDCl$_3$, 400 MHz) δ 8.45-8.39 (m, 1H), 7.74 (d, 2H, J=8.1 Hz), 7.59 (s, 1H), 7.39-7.30 (m, 3H), 7.29 (d, 2H, J=8.1 Hz), 6.01 (ddt, 1H, J=17.1, 10.3, 5.4 Hz), 5.28 (brd, 1H, J=10.3 Hz), 5.16 (brd, 1H, J=17.1 Hz), 4.78 (ddd, 2H, J=5.4, 1.6, 1.6 Hz), 2.45 (s, 3H).

Reference Example 32

(1-Allyl-6-methoxy-2-methyl-1H-indol-3-yl)(4-methylphenyl)methanone

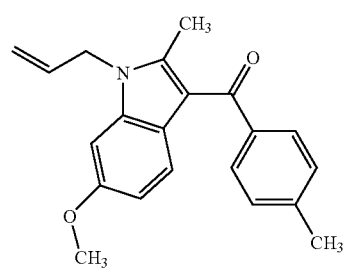

The subject compound was prepared in the same method as Reference example 27 by using the compound of Reference example 12.

$^1$H NMR (CDCl$_3$, 400 MHz) δ 7.68 (d, 2H, J=8.1 Hz), 7.25 (d, 1H, J=9.3 Hz), 7.25 (d, 2H, J=8.1 Hz), 6.75 (d, 1H, J=2.3 Hz), 6.74 (dd, 1H, J=9.3, 2.3 Hz), 5.96 (ddt, 1H, J=17.1, 10.3, 4.6 Hz), 5.21 (brdd, 1H, J=10.1, 1.8 Hz), 4.92 (brdd, 1H, J=17.1, 1.8 Hz), 4.72 (ddd, 2H, J=4.6, 1.8, 1.8 Hz), 3.85 (s, 3H), 2.52 (s, 3H), 2.44 (s, 3H).

Reference Example 33

(1-Allyl-6-methoxy-2-methyl-1H-indol-3,5-diyl)bis[(4-methylphenyl)methanone]

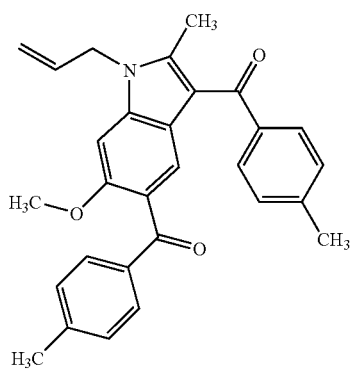

The subject compound was prepared in the same method as Reference example 27 by using the compound of Reference example 13.

$^1$H NMR (CDCl$_3$, 400 MHz) δ 7.67 (d, 2H, J=8.2 Hz), 7.65 (d, 2H, J=8.2 Hz), 7.36 (s, 1H), 7.19 (s, 2H), 7.17 (s, 2H), 6.78 (s, 1H), 5.99 (ddt, 1H, J=17.1, 10.3, 4.4 Hz), 5.25 (brd, 1H, J=10.3 Hz), 4.93 (brd, 1H, J=17.1 Hz), 4.77 (ddd, 2H, J=4.4, 2.2, 2.2 Hz), 3.76 (s, 3H), 2.52 (s, 3H), 2.40 (s, 3H), 2.36 (s, 3H).

Reference Example 34

(1-Allyl-4-methoxy-2-methyl-1H-indol-3-yl)(4-methylphenyl)methanone

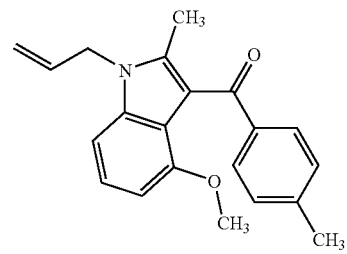

The subject compound was prepared in the same method as Reference example 27 by using the compound of Reference example 14.

$^1$H NMR (CDCl$_3$, 400 MHz) δ 7.69 (d, 2H, J=8.2 Hz), 7.16 (d, 2H, J=8.2 Hz), 7.13 (dd, 1H, J=8.0, 8.0 Hz), 6.92 (d, 1H, J=8.0 Hz), 6.49 (d, 1H, J=8.0 Hz), 5.97 (ddt, 1H, J=17.1, 10.3, 4.6 Hz), 5.19 (brd, 1H, J=10.3 Hz), 4.90 (brd, 1H, J=17.1 Hz), 4.74 (ddd, 2H, J=4.6, 1.8, 1.8 Hz), 3.38 (s, 3H), 2.46 (s, 3H), 2.40 (s, 3H).

Reference Example 35

(1-Allyl-2,5-dimethyl-1H-indol-3-yl)(4-methylphenyl)methanone

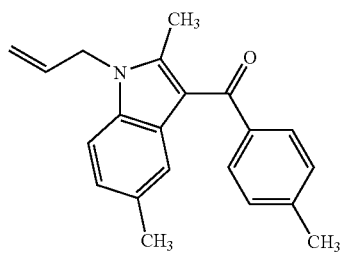

The subject compound was prepared in the same method as Reference example 27 by using the compound of Reference example 15.

$^1$H NMR (CDCl$_3$, 400 MHz) δ 7.69 (d, 2H, J=8.1 Hz), 7.25 (d, 2H, J=8.1 Hz), 7.27-7.24 (m, 1H), 7.17 (d, 1H, J=8.3 Hz), 7.02 (dd, 1H, J=8.3, 1.4 Hz), 5.95 (ddt, 1H, J=17.1, 10.3, 4.3 Hz), 5.19 (brd, 1H, J=10.3 Hz), 4.89 (brd, 1H, J=17.1 Hz), 4.74 (ddd, 2H, J=4.3, 1.8, 1.8 Hz), 2.49 (s, 3H), 2.44 (s, 3H), 2.34 (s, 3H).

Reference Example 36

(1-Allyl-5-chloro-1H-indol-3-yl)(4-methylphenyl)methanone

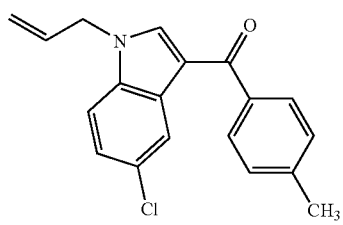

The subject compound was prepared in the same method as Reference example 27 by using the compound of Reference example 16.

$^1$H NMR (CDCl$_3$, 400 MHz) δ 8.44 (dd, 1H, J=1.3, 1.3 Hz), 7.73 (d, 2H, J=8.1 Hz), 7.59 (s, 1H), 7.30 (d, 2H, J=8.1 Hz), 7.28 (d, 2H, J=1.3 Hz), 5.99 (ddt, 1H, J=17.1, 10.3, 5.4 Hz), 5.29 (ddd, 1H, J=10.3, 2.2, 1.6 Hz), 5.14 (ddd, 1H, J=17.1, 2.2, 1.6 Hz), 4.76 (ddd, 2H, J=5.4, 1.6, 1.6 Hz), 2.45 (s, 3H).

Reference Example 37

(1-Allyl-5-fluoro-1H-indol-3-yl)(4-methylphenyl)methanone

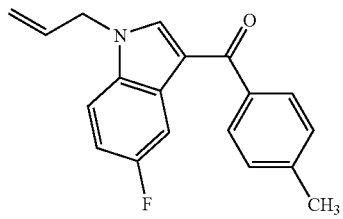

The subject compound was prepared in the same method as Reference example 27 by using the compound of Reference example 17.

$^1$H NMR (CDCl$_3$, 400 MHz) δ 8.11 (dd, 1H, J=9.0, 2.5 Hz), 7.73 (d, 2H, J=8.1 Hz), 7.61 (s, 1H), 7.30 (d, 2H, J=8.1 Hz), 7.28 (dd, 1H, J=9.0, 4.3 Hz), 7.07 (ddd, 1H, J=9.0, 9.0, 2.6 Hz), 5.99 (ddt, 1H, J=17.1, 10.3, 5.4 Hz), 5.29 (ddd, 1H, J=10.3, 2.2, 1.6 Hz), 5.16 (ddd, 1H, J=17.1, 2.2, 1.6 Hz), 4.76 (ddd, 2H, J=5.4, 1.6, 1.6 Hz), 2.45 (s, 3H).

Reference Example 38

(1-Allyl-1H-pyrrolo[2,3-b]pyridin-3-yl)(4-methylphenyl)methanone

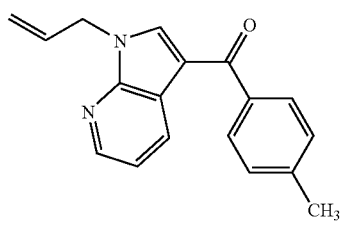

The subject compound was prepared in the same method as Reference example 27 by using the compound of Reference example 19.

$^1$H NMR (CDCl$_3$, 400 MHz) δ 8.65 (dd, 1H, J=7.9, 1.6 Hz), 8.43 (dd, 1H, J=4.7, 1.6 Hz), 7.75 (d, 2H, J=8.1 Hz), 7.73 (s, 1H), 7.31 (d, 2H, J=8.1 Hz), 7.28 (dd, 1H, J=7.9, 4.7 Hz), 6.07 (ddt, 1H, J=17.1, 10.3, 5.6 Hz), 5.27 (ddd, 1H, J=10.3, 2.6, 1.5 Hz), 5.17 (ddd, 1H, J=17.1, 2.6, 1.5 Hz), 4.97 (ddd, 2H, J=5.6, 1.5, 1.5 Hz), 2.46 (s, 3H).

Reference Example 39

(1-Allyl-2-methyl-1H-pyrrolo[2,3-b]pyridin-3-yl)(4-methylphenyl)methanone

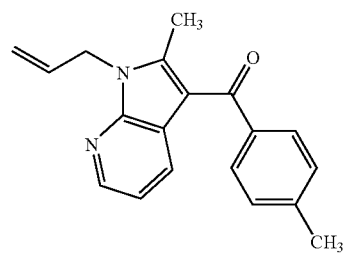

The subject compound was prepared in the same method as Reference example 27 by using the compound of Reference example 20.

$^1$H NMR (CDCl$_3$, 400 MHz) δ 8.28 (dd, 1H, J=4.7, 1.5 Hz), 7.67 (d, 2H, J=8.1 Hz), 7.62 (dd, 1H, J=7.9, 1.5 Hz), 7.27 (d, 2H, J=8.1 Hz), 7.04 (dd, 1H, J=7.9, 4.7 Hz), 6.03 (ddt, 1H, J=17.1, 10.4, 4.8 Hz), 5.20 (ddd, 1H, J=10.4, 2.6, 1.8 Hz), 5.01 (ddd, 2H, J=4.8, 1.8, 1.8 Hz), 4.91 (ddd, 1H, J=17.1, 2.6, 1.8 Hz), 2.62 (s, 3H), 2.45 (s, 3H).

Reference Example 40

2-[(4-Iodobenzyl)oxy]-2-methylpropionic acid

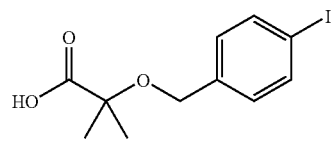

To a solution of the compound of Reference example 3-1 (29.23 g, 87.47 mmol) in THF (50 ml) and methanol (50 ml) was added 3N aqueous potassium hydroxide solution (40 ml) and the mixture was stirred for 1 hour at 30° C. Thereto was added toluene (70 ml) and the mixture was poured into a separating funnel. After washing with toluene (10 ml) and water (20 ml), the mixture was separated. The aqueous layer was acidified to pH 1 to 2 with concentrated hydrochloric acid (about 17 ml) and extracted with toluene (100 ml). The organic layer was washed with water (60 ml), concentrated to dryness and dried in vacuo to give a mixture of the subject compound (12.9 g). The mixture of the subject compound (22.7 g) was suspended in toluene (70 ml), and dissolved by warming to 60° C. By stopping heating under a water bath the solution was stirred while being gradually cooled. As crystals begin to separate at 45° C., the solution was stirred for 10 minutes at 50° C. Thereto was added hexane (70 ml) and the mixture was stirred for 10 minutes at 50° C. After removal of the water bath for heating, the mixture was stirred at room temperature for 20 minutes and under ice-cooling for 20 minutes. The resulting crystals were collected by filtration to give the subject compound (21.0 g, 75%).

$^1$H NMR (CDCl$_3$, 400 MHz) δ 7.67 (d, 2H, J=8.3 Hz), 7.13 (d, 2H, J=8.3 Hz), 4.47 (s, 2H), 1.55 (s, 6H).

Reference Example 41

(2R)-2-[(4-Iodobenzyl)oxy]propionic acid

Reference Example 41-1

(2R)-2-[(4-Iodo-benzyl)oxy]propionic acid (1S)-1-phenylethanamine salt

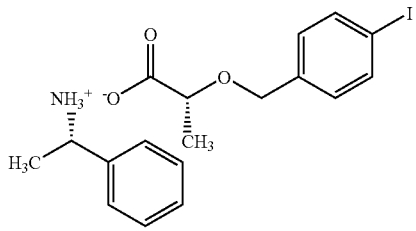

To a solution of (R)-methyl lactate (116 mg, 1.12 mmol) in THF (20 ml) was added at 0° C. sodium hydride (60% in paraffin liquid) (45 mg, 1.12 mmol) and the mixture was stirred for 15 minutes at room temperature. Thereto was added 4-iodobenzyl bromide (300 mg, 1.12 mmol), followed by stirring for 5 hours at room temperature. Thereto was added a saturated ammonia solution and the mixture was extracted with ethyl acetate. The organic layer was dried over anhydrous sodium sulfate and filtered. After removal of the solvent, thereto were added 3N aqueous sodium hydroxide solution (1 ml), THF (1 ml) and methanol (1 ml) and the mixture was stirred for 3 hours at room temperature. Thereto was added toluene (3 ml) and the aqueous layer was extracted. The aqueous layer was acidified to pH 2 with 1N hydrochloric acid. Thereto was added toluene (3 ml) and the organic layer was extracted and dried over anhydrous sodium sulfate and filtered. The solvent was removed to give a carboxylic acid compound (210 mg, 67%, 60% ee). To this carboxylic acid compound (100 mg) was added (S)-1-phenylethylamine (40 mg) and the mixture was dissolved in chloroform (1.75 ml) at 70° C. After hexane (1.75 ml) was dropped therein, the mixture was cooled to 0° C. in a period of 10 hours and stirred for additional 3 hours at 0° C. The resulted white crystals were collected by filtration to give the subject compound as a white solid (85 mg, 63%).

$^1$H NMR (CDCl$_3$, 400 MHz) δ 7.61 (d, 2H, J=8.3 Hz), 7.40-7.20 (m, 5H), 7.00 (d, 2H, J=8.3 Hz), 4.34 (d, 1H, J=12 Hz), 4.15 (d, 1H, J=12 Hz), 4.02 (q, 1H, 6.8 Hz), 3.71 (q, 1H, 6.8 Hz), 1.47 (d, 3H, J=6.8 Hz), 1.20 (d, 3H, J=6.8 Hz).

Result of analysis: Optical purity 99.5% ee.

(Condition for resolution: 11.8 min, HPLC: Column: CHIRALCEL OD-RH (5 μm 6 mmφ×15 cm), eluate: solution A 0.1% trifluoroacetic acid/water, solution B acetonitrile, A:B=2:1 (constant), flow rate: 1 ml/min, UV: 254 nm

Reference Example 41-2

(2R)-2-[(4-Iodobenzyl)oxy]propionic acid

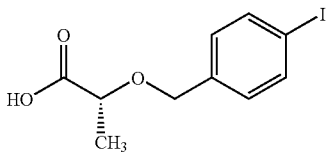

To the compound of Reference example 41-1 (500 mg, 1.17 mmol) was added water and the solution was acidified to pH2 with 1N hydrochloric acid. Thereto was added toluene (1 ml) and the organic layer was extracted to give the subject compound (336 mg, 94%).

$^1$H NMR (CDCl$_3$, 400 MHz) δ 7.70 (d, 2H, J=8.0 Hz), 7.12 (d, 2H, J=8.0 Hz), 4.64 (d, 1H, J=12.0 Hz), 4.49 (d, 1H, J=12.0 Hz), 4.11 (q, 1H, J=6.8 Hz), 1.50 (d, 3H, J=6.8 Hz).

Reference Example 42

4-{(2R)-2-[(3-Bromobenzyl)oxy]propanoyl}morphline

Reference Example 42-1

(2R)-1-Morpholin-4-yl-1-oxopropan-2-ol

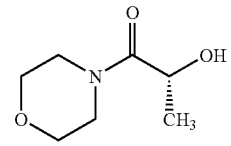

To (R)-methyl lactate (24.42 g, 0.23 mol) were added morphline (21.46 g, 0.25 mol) and sodium methoxide in methanol (14%, 9.04 g, 0.02 mol) and the mixture was stirred for 3 hours at 50° C. After removal of the solvent in vacuo, the residue was subjected to azeotropic distillation three times with toluene to give the subject compound (quant.).

$^1$H NMR (CDCl$_3$, 400 MHz) δ 4.44 (q, 1H, J=6.6 Hz), 3.77-3.58 (m, 6H), 3.45-3.40 (m, 2H), 1.33 (d, 3H, J=6.6 Hz).

Reference Example 42-2

4-{(2R)-2-[(3-Bromobenzyl)oxy]propanoyl}morpholine

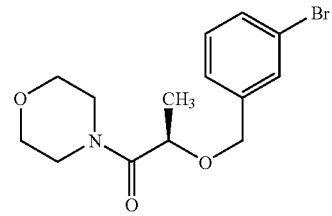

In a suspension of sodium hydride (60% in paraffin liquid) (2.08 g, 52.0 mmol) in THF (80 ml) was dropped the compound of Reference example 42-1 (8.28 g, 52.0 mmol) in THF (20 ml) and the mixture was stirred for 30 minutes at 50° C. Thereto was added 3-bromobenzyl bromide (10.0 g, 40.0 mmol) in THF (25 ml) and the mixture was stirred for 1 hour at room temperature and 1 hour at 50° C. After being cooled to room temperature, an aqueous saturated ammonium chloride solution was added thereto. The mixture was extracted with ethyl acetate and separated by a separating funnel. The organic layer was washed with saturated brine, dried over anhydrous sodium sulfate and filtered. The solvent was removed in vacuo and the residue was purified by silica gel column chromatography to give the subject compound (quant.).

$^1$H NMR (CDCl$_3$, 300 MHz) δ 7.49 (brs, 1H), 7.43 (ddd, 1H, J=6.6, 2.0, 2.0 Hz), 7.29-7.19 (m, 2H), 4.56 (d, 1H, J=11.9 Hz), 4.42 (d, 1H, J=11.9 Hz), 4.32 (q, 1H, 6.8 Hz), 3.72-3.58 (m, 8H), 1.46 (d, 3H, J=6.8 Hz).

Reference Example 43

(1-Allyl-1H-pyrazol-3-yl)(4-methylphenyl)methanone

Reference Example 43-1

1-Allyl-1H-pyrazole-3-carbaldehyde

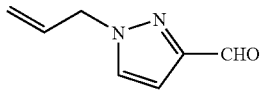

While stirring pyrazole-3-cabaldehyde (3.00 g, 31.2 mmol) in DMF (20 ml), thereto were added potassium carbonate (6.47 g, 46.8 mmol) and allyl bromide (3.50 g, 32.8 mmol). After stirring for 6 hours at room temperature, water was added thereto and the mixture was extracted with ethyl acetate. The organic layer was washed with water and saturated brine, dried over anhydrous magnesium sulfate and filtered. The solvent was removed in vacuo and the residue was purified by silica gel column chromatography to give the subject compound (3.27 g, 77%).

$^1$H NMR (CDCl$_3$, 400 MHz) δ 9.99 (s, 1H), 7.47 (d, 1H, J=2.0 Hz), 6.83 (d, 1H, J=2.0 Hz), 6.05 (ddt, 1H, J=17.6, 10.2, 6.0 Hz), 5.35 (d, 1H J=10.2 Hz), 5.28 (d, 1H, J=17.6 Hz), 4.84 (d, 2H, J=6.0 Hz).

Reference Example 43-2

(1-Allyl-1H-pyrazol-3-yl)(4-methylphenyl)methanone

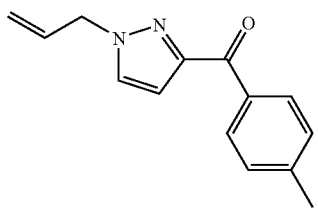

To the compound of Reference example 43-1 (1.36 g, 10.0 mmol) in THF (10 ml) was added under stirring at room temperature p-tolylmagnesium bromide (1.0 M diethyl ether, 20.0 ml, 20.0 mmol), followed by stirring for 2 hours at room temperature. Thereto was added an aqueous saturated ammonium chloride solution, and the mixture was extracted with ethyl acetate. The organic layer was washed with water and saturated brine, dried over anhydrous magnesium sulfate and the solvent was removed in vacuo. The residue was dissolved in chloroform (30 ml) and thereto was added magnesium dioxide (10.0 g, 115 mmol), followed by stirring for 3 hours at 50° C. The reaction mixture was cooled to room temperature and filtered through Celite. After removal of the solvent in the filtrate in vacuo, the residue was purified by silica gel column chromatography to give the subject compound (1.43 g, 63%).

$^1$H NMR (CDCl$_3$, 400 MHz) δ 8.15 (d, 2H, J=8.3 Hz), 7.46 (d, 1H, J=2.4 Hz), 7.28 (d, 2H, J=8.3 Hz), 6.96 (d, 1H, J=2.4 Hz), 6.06 (ddt, 1H, J=17.0, 10.2, 6.0 Hz), 5.32 (d, 1H, J=10.2 Hz), 5.27 (d, 1H, J=17.0 Hz), 4.86 (d, 2H, J=6.0 Hz), 2.42 (s, 3H).

Reference Example 44

(1-Allyl-4,5,6,7-tetrahydro-1H-benzimidazol-2-yl)[4-(trifluoromethyl)phenyl]methanone Reference Example 44-1

4,5,6,7-Tetrahydro-1H-benzimidazole

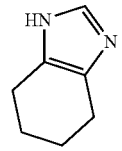

In formamide (84.9 g, 1.89 mmol) was dropped under stirring at 170° C. 2-chlorocyclohexanone (25.0 g, 189 mmol) in a period of 30 minutes, followed by stirring for 4 hours at 170° C. After being cooled to room temperature, water was added thereto, and the aqueous layer was washed twice with toluene-hexane (1:1). The aqueous layer was neutralized with 4N aqueous sodium hydroxide solution and the solution was extracted with chloroform. The chloroform layer was washed with water and saturated brine, dried over anhydrous sodium sulfate and filtered. The solvent was removed in vacuo and the residue was purified by silica gel column chromatography to give the subject compound (12.9 g, 61%).

$^1$H NMR (CDCl$_3$, 400 MHz) δ 7.47 (s, 1H), 2.61-2.58 (m, 4H), 1.84-1.80 (m, 4H).

Reference Example 44-2

4,5,6,7-Tetrahydro-1H-benzimidazol-2-yl[4-(trifluoromethyl)phenyl]methanone

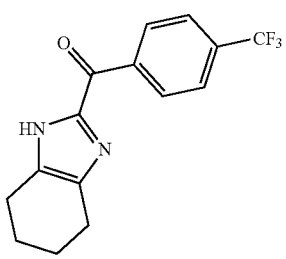

The compound of Reference example 44-1 (3.13 g, 25.6 mmol) and 4-(trifluoromethyl)benzoyl chloride (10.0 g, 47.9 mmol) were dissolve in pyridine (20 ml) and the solution was stirred at room temperature. Therein was dropped triethylamine (4.85 g, 47.9 mmol) and the mixture was stirred for 4 hours at 60° C. Thereto was added 4N aqueous sodium hydroxide solution (20 ml) and the mixture was stirred for 3 hours at room temperature. The reaction mixture was neutralized with 1N diluted hydrochloric acid and the mixture was extracted with ethyl acetate. The organic layer was washed with water and saturated brine, dried over anhydrous sodium sulfate and filtered. The solvent was removed in vacuo and the residue was recrystallized from toluene to give the subject compound (5.24 g, 70%).

¹H NMR (CDCl₃, 400 MHz) δ 8.22 (d, 2H, J=8.0 Hz), 7.48 (d, 2H, J=8.0 Hz), 2.40-2.35 (m, 4H), 1.72-1.67 (m, 4H).

Reference Example 44-3

(1-Allyl-4,5,6,7-tetrahydro-1H-benzimidazol-2-yl)[4-(trifluoromethyl)phenyl]methanone

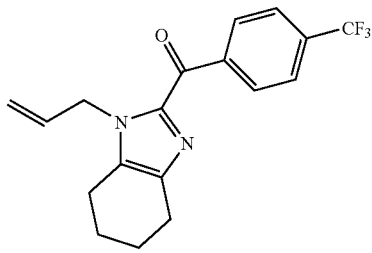

To a solution of the compound of Reference example 44-2 (2.00 g, 6.80 mmol) in 2-propanol (50 ml) were added potassium carbonate (1.41 g, 10.2 mmol) and 3-bromopropene (1.65 g, 13.6 mmol) and the mixture was stirred for 16 hours at 80° C. Thereto was added ethyl acetate (150 ml) to remove insoluble materials. The solvent in the filtrate was removed in vacuo and the residue was purified by silica gel column chromatography to give the subject compound (880 mg, 39%).

¹H NMR (CDCl₃, 400 MHz) δ 8.29 (d, 2H, J=8.1 Hz), 7.72 (d, 2H, J=8.1 Hz), 6.03 (ddt, 1H, J=17.3, 10.4, 5.6 Hz), 5.20 (d, 1H, J=10.4 Hz), 5.02 (d, 2H, J=5.6 Hz), 4.98 (d, 1H, J=17.3 Hz), 2.70-2.60 (m, 4H), 1.93-1.84 (m, 4H).

Reference Example 45

(1-Allyl-4,5,6,7-tetrahydro-1H-benzimidazol-2-yl)(4-methylphenyl)methanone

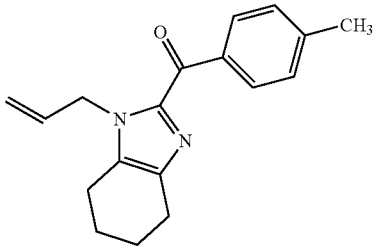

The subject compound was prepared in the same method as Reference example 44.

¹H NMR (CDCl₃, 400 MHz) δ 8.12 (d, 2H, J=8.2 Hz), 7.25 (d, 2H, J=8.2 Hz), 6.07-5.98 (ddt, 1H, J=17.0, 10.4, 6.0 Hz), 5.15 (d, 1H, J=10.4 Hz), 4.97 (d, 2H, J=6.0 Hz), 4.95 (d, 1H, J=17.0 Hz), 2.70-2.67 (m, 2H), 2.61-2.58 (m, 2H), 2.40 (s, 3H), 1.91-1.82 (m, 4H).

Reference Example 46

(1-allyl-1H-indazol-3-yl)(4-methylphenyl)methanone

Reference Example 46-1

{2-[(4-Methylphenyl)ethynyl]phenyl}amine

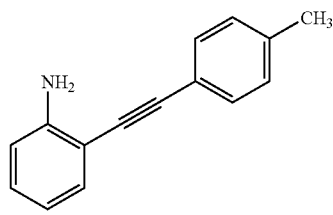

To 2-iodoaniline (2.19 g, 10.0 mmol) in diethylamine (40 ml) were added 4-ethynyltoluene (1.16 g, 10.0 mmol), bis (triphenylphosphine) palladium(II) chloride (702 mg, 1.00 mmol) and copper iodide (190 mg, 1.00 mmol) successively, and the mixture was stirred for 6 hours at 50° C. After adding water, the reaction mixture was extracted with ethyl acetate. The organic layer was washed with water and saturated brine, dried over anhydrous sodium sulfate and filtered. The solvent was removed in vacuo and the residue was purified by silica gel column chromatography to give the subject compound (1.80 g, 87%).

¹H NMR (CDCl₃, 400 MHz) δ 7.42 (d, 2H, J=8.1 Hz), 7.35 (d, 1H, J=8.2 Hz), 7.16 (d, 2H, J=8.1 Hz), 7.12 (d, 1H, J=7.6 Hz), 6.71 (dd, 1H, J=7.6, 7.4 Hz), 6.70 (dd, 1H, J=8.1, 7.4 Hz), 4.27 (brs, 2H), 2.37 (s, 3H).

Reference Example 46-2

1H-Indazol-3-yl(4-methylphenyl)methanone

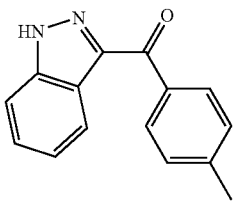

To the compound of Reference example 46-1 (1.49 g, 7.19 mmol) in dioxane (20 ml) was added 1N diluted hydrochloric acid (20 ml), and in the suspension was dropped under stirring at room temperature sodium nitrite solution (595 mg, 8.63 mmol) in water (5 ml), followed by stirring for 2 hours at room temperature. Thereto was added water and the mixture was extracted with ethyl acetate. The organic layer was washed with water and saturated brine, dried over anhydrous sodium sulfate and filtered. The solvent was removed in vacuo and the residue was purified by silica gel column chromatography to give the subject compound (570 mg, 34%).

¹H NMR (CDCl₃, 400 MHz) δ 10.72 (brs, 1H), 8.46 (d, 1H, J=8.2 Hz), 8.22 (d, 2H, J=8.2 Hz), 7.54 (d, 1H, J=8.4 Hz), 7.48 (dd, 1H, J=8.3, 8.2 Hz), 7.37 (dd, 1H, J=8.4, 8.3 Hz), 7.32 (d, 2H, J=8.2 Hz), 2.45 (s, 3H).

Reference Example 47

(4-Methylphenyl)[6-(trifluoromethyl)-1H-indazol-3-yl]methanone

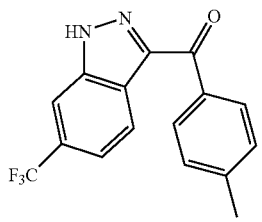

The subject compound was prepared in the same method as Reference example 46 by using 5-(trifluoromethyl)-2-bromoaniline.

$^1$H NMR (CDCl$_3$, 400 MHz) δ 8.60 (d, 1H, J=8.6 Hz), 8.24 (d, 2H, J=8.2 Hz), 7.88 (s, 1H), 7.60 (d, 1H, J=8.6 Hz), 7.35 (d, 2H, J=8.2 Hz), 2.47 (s, 3H).

Reference Example 48

(4-Methylphenyl)(1H-pyrazolo[4,3-b]pyridin-3-yl)methanone

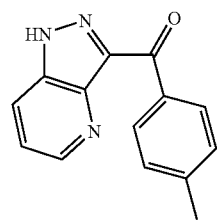

The subject compound was prepared in the same method as Reference example 46 by using 2-bromo-3-aminopyridine.

$^1$H NMR (CDCl$_3$, 400 MHz) δ 8.69 (d, 1H, J=4.3 Hz), 8.19 (d, 1H, J=8.4 Hz), 8.01 (d, 2H, J=8.2 Hz), 7.49 (dd, 1H, J=4.3, 8.4 Hz), 7.38 (d, 2H, J=8.2 Hz), 2.51 (s, 3H).

Reference Example 49

(1-Allyl-1H-indazol-3-yl)(4-methylphenyl)methanone

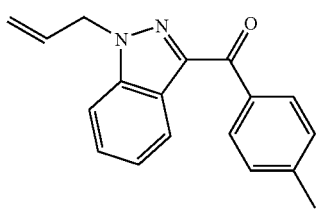

To the compound of Reference example 46 (236 mg, 1.00 mmol) in 2-propanol (10 ml) were added potassium carbonate (181 mg, 1.50 mmol) and 3-bromopropene (242 mg, 2.00 mmol) and the mixture was stirred for 6 hours at 80° C. Thereto was added ethyl acetate (100 ml) to remove insoluble materials. The solvent in the filtrate was removed in vacuo and the residue was purified by silica gel column chromatography to give the subject compound (228 mg, 83%).

$^1$H NMR (CDCl$_3$, 400 MHz) δ 8.46 (d, 1H, J=7.3 Hz), 8.24 (d, 2H, J=8.2 Hz), 7.48 (d, 1H, J=7.3 Hz), 7.47 (dd, 1H, J=7.3, 7.2 Hz), 7.37 (dd, 1H, J=7.3, 7.2 Hz), 7.32 (d, 2H, J=8.2 Hz), 6.07 (ddt, 1H, J=17.1, 10.2, 5.6 Hz), 5.29 (d, 1H, J=10.2 Hz), 5.20 (d, 1H, J=17.1 Hz), 5.15 (d, 2H, J=5.6 Hz), 2.45 (s, 3H).

Reference Example 50

(1-Allyl-1H-indazol-3-yl)(4-chlorophenyl)methanone

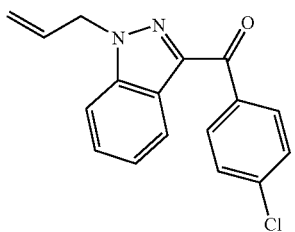

The subject compound was prepared in the same methods as Reference example 46 and then Reference example 49 by using 2-iodoaniline and 4'-chlorophenylacetylene.

$^1$H NMR (CDCl$_3$, 400 MHz) δ 8.46 (d, 1H, J=7.1 Hz), 8.32 (d, 2H, J=8.8 Hz), 7.50 (d, 2H, J=8.8 Hz), 7.50-7.45 (m, 2H), 7.38 (m, 1H), 6.08 (ddt, 1H, J=10.3, 17.1, 7.0 Hz), 5.30 (d, 1H, J=10.3 Hz), 5.21 (d, 1H, J=17.1 Hz), 5.15 (d, 2H, J=7.0 Hz).

Reference Example 51

(1-Allyl-1H-indazol-3-yl)(4-ethylphenyl)methanone

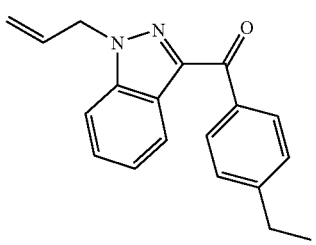

The subject compound was prepared in the same methods as Reference example 46 and then Reference example 49 by using 2-iodoaniline and 1-ethyl-4-ethynylbenzene.

$^1$H NMR (CDCl$_3$, 400 MHz) δ 8.46 (d, 1H, J=7.2 Hz), 8.27 (d, 2H, J=8.3 Hz), 7.50-7.43 (m, 2H), 7.37 (d, 1H, J=6.4 Hz), 7.34 (d, 2H, J=8.3 Hz), 6.08 (ddt, 1H, J=10.3, 17.0, 5.6 Hz), 5.28 (d, 1H, J=10.3 Hz), 5.14 (d, 1H, J=17.0 Hz), 5.14 (d, 2H, J=5.6 Hz), 2.74 (q, 2H, J=7.6 Hz), 1.29 (t, 3H, J=7.6 Hz).

Reference Example 52

[1-Allyl-6-(trifluoromethyl)-1H-indazol-3-yl](4-methylphenyl)methanone

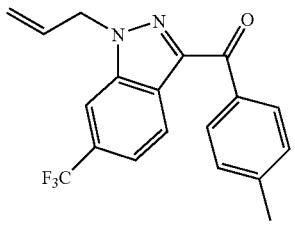

The subject compound was prepared in the same method as Reference example 49 by using the compound of Reference example 47.

$^1$H NMR (CDCl$_3$, 400 MHz) δ 8.59 (d, 1H, J=8.8 Hz), 8.26 (d, 2H, J=8.2 Hz), 7.78 (s, 1H), 7.59 (d, 1H, J=8.8 Hz), 7.34 (d, 2H, J=8.2 Hz), 6.11 (ddt, 1H, J=10.3, 17.4, 5.7 Hz), 5.34 (d, 1H, J=10.3 Hz), 5.22 (d, 1H, J=17.4 Hz), 5.20 (d, 2H, J=5.7 Hz), 2.46 (s, 3H).

Reference Example 53

[1-Allyl-5-(trifluoromethoxy-)-1H-indazol-3-yl](4-methylphenyl)methanone

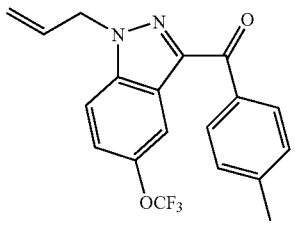

The subject compound was prepared in the same method as Reference example 46 and then Reference example 49 by using 4-(trifluoromethoxy)-2-bromoaniline and 4-ethynyl-toluene.

$^1$H NMR (CDCl$_3$, 400 MHz) δ 8.36 (s, 1H), 8.26 (d, 2H, J=8.2 Hz), 7.49 (d, 1H, J=9.0 Hz), 7.34 (d, 1H, J=9.0 Hz), 7.33 (d, 2H, J=8.2 Hz), 6.07 (ddt, 1H, J=10.2, 17.2, 5.5 Hz), 5.33 (d, 1H, J=10.2 Hz), 5.23 (d, 1H, J=17.2 Hz), 5.15 (d, 2H, J=5.5 Hz).

Reference Example 54

(4-Methylphenyl)(1-vinyl-1H-indazol-3-yl)methanone

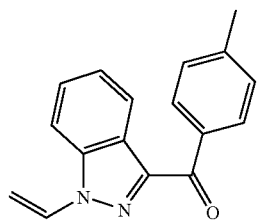

To the compound of Reference example 46 (236 mg, 1.00 mmol) in methyl ethyl ketone (5 ml) were added 1-chloro-2-bromoethane (430 mg, 3.00 mmol) and potassium carbonate (414 mg, 3.00 mmol), and the mixture was stirred for 5 hours at 70° C. Thereto was added ethyl acetate (20 ml) to remove insoluble materials. The solvent in the filtrate was removed in vacuo and the residue was dissolved in dioxane (5 ml). Thereto was added DBU (2 ml) and the mixture was stirred for 2 hours at 50° C. The solvent was removed in vacuo and the residue was purified by silica gel column chromatography to give the subject compound.

$^1$H NMR (CDCl$_3$, 400 MHz) δ 8.47 (d, 1H, J=8.2 Hz), 8.31 (d, 2H, J=8.2 Hz), 7.64 (d, 1H, J=8.4 Hz), 7.53 (m, 1H), 7.44 (dd, 1H, J=8.8, 15.6 Hz), 7.41 (m, 1H), 7.34 (d, 2H, J=8.2 Hz), 5.92 (d, 1H, J=15.6 Hz), 5.11 (d, 1H, J=8.8 Hz), 2.46 (s, 3H).

Reference Example 55

4-((2R)-2-{[4-(Bromomethyl)benzyl]oxy}propanoyl)morpholine

Reference Example 55-1

[4-({[tert-Butyl(dimethyl)sillyl]oxy}methyl)phenyl]methanol

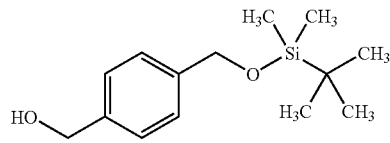

To 1,4-benzene dimethanol (499 mg, 3.61 mmol) in dichloromethane (15 ml) were added at 0° C. triethylamine (731 mg, 7.22 mmol), 4-dimethylaminopyridine (44 mg, 0.36 mmol) and t-butyldimethylchlorosilane (544 mg, 3.61 mmol) successively, and the mixture was stirred for 20 hours at room temperature. Thereto was added a saturated ammonia solution. The mixture was extracted with ethyl acetate and separated by a separating funnel. The organic layer was washed with water and saturated brine, dried over magnesium sulfate and filtered. The solvent was removed in vacuo and the residue was purified by silica gel column chromatography to give the subject compound (415 mg, 45%).

$^1$H NMR (CDCl$_3$, 400 MHz) δ 7.33 (s, 4H), 4.74 (s, 2H), 4.68 (d, 2H, J=5.8 Hz), 1.60 (t, 1H, J=5.8 Hz), 0.95 (s, 9H), 0.10 (s, 6H).

Reference Example 55-2

{[4-(Bromomethyl)benzyl]oxy}(tert-butyl)dimethyl-silane

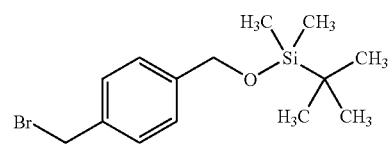

To the compound of Reference example 55-1 (415 mg, 1.64 mmol) in dichloromethane (6 ml) were added at 0° C. triphenylphosphine (732 mg, 2.79 mmol) and carbontetrachloride (1.09 g, 3.29 mmol), and the mixture was stirred for 2 hours at room temperature. Thereto was added an aqueous saturated sodium hydrogen carbonate solution. The mixture was extracted with ethyl acetate and separated by a separating funnel. The organic layer was washed with saturated brine, dried over anhydrous sodium sulfate and filtered. The solvent was removed in vacuo and the residue was purified by silica gel column chromatography to give the subject compound (414 mg, 80%).

$^1$H NMR (CDCl$_3$, 400 MHz) δ 7.36 (d, 2H, J=8.2 Hz), 7.30 (d, 2H, J=8.2 Hz), 4.73 (s, 2H), 4.50 (s, 2H), 0.94 (s, 9H), 0.10 (s, 6H).

Reference Example 55-3

4-((2R)-2-{[4-({[tert-Butyl(dimethyl)silyl] oxy}methyl)benzyl]oxy}propanoyl)morpholine

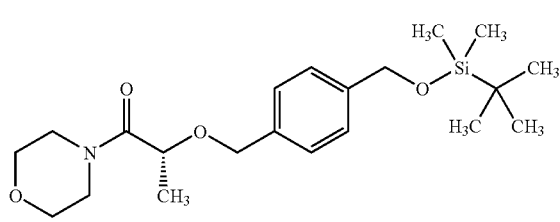

To the compound of Reference example 42-1 (248 mg, 1.56 mmol) in THF (6 ml) were added at 0° C. sodium hydride (55% in liquid paraffin) (79 mg, 1.82 mmol), the compound of Reference example 55-2 (410 mg, 1.30 mmol) and tetra n-butylammonium iodide (48 mg, 0.13 mmol), and the mixture was stirred for 2.5 hours at room temperature. Thereto was added 5% aqueous potassium hydrogen sulfate solution. The mixture was extracted with ethyl acetate and separated by a separating funnel. After the organic layer was washed with saturated brine, it was dried over anhydrous sodium sulfate, filtered and the solvent was removed in vacuo. The obtained residue was purified by silica gel column chromatography to give the subject compound (294 mg, 57%).

$^1$H NMR (CDCl$_3$, 400 MHz) δ 7.31 (d, 2H, J=8.4 Hz), 7.28 (d, 2H, J=8.4 Hz), 4.74 (s, 2H), 4.58 (d, 1H, J=11.6 Hz), 4.45 (d, 1H, J=11.6 Hz), 4.32 (q, 1H, J=6.9 Hz), 3.73-357 (m, 8H), 1.44 (d, 3H, J=6.9 Hz), 0.94 (s, 9H), 0.10 (s, 6H).

Reference Example 55-4

(4-{[(1R)-1-Methyl-2-morpholin-4-yl-2-oxoethoxy] methyl}phenyl)methanol

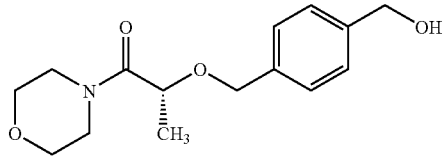

To the compound of Reference example 55-3 (294 mg, 0.75 mmol) in THF (4 ml) was added at 0° C. tetra-n-butylammonium fluoride in THF (1 mol/l, 1.1 ml) and the mixture was stirred for 1.5 hours. After warming to room temperature, thereto was added water and the mixture was ethyl acetate and separated by a separating funnel. The organic layer was washed with saturated brine and the aqueous layer was extracted twice with ethyl acetate. The extract combined with the organic layer was dried over anhydrous sodium sulfate and filtered. The solvent was removed in vacuo and the residue was purified by silica gel column chromatography to give the subject compound (171 mg, 82%).

$^1$H NMR (CDCl$_3$, 400 MHz) δ 7.36 (d, 2H, J=8.2 Hz), 7.32 (d, 2H, J=8.2 Hz), 4.70 (s, 2H), 4.59 (d, 1H, J=11.6 Hz), 4.46 (d, 1H, J=11.6 Hz), 4.33 (q, 1H, J=6.8 Hz), 3.74-3.57 (m, 8H), 1.45 (d, 3H, J=6.8 Hz).

Reference Example 55-5

4-((2R)-2-{[4-(Bromomethyl)benzyl] oxy}propanoyl)morpholine

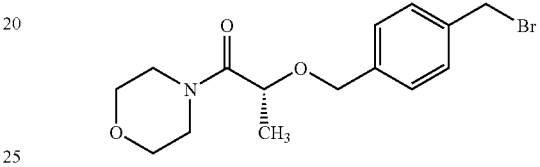

To the compound of Reference example 55-4 (171 mg, 0.61 mmol) in dichloromethane (3 ml) were added at 0° C. N-bromosuccinimide (109 mg, 0.61 mmol) and triphenylphosphine (161 mg, 0.61 mmol), and the mixture was stirred for 2 hours at room temperature. Additionally N-bromosuccinimide (54 mg, 0.31 mmol) and triphenylphosphine (80 mg, 0.31 mmol) were added at room temperature thereto. After stirring for 1.5 hours, thereto was added an aqueous saturated sodium hydrogen carbonate solution and the mixture was extracted with ethyl acetate and separated by a separating funnel. The organic layer was washed with saturated brine, dried over anhydrous sodium sulfate and filtered. The solvent was removed in vacuo and the residue was purified by silica gel column chromatography to give the subject compound (174 mg, 83%).

$^1$H NMR (CDCl$_3$, 400 MHz) δ 7.38 (d, 2H, J=8.1 Hz), 7.31 (d, 2H, J=8.1 Hz), 4.58 (d, 1H, J=11.8 Hz), 4.49 (s, 2H), 4.46 (d, 1H, J=11.8 Hz), 4.33 (q, 1H, J=6.8 Hz), 3.72-3.57 (m, 8H), 1.45 (d, 3H, J=6.8 Hz).

Reference Example 56

(3-{[(1R)-1-Methyl-2-morpholin-4-yl-2-oxoethoxy] methyl}phenyl)methanol

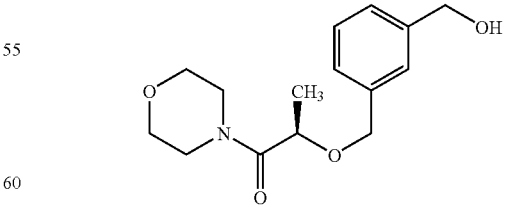

The subject compound was prepared in the same methods of Reference examples 55-1~55-4 using 1,3-benzenedimethanol.

$^1$H NMR (CDCl$_3$, 400 MHz) δ 7.35 (dd, 1H, J=7.6 Hz), 7.35 (brs, 1H), 7.31 (brd, 1H, J=7.6 Hz), 7.25 (brd, 1H, J=7.6

Hz), 4.70 (d, 2H, J=5.7 Hz), 4.59 (d, 1H, J=11.6 Hz), 4.47 (d, 1H, J=11.6 Hz), 4.33 (q, 1H, J=6.8 Hz), 3.73-3.55 (m, 8H), 1.96 (t, 1H, J=5.7 Hz), 1.45 (d, 3H, J=6.8 Hz).

Reference Example 57

{1-[3-(Bromomethyl)benzyl]-6-methoxy-2-methyl-1H-indol-3-yl}(4-methylphenyl)methanone

Reference Example 57-1

[3-({[tert-Butyl(dimethyl)silyl]oxy}methyl)phenyl]methanol

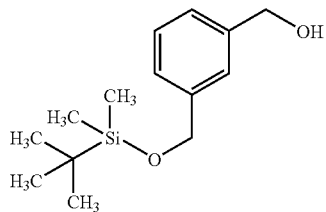

To 1,3-benzenedimethanol (5.10 g, 36.91 mmol) in dichloromethane (70 ml) was added at 0° C. triethylamine (7.47 g, 73.82 mmol), 4-dimethyl-aminopyridine (451 mg, 3.61 mmol) and t-butyldimethylchlorosilane (5.56 g, 36.91 mmol) successively, and the mixture was stirred for 20 hours at room temperature. Thereto was added a saturated ammonia solution and the mixture was extracted with ethyl acetate and separated by a separating funnel. The organic layer was washed with water and saturated brine, dried over magnesium sulfate and filtered. The solvent was removed in vacuo and the residue was purified by silica gel column chromatography to give the subject compound (4.23 g, 45%).

$^1$H NMR (CDCl$_3$, 400 MHz) δ 7.34 (dd, 1H, J=7.6, 7.6 Hz), 7.33 (brs, 1H), 7.27 (brd, 1H, J=7.6 Hz), 7.25 (brd, 1H, J=7.6 Hz), 4.75 (s, 2H), 4.70 (d, 2H, J=6.0 Hz), 1.64 (t, 1H, J=6.0 Hz), 0.95 (s, 9H), 0.11 (s, 6H).

Reference Example 57-2

{1-[3-({[tert-Butyl(dimethyl)silyl]oxy}methyl)benzyl]-6-methoxy-2-methyl-1H-indol-3-yl}(4-methylphenyl)methanone

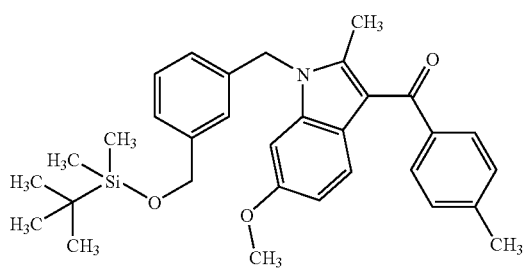

To the compound of Reference example 57-1 (303 mg, 1.20 mmol) in THF (6 ml) was added triethylamine (364 mg, 3.60 mmol) and added under ice cooling methanesulfonyl chloride (139 μl, 1.80 mmol). After stirring under ice cooling for 45 minutes, thereto was added a saturated ammonium chloride solution. The mixture was extracted with ethyl acetate and the organic layer was washed with saturated brine, dried over sodium sulfate and dried. The solvent was removed in vacuo to give the residue.

To the compound of Reference example 12 (369 mg, 1.32 mmol) in DMF (6 ml) was added potassium carbonate (498 mg, 3.60 mmol) and the mixture was stirred for 30 minutes at room temperature. To this mixture were added the above residue in DMF (2 ml) and tetra n-butylammonium iodide (44 mg, 0.12 mmol) and the mixture was stirred for 4 hours at 60° C. After being cooled to room temperature, thereto was added an aqueous saturated ammonium chloride solution and the mixture was extracted with ethyl acetate. The organic layer was washed with water and saturated brine, dried over sodium sulfate and dried. The solvent was removed in vacuo and the residue was purified by silica gel column chromatography to give the subject compound (419 mg, 68%).

$^1$H NMR (CDCl$_3$, 400 MHz) δ 7.69 (d, 2H, J=8.1 Hz), 7.37-7.19 (m, 5H), 7.03 (brs, 1H), 6.92 (brd, 1H, J=7.6 Hz), 6.74 (dd, 1H, J=8.2, 2.2 Hz), 6.73 (d, 1H, J=2.2 Hz), 5.33 (s, 2H), 4.68 (s, 2H), 3.77 (s, 3H), 2.49 (s, 3H), 2.44 (s, 3H), 0.88 (s, 9H), 0.03 (s, 6H).

Reference Example 57-3

{1-[3-(Hydroxymethyl)benzyl]-6-methoxy-2-methyl-1H-indol-3-yl}(4-methylphenyl)methanone

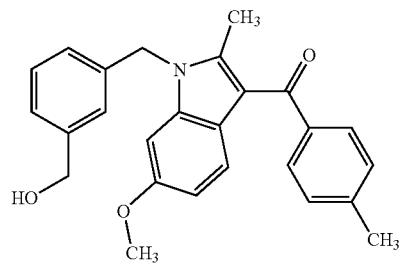

To the compound of Reference example 57-2 (419 mg, 0.82 mmol) in THF (4 ml), was added at 0° C. tetra n-butylammonium fluoride in THF (1 mol/l, 1.1 ml) and the mixture was stirred for 1.5 hours. After warming to room temperature, thereto was added water and the mixture was extracted with ethyl acetate and separated by a separating funnel. The organic layer was washed with saturated brine and the aqueous layer was extracted with ethyl acetate. The organic layer was dried over anhydrous sodium sulfate and filtered. The solvent was removed in vacuo and the residue was purified by silica gel column chromatography to give the subject compound (299 mg, 92%).

$^1$H NMR (CDCl$_3$, 400 MHz) δ 7.70 (d, 2H, J=8.1 Hz), 7.30 (dd, 1H, J=7.6, 7.6 Hz), 7.29 (d, 1H, J=8.6 Hz), 7.25 (d, 2H, J=8.1 Hz), 7.31-7.23 (m, 1H), 7.10 (brs, 1H), 6.93 (brd, 1H, J=7.6 Hz), 6.75 (dd, 1H, J=8.6, 2.3 Hz), 6.72 (d, 1H, J=2.3 Hz), 5.34 (s, 2H), 4.66 (d, 2H, J=4.9 Hz), 3.78 (s, 3H), 2.49 (s, 3H), 2.44 (s, 3H), 1.74 (t, 1H, J=4.9 Hz).

Reference Example 57-4

{1-[3-(Bromomethyl)benzyl]-6-methoxy-2-methyl-1H-indol-3-yl}(4-methylphenyl)methanone

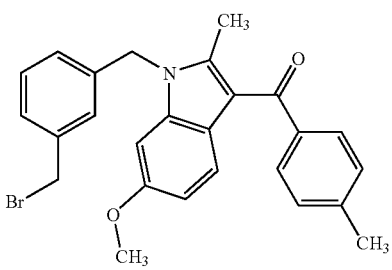

To the compound of Reference example 57-3 (149 mg, 0.37 mmol) in THF (2 ml) was added triethylamine (57 mg, 0.56 mmol), and thereto was added under ice cooling methanesulfonyl chloride (38 μl, 0.48 mmol). After stirring for 30 minutes, thereto was added a 5% aqueous potassium hydrogen sulfate solution and the mixture was extracted with ethyl acetate. The organic layer was washed with saturated brine, dried over sodium sulfate and dried. The solvent was removed in vacuo, and the residue was subjected to azeotropic distillation twice with toluene. To the residue in THF (2 ml) was added lithium bromide (65 mg, 0.74 mmol) and the mixture was stirred for 3 hours at room temperature. Thereto was added water and the mixture was extracted with ethyl acetate and the organic layer was washed with saturated brine, dried over magnesium sulfate and filtered. The solvent was removed in vacuo. The residue was purified by silica gel column chromatography to give the subject compound (151 mg, 88%).

$^1$H NMR (CDCl$_3$, 400 MHz) δ 7.70 (d, 2H, J=8.1 Hz), 7.30 (dd, 1H, J=7.6, 7.6 Hz), 7.29 (d, 1H, J=8.8 Hz), 7.25 (d, 2H, J=8.1 Hz), 7.33-7.23 (m, 1H), 7.13 (brs, 1H), 6.92 (brd, 1H, J=7.6 Hz), 6.76 (dd, 1H, J=8.8, 2.3 Hz), 6.71 (d, 1H, J=2.3 Hz), 5.32 (s, 2H), 4.44 (s, 2H), 3.78 (s, 3H), 2.48 (s, 3H), 2.44 (s, 3H).

Reference Example 58

(1-Allyl-1H-pyrrol-3-yl)(4-methylphenyl)

Reference Example 58-1

(1-Benzenesulfonyl-1H-pyrrol-3-yl)(4-methylphenyl)ketone

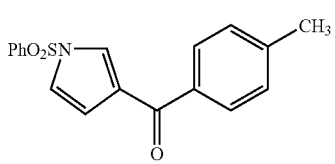

To a suspension of alminium chloride (4.62 g, 34.7 mmol) in ethylene chloride (50 mL) was added under a nitrogen atmosphere p-toluoyl chloride (4.91 g, 31.8 mmol) in ethylene chloride (5 mL) at room temperature in a period of 10 minutes. After stirring for 30 minutes to the mixture was added 1-benzenesulfonyl-1H-pyrrole (6.00 g, 28.9 mmol) in ethylene chloride (10 mL) in a period of 10 minutes. After stirring for 2 hours at room temperature, the reaction mixture was poured into ice water and the aqueous layer was extracted twice with dichloromethane. The organic layer combined was dried over magnesium sulfate and filtered. The filtrate was concentrated and the residue was purified by silica gel column chromatography to give the subject compound (9.9 g, 100%).

$^1$H NMR (CDCl$_3$, 300 MHz) δ 7.89 (brd, 2H, J=7.9 Hz), 7.73 (d, 2H, J=8.0 Hz), 7.65 (brt, 1H, J=7.9 Hz), 7.65 (brs, 1H), 7.34 (brt, 2H, J=7.9 Hz), 7.29 (d, 2H, J=8.0 Hz), 7.22 (dd, 1H, J=2.2, 2.8 Hz), 6.80 (dd, 1H, J=1.5, 2.8 Hz), 2.44 (s, 3H).

Reference Example 58-2

(1H-Pyrrol-3-yl)(4-methylphenyl)ketone

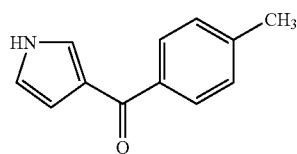

A mixture of the compound of Reference example 58-1 (6.50 g, 20.0 mmol), 5N aqueous sodium hydroxide solution (70 mL) and THF (70 mL) were stirred for 6 hours at 45° C. After separating the organic layer, it was concentrated until the volume of the solvent became 5 mL, followed by standing it for 2 days at room temperature. The resulted crystals were collected and washed with cooled THF to give the subject compound (3.1 g, 84%).

$^1$H NMR (CDCl$_3$, 300 MHz) δ 7.76 (d, 2H, J=8.1 Hz), 7.35 (brquint., 1H, J=1.5 Hz), 7.26 (d, 2H, J=8.1 Hz), 6.84 (brq, 1H, J=1.5 Hz), 6.76 (brs, 1H), 2.43 (s, 3H).

Reference Example 59

[1-(4-Iodobenzyl)-1H-pyrrol-2-yl](4-methylphenyl)methanone

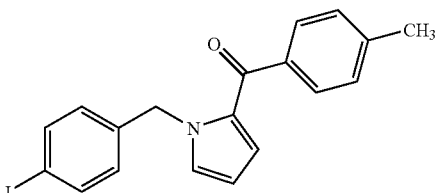

To the compound of Reference example 1-2 (400 mg, 2.16 mmol) in THF (10 ml) was added potassium t-butoxide (291 mg, 2.59 mmol) and the mixture was stirred for 1 hour at 40° C. Thereto were added 4-iodobenzyl bromide (769 mg, 2.59 mmol), tetra n-butylammonium iodide (80 mg, 0.22 mmol) and the mixture was stirred for 6 hours at 40° C. Thereto was added 5% aqueous potassium hydrogen sulfate solution and the mixture was extracted with ethyl acetate. The organic layer was washed with saturated brine, dried over magnesium sulfate and filtered. The solvent was removed in vacuo and the residue was purified by silica gel column chromatography to give the subject compound (quant.).

$^1$H NMR (CDCl$_3$, 400 MHz) δ 7.68 (d, 2H, J=8.1 Hz), 7.62 (d, 2H, J=8.4 Hz), 7.23 (d, 2H, J=8.1 Hz), 6.99 (dd, 1H, J=2.6, 1.7 Hz), 6.91 (d, 2H, J=8.4 Hz), 6.78 (dd, 1H, J=4.0, 1.7 Hz), 6.22 (dd, 1H, J=4.0, 2.6 Hz), 5.58 (s, 2H), 2.41 (s, 3H).

Reference Example 60

[1-(4-Iodobenzyl)-1H-pyrrol-3-yl](4-methylphenyl)methanone

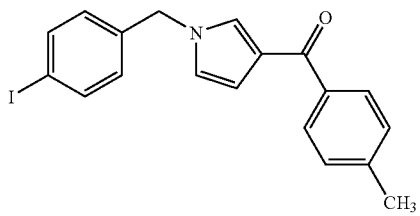

The subject compound was prepared in the same method as Reference example 59 by using the compound of Reference example 58-2.

$^1$H NMR (CDCl$_3$, 400 MHz) δ 7.74 (d, 2H, J=8.1 Hz), 7.68 (d, 2H, J=8.4 Hz), 7.25 (d, 2H, J=8.1 Hz), 7.27-7.23 (m, 1H), 6.89 (d, 2H, J=8.4 Hz), 6.72 (dd, 1H, J=2.9, 1.7 Hz), 6.67 (dd, 1H, J=2.9, 2.3 Hz), 5.03 (s, 2H), 2.42 (s, 3H).

Reference Example 61

[1-(4-Iodobenzyl)-1H-indol-3-yl](4-methylphenyl)methanone

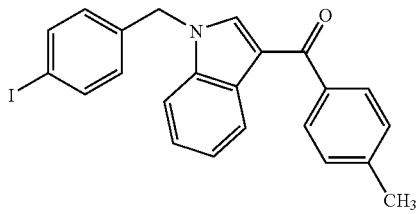

The subject compound was prepared in the same method as Reference example 59 by using the compound of Reference example 22.

$^1$H NMR (CDCl$_3$, 400 MHz) δ 8.42 (dd, 1H, J=8.2, 1.6 Hz), 7.74 (d, 2H, J=8.1 Hz), 7.64 (d, 2H, J=8.4 Hz), 7.61 (s, 1H), 7.33 (ddd, 1H, J=8.2, 6.7, 1.6 Hz), 7.32-7.23 (m, 4H), 6.86 (d, 2H, J=8.4 Hz), 5.31 (s, 2H), 2.44 (s, 3H).

Reference Example 62

[1-(4-Iodobenzyl)-2,5-dimethyl-1H-indol-3-yl](4-methylphenyl)methanone

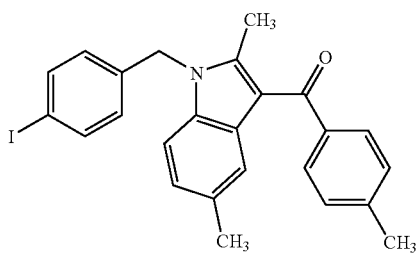

The subject compound was prepared in the same method as Reference example 59 by using the compound of Reference example 15.

$^1$H NMR (CDCl$_3$, 400 MHz) δ 7.70 (d, 2H, J=8.1 Hz), 7.62 (d, 2H, J=8.4 Hz), 7.29 (brs, 1H), 7.26 (d, 2H, J=8.1 Hz), 7.10 (d, 1H, J=8.3 Hz), 6.99 (dd, 1H, J=8.3, 1.4 Hz), 6.76 (d, 2H, J=8.4 Hz), 5.30 (s, 2H), 2.45 (s, 6H), 2.34 (s, 3H).

Reference Example 63

4-[(2R)-2-(Allyloxy)propanoyl]morpholine

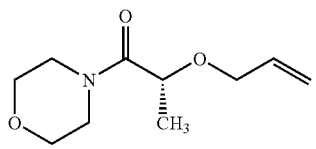

To the compound of Reference example 42-1 (3.27 g, 20.5 mmol) in THF (50 ml) was added sodium hydride (55% in liquid paraffin) (2.08 g, 52.0 mmol) and the mixture was stirred for 30 minutes at room temperature. Thereto was added allyl bromide (10.0 g, 40.0 mmol) and the mixture was stirred for 2.5 hours at 60° C. After being cooled to room temperature, thereto was added 5% aqueous potassium hydrogen sulfate solution and the mixture was extracted with ethyl acetate and separated by a separating funnel. The organic layer was washed with saturated brine, dried over anhydrous sodium sulfate and filtered. The solvent was removed in vacuo and the residue was purified by silica gel column chromatography to give the subject compound (3.04 g, 74%).

$^1$H NMR (CDCl$_3$, 400 MHz) δ 5.91 (dddd, 1H, J=17.2, 10.4, 5.5, 5.5 Hz), 5.29 (ddd, 1H, J=17.2, 1.4, 1.4 Hz), 5.21 (ddd, 1H, J=10.4, 1.4, 1.4 Hz), 4.29 (q, 1H, 6.8 Hz), 4.05 (dddd, 1H, J=12.5, 5.5, 1.4, 1.4 Hz), 3.95 (dddd, 1H, J=12.5, 5.5, 1.4, 1.4 Hz), 3.81-3.58 (m, 8H), 1.42 (d, 3H, J=6.8 Hz).

Reference Example 64

Ethyl 2-(allyloxy)-2-methylpropionate

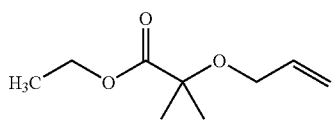

The subject compound was prepared in the same method as Reference example 63 by using ethyl 2-hydroxyisobutyrate.

$^1$H NMR (CDCl$_3$, 400 MHz) δ 5.95 (ddt, 1H, J=17.3, 10.3, 5.6 Hz), 5.30 (ddd, 1H, J=17.3, 2.7, 1.4 Hz), 5.16 (ddd, 1H, J=10.3, 2.7, 1.4 Hz), 4.20 (q, 2H, 7.1 Hz), 3.95 (ddd, 2H, J=5.6, 1.4, 1.4 Hz), 1.45 (s, 6H), 1.29 (t, 3H, J=7.1 Hz).

Reference Example 65

(4-{(1E)-3-[(1R)-1-Methyl-2-morpholin-4-yl-2-oxo-ethoxy]prop-1-en-1-yl}phenyl)methanol

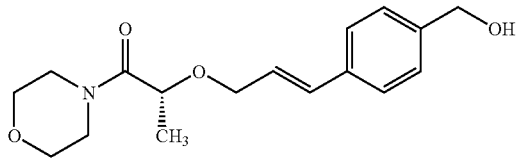

The compound of Reference example 63 (323 mg, 1.62 mmol), 4-iodo-benzylalcohol (418 mg, 1.78 mmol), palladium acetate (36 mg, 0.16 mmol), tri n-butylphosphine (66 mg, 0.32 mmol) and potassium carbonate (291 mg, 2.11 mmol) were dissolved in DMF (8 ml) and the solution was stirred for 9 hours at 80° C. Thereto was added 10% aqueous thiosodium sulfate solution and the mixture was extracted with ethyl acetate. The organic layer was washed with 10% aqueous thiosodium sulfate solution and saturated brine, dried over anhydrous sodium sulfate and filtered. The solvent was removed in vacuo and the residue was purified by silica gel column chromatography to give the subject compound (149 mg, 33%).

$^1$H NMR (CDCl$_3$, 400 MHz) δ 7.38 (d, 2H, J=8.2 Hz), 7.33 (d, 2H, J=8.2 Hz), 6.60 (brd, 1H, J=15.9 Hz), 6.28 (ddd, 1H, J=15.9, 6.0, 6.0 Hz), 4.69 (brd, 2H, J=5.4 Hz), 4.34 (q, 1H, J=6.8 Hz), 4.21 (ddd, 1H, J=12.4, 6.0, 1.4 Hz), 4.12 (ddd, 1H, J=12.4, 6.0, 1.4 Hz), 3.80-3.51 (m, 8H), 1.76 (brt, 1H, J=5.4 Hz), 1.45 (d, 3H, J=6.8 Hz).

Reference Example 66

Ethyl 2-({(2E)-3-[4-(hydroxymethyl)phenyl]prop-2-en-1-yl}oxy)-2-methylpropionate

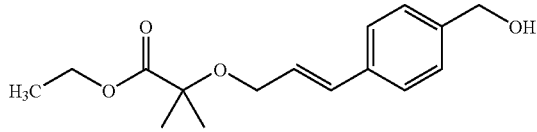

The subject compound was prepared in the same method as Reference example 65 by using the compound of Reference example 64.

$^1$H NMR (CDCl$_3$, 400 MHz) δ 7.38 (d, 2H, J=8.2 Hz), 7.30 (d, 2H, J=8.2 Hz), 6.62 (brd, 1H, J=15.9 Hz), 6.32 (dt, 1H, J=15.9, 6.0 Hz), 4.68 (d, 2H, J=6.0 Hz), 4.22 (q, 2H, J=7.1 Hz), 4.12 (dd, 2H, J=6.0, 1.4 Hz), 1.65 (t, 1H, J=6.0 Hz), 1.49 (s, 6H), 1.30 (t, 3H, J=7.1 Hz).

Reference Example 67

1H-Imidazol-2-yl(4-methylphenoxy)methanone

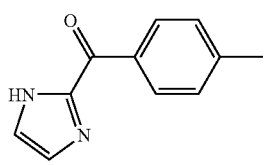

To imidazole (6.80 g, 100 mmol) in pyridine (30 ml) was added triethylamine (20.2 g, 200 mmol) and the mixture was stirred under ice cooling. Therein was dropped p-toluoyl chloride (30.9 g, 200 mmol) in a period of 10 minutes. After addition of pyridine (70 ml) the mixture was stirred for 3 hours at room temperature. Thereto was added 4N aqueous sodium hydroxide solution (100 ml) and the mixture was stirred 3 hours at 80° C. The reaction mixture was allowed to stand at room temperature. After addition of water (200 ml), the mixture was stirred to give crystals. The crystals were taken by filtration and washed with water-methanol (1:1) to give the subject compound (9.83 g, 51%).

$^1$H NMR (CDCl$_3$, 400 MHz) δ 8.52 (d, 2H, J=8.0 Hz), 7.39 (m, 1H), 7.33 (d, 2H, J=8.0 Hz), 7.29 (m, 1H), 2.44 (s, 3H).

Reference Example 68

1H-Benzimidazol-2-yl(4-methylphenoxy)methanone

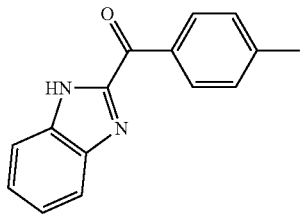

The subject compound was prepared in the same method as Reference example 67 by using benzimidazole.

$^1$H NMR (CDCl$_3$, 400 MHz) δ 10.50 (brs, 1H), 8.62 (d, 2H, J=8.0 Hz), 7.98 (m, 1H), 7.59 (m, 1H), 7.41 (m, 1H), 7.37 (d, 2H, J=8.0 Hz), 2.47 (s, 3H).

Reference Example 69

{1-[4-(Bromomethyl)phenyl]-2-methyl-1H-indol-3-yl}(4-methylphenyl)methanone

Reference Example 69-1

Ethyl 4-[2-methyl-3-(4-methylbenzoyl)-1H-indol-1-yl]benzoate

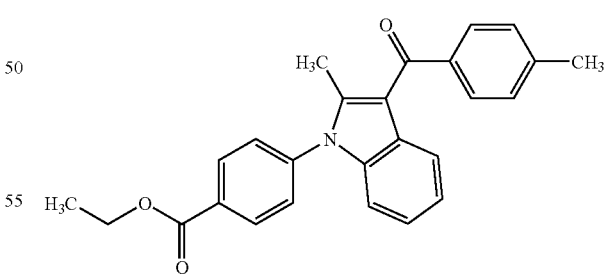

The compound of Reference example 23 (99 mg, 0.40 mmol), ethyl 4-iodobenzoate (109 mg, 0.48 mmol), calcium phosphate (177 mg, 0.83 mmol), N,N'-dimethylethylenediamine (8 mg, 0.08 mmol) and copper iodide (4 mg, 0.02 mmol) were dissolved in toluene (2 ml), and the mixture was stirred for 21 hours at 110° C. After being cooled to room temperature, to the reaction mixture was added ethyl acetate, followed by filtration over silica gel. The solvent was removed in vacuo and the residue was purified by silica gel column chromatography to give the subject compound (76 mg, 48%).

¹H NMR (CDCl₃, 400 MHz) δ 8.28 (d, 2H, J=8.5 Hz), 7.77 (d, 2H, J=8.1 Hz), 7.48 (d, 2H, J=8.5 Hz), 7.42 (dd, 1H, J=7.1, 1.5 Hz), 7.28 (d, 2H, J=8.1 Hz), 7.15 (ddd, 1H, J=7.1, 7.1, 1.5 Hz), 7.12 (ddd, 1H, J=7.1, 7.1, 1.5 Hz), 7.06 (dd, 1H, J=7.1, 1.5 Hz), 4.46 (q, 2H, J=7.1 Hz), 2.46 (s, 3H), 2.42 (s, 3H), 1.45 (t, 3H, J=7.1 Hz).

Reference Example 69-2

{1-[4-(Hydroxymethyl)phenyl]-2-methyl-1H-indol-3-yl}(4-methylphenyl)methanone

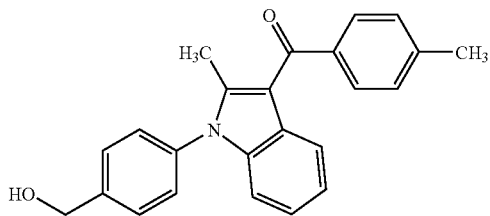

The compound of Reference example 69-1 (1.27 g, 3.20 mmol) in 1N aqueous sodium hydroxide solution (13 ml), THF (13 ml) and methanol (13 ml) were stirred for 3 hours at room temperature. The mixture was acidified with 5% aqueous potassium hydrogen sulfate solution and the mixture was extracted with chloroform. The organic layer was washed with saturated brine and dried over anhydrous sodium sulfate. The solvent was removed in vacuo. To the residue in THF (15 ml) was added under a nitrogen atmosphere triethylamine (485 mg, 4.79 mmol). After ice cooling, thereto was added ethyl chloroformate (416 mg, 3.83 mmol). After stirring for 30 minutes at ice cooling, triethylamine hydrochloride resulted as crystals was filtered off and the filtrate was washed with THF. The filtrate and washings were combined and therein was dropped under ice cooling sodium borohydride (181 mg, 4.79 mmol) in water (2 ml), followed by stirring under ice cooling for 2 hours. The reaction mixture was acidified with 5% aqueous potassium hydrogen sulfate solution and the mixture was extracted with ethyl acetate. The organic layer was washed with saturated brine and dried over anhydrous sodium sulfate. The solvent was removed in vacuo and the residue was purified by silica gel chromatography to give the subject compound (1.12 g, 98%).

¹H NMR (CDCl₃, 400 MHz) δ 7.76 (d, 2H, J=8.1 Hz), 7.60 (d, 2H, J=8.5 Hz), 7.42 (dd, 1H, J=7.1, 1.6 Hz), 7.37 (d, 2H, J=8.5 Hz), 7.28 (d, 2H, J=8.1 Hz), 7.13 (ddd, 1H, J=7.1, 7.1, 1.6 Hz), 7.10 (ddd, 1H, J=7.1, 7.1, 1.6 Hz), 7.04 (dd, 1H, J=7.1, 1.6 Hz), 4.85 (d, 2H, J=3.8 Hz), 2.45 (s, 3H), 2.40 (s, 3H), 1.99 (t, 1H, J=3.8 Hz).

Reference Example 69-3

{1-[4-(Bromomethyl)phenyl]-2-methyl-1H-indol-3-yl}(4-methylphenyl)methanone

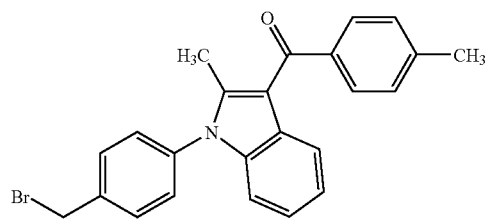

To the compound of Reference example 69-2 (640 mg, 1.80 mmol) in THF (9 ml) was added triethylamine (273 mg, 2.70 mmol) and thereto was added under ice cooling methanesulfonyl chloride (181 μl, 2.34 mmol). After stirring for 1 hour, thereto was added a 5% aqueous potassium hydrogen sulfate solution and the mixture was extracted with ethyl acetate. The organic layer was washed with saturated brine, dried over anhydrous magnesium sulfate and filtered. The solvent was removed in vacuo and the residue was subjected to azeotropic distillation twice with toluene. To the residue in THF (9 ml) was added lithium bromide (313 mg, 3.60 mmol) and the mixture was stirred for 3 hours at room temperature. Thereto was added water and the mixture was extracted with ethyl acetate. The organic layer was washed with saturated brine, dried over anhydrous magnesium sulfate and filtered. The solvent was removed in vacuo and the residue was purified by silica gel column chromatography to give the subject compound (quant.).

¹H NMR (CDCl₃, 400 MHz) δ 7.76 (d, 2H, J=8.1 Hz), 7.62 (d, 2H, J=8.3 Hz), 7.41 (dd, 1H, J=7.0, 1.6 Hz), 7.37 (d, 2H, J=8.3 Hz), 7.28 (d, 2H, J=8.1 Hz), 7.14 (ddd, 1H, J=7.0, 7.0, 1.6 Hz), 7.10 (ddd, 1H, J=7.0, 7.0, 1.6 Hz), 7.06 (dd, 1H, J=7.0, 1.6 Hz), 4.60 (s, 2H), 2.46 (s, 3H), 2.41 (s, 3H).

Reference Example 70

1H-Pyrrolo[2,3-c]pyridine hydrochloride

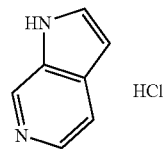

A solution of 2-chloro-3-nitropyridine (4.76 g, 30.0 mmol) in THF (50 ml) was stirred at −70° C. and therein was dropped in a period of 40 minutes vinyl magnesium bromide (1.0 M in THF, 80.0 ml, 80.0 mmol). The mixture was warmed to room temperature and stirred over night. The reaction mixture was quenched with aqueous ammonium solution, made alkaline with aqueous sodium bicarbonate solution and extracted with chloroform. The organic layer was washed with water, dried over magnesium sulfate and filtered. The solvent was removed in vacuo and the residue was purified by silica gel column chromatography. Thus obtained compound was dissolved in methanol (20 ml), and thereto was added 10% palladium hydroxide-carbon (50% wet)(40 mg). The mixture was stirred at room temperature under a hydrogen atmosphere at ordinary pressure for 5 hours. The reaction mixture was filtered through Celite and the filtrate was concentrated in vacuo to give the subject compound (595 mg, 13%).

¹H NMR (CDCl₃, 400 MHz) δ 15.27 (s, 1H), 13.11 (s, 1H), 9.17 (s, 1H), 8.31 (d, 1H, J=5.2 Hz), 8.28 (d, 1H, J=6.4 Hz), 8.13 (d, 1H, J=6.4 Hz), 6.95 (d, 1H, J=5.2 Hz).

Reference Example 71

(4-Methylphenyl)(1H-pyrrolo[2,3-c]pyridin-3-yl)methanone

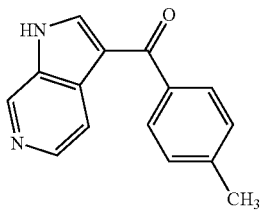

The subject compound was prepared in the same method as Reference example 11 by using the compound of Reference example 70.

$^1$H NMR (CDCl$_3$, 400 MHz) δ 9.70 (s, 1H), 8.76 (d, 1H, J=6.4 Hz), 8.25 (d, 1H, J=6.4 Hz), 7.79 (d, 2H, J=7.8 Hz), 7.37 (d, 2H, J=7.8 Hz), 7.04 (m, 2H), 2.49 (s, 3H).

Example 1

2-Methyl-2-[(4-{(1Z)-3-[2-(4-methylbenzoyl)-1H-pyrrol-1-yl]prop-1-en-1-yl}benzyl)oxy]propionic acid

Example 1-1

Methyl 2-methyl-2-[(4-{(1Z)-3-[2-(4-methylbenzoyl)-1H-pyrrol-1-yl]prop-1-en-1-yl}benzyl)oxy]propionate

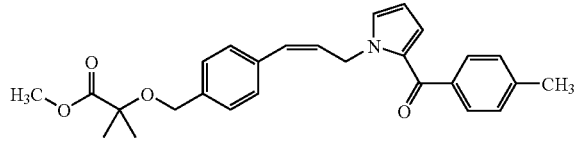

To the compound of Reference example 1-2 (263 mg, 1.42 mmol) in THF (8 ml) was added potassium t-butoxide (188 mg, 1.67 mmol) and the mixture was stirred for 30 minutes at room temperature. Thereto was added at room temperature the compound of Reference example 3-4 (215 mg, 1.41 mmol) and the mixture was stirred for 15 hours. Thereto was added 5% aqueous potassium hydrogen sulfate solution and the mixture was extracted with ethyl acetate. The organic layer was washed with saturated brine, dried over magnesium sulfate and filtered. The solvent was removed in vacuo and the residue was purified by silica gel column chromatography to give the subject compound (505 mg, 71%).

$^1$H NMR (CDCl$_3$, 400 MHz) δ 7.74 (d, 2H, J=8.1 Hz), 7.40 (d, 2H, J=8.1 Hz), 7.27 (d, 2H, J=8.1 Hz), 7.26 (d, 2H, J=8.1 Hz), 6.92 (dd, 1H, J=2.5, 1.7 Hz), 6.75 (dd, 1H, J=4.0, 1.7 Hz), 6.64 (brd, 1H, J=11.6 Hz), 6.16 (dd, 1H, J=4.0, 2.5 Hz), 5.89 (dt, 1H, J=11.6, 6.4 Hz), 5.32 (dd, 2H, J=6.4, 1.8 Hz), 4.48 (s, 2H), 3.77 (s, 3H), 2.43 (s, 3H), 1.53 (s, 6H).

Example 1-2

2-Methyl-2-[(4-{(1Z)-3-[2-(4-methylbenzoyl)-1H-pyrrol-1-yl]prop-1-en-1-yl}benzyl)oxy]propionic acid

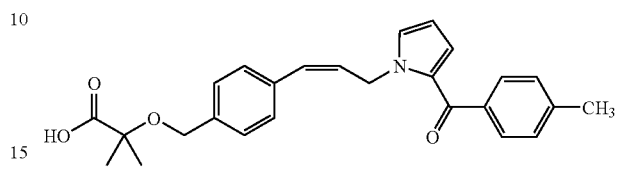

To the compound of Example 1-1 (410 mg, 0.95 mmol) in THF (4 ml) were added methanol (4 ml) and 1N aqueous lithium hydroxide solution (4 ml), followed by stirring for 8 hours at room temperature. The reaction mixture was diluted with water and washed with diethyl ether. To the aqueous layer was added 5% aqueous potassium hydrogen sulfate solution and the solution was adjusted around pH3 and extracted with ethyl acetate. The organic layer was washed with water, saturated brine, dried over magnesium sulfate and filtered. The solvent was removed in vacuo to give the subject compound (262 mg, 66%).

$^1$H NMR (CDCl$_3$, 400 MHz) δ 7.73 (d, 2H, J=8.1 Hz), 7.38 (d, 2H, J=8.1 Hz), 7.28 (d, 2H, J=8.1 Hz), 7.25 (d, 2H, J=8.1 Hz), 6.94 (dd, 1H, J=2.5, 1.7 Hz), 6.75 (dd, 1H, J=4.0, 1.7 Hz), 6.64 (brd, 1H, J=11.6 Hz), 6.17 (dd, 1H, J=4.0, 2.5 Hz), 5.90 (dt, 1H, J=11.6, 6.4 Hz), 5.33 (dd, 2H, J=6.4, 1.8 Hz), 4.55 (s, 2H), 2.43 (s, 3H), 1.58 (s, 6H).

Example 2

Sodium 2-methyl-2-[(4-{(1Z)-3-[2-(4-methylbenzoyl)-1H-pyrrol-1-yl]prop-1-en-1-yl}benzyl)oxy]propionate

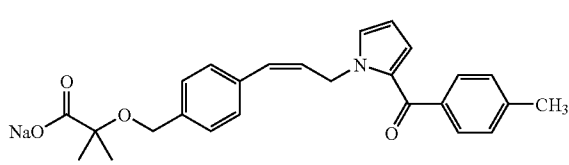

To the compound of Example 1-2 (384 mg, 0.92 mmol) was added sodium hydroxide in methanol (0.1 mol/l, 9.2 ml, 0.92 mmol) and the solvent was removed in vacuo. The residue was subjected to azeotropic distillation with diethyl ether to give the subject compound (quant.).

$^1$H NMR (DMSO-d$_6$, 400 MHz) δ 7.65 (d, 2H, J=8.1 Hz), 7.41 (d, 2H, J=8.1 Hz), 7.32 (d, 2H, J=8.1 Hz), 7.32-7.27 (m, 1H), 7.27 (d, 2H, J=8.1 Hz), 6.69 (dd, 1H, J=4.0, 1.6 Hz), 6.53 (brd, 1H, J=11.8 Hz), 6.20 (dd, 1H, J=4.0, 2.6 Hz), 5.68 (dt, 1H, J=11.8, 5.9 Hz), 5.33 (dd, 2H, J=5.9, 1.8 Hz), 4.48 (s, 2H), 2.39 (s, 3H), 1.28 (s, 6H).

Example 3

Ethyl 2-[(4-{(1Z)-3-[2-(4-methylbenzoyl)-1H-pyr-rol-yl]prop-1-en-1-yl}benzyl)oxy]propionate

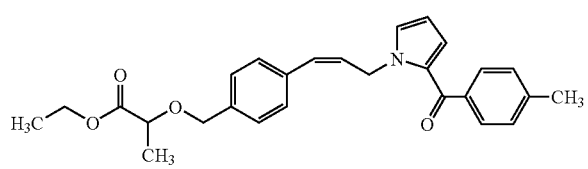

The subject compound was prepared in the same method as Example 1-1 by using the compounds of Reference example 1-2 and Reference example 4.

$^1$H NMR (CDCl$_3$, 400 MHz) δ 7.74 (d, 2H, J=8.1 Hz), 7.38 (d, 2H, J=8.1 Hz), 7.27 (d, 2H, J=8.1 Hz), 7.26 (d, 2H, J=8.1 Hz), 6.93 (dd, 1H, J=2.4, 1.7 Hz), 6.75 (dd, 1H, J=4.0, 1.7 Hz), 6.64 (brd, 1H, J=11.6 Hz), 6.16 (dd, 1H, J=4.0, 2.4 Hz), 5.90 (dt, 1H, J=11.6, 6.4 Hz), 5.33 (dd, 2H, J=6.4, 1.8 Hz), 4.70 (d, 1H, J=11.7 Hz), 4.46 (d, 1H, J=11.7 Hz), 4.25 (dq, 1H, J=10.8, 7.1 Hz), 4.22 (dq, 1H, J=10.8, 7.1 Hz), 4.07 (q, 1H, J=6.9 Hz), 2.43 (s, 3H), 1.45 (d, 3H, J=6.9 Hz), 1.31 (t, 3H, J=7.1 Hz).

Example 4

Methyl 4-{[1-((2Z)-3-{4-[(2-ethoxy-1-methyl-2-oxoethoxy)methyl]phenyl}prop-2-en-1-yl)-1H-pyr-rol-2-yl]carbonyl}benzoate

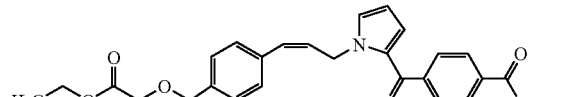

The subject compound was prepared in the same method as Example 1-1 by using the compounds of Reference example 2 and Reference example 4.

$^1$H NMR (CDCl$_3$, 400 MHz) δ 8.12 (d, 2H, J=8.5 Hz), 7.84 (d, 2H, J=8.5 Hz), 7.39 (d, 2H, J=8.1 Hz), 7.28 (d, 2H, J=8.1 Hz), 6.98 (dd, 1H, J=2.3, 1.7 Hz), 6.72 (dd, 1H, J=4.1, 1.7 Hz), 6.67 (brd, 1H, J=11.6 Hz), 6.18 (dd, 1H, J=4.1, 2.3 Hz), 5.89 (dt, 1H, J=11.6, 6.4 Hz), 5.35 (dd, 2H, J=6.4, 1.8 Hz), 4.71 (d, 1H, J=11.7 Hz), 4.47 (d, 1H, J=11.7 Hz), 4.25 (dq, 1H, J=10.8, 7.1 Hz), 4.22 (dq, 1H, J=10.8, 7.1 Hz), 4.08 (q, 1H, J=6.9 Hz), 3.96 (s, 3H), 1.46 (d, 3H, J=6.9 Hz), 1.31 (t, 3H, J=7.1 Hz).

Example 5

(2R)-2-[(4-{(1E)-3-[5-Methoxy-2-methyl-3-(4-methylbenzoyl)-1H-indol-1-yl]prop-1-en-1-yl}benzyl)oxy]propionic acid

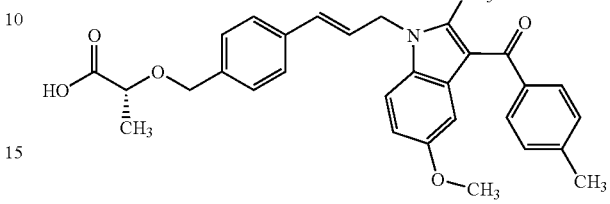

The compound of Reference example 27 (186 mg, 0.58 mmol), the compound of Reference example 41-2 (205 mg, 0.58 mmol), palladium acetate (7 mg, 0.029 mmol), N,N-dicyclohexylmethylamine (227 mg, 1.16 mmol) and triethylbenzylammonium chloride (132 mg, 0.58 mmol) were dissolved in DMF (3 ml) and the solution was stirred for 6 hours at 70° C. After adding 5% aqueous potassium hydrogen sulfate solution, the solution was extracted with ethyl acetate. The organic layer was washed with water, saturated brine, dried over anhydrous sodium sulfate and filtered. The solvent was removed in vacuo and the residue was purified by silica gel column chromatography to give the subject compound (quant.).

$^1$H NMR (CDCl$_3$, 400 MHz) δ 7.69 (d, 2H, J=8.1 Hz), 7.30-7.22 (m, 6H), 7.23 (d, 1H, J=8.9 Hz), 7.00 (d, 1H, J=2.4 Hz), 6.84 (dd, 1H, J=8.9, 2.4 Hz), 6.34-6.22 (m, 2H), 4.89 (brs, 2H), 4.63 (d, 1H, J=11.8 Hz), 4.51 (d, 1H, J=11.8 Hz), 4.06 (q, 1H, J=6.9 Hz), 3.70 (s, 3H), 2.52 (s, 3H), 2.43 (s, 3H), 1.46 (d, 3H, J=6.9 Hz).

Example 6

(2R)-2-[(4-{(1E)-3-[5-Chloro-2-methyl-3-(4-methylbenzoyl)-1H-indol-1-yl]prop-1-en-1-yl}benzyl)oxy]propionic acid

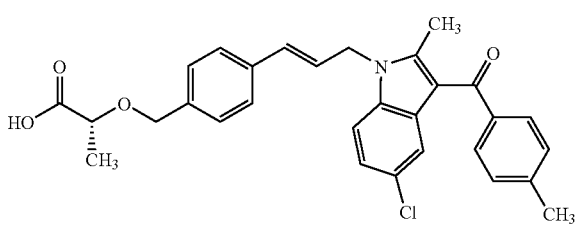

The subject compound was prepared in the same method as Example 5 by using the compounds of Reference example 29 and Reference example 41-2.

$^1$H NMR (CDCl$_3$, 400 MHz) δ 7.68 (d, 2H, J=8.1 Hz), 7.42 (d, 1H, J=2.0 Hz), 7.29 (s, 4H), 7.27 (d, 2H, J=8.1 Hz), 7.26 (d, 1H, J=8.6 Hz), 7.16 (dd, 1H, J=8.6, 2.0 Hz), 6.33-6.22 (m, 2H), 4.92 (brd, 2H, J=2.2 Hz), 4.66 (d, 1H, J=11.8 Hz), 4.49 (d, 1H, J=11.8 Hz), 4.07 (q, 1H, J=6.9 Hz), 2.56 (s, 3H), 2.45 (s, 3H), 1.47 (d, 3H, J=6.9 Hz).

Example 7

(2R)-2-[(4-{(1E)-3-[2-Methyl-3-(4-methyl-benzoyl)-1H-indol-1-yl]prop-1-en-1-yl}benzyl)oxy]propionate acid

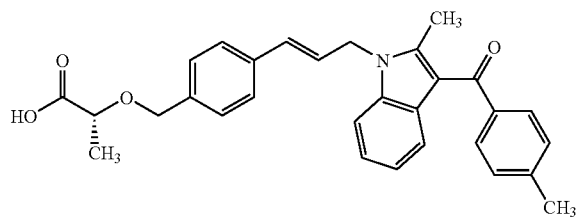

The subject compound was prepared in the same method as Example 5 by using the compounds of Reference example 30 and Reference example 41-2.

¹H NMR (CDCl₃, 400 MHz) δ 7.71 (d, 2H, J=8.1 Hz), 7.38 (brd, 1H, J=8.0 Hz), 7.35 (brd, 1H, J=8.2 Hz), 7.34-7.24 (m, 4H), 7.26 (d, 2H, J=8.1 Hz), 7.20 (ddd, 1H, J=8.2, 7.1, 1.1 Hz), 7.09 (ddd, 1H, J=8.0, 7.1, 1.0 Hz), 6.38-6.26 (m, 2H), 4.95 (d, 2H, J=3.3 Hz), 4.66 (d, 1H, J=11.8 Hz), 4.50 (d, 1H, J=11.8 Hz), 4.07 (q, 1H, J=6.9 Hz), 2.61 (s, 3H), 2.44 (s, 3H), 1.47 (d, 3H, J=6.9 Hz).

Example 8

(2R)-2-[(4-{(1E)-3-[2-Methyl-3-(4-methylbenzoyl)-5-(trifluoromethoxy)-1H-indol-1-yl]prop-1-en-1-yl}benzyl)oxy]propionic acid

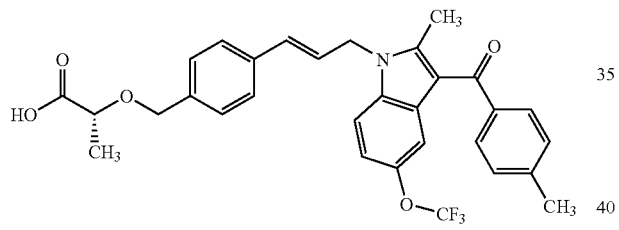

The subject compound was prepared in the same method as Example 5 by using the compounds of Reference example 28 Reference example 41-2.

¹H NMR (CDCl₃, 400 MHz) δ 7.68 (d, 2H, J=8.1 Hz), 7.34-7.23 (m, 8H), 7.07 (brd, 1H, J=8.9 Hz), 6.36-6.24 (m, 2H), 4.94 (d, 2H, J=3.6 Hz), 4.65 (d, 1H, J=11.8 Hz), 4.52 (d, 1H, J=11.8 Hz), 4.08 (q, 1H, J=6.9 Hz), 2.59 (s, 3H), 2.45 (s, 3H), 1.48 (d, 3H, J=6.9 Hz).

Example 9

2-[(4-{(1E)-3-[5-Methoxy-2-methyl-3-(4-methyl-benzoyl)-1H-indol-1-yl]prop-1-en-1-yl}benzyl)oxy]-2-methylpropionic acid

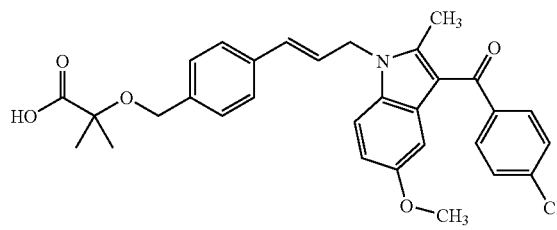

The subject compound was prepared in the same method as Example 5 by using the compounds of Reference example 27 and Reference example 40.

¹H NMR (CDCl₃, 400 MHz) δ 7.69 (d, 2H, J=8.1 Hz), 7.29 (s, 4H), 7.26 (d, 2H, J=8.1 Hz), 7.23 (d, 1H, J=8.9 Hz), 7.00 (d, 1H, J=2.4 Hz), 6.84 (dd, 1H, J=8.9, 2.4 Hz), 6.34-6.22 (m, 2H), 4.89 (d, 2H, J=3.3 Hz), 4.49 (s, 2H), 3.70 (s, 3H), 2.52 (s, 3H), 2.43 (s, 3H), 1.54 (s, 6H).

Example 10

(2R)-2-[(4-{(1E)-3-[3-(4-Methylbenzoyl)-1H-indol-1-yl]prop-1-en-1-yl}benzyl)oxy]propionic acid

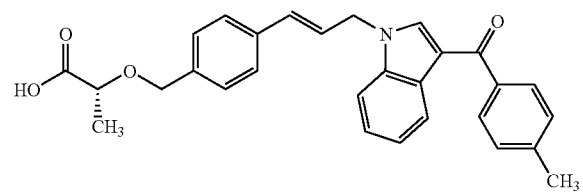

The subject compound was prepared in the same method as Example 5 by using the compounds of Reference example 31 and Reference example 41-2.

¹H NMR (CDCl₃, 400 MHz) δ 8.45-8.40 (m, 1H), 7.75 (d, 2H, J=8.1 Hz), 7.64 (s, 1H), 7.44-7.40 (m, 1H), 7.37-7.25 (m, 6H), 7.29 (d, 2H, J=8.1 Hz), 6.51 (brd, 1H, J=15.9 Hz), 6.33 (dt, 1H, J=15.9, 5.8 Hz), 4.94 (dd, 2H, J=5.8, 1.3 Hz), 4.65 (d, 1H, J=11.7 Hz), 4.51 (d, 1H, J=11.7 Hz), 4.08 (q, 1H, J=6.9 Hz), 2.43 (s, 3H), 1.47 (d, 3H, J=6.9 Hz).

Example 11

(2R)-2-[(4-{(1E)-3-[6-Methoxy-2-methyl-3-(4-methylbenzoyl)-1H-indol-1-yl]prop-1-en-1-yl}benzyl)oxy]propionic acid

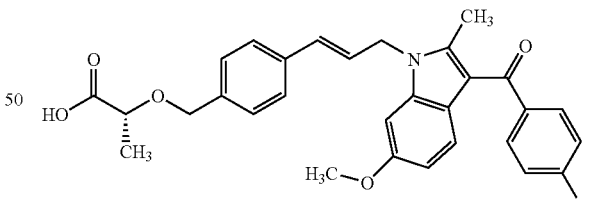

The subject compound was prepared in the same method as Example 5 by using the compounds of Reference example 32 and Reference example 41-2.

¹H NMR (CDCl₃, 400 MHz) δ 7.69 (d, 2H, J=8.1 Hz), 7.31 (d, 2H, J=6.7 Hz), 7.28 (d, 2H, J=6.7 Hz), 7.28 (d, 1H, J=8.8 Hz), 7.25 (d, 2H, J=8.1 Hz), 6.81 (d, 1H, J=2.3 Hz), 6.75 (dd, 1H, J=8.8, 2.3 Hz), 6.32-6.28 (m, 2H), 4.89 (brd, 2H, J=2.0 Hz), 4.65 (d, 1H, J=11.7 Hz), 4.52 (d, 1H, J=11.7 Hz), 4.09 (q, 1H, J=6.9 Hz), 3.84 (s, 3H), 2.56 (s, 3H), 2.44 (s, 3H), 1.48 (d, 3H, J=6.9 Hz).

Example 12

(2R)-2-[(4-{(1E)-3-[6-Methoxy-2-methyl-3,5-bis(4-methylbenzoyl)-1H-indol-1-yl]prop-1-en-1-yl}benzyl)oxy]propionic acid

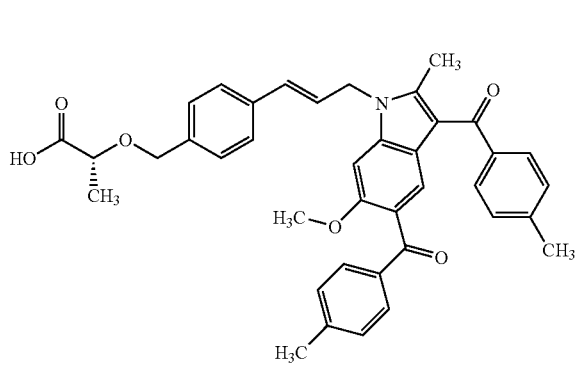

The subject compound was prepared in the same method as Reference example 5 by using the compounds of Reference example 33 and Reference example 41-2.

$^1$H NMR (CDCl$_3$, 400 MHz) δ 7.68 (d, 2H, J=8.2 Hz), 7.67 (d, 2H, J=8.1 Hz), 7.38 (s, 1H), 7.33 (d, 2H, J=8.6 Hz), 7.30 (d, 2H, J=8.6 Hz), 7.25 (d, 2H, J=8.1 Hz), 7.18 (d, 2H, J=8.2 Hz), 6.85 (s, 1H), 6.33-6.29 (m, 2H), 4.94 (brd, 2H, J=1.3 Hz), 4.67 (d, 1H, J=11.8 Hz), 4.49 (d, 1H, J=11.8 Hz), 4.08 (q, 1H, J=6.9 Hz), 3.76 (s, 3H), 2.57 (s, 3H), 2.39 (s, 3H), 2.36 (s, 3H), 1.48 (d, 3H, J=6.9 Hz).

Example 13

(2R)-2-[(4-{(1E)-3-[4-Methoxy-2-methyl-3-(4-methylbenzoyl)-1H-indol-1-yl]prop-1-en-1-yl}benzyl)oxy]propionic acid

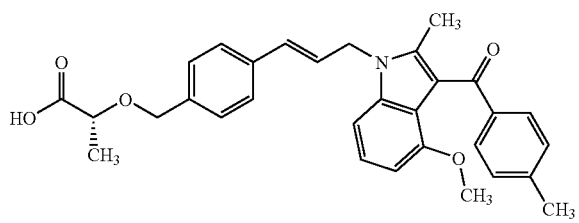

The subject compound was prepared in the same method as Example 5 by using the compounds of Reference example 34 and Reference example 41-2.

$^1$H NMR (CDCl$_3$, 400 MHz) δ 7.71 (d, 2H, J=8.1 Hz), 7.30 (d, 2H, J=8.4 Hz), 7.27 (d, 2H, J=8.4 Hz), 7.17 (d, 2H, J=8.1 Hz), 7.14 (dd, 1H, J=8.0, 8.0 Hz), 6.98 (d, 1H, J=8.0 Hz), 6.51 (d, 1H, J=8.0 Hz), 6.33-6.29 (m, 2H), 4.91 (brd, 2H, J=2.3 Hz), 4.64 (d, 1H, J=11.8 Hz), 4.51 (d, 1H, J=11.8 Hz), 4.08 (q, 1H, J=6.9 Hz), 3.40 (s, 3H), 2.51 (s, 3H), 2.40 (s, 3H), 1.47 (d, 3H, J=6.9 Hz).

Example 14

(2R)-2-[(4-{(1E)-3-[2,5-Dimethyl-3-(4-methylbenzoyl)-1H-indol-1-yl]prop-1-en-1-yl}benzyl)oxy]propionic acid

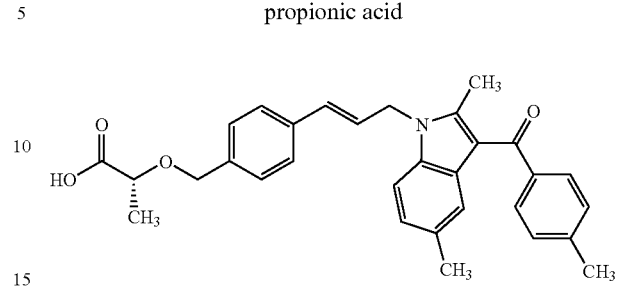

The subject compound was prepared in the same method as Example 5 by using the compounds of Reference example 35 and Reference example 41-2.

$^1$H NMR (CDCl$_3$, 400 MHz) δ 7.71 (d, 2H, J=8.1 Hz), 7.30-7.21 (m, 8H), 7.03 (dd, 1H, J=8.4, 1.3 Hz), 6.30-6.27 (m, 2H), 4.91 (brs, 2H), 4.66 (d, 1H, J=11.8 Hz), 4.47 (d, 1H, J=11.8 Hz), 4.06 (q, 1H, J=6.9 Hz), 2.53 (s, 3H), 2.44 (s, 3H), 2.35 (s, 3H), 1.47 (d, 3H, J=6.9 Hz).

Example 15

(2R)-2-[(4-{(1E)-3-[5-Chloro-3-(4-methylbenzoyl)-1H-indol-1-yl]prop-1-en-1-yl}benzyl)oxy]propionic acid

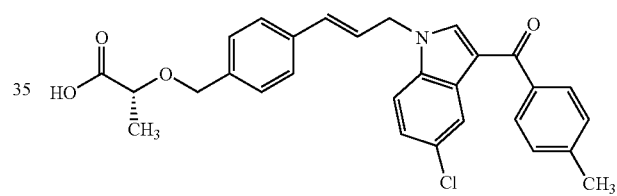

The subject compound was prepared in the same method as Example 5 by using the compounds of Reference example 36 and Reference example 41-2.

$^1$H NMR (CDCl$_3$, 400 MHz) δ 8.45 (d, 1H, J=1.7 Hz), 7.74 (d, 2H, J=8.1 Hz), 7.65 (s, 1H), 7.36-7.24 (m, 8H), 6.49 (brd, 1H, J=15.9 Hz), 6.31 (dt, 1H, J=15.9, 5.8 Hz), 4.93 (dd, 2H, J=5.8, 1.3 Hz), 4.65 (d, 1H, J=11.7 Hz), 4.53 (d, 1H, J=11.7 Hz), 4.09 (q, 1H, J=6.9 Hz), 2.44 (s, 3H), 1.48 (d, 3H, J=6.9 Hz).

Example 16

(2R)-2-[(4-{(1E)-3-[5-Fluoro-3-(4-methylbenzoyl)-1H-indol-1-yl]prop-1-en-1-yl}benzyl)oxy]propionic acid

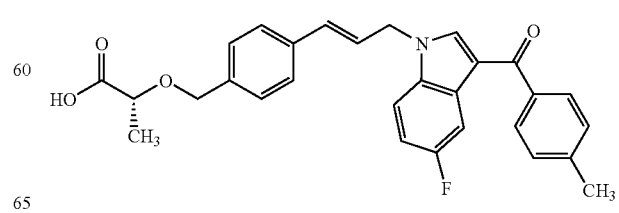

The subject compound was prepared in the same method as Example 5 by using the compounds of Reference example 37 and Reference example 41-2.

¹H NMR (CDCl₃, 400 MHz) δ 8.12 (dd, 1H, J=9.6, 2.6 Hz), 7.74 (d, 2H, J=8.1 Hz), 7.67 (s, 1H), 7.34 (dd, 1H, J=9.0, 4.2 Hz), 7.33 (d, 2H, J=8.6 Hz), 7.30 (d, 2H, J=8.6 Hz), 7.29 (d, 2H, J=8.1 Hz), 7.07 (ddd, 1H, J=9.0, 9.0, 2.6 Hz), 6.51 (brd, 1H, J=15.8 Hz), 6.32 (dt, 1H, J=15.8, 5.8 Hz), 4.93 (dd, 2H, J=5.8, 1.3 Hz), 4.66 (d, 1H, J=11.7 Hz), 4.52 (d, 1H, J=11.7 Hz), 4.09 (q, 1H, J=6.9 Hz), 2.44 (s, 3H), 1.48 (d, 3H, J=6.9 Hz).

Example 17

(2R)-2-[(4-{(1E)-3-[3-(4-Methylbenzoyl)-1H-pyrrolo[2,3-b]pyridin-1-yl]prop-1-en-1-yl}benzyl)oxy]propionic acid

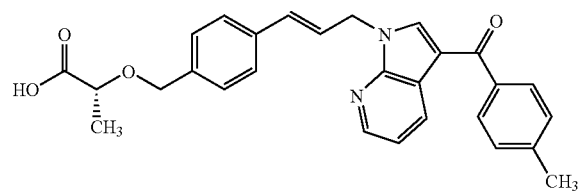

The subject compound was prepared in the same method as Example 5 by using the compounds of Reference example 38 and Reference example 41-2.

¹H NMR (CDCl₃, 400 MHz) δ 8.72 (dd, 1H, J=7.9, 1.6 Hz), 8.50 (dd, 1H, J=4.9, 1.6 Hz), 7.80 (s, 1H), 7.74 (d, 2H, J=8.1 Hz), 7.34 (dd, 1H, J=7.9, 4.9 Hz), 7.27 (d, 2H, J=8.1 Hz), 7.34-7.27 (m, 4H), 6.56 (d, 1H, J=15.9 Hz), 6.38 (dt, 1H, J=15.9, 6.1 Hz), 5.14 (d, 2H, J=6.1 Hz), 4.66 (d, 1H, J=11.8 Hz), 4.46 (d, 1H, J=11.8 Hz), 4.08 (q, 1H, J=6.9 Hz), 2.44 (s, 3H), 1.47 (d, 3H, J=6.9 Hz).

Example 18

(2R)-2-[(4-{(1E)-3-[2-Methyl-3-(4-methylbenzoyl)-1H-pyrrolo[2,3-b]pyridin-1-yl]prop-1-en-1-yl}benzyl)oxy]propionic acid

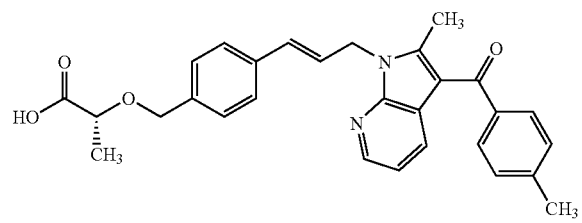

The subject compound was prepared in the same method as Example 5 by using the compounds of Reference example 39 and Reference example 41-2.

¹H NMR (CDCl₃, 400 MHz) δ 8.33 (dd, 1H, J=4.8, 1.5 Hz), 7.68 (d, 2H, J=8.1 Hz), 7.67 (dd, 1H, J=7.9, 1.5 Hz), 7.30 (d, 2H, J=8.5 Hz), 7.25 (d, 2H, J=8.1 Hz), 7.30-7.24 (m, 2H), 7.08 (dd, 1H, J=7.9, 4.8 Hz), 6.41-6.30 (m, 2H), 5.17 (d, 2H, J=1.7 Hz), 4.64 (d, 1H, J=11.8 Hz), 4.49 (d, 1H, J=11.8 Hz), 4.07 (q, 1H, J=6.9 Hz), 2.67 (s, 3H), 2.45 (s, 3H), 1.47 (d, 3H, J=6.9 Hz).

Example 19

2-Methyl-2-[(4-{(1E)-3-[3-(4-methylbenzoyl)-1H-indol-1-yl]prop-1-en-1-yl}benzyl)oxy]propionic acid

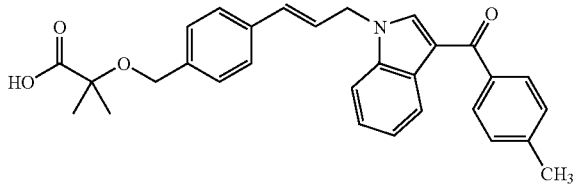

The subject compound was prepared in the same method as Example 5 by using the compounds of Reference example 31 and Reference example 40.

¹H NMR (CDCl₃, 400 MHz) δ 8.46-8.41 (m, 1H), 7.75 (d, 2H, J=8.1 Hz), 7.65 (s, 1H), 7.46-7.40 (m, 1H), 7.37-7.31 (m, 2H), 7.31 (s, 4H), 7.28 (d, 2H, J=8.1 Hz), 6.52 (brd, 1H, J=15.8 Hz), 6.33 (dt, 1H, J=15.8, 5.8 Hz), 4.95 (dd, 2H, J=5.8, 1.3 Hz), 4.50 (s, 2H), 2.44 (s, 3H), 1.55 (s, 6H).

Example 20

2-Methyl-2-[(4-{(1E)-3-[2-Methyl-3-(4-methylbenzoyl)-1H-pyrrolo[2,3-b]pyridin-1-yl]prop-1-en-1-yl}benzyl)oxy]propionic acid

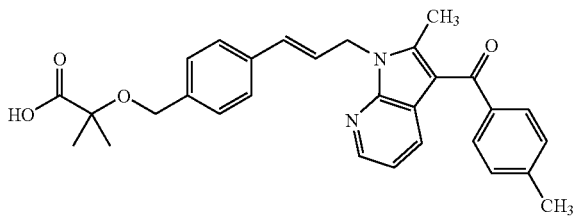

The subject compound was prepared in the same method as Example 5 by using the compounds of Reference example 39 and Reference example 40.

¹H NMR (CDCl₃, 400 MHz) δ 8.33 (dd, 1H, J=4.8, 1.5 Hz), 7.67 (d, 2H, J=8.2 Hz), 7.69-7.65 (m, 1H), 7.27 (d, 2H, J=8.2 Hz), 7.30-7.23 (m, 4H), 7.08 (dd, 1H, J=8.0, 4.8 Hz), 6.38 (d, 1H, J=15.9 Hz), 6.32 (dt, 1H, J=15.9, 4.3 Hz), 5.16 (d, 2H, J=4.3 Hz), 4.47 (s, 2H), 2.66 (s, 3H), 2.45 (s, 3H), 1.54 (s, 6H).

Example 21

(2R)-2-[(4-{(1E)-3-[3-(4-Methylbenzoyl)-1H-pyrazol-1-yl]prop-1-en-1-yl}benzyl)oxy]propanoic acid

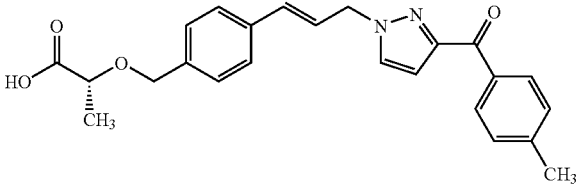

The subject compound was prepared in the same method as Example 5 by using the compounds of Reference example 41 and Reference example 43.

¹H NMR (CDCl₃, 400 MHz) δ 8.15 (d, 2H, J=8.4 Hz), 7.52 (d, 1H, J=2.4 Hz), 7.39 (d, 2H, J=8.2 Hz), 7.33 (d, 2H, J=8.2 Hz), 7.28 (d, 2H, J=8.4 Hz), 6.97 (d, 1H, J=2.4 Hz), 6.62 (d,

1H, J=15.8 Hz), 6.41 (dt, 1H, J=15.8, 6.4 Hz), 5.02 (d, 2H, J=6.4 Hz), 4.68 (d, 1H, J=11.7 Hz), 4.52 (d, 1H, J=11.7 Hz), 4.10 (q, 1H, J=6.9 Hz), 2.43 (s, 3H), 1.49 (d, 3H, J=6.9 Hz).

Example 22

Sodium (2R)-2-[(4-{(1E)-3-[3-(4-methylbenzoyl)-1H-pyrazol-1-yl]prop-1-en-1-yl}benzyl)oxy]propanoate

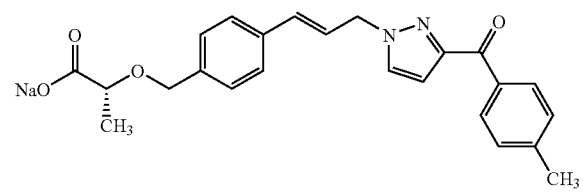

The subject compound was prepared in the same method as Example 2 by using the compound of Reference example 21.

$^1$H NMR (DMSO-d$_6$, 400 MHz) δ 8.11 (d, 2H, J=8.2 Hz), 8.00 (d, 1H, J=2.3 Hz), 7.42 (d, 2H, J=8.1 Hz), 7.35 (d, 2H, J=8.1 Hz), 7.28 (d, 2H, J=8.2 Hz), 6.91 (d, 1H, J=2.3 Hz), 6.61 (d, 1H, J=16.0 Hz), 6.52 (dt, 1H, J=16.0, 6.0 Hz), 5.07 (d, 2H, J=6.0 Hz), 4.61 (d, 1H, J=12.0 Hz), 4.22 (d, 1H, J=12.0 Hz), 3.52 (q, 1H, J=6.8 Hz), 2.39 (s, 3H), 1.15 (d, 3H, J=6.8 Hz).

Example 23

(2R)-2-[(4-{(1E)-3-[3-(4-Propylbenzoyl)-1H-pyrazol-1-yl]prop-1-en-1-yl}benzyl)oxy]propanoic acid

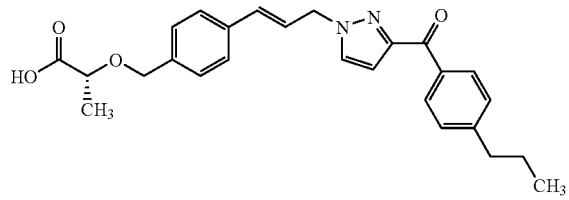

The subject compound was prepared in the same method as Example 5 by using (1-allyl-1H-pyrazol-3-yl)(4-propylphenyl)methanone prepared by the same method as Reference example 43 and the compound of Reference example 41.

$^1$H NMR (CDCl$_3$, 400 MHz) δ 8.18 (d, 2H, J=8.3 Hz), 7.52 (d, 1H, J=2.4 Hz), 7.39 (d, 2H, J=8.2 Hz), 7.33 (d, 2H, J=8.2 Hz), 7.29 (d, 2H, J=8.3 Hz), 6.98 (d, 1H, J=2.4 Hz), 6.62 (d, 1H, J=15.8 Hz), 6.42 (dt, 1H, J=15.8, 6.4 Hz), 5.03 (d, 2H, J=6.4 Hz), 4.68 (d, 1H, J=11.7 Hz), 4.54 (d, 1H, J=11.7 Hz), 4.10 (q, 1H, J=6.9 Hz), 2.66 (t, 2H, J=8.0 Hz), 1.68 (tq, 2H, J=8.0, 7.2 Hz), 1.49 (d, 3H, J=6.9 Hz), 0.96 (t, 3H, J=7.2 Hz).

Example 24

(2R)-2-{[4-((1E)-3-{3-[4-(Trifluoromethyl)benzoyl]-1H-pyrazol-1-yl}prop-1-en-1-yl)benzyl]oxy}propanoic acid

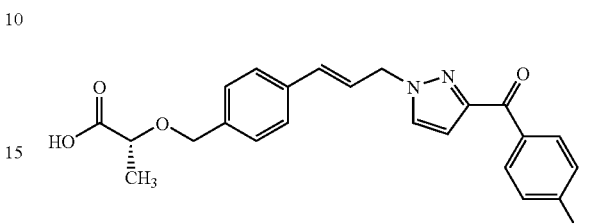

The subject compound was prepared in the same method as Example 5 by using (1-allyl-1H-pyrazol-3-yl)(4-trifluoromethylphenyl)methanone prepared by the same method as Reference example 43 and the compound of Reference example 41.

$^1$H NMR (CDCl$_3$, 400 MHz) δ 8.36 (d, 2H, J=8.0 Hz), 7.74 (d, 2H, J=8.0 Hz), 7.56 (d, 1H, J=2.4 Hz), 7.39 (d, 2H, J=8.2 Hz), 7.33 (d, 2H, J=8.2 Hz), 7.04 (d, 1H, J=2.4 Hz), 6.63 (d, 1H, J=15.8 Hz), 6.40 (dt, 1H, J=15.8, 6.5 Hz), 5.02 (d, 2H, J=6.5 Hz), 4.69 (d, 1H, J=11.8 Hz), 4.53 (d, 1H, J=11.8 Hz), 4.10 (q, 1H, J=6.9 Hz), 1.50 (d, 3H, J=6.9 Hz).

Example 25

(2R)-2-{[4-((1E)-3-{2-[4-(Trifluoromethyl)benzoyl]-4,5,6,7-tetrahydro-1H-benzimidazol-1-yl}prop-1-en-1-yl)benzyl]oxy}propanoic acid

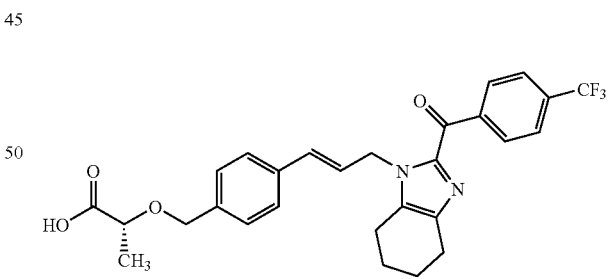

The subject compound was prepared in the same method as Example 5 by using the compounds of Reference example 41 and Reference example 44.

$^1$H NMR (CDCl$_3$, 400 MHz) δ 8.31 (d, 2H, J=8.1 Hz), 7.72 (d, 2H, J=8.1 Hz), 7.36 (d, 2H, J=8.2 Hz), 7.28 (d, 2H, J=8.2 Hz), 6.46 (d, 1H, J=16.0 Hz), 6.39 (dt, 1H, J=16.0, 5.3 Hz), 5.16 (d, 2H, J=5.3 Hz), 4.64 (d, 1H, J=11.8 Hz), 4.53 (d, 1H, J=11.8 Hz), 4.07 (q, 1H, J=6.9 Hz), 2.71-2.66 (m, 4H), 1.92-1.86 (m, 4H), 1.46 (d, 3H, J=6.9 Hz).

Example 26

(2R)-2-[(4-{(1E)-3-[2-(4-Methylbenzoyl)-4,5,6,7-tetrahydro-1H-benzimidazol-1-yl]prop-1-en-1-yl}benzyl)oxy]propanoic acid

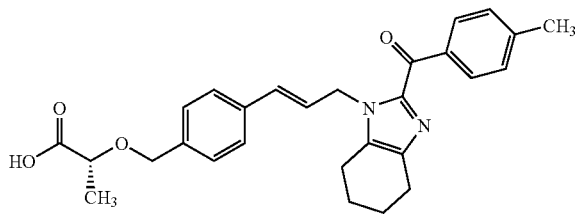

The subject compound was prepared in the same method as Example 5 by using the compounds of Reference example 41 and Reference example 45.

$^1$H NMR (CDCl$_3$, 400 MHz) δ 8.14 (d, 2H, J=8.2 Hz), 7.35 (d, 2H, J=8.2 Hz), 7.28 (d, 2H, J=8.2 Hz), 7.27 (d, 2H, J=8.2 Hz), 6.41 (d, 1H, J=8.6 Hz), 6.40 (dt, 1H, J=8.6, 4.4 Hz), 5.12 (d, 2H, J=4.4 Hz), 4.62 (d, 1H, J=11.7 Hz), 4.53 (d, 1H, J=11.7 Hz), 4.06 (q, 1H, J=6.9 Hz), 2.71-2.64 (m, 4H), 2.40 (s, 3H), 1.89-1.84 (m, 4H), 1.45 (d, 3H, J=6.9 Hz).

Example 27

2-Methyl-2-[(4-{(1E)-3-[2-(4-methylbenzoyl)-4,5,6,7-tetrahydro-1H-benzimidazol-1-yl]prop-1-en-1-yl}benzyl)oxy]propanoic acid

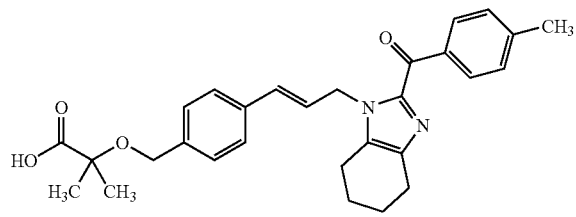

The subject compound was prepared in the same method as Example 5 by using the compounds of Reference example 40 and Reference example 45.

$^1$H NMR (CDCl$_3$, 400 MHz) δ 8.12 (d, 2H, J=8.1 Hz), 7.35 (d, 2H, J=8.2 Hz), 7.28 (d, 2H, J=8.1 Hz), 7.27 (d, 2H, J=8.2 Hz), 6.42 (d, 1H, J=8.8 Hz), 6.41 (dt, 1H, J=8.8, 4.8 Hz), 5.12 (d, 2H, J=4.8 Hz), 4.53 (s, 2H), 2.71-2.64 (m, 4H), 2.41 (s, 3H), 1.89-1.86 (m, 4H), 1.55 (s, 6H).

Example 28

(2R)-2-[(4-{(1E)-3-[3-(4-Methylbenzoyl)-1H-indazol-1-yl]prop-1-en-1-yl}benzyl)oxy]propanoic acid

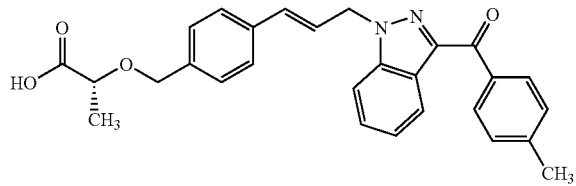

The subject compound was prepared in the same method as Example 5 by using the compounds of Reference example 41 and Reference example 49.

$^1$H NMR (CDCl$_3$, 400 MHz) δ 8.47 (d, 1H, J=8.1 Hz), 8.26 (d, 2H, J=8.2 Hz), 7.54 (d, 1H, J=8.4 Hz), 7.46 (dd, 1H, J=8.2, 8.1 Hz), 7.45-7.28 (m, 7H), 6.59 (d, 1H, J=15.8 Hz), 6.44 (dt, 1H, J=15.8, 6.0 Hz), 5.31 (d, 2H, J=6.0 Hz), 4.64 (d, 1H, J=11.8 Hz), 4.54 (d, 1H, J=11.8 Hz), 4.09 (q, 1H, J=6.9 Hz), 2.45 (s, 3H), 1.47 (d, 3H, J=6.9 Hz).

Example 29

(2R)-2-[(4-{(1E)-3-[3-(4-Chlorobenzoyl)-1H-indazol-1-yl]prop-1-en-1-yl}benzyl)oxy]propanoic acid

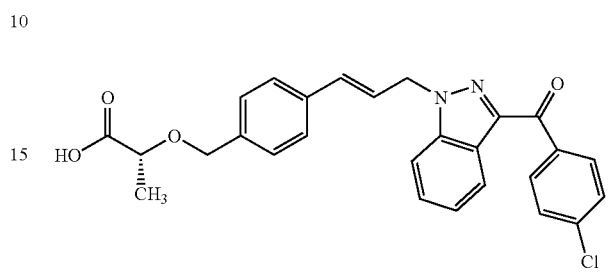

The subject compound was prepared in the same method as Example 5 by using the compounds of Reference example 41 and Reference example 50.

LC-MS R.T. 4.03 min., m/z 475 (M+1)

Example 30

(2R)-2-[(4-{(1E)-3-[3-(4-Ethylbenzoyl)-1H-indazol-yl]prop-1-en-1-yl}benzyl)oxy]propanoic acid

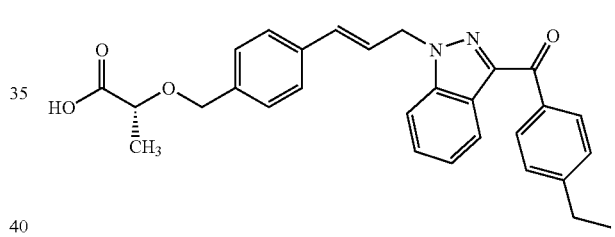

The subject compound was prepared in the same method as Example 5 by using the compounds of Reference example 41 and Reference example 51.

LC-MS R.T. 4.09 min., m/z 469 (M+1)

Example 31

2-[(4-{(1E)-3-[3-(4-Chlorobenzoyl)-1H-indazol-1-yl]prop-1-en-1-yl}benzyl)oxy]-2-methylpropanoic acid

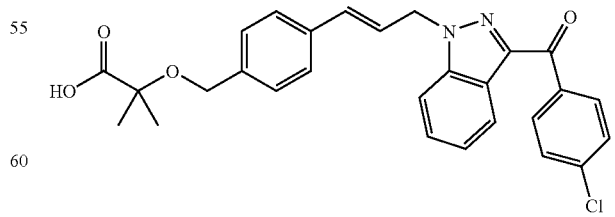

The subject compound was prepared in the same method as Example 5 by using the compounds of Reference example 40 and Reference example 50.

LC-MS R.T. 4.15 min., m/z 511% (M+Na)

Example 32

2-[(4-{(1E)-3-[3-(4-Ethylbenzoyl)-1H-indazol-1-yl]prop-1-en-1-yl}benzyl)oxy]-2-methylpropanoic acid

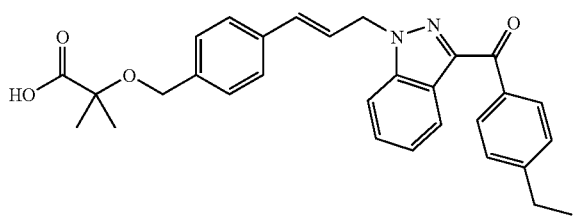

The subject compound was prepared in the same method as Example 5 by using the compounds of Reference example 40 and Reference example 51.

LC-MS R.T. 4.13 min., m/z 483 (M+1)

Example 33

(2R)-2-[(4-{(1E)-3-[3-(4-Methylbenzoyl)-1H-pyrazolo[4,3-b]pyridin-1-yl]prop-1-en-1-yl}benzyl)oxy]propanoic acid

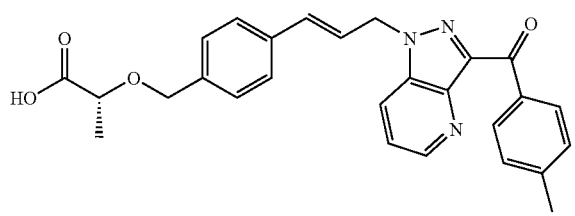

The subject compound was prepared in the same method as Example 5 by using the compound of Reference example 41 and the compound of Reference example 48.

LC-MS R.T. 4.13 min., m/z 483 (M+1)

Example 34

(2R)-2-[(4-{(E)-2-[3-(4-Methylbenzoyl)-1H-indazol-1-yl]vinyl}benzyl)oxy]propanoic acid

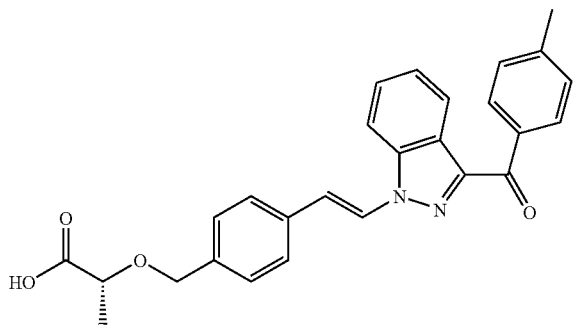

The subject compound was prepared in the same method as Example 5 by using the compounds of Reference example 41 and Reference example 54.

LC-MS R.T. 4.09 min., m/z 441 (M+1)

Example 35

2-Methyl-2-[(4-{(1E)-3-[3-(4-methylbenzoyl)-1H-indazol-1-yl]prop-1-en-1-yl}benzyl)oxy]propanoic acid

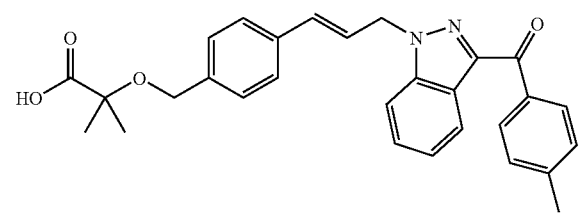

The subject compound was prepared in the same method as Example 5 by using the compounds of Reference example 40 and Reference example 49.

LC-MS R.T. 4.01 min., m/z 469 (M+1)

Example 36

(2R)-2-[(4-{(1E)-3-[3-(4-Methylbenzoyl)-6-(trifluoromethyl)-1H-indazol-1-yl]prop-1-en-1-yl}benzyl)oxy]propanoic acid

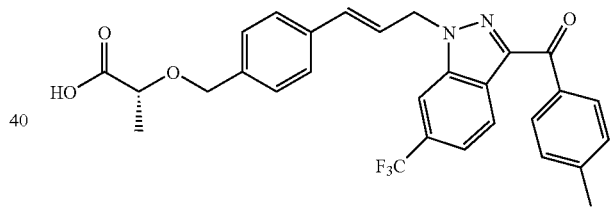

The subject compound was prepared in the same method as Example 5 by using the compounds of Reference example 41 and Reference example 52.

LC-MS R.T. 4.29 min., m/z 523 (M+1)

Example 37

(2R)-2-[(4-{(1E)-3-[3-(4-Methylbenzoyl)-5-(trifluoromethoxy-)-1H-indazol-1-yl]prop-1-en-1-yl}benzyl)oxy]propanoic acid

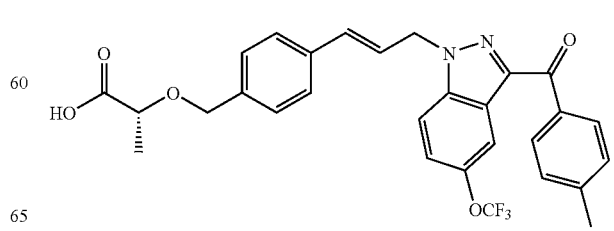

The subject compound was prepared in the same method as Example 5 by using the compounds of Reference example 41 and Reference example 53.
LC-MS R.T. 4.30 min., m/z 539 (M+1)

Example 38

(2R)-2-[(4-{3-[5-Methoxy-2-methyl-3-(4-methyl-benzoyl)-1H-indol-1-yl]propyl}benzyl)oxy]propionate acid

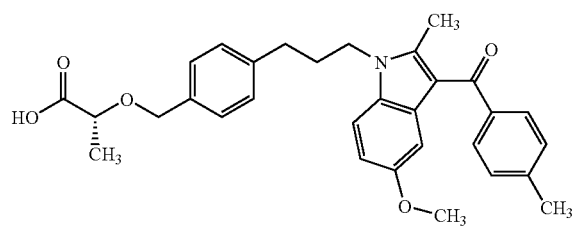

To the compound of Example 5 (134 mg, 0.269 mmol) in methanol (2 ml) was added 10% palladium-carbon (50% wet, 13.4 mg) and the mixture was stirred for 5 hours at room temperature under a hydrogen atmosphere at ordinary pressure, and the catalyst was filtered off over Celite. The solvent of the filtrate was removed in vacuo to give the subject compound (quant.).

$^1$H NMR (CDCl$_3$, 400 MHz) δ 7.65 (d, 2H, J=7.9 Hz), 7.30 (d, 2H, J=7.9 Hz), 7.24 (d, 2H, J=7.9 Hz), 7.18 (d, 2H, J=7.9 Hz), 7.09 (d, 1H, J=8.9 Hz), 6.92 (d, 1H, J=2.4 Hz), 6.81 (dd, 1H, J=8.9, 2.4 Hz), 4.67 (d, 1H, J=11.5 Hz), 4.51 (d, 1H, J=11.5 Hz), 4.11 (q, 1H, J=6.8 Hz), 4.12-4.05 (m, 2H), 3.68 (s, 3H), 2.75-2.68 (m, 2H), 2.45 (s, 3H), 2.42 (s, 3H), 2.16-2.06 (m, 2H), 1.48 (d, 3H, J=6.8 Hz).

Example 39

(2R)-2-[(3-{(1E)-3-[5-Chloro-2-methyl-3-(4-methyl-benzoyl)-1H-indol-1-yl]prop-1-en-1-yl}benzyl)oxy] propionic acid Example 39-1

{5-Chloro-2-methyl-1-[(2E)-3-(3-{[(1R)-1-methyl-2-morpholin-4-yl-2-oxoethoxy]methyl-}phenyl) prop-2-ene-1-yl]-1H-indol-3-yl}(4-methylphenyl) methanone

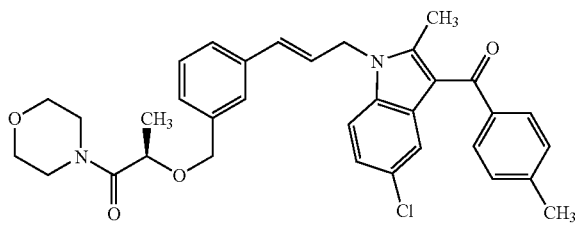

The compound of Reference example 29 (91 mg, 0.28 mmol), the compound of Reference example 42-2 (92 mg, 0.28 mmol), bis(tri t-butylphospine)palladium (15 mg, 0.028 mmol) and N,N-dicyclohexylmethylamine (110 mg, 0.56 mmol) were dissolved in dioxane (1 ml) and the solution was stirred for 4 hours at 70° C. Thereto was added 5% aqueous thiosodium sulfate solution, and the mixture was extracted with ethyl acetate. The organic layer was washed with water and saturated brine, dried over magnesium sulfate and filtered. The solvent was removed in vacuo and the residue was purified by silica gel column chromatography to give the subject compound (160 mg, 71%).

$^1$H NMR (CDCl$_3$, 400 MHz) δ 7.69 (d, 2H, J=8.0 Hz), 7.43 (d, 1H, J=2.0 Hz), 7.31-7.19 (m, 7H), 7.16 (dd, 1H, J=8.4, 2.0 Hz), 6.29-6.20 (m, 2H), 4.93 (d, 2H, J=3.2 Hz), 4.55 (d, 1H, J=11.5 Hz), 4.42 (d, 1H, J=11.5 Hz), 4.31 (q, 1H, J=6.8 Hz), 3.70-3.50 (m, 8H), 2.57 (s, 3H), 2.45 (s, 3H), 1.44 (d, 3H, J=6.8 Hz).

Example 39-2

(2R)-2-[(3-{(1E)-3-[5-Chloro-2-methyl-3-(4-methyl-benzoyl)-1H-indol-1-yl]prop-1-en-1-yl}benzyl)oxy] propionic acid

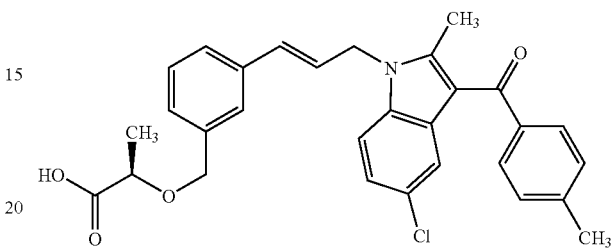

The compound of Example 39-1 (114 mg, 0.20 mmol) was dissolved in methanol (0.75 ml) and THF (0.75 ml) and thereto was added 2N aqueous lithium hydroxide solution (0.2 ml), followed by stirring under reflux for 4 hours. After being cooled to room temperature, the solution was adjusted around pH2 with 1N diluted hydrochloric acid. The solution was extracted with ethyl acetate and the organic layer was washed with saturated brine, dried over magnesium sulfate and filtered. The solvent was removed in vacuo to give the subject compound (99 mg, 92%).

$^1$H NMR (CDCl$_3$, 400 MHz) δ 7.69 (d, 2H, J=8.1 Hz), 7.41 (d, 1H, J=2.0 Hz), 7.33-7.08 (m, 7H), 7.15 (dd, 1H, J=8.8, 2.0 Hz), 6.33-6.18 (m, 2H), 4.90 (d, 2H, J=3.2 Hz), 4.64 (d, 1H, J=11.5 Hz), 4.47 (d, 1H, J=11.5 Hz), 4.08 (q, 1H, J=6.9 Hz), 2.55 (s, 3H), 2.44 (s, 3H), 1.48 (d, 3H, J=6.9 Hz).

Example 40

(2R)-2-[(4-{[5-Methoxy-2-methyl-3-(4-methylbenzoyl)-1H-indol-1-yl]methyl-}benzyl)oxy]propionic acid Example 40-1

[5-Methoxy-2-methyl-1-(4-{[(1R)-1-methyl-2-morpholin-4-yl-2-oxoethoxy]methyl-}benzyl)-1H-indol-3-yl] (4-methylphenyl)methanone

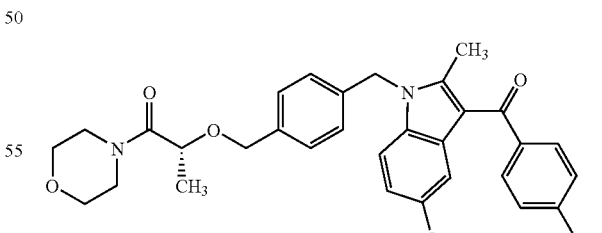

To the compound of Reference example 11 (131 mg, 0.47 mmol) in DMF (2 ml) was added potassium carbonate (129 mg, 0.94 mmol). After stirring for 30 minutes at room temperature, thereto were added the compound of Reference example 55-5 (160 mg, 0.47 mmol) and tetra n-butylammonium iodide (17 mg, 0.05 mmol), and the mixture was stirred for 4.5 hours at 80° C. and then for 5.5 hours at 100° C. After being cooled to room temperature, thereto was added 5% aqueous potassium hydrogen sulfate solution and the mixture was extracted with ethyl acetate. The organic layer was washed with saturated brine, dried over anhydrous sodium sulfate and filtered. The solvent was removed in vacuo and purified by silica gel column chromatography to give the subject compound (145 mg, 56%).

$^1$H NMR (CDCl$_3$, 400 MHz) δ 7.69 (d, 2H, J=8.1 Hz), 7.29 (d, 2H, J=8.1 Hz), 7.26 (d, 2H, J=8.1 Hz), 7.12 (d, 1H, J=8.9 Hz), 7.00 (d, 2H, J=8.1 Hz), 7.00 (d, 1H, J=2.5 Hz), 6.79 (dd, 1H, J=8.9, 2.5 Hz), 5.34 (s, 2H), 4.55 (d, 1H, J=11.6 Hz), 4.41 (d, 1H, J=11.6 Hz), 4.31 (q, 1H, J=6.8 Hz), 3.71-3.56 (m, 8H), 3.69 (s, 3H), 2.46 (s, 3H), 2.44 (s, 3H), 1.43 (d, 3H, J=6.8 Hz).

Example 40-2

(2R)-2-[(4-{[5-Methoxy-2-methyl-3-(4-methylbenzoyl)-1H-indol-1-yl]methyl-}benzyl)oxy]propionic acid

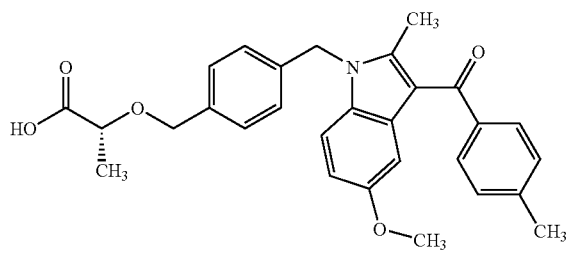

The compound of Example 40-1 (142 mg, 0.26 mmol) was dissolved in methanol (1 ml) and THF (1 ml) and thereto was added 2N lithium hydroxide solution (0.5 ml), followed by stirring under reflux for 15 hours. The reaction mixture was diluted with water and washed with diethyl ether. The aqueous layer was adjusted to around pH4 with 5% aqueous potassium hydrogen sulfate solution and extracted with ethyl acetate. The organic layer was washed with saturated brine, dried over anhydrous sodium sulfate and filtered. The solvent was removed in vacuo to give the subject compound (39 mg, 31%).

$^1$H NMR (CDCl$_3$, 400 MHz) δ 7.69 (d, 2H, J=8.1 Hz), 7.29 (d, 2H, J=8.1 Hz), 7.26 (d, 2H, J=8.1 Hz), 7.11 (d, 1H, J=8.9 Hz), 7.00 (d, 2H, J=8.1 Hz), 7.00 (d, 1H, J=2.5 Hz), 6.79 (dd, 1H, J=8.9, 2.5 Hz), 5.34 (s, 2H), 4.64 (d, 1H, J=11.6 Hz), 4.48 (d, 1H, J=11.6 Hz), 4.08 (q, 1H, J=6.9 Hz), 3.69 (s, 3H), 2.45 (s, 3H), 2.43 (s, 3H), 1.47 (d, 3H, J=6.9 Hz).

Example 41

[1-(3-{[(1R)-1-Methyl-2-morphplin-4-yl-2-oxoethoxy]methyl}benzyl)-1H-pyrrolo[2,3-c]pyridin-3-yl] (4-methylphenyl)methanone

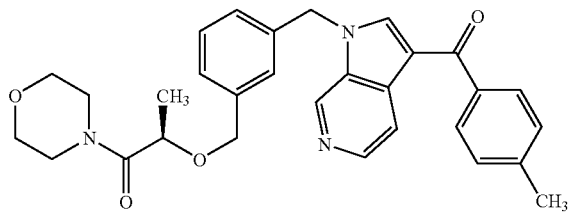

The subject compound was prepared in the same method as Example 50-1 by using the compounds of Reference example 71 and Reference example 56.

LC-MS R.T. 2.67 min, m/z 498 (M+1)

Example 42

(2R)-2-[(4-{[3-(4-Methylbenzoyl)-1H-pyrrol-1-yl]methyl}benzyl)oxy]propionic acid

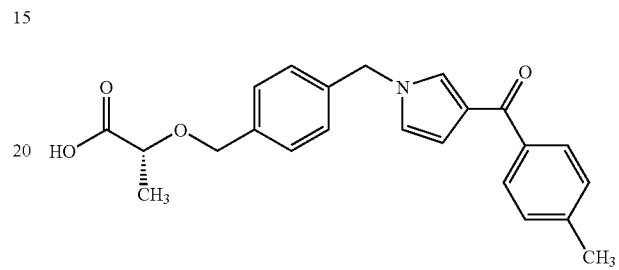

The subject compound was prepared in the same method as Example 41 by using the compounds of Reference example 58-2 and Reference example 55-5.

$^1$H NMR (CDCl$_3$, 400 MHz) δ 7.74 (d, 2H, J=8.1 Hz), 7.35 (d, 2H, J=8.1 Hz), 7.27 (dd, 1H, J=1.9, 1.9 Hz), 7.25 (d, 2H, J=8.1 Hz), 7.16 (d, 2H, J=8.1 Hz), 6.71 (dd, 1H, J=2.9, 1.9 Hz), 6.69 (dd, 1H, J=2.9, 1.9 Hz), 5.09 (s, 2H), 4.67 (d, 1H, J=11.6 Hz), 4.54 (d, 1H, J=11.6 Hz), 4.10 (q, 1H, J=6.9 Hz), 2.41 (s, 3H), 1.49 (d, 3H, J=6.9 Hz).

Example 43

(2R)-2-[(4-{[3-(4-Methylbenzoyl)-1H-indol-1-yl]methyl}benzyl)oxy]propionic acid

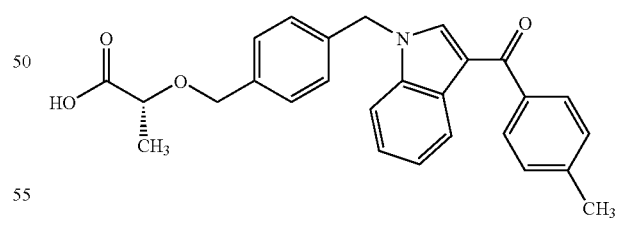

The subject compound was prepared in the same method as Example 41 by using the compounds of Reference example 22 and Reference example 55-5.

$^1$H NMR (CDCl$_3$, 400 MHz) δ 8.41 (d, 1H, J=6.1 Hz), 7.75 (d, 2H, J=8.1 Hz), 7.63 (s, 1H), 7.37-7.25 (m, 7H), 7.13 (d, 2H, J=8.1 Hz), 5.36 (s, 2H), 4.64 (d, 1H, J=11.6 Hz), 4.50 (d, 1H, J=11.6 Hz), 4.08 (q, 1H, J=6.9 Hz), 2.43 (s, 3H), 1.48 (d, 3H, J=6.9 Hz).

Example 44

(2R)-2-[(4-{[2,5-Dimethyl-3-(4-methylbenzoyl)-1H-indol-1-yl]methyl}benzyl)oxy]propionic acid

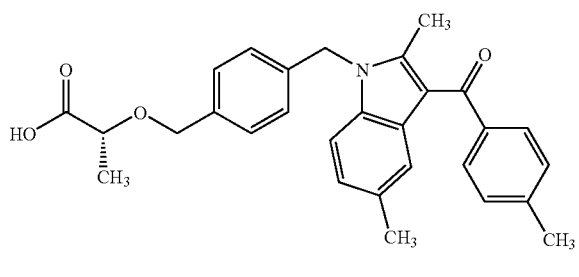

The subject compound was prepared in the same method as Example 41 by using the compounds of Reference example 15 and Reference example 55-5.

$^1$H NMR (CDCl$_3$, 400 MHz) δ 7.71 (d, 2H, J=8.0 Hz), 7.29 (d, 2H, J=8.0 Hz), 7.28 (d, 1H, J=1.5 Hz), 7.25 (d, 2H, J=8.0 Hz), 7.13 (d, 1H, J=8.3 Hz), 7.01 (d, 2H, J=8.0 Hz), 6.98 (dd, 1H, J=8.3, 1.5 Hz), 5.36 (s, 2H), 4.63 (d, 1H, J=11.6 Hz), 4.50 (d, 1H, J=11.6 Hz), 4.09 (q, 1H, J=6.9 Hz), 2.46 (s, 3H), 2.45 (s, 3H), 2.34 (s, 3H), 1.48 (d, 3H, J=6.9 Hz).

Example 45

(2R)-2-[(4-{[3-(4-Methylbenzoyl)-1H-indol-1-yl]methyl}benzyl)oxy]propionic acid

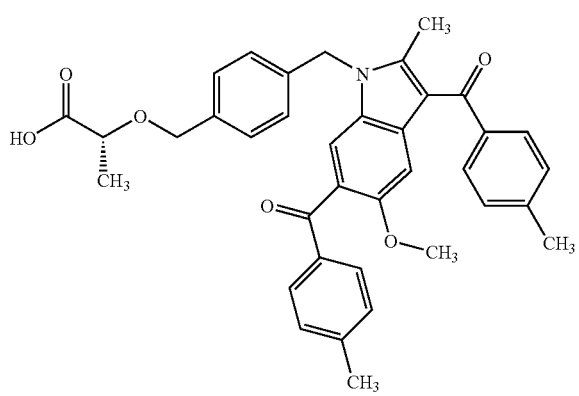

The subject compound was prepared in the same method as Example 41 by using the compounds of Reference example 25 and Reference example 55-5.

LC-MS: R.T. 4.25 min., m/z 590 (M+1)

Example 46

(2R)-2-[(4-{[6-Methoxy-2-methyl-3-(4-methylbenzoyl)-1H-indol-1-yl]methyl-}benzyl)oxy]propionic acid

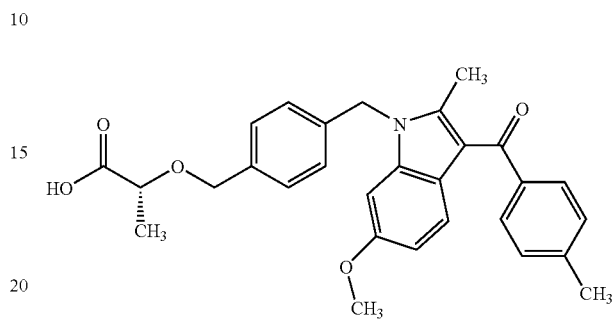

The subject compound was prepared in the same method as Example 41 by using the compounds of Reference example 12 and Reference example 55-5.

$^1$H NMR (CDCl$_3$, 400 MHz) δ 7.69 (d, 2H, J=8.1 Hz), 7.31 (d, 2H, J=8.1 Hz), 7.28 (d, 1H, J=8.7 Hz), 7.25 (d, 2H, J=8.1 Hz), 7.03 (d, 2H, J=8.1 Hz), 6.74 (dd, 1H, J=8.7, 2.3 Hz), 6.71 (d, 1H, J=2.3 Hz), 5.33 (s, 2H), 4.64 (d, 1H, J=11.6 Hz), 4.51 (d, 1H, J=11.6 Hz), 4.09 (q, 1H, J=6.9 Hz), 3.78 (s, 3H), 2.49 (s, 3H), 2.44 (s, 3H), 1.48 (d, 3H, J=6.9 Hz).

Example 47

(2R)-2-[(4-{[6-Bromo-3-(4-methylbenzoyl)-1H-indol-1-yl]methyl-}benzyl)oxy]propionic acid

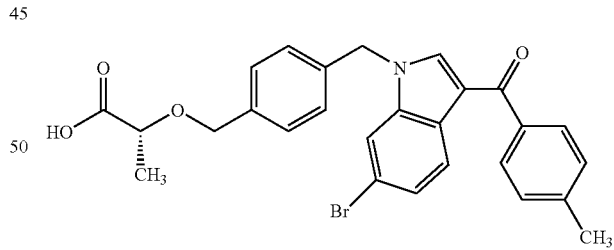

The subject compound was prepared in the same method as Example 41 by using the compounds of Reference example 21 and Reference example 55-5.

$^1$H NMR (CDCl$_3$, 400 MHz) δ 8.27 (d, 1H, J=8.5 Hz), 7.72 (d, 2H, J=8.1 Hz), 7.59 (s, 1H), 7.45 (d, 1H, J=1.7 Hz), 7.42 (dd, 1H, J=8.5, 1.7 Hz), 7.33 (d, 2H, J=8.1 Hz), 7.28 (d, 2H, J=8.1 Hz), 7.11 (d, 2H, J=8.1 Hz), 5.31 (s, 2H), 4.65 (d, 1H, J=11.7 Hz), 4.52 (d, 1H, J=11.7 Hz), 4.09 (q, 1H, J=6.9 Hz), 2.43 (s, 3H), 1.48 (d, 3H, J=6.9 Hz).

Example 48

(2R)-2-[(4-{[2-Methyl-3-(4-methylbenzoyl)-1H-indol-1-yl]methyl-}benzyl)oxy]propionic acid

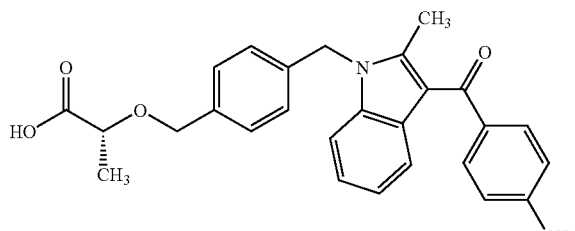

The subject compound was prepared in the same method as Example 41 by using the compounds of Reference example 23 and Reference example 55-5.

$^1$H NMR (CDCl$_3$, 400 MHz) δ 7.71 (d, 2H, J=8.1 Hz), 7.38 (brd, 1H, J=8.0 Hz), 7.30 (d, 2H, J=8.1 Hz), 7.28-7.22 (m, 3H), 7.15 (ddd, 1H, J=8.0, 7.1, 1.1 Hz), 7.08 (ddd, 1H, J=8.0, 7.1, 1.1 Hz), 7.02 (d, 2H, J=8.1 Hz), 5.39 (s, 2H), 4.63 (d, 1H, J=11.6 Hz), 4.50 (d, 1H, J=11.6 Hz), 4.08 (q, 1H, J=6.9 Hz), 2.53 (s, 3H), 2.44 (s, 3H), 1.47 (d, 3H, J=6.9 Hz).

Example 49

(2R)-2-[(4-{[2-Methyl-3-(4-methylbenzoyl)-6-(trifluoromethyl)-1H-indol-1-yl]methyl-}benzyl)oxy]propionic acid

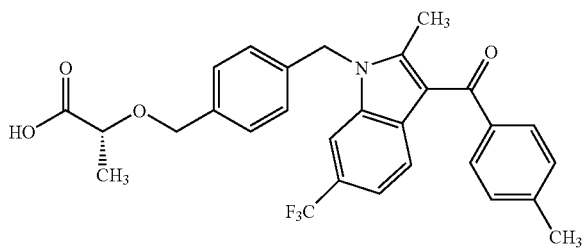

The subject compound was prepared in the same method as Example 41 by using the compounds of Reference example 26 and Reference example 55-5.

$^1$H NMR (CDCl$_3$, 400 MHz) δ 7.69 (d, 2H, J=8.1 Hz), 7.53 (brs, 1H), 7.46 (d, 1H, J=8.3 Hz), 7.33 (d, 2H, J=8.1 Hz), 7.32 (dd, 1H, J=8.3, 1.2 Hz), 7.27 (d, 2H, J=8.1 Hz), 7.01 (d, 2H, J=8.1 Hz), 5.44 (s, 2H), 4.66 (d, 1H, J=11.6 Hz), 4.51 (d, 1H, J=11.6 Hz), 4.10 (q, 1H, J=6.9 Hz), 2.55 (s, 3H), 2.45 (s, 3H), 1.49 (d, 3H, J=6.9 Hz).

Example 50

(2R)-2-[(3-{[2-Methyl-3-(4-methylbenzoyl)-1H-indol-1-yl]methyl}benzyl)oxy]propionic acid

Example 50-1

[2-Methyl-1-(3-{[(1R)-1-methyl-2-morpholin-4-yl-2-oxoethoxy]methyl}benzyl)-1H-indol-3-yl] (4-methylphenyl)methanone

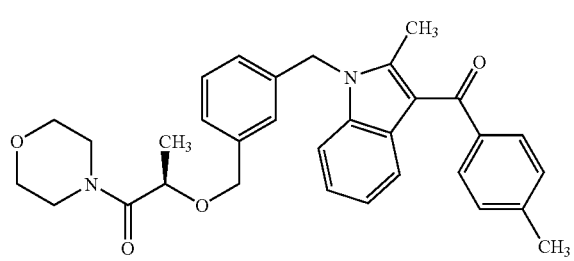

To the compound of Reference example 56 (166 mg, 0.60 mmol) in methylene chloride (3 ml) was added under ice cooling thionyl chloride (87 µl, 1.19 mmol). After stirring for 1 hour, the solvent was removed in vacuo to give the residue. To the compound of Reference example 23 (178 mg, 0.72 mmol) in DMF (3 ml) was added potassium carbonate (200 mg, 1.79 mmol) and the mixture was stirred for 30 minutes at room temperature. Thereto were added the above residue and tetra n-butylammonium iodide (22 mg, 0.06 mmol) and the mixture was stirred for 4.5 hours at 70° C. After being cooled to room temperature, thereto was added 5% aqueous potassium hydrogen sulfate solution and the mixture was extracted with ethyl acetate. The organic layer was washed with water and saturated brine, dried over anhydrous sodium sulfate and filtered. The solvent was removed in vacuo and purified by silica gel column chromatography to give the subject compound (169 mg, 55%).

$^1$H NMR (CDCl$_3$, 400 MHz) δ 7.71 (d, 2H, J=8.1 Hz), 7.39 (brd, 1H, J=8.0 Hz), 7.29 (dd, 1H, J=7.6, 7.6 Hz), 7.26 (d, 2H, J=8.1 Hz), 7.23 (brd, 1H, J=7.6 Hz), 7.28-7.21 (m, 1H), 7.16 (ddd, 1H, J=8.0, 7.1, 1.0 Hz), 7.09 (ddd, 1H, J=8.0, 7.1, 1.0 Hz), 7.02 (brs, 1H), 6.94 (brd, 1H, J=7.6 Hz), 5.40 (s, 2H), 4.53 (d, 1H, J=11.7 Hz), 4.38 (d, 1H, J=11.7 Hz), 4.28 (q, 1H, J=6.8 Hz), 3.70-3.49 (m, 8H), 2.54 (s, 3H), 2.45 (s, 3H), 1.40 (d, 3H, J=6.8 Hz).

Example 50-2

(2R)-2-[(3-{[2-Methyl-3-(4-methylbenzoyl)-1H-indol-1-yl]methyl-}benzyl)oxy]propionic acid

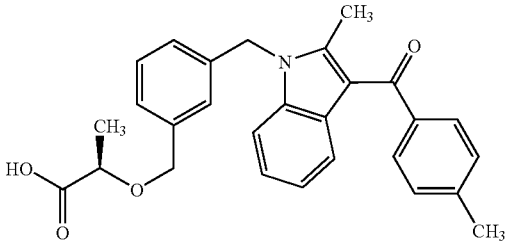

The compound of Example 50-1 (169 mg, 0.33 mmol) was dissolved in methanol (2 ml) and THF (2 ml) and thereto was 2N aqueous lithium hydroxide solution (2 ml). After stirring under reflux for 9.5 hours, the reaction mixture was diluted with water and washed with diethyl ether. The aqueous layer was adjusted to around pH 4 with 5% aqueous potassium hydrogen sulfate solution and extracted with ethyl acetate. The organic layer was washed with saturated brine, dried over anhydrous sodium sulfate and filtered. The solvent was removed in vacuo to give the subject compound (138 mg, 94%).

$^1$H NMR (CDCl$_3$, 400 MHz) δ 7.74 (d, 2H, J=8.1 Hz), 7.36 (brd, 1H, J=8.0 Hz), 7.30 (dd, 1H, J=7.8, 7.8 Hz), 7.29-7.22 (m, 4H), 7.15 (ddd, 1H, J=8.0, 7.1, 1.0 Hz), 7.08 (ddd, 1H, J=8.0, 7.1, 1.0 Hz), 7.00 (brs, 1H), 6.99 (brd, 1H, J=7.8 Hz), 5.41 (s, 2H), 4.58 (d, 1H, J=11.8 Hz), 4.50 (d, 1H, J=11.8 Hz), 4.01 (q, 1H, J=6.9 Hz), 2.54 (s, 3H), 2.45 (s, 3H), 1.44 (d, 3H, J=6.9 Hz).

Example 51

(2R)-2-[(3-{[3-(4-Methylbenzoyl)-1H-indol-1-yl]methyl}benzyl)oxy]propionic acid

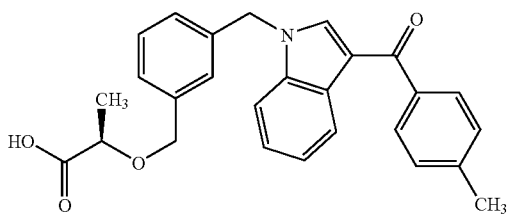

The subject compound was prepared in the same method as Example 50 by using the compounds of Reference example 22 and Reference example 56.

$^1$H NMR (CDCl$_3$, 400 MHz) δ 8.38-8.33 (m, 1H), 7.75 (d, 2H, J=8.1 Hz), 7.66 (s, 1H), 7.34-7.24 (m, 7H), 7.16 (brs, 1H), 7.07 (brd, 1H, J=7.1 Hz), 5.37 (s, 2H), 4.60 (d, 1H, J=11.7 Hz), 4.49 (d, 1H, J=11.7 Hz), 4.03 (q, 1H, J=6.9 Hz), 2.43 (s, 3H), 1.44 (d, 3H, J=6.9 Hz).

Example 52

(2R)-2-[(3-{[6-Bromo-3-(4-methylbenzoyl)-1H-indol-1-yl]methyl-}benzyl)oxy]propionic acid

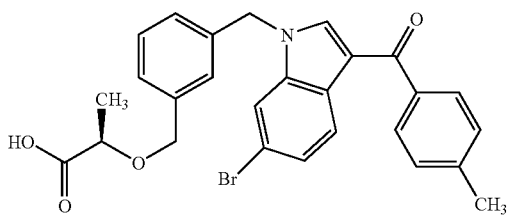

The subject compound was prepared in the same method as Example 50 by using the compounds of Reference example 21 and Reference example 56.

$^1$H NMR (CDCl$_3$, 400 MHz) δ 8.22 (d, 1H, J=8.5 Hz), 7.73 (d, 2H, J=8.1 Hz), 7.61 (s, 1H), 7.47 (d, 1H, J=1.6 Hz), 7.41 (dd, 1H, J=8.5, 1.6 Hz), 7.33 (dd, 1H, J=7.6, 7.6 Hz), 7.32-7.25 (m, 3H), 7.15 (brs, 1H), 7.05 (brd, 1H, J=7.6 Hz), 5.32 (s, 2H), 4.63 (d, 1H, J=11.7 Hz), 4.51 (d, 1H, J=11.7 Hz), 4.06 (q, 1H, J=6.9 Hz), 2.43 (s, 3H), 1.46 (d, 3H, J=6.9 Hz).

Example 53

(2R)-2-[(3-{[3-(4-Methylbenzoyl)-1H-pyrrol-1-yl]methyl}benzyl)oxy]propionic acid

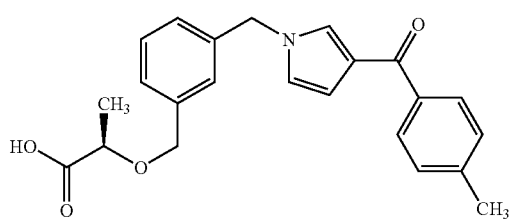

The subject compound was prepared in the same method as Example 50 by using the compounds of Reference example 58-2 and Reference example 56.

$^1$H NMR (CDCl$_3$, 400 MHz) δ 7.76 (d, 2H, J=8.1 Hz), 7.35 (dd, 1H, J=7.4, 7.4 Hz), 7.31 (dd, 1H, J=2.0, 2.0 Hz), 7.31 (brd, 1H, J=7.4 Hz), 7.25 (d, 2H, J=8.1 Hz), 7.18 (brs, 1H), 7.12 (brd, 1H, J=7.4 Hz), 6.71 (dd, 1H, J=2.9, 2.0 Hz), 6.68 (dd, 1H, J=2.9, 2.0 Hz), 5.10 (s, 2H), 4.64 (d, 1H, J=11.8 Hz), 4.58 (d, 1H, J=11.8 Hz), 4.06 (q, 1H, J=6.9 Hz), 2.42 (s, 3H), 1.48 (d, 3H, J=6.9 Hz).

Example 54

(2R)-2-[(3-{[6-Methoxy-2-methyl-3-(4-methylbenzoyl)-1H-indol-1-yl]methyl-}benzyl)oxy]propionic acid

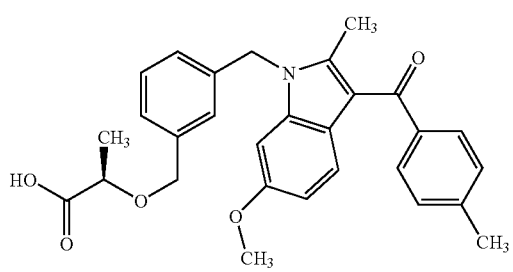

The subject compound was prepared in the same method as Example 50 by using the compounds of Reference example 12 and Reference example 56.

$^1$H NMR (CDCl$_3$, 400 MHz) δ 7.72 (d, 2H, J=8.1 Hz), 7.30 (dd, 1H, J=7.5, 7.5 Hz), 7.25 (d, 2H, J=8.1 Hz), 7.29-7.25 (m, 2H), 7.04 (brs, 1H), 6.97 (brd, 1H, J=7.5 Hz), 6.74 (dd, 1H, J=8.6, 2.3 Hz), 6.72 (d, 1H, J=2.3 Hz), 5.34 (s, 2H), 4.60 (d, 1H, J=11.8 Hz), 4.50 (d, 1H, J=11.8 Hz), 4.03 (q, 1H, J=6.9 Hz), 3.78 (s, 3H), 2.49 (s, 3H), 2.44 (s, 3H), 1.45 (d, 3H, J=6.9 Hz).

Example 55

(2R)-2-[(3-{[6-Methoxy-2-methyl-3,5-bis(4-methyl-benzoyl)-1H-indol-1-yl]methyl}benzyl)oxy]propionic acid

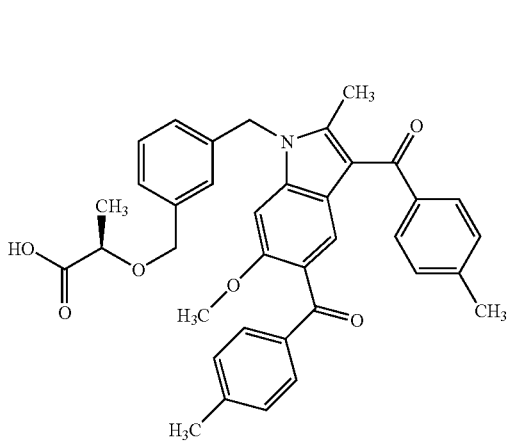

The subject compound was prepared in the same method as Example 50 by using the compounds of Reference example 13 and Reference example 56.

¹H NMR (CDCl₃, 400 MHz) δ 7.68 (d, 4H, J=8.0 Hz), 7.35 (s, 1H), 7.33 (dd, 1H, J=7.6, 7.6 Hz), 7.27 (brd, 1H, J=7.6 Hz), 7.19 (d, 2H, J=8.0 Hz), 7.18 (d, 2H, J=8.0 Hz), 7.04 (brs, 1H), 7.01 (brd, 1H, J=7.6 Hz), 6.76 (s, 1H), 5.40 (s, 2H), 4.60 (d, 1H, J=11.7 Hz), 4.51 (d, 1H, J=11.7 Hz), 4.03 (q, 1H, J=6.9 Hz), 3.69 (s, 3H), 2.50 (s, 3H), 2.39 (s, 3H), 2.36 (s, 3H), 1.45 (d, 3H, J=6.9 Hz).

Example 56

(2R)-2-[(3-{[5-Fluoro-3-(4-methylbenzoyl)-1H-indol-1-yl]methyl}benzyl)oxy]propionic acid

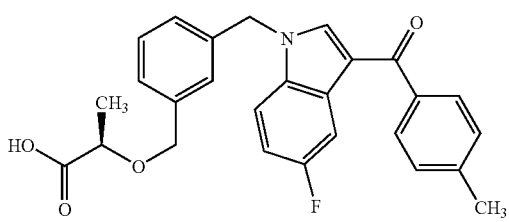

The subject compound was prepared in the same method as Example 50 by using the compounds of Reference example 17 and Reference example 56.

¹H NMR (CDCl₃, 400 MHz) δ 8.05 (dd, 1H, J=9.7, 2.6 Hz), 7.74 (d, 2H, J=8.1 Hz), 7.68 (s, 1H), 7.32 (dd, 1H, J=7.5, 7.5 Hz), 7.29 (brd, 1H, J=7.5 Hz), 7.28 (d, 2H, J=8.1 Hz), 7.21 (dd, 1H, J=9.0, 4.2 Hz), 7.15 (brs, 1H), 7.06 (brd, 1H, J=7.5 Hz), 7.01 (ddd, 1H, J=9.0, 9.0, 2.6 Hz), 5.35 (s, 2H), 4.61 (d, 1H, J=11.7 Hz), 4.50 (d, 1H, J=11.7 Hz), 4.05 (q, 1H, J=6.9 Hz), 2.43 (s, 3H), 1.45 (d, 3H, J=6.9 Hz).

Example 57

(2R)-2-[(3-{[5-Chloro-3-(4-methylbenzoyl)-1H-indol-1-yl]methyl}benzyl)oxy]propionic acid

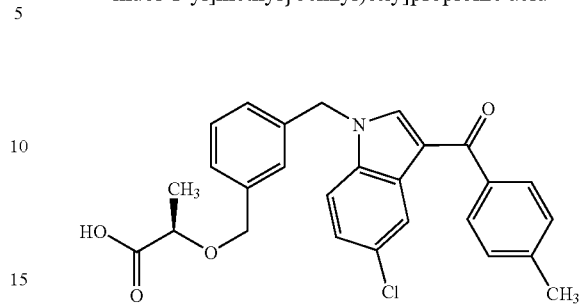

The subject compound was prepared in the same method as Example 50 by using the compounds of Reference example 16 and Reference example 56.

¹H NMR (CDCl₃, 400 MHz) δ 8.39 (dd, 1H, J=1.9, 0.6 Hz), 7.73 (d, 2H, J=8.1 Hz), 7.66 (s, 1H), 7.32 (dd, 1H, J=7.5, 7.5 Hz), 7.29 (brd, 1H, J=7.5 Hz), 7.28 (d, 2H, J=8.1 Hz), 7.23 (dd, 1H, J=8.8, 1.9 Hz), 7.20 (dd, 1H, J=8.8, 0.6 Hz), 7.14 (brs, 1H), 7.05 (brd, 1H, J=7.5 Hz), 5.35 (s, 2H), 4.61 (d, 1H, J=11.7 Hz), 4.50 (d, 1H, J=11.7 Hz), 4.05 (q, 1H, J=6.9 Hz), 2.43 (s, 3H), 1.46 (d, 3H, J=6.9 Hz).

Example 58

(2R)-2-[(3-{[2-Methyl-3-(4-methylbenzoyl)-5-(trifluoromethoxy)-1H-indol-1-yl]methyl}benzyl)oxy] propionic acid

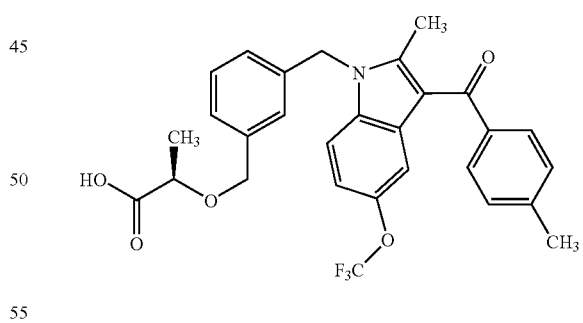

The subject compound was prepared in the same method as Example 50 by using the compounds of Reference example 24 and Reference example 56.

¹H NMR (CDCl₃, 400 MHz) δ 7.69 (d, 2H, J=8.1 Hz), 7.30 (dd, 1H, J=7.3, 7.3 Hz), 7.26 (d, 2H, J=8.1 Hz), 7.29-7.24 (m, 2H), 7.21 (d, 1H, J=8.9 Hz), 7.05 (brs, 1H), 7.02 (brdd, 1H, J=8.9, 1.4 Hz), 6.93 (brd, 1H, J=7.3 Hz), 5.39 (s, 2H), 4.63 (d, 1H, J=11.8 Hz), 4.48 (d, 1H, J=11.8 Hz), 4.04 (q, 1H, J=6.9 Hz), 2.52 (s, 3H), 2.44 (s, 3H), 1.44 (d, 3H, J=6.9 Hz).

Example 59

(2R)-2-[(3-{[2-Methyl-3-(4-methylbenzoyl)-1H-pyrrolo[2,3-b]pyridin-1-yl]methyl-}benzyl)oxy]propionic acid

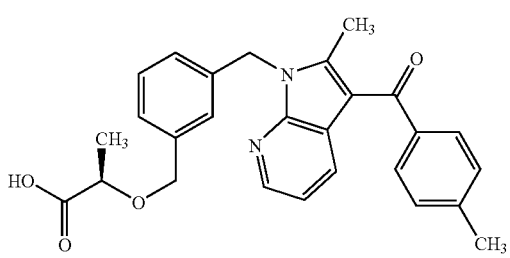

The subject compound was prepared in the same method as Example 50 by using the compounds of Reference example 20 and Reference example 56.

$^1$H NMR (CDCl$_3$, 400 MHz) δ 8.31 (dd, 1H, J=4.8, 1.5 Hz), 7.68 (d, 2H, J=8.1 Hz), 7.67 (dd, 1H, J=7.9, 1.5 Hz), 7.29-7.23 (m, 1H), 7.27 (d, 2H, J=8.1 Hz), 7.23 (brd, 1H, J=7.6 Hz), 7.12 (brs, 1H), 7.09 (dd, 1H, J=7.9, 4.8 Hz), 7.00 (brd, 1H, J=7.6 Hz), 5.67 (d, 1H, J=16.3 Hz), 5.59 (d, 1H, J=16.3 Hz), 4.57 (d, 1H, J=11.9 Hz), 4.43 (d, 1H, J=11.9 Hz), 4.00 (q, 1H, J=6.9 Hz), 2.54 (s, 3H), 2.44 (s, 3H), 1.41 (d, 3H, J=6.9 Hz).

Example 60

(2R)-2-[(3-[2-Methyl-3-(4-methylbenzoyl)-6-(trifluoromethyl)-1H-indol-1-yl]methyl}benzyl)oxy]propionic acid

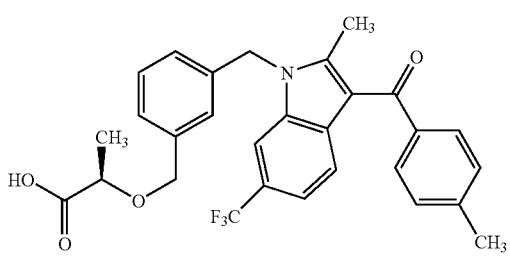

The subject compound was prepared in the same method as Example 50 by using the compounds of Reference example 26 and Reference example 56.

$^1$H NMR (CDCl$_3$, 400 MHz) δ 7.72 (d, 2H, J=8.1 Hz), 7.53 (brs, 1H), 7.43 (d, 1H, J=8.5 Hz), 7.33 (dd, 1H, J=7.6, 7.6 Hz), 7.27 (d, 2H, J=8.1 Hz), 7.31-7.24 (m, 2H), 7.00 (brs, 1H), 6.96 (brd, 1H, J=7.6 Hz), 5.48 (d, 1H, J=17.6 Hz), 5.43 (d, 1H, J=17.6 Hz), 4.60 (d, 1H, J=11.9 Hz), 4.51 (d, 1H, J=11.9 Hz), 4.02 (q, 1H, J=6.9 Hz), 2.56 (s, 3H), 2.45 (s, 3H), 1.44 (d, 3H, J=6.9 Hz).

Example 61

(2R)-2-[(3-{[3-(4-Methylbenzoyl)-1H-indazol-1-yl]methyl}benzyl)oxy]propanoic acid

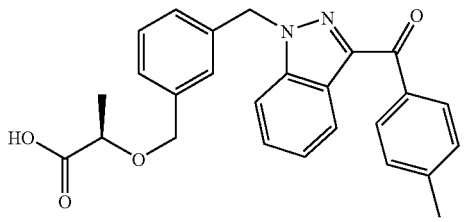

The subject compound was prepared in the same method as Example 5 by using the compounds of Reference example 56 and Reference example 46.

LC-MS R.T. 4.31 min., m/z 429.4 (M+1)

Example 62

(2R)-2-[(3-{[3-(4-Methylbenzoyl)-6-(trifluoromethyl)-1H-indazol-1-yl]methyl-}benzyl)oxy]propanoic acid

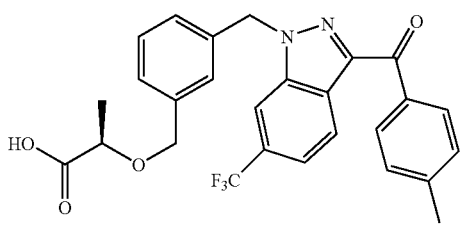

The subject compound was prepared in the same method as Example 5 by using the compounds of Reference example 56 and Reference example 47.

LC-MS R.T. 4.64 min., m/z 497.5 (M+1)

Example 63

1-[(3-{[6-Methoxy-2-methyl-3-(4-methylbenzoyl)-1H-indol-1-yl]methyl-}benzyl)oxy]cyclobutanecarboxylic acid

Example 63-1

Ethyl 1-[(3-{[6-methoxy-2-methyl-3-(4-methylbenzoyl)-1H-indol-1-yl]methyl}benzyl)oxy]cyclobutancarboxylate

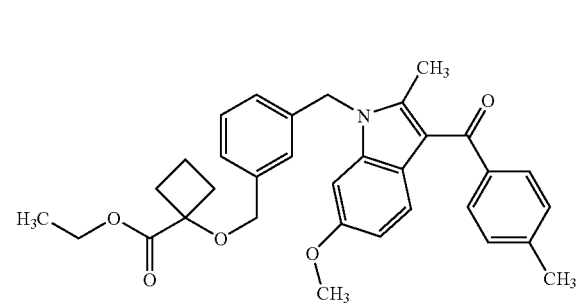

To the compound of Reference example 57-3 (50 mg, 0.13 mmol) in THF (1 ml) was added sodium hydride (55% in paraffin liquid) (8 mg, 0.19 mmol) and the mixture was stirred for 30 minutes at room temperature. Thereto was added ethyl 1-bromocyclobutanecarboxylate and the mixture was stirred for 5 hours at 60° C. After being cooled to room temperature, thereto was added 5% aqueous potassium hydrogen sulfate solution and the mixture was extracted with ethyl acetate. The organic layer was washed with saturated brine, dried over anhydrous sodium sulfate and filtered. The solvent was removed in vacuo and the residue was purified by silica gel column chromatography to give the subject compound (14 mg, 22%).

LC-MS: R.T. 4.67 min., m/z 526 (M+1)

Example 63-2

1-[(3-{[6-Methoxy-2-methyl-3-(4-methyl-benzoyl)-1H-indol-1-yl]methyl}benzyl)oxy]cyclobutanecarboxylic acid

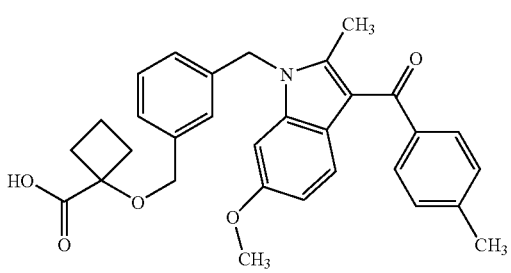

The compound of Example 63-1 (14 mg, 0.03 mmol) was dissolved in methanol (1 ml) and THF (1 ml) and thereto was added 1N aqueous sodium hydroxide solution (1 ml), followed by stirring for 20 hours. The reaction mixture was diluted with water and washed with diethyl ether. The aqueous layer was adjusted to around pH 4 with 5% aqueous potassium hydrogen sulfate solution and the solution was extracted with ethyl acetate. The organic layer was washed with saturated brine, dried over anhydrous sodium sulfate and filtered. The solvent was removed in vacuo to give the subject compound (6 mg, 45%).

LC-MS: R.T. 4.11 min., m/z 498 (M+1)

Example 64

[(3-{[6-Methoxy-2-methyl-3-(4-methylbenzoyl)-1H-indol-1-yl]methyl}benzyl)oxy]acetic acid

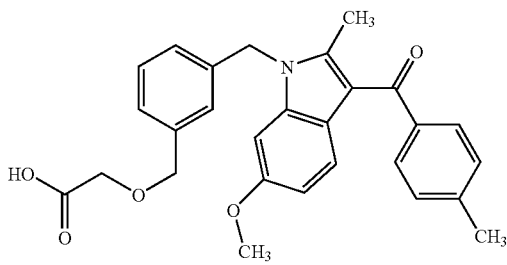

The subject compound was prepared in the same method as Example 63 by using the compound of Reference example 57-3 and t-butyl 2-bromoacetate.

$^1$H NMR (CDCl$_3$, 400 MHz) δ 7.72 (d, 2H, J=8.0 Hz), 7.31 (dd, 1H, J=7.6, 7.6 Hz), 7.25 (d, 2H, J=8.0 Hz), 7.28-7.22 (m, 2H), 7.04 (brs, 1H), 7.00 (brd, 1H, J=7.6 Hz), 6.74 (dd, 1H, J=8.7, 2.3 Hz), 6.71 (d, 1H, J=2.3 Hz), 5.35 (s, 2H), 4.58 (s, 2H), 4.09 (s, 2H), 3.78 (s, 3H), 2.49 (s, 3H), 2.44 (s, 3H).

Example 65

Methyl 1-[(3-{[6-methoxy-2-methyl-3-(4-methylbenzoyl)-1H-indol-1-yl]methyl}benzyl)oxy]cyclohexanecarboxylate

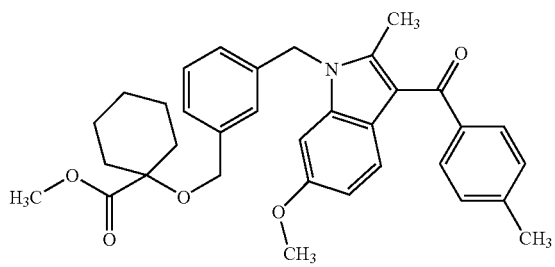

The subject compound was prepared in the same method as Example 63-1 by using the compound of Reference example 57-3 and methyl 1-bromocyclohexanecarboxylate.

LC-MS: R.T. 4.52 min., m/z 540 (M+1)

Example 66

1-[(3-{[6-Methoxy-2-methyl-3-(4-methylbenzoyl)-1H-indol-1-yl]methyl-}benzyl)oxy]cyclopropanecarboxylic acid Example 66-1

Ethyl 1-[(3-{[6-methoxy-2-methyl-3-(4-methylbenzoyl)-1H-indol-1-yl]methyl-}benzyl)oxy]cyclopropanecarboxylate

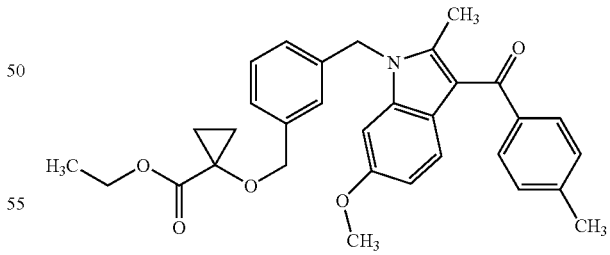

To ethyl 1-hydroxycyclopropanecarboxylate (32 mg, 0.24 mmol) in THF (1 ml) was added sodium hydride (55% in paraffin liquid)(11 mg, 0.24 mmol) and the mixture was stirred for 30 minutes at room temperature. Thereto was added the compound of Reference example 57-4 (75 mg, 0.16 mmol) and the mixture was stirred for 5 hours at 60° C. After being cooled to room temperature, thereto was added 5% aqueous potassium hydrogen sulfate solution and the mixture was extracted with ethyl acetate. The organic layer was washed with saturated brine, dried over anhydrous sodium sulfate and filtered. The solvent was removed in vacuo and the residue was purified by silica gel column chromatography to give the subject compound (10 mg, 12%).

$^1$H NMR (CDCl$_3$, 400 MHz) δ 7.69 (d, 2H, J=8.1 Hz), 7.29 (d, 1H, J=8.7 Hz), 7.25 (d, 2H, J=8.1 Hz), 7.31-7.23 (m, 2H), 7.14 (brs, 1H), 6.86 (brd, 1H, J=7.6 Hz), 6.74 (dd, 1H, J=8.7, 2.3 Hz), 6.71 (d, 1H, J=2.3 Hz), 5.33 (s, 2H), 4.60 (s, 2H), 4.20 (q, 2H, J=7.2 Hz), 3.78 (s, 3H), 2.48 (s, 3H), 2.44 (s, 3H), 1.36-1.32 (m, 2H), 1.27 (t, 3H, J=7.2 Hz), 1.22-1.17 (m, 2H).

Example 66-2

1-[(3-{[6-Methoxy-2-methyl-3-(4-methylbenzoyl)-1H-indol-1-yl]methyl-}benzyl)oxy]cyclopropanecarboxylic acid

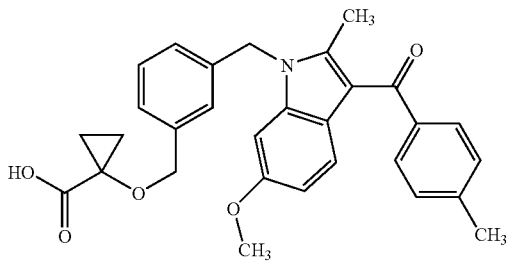

The compound of Example 66-1 (10 mg, 0.02 mmol) was dissolved in methanol (1 ml) and THF (1 ml) and thereto was added 1N aqueous sodium hydroxide solution (1 ml), followed by stirring for 20 hours. The reaction mixture was diluted with water and washed with diethyl ether. The aqueous layer was adjusted to around pH4 with 5% aqueous potassium hydrogen sulfate solution and the solution was extracted with ethyl acetate. The organic layer was washed with saturated brine, dried over anhydrous sodium sulfate and filtered. The solvent was removed in vacuo to give the subject compound (quant.).

$^1$H NMR (CDCl$_3$, 400 MHz) δ 7.72 (d, 2H, J=8.1 Hz), 7.28 (dd, 1H, J=7.5, 7.5 Hz), 7.26 (d, 1H, J=8.6 Hz), 7.25 (d, 2H, J=8.1 Hz), 7.28-7.23 (m, 1H), 7.09 (brs, 1H), 6.93 (brd, 1H, J=7.5 Hz), 6.73 (dd, 1H, J=8.6, 2.3 Hz), 6.72 (d, 1H, J=2.3 Hz), 5.34 (s, 2H), 4.59 (s, 2H), 3.77 (s, 3H), 2.49 (s, 3H), 2.44 (s, 3H), 1.43-1.38 (m, 2H), 1.29-1.23 (m, 2H).

Example 67

2-[(3-{[6-Methoxy-2-methyl-3-(4-methylbenzoyl)-1H-indol-1-yl]methyl}benzyl)oxy]-2-methylpropionic acid

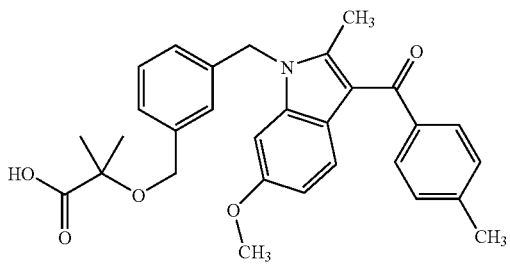

The subject compound was prepared in the same method as Example 66 by using the compound of Reference example 57-4 and ethyl 2-hydroxyisobutyrate.

$^1$H NMR (CDCl$_3$, 400 MHz) δ 7.73 (d, 2H, J=8.1 Hz), 7.30 (dd, 1H, J=7.8, 7.8 Hz), 7.29-7.23 (m, 4H), 7.02-6.99 (m, 2H), 6.74 (dd, 1H, J=8.5, 2.3 Hz), 6.72 (d, 1H, J=2.3 Hz), 5.35 (s, 2H), 4.42 (s, 2H), 3.78 (s, 3H), 2.51 (s, 3H), 2.44 (s, 3H), 1.51 (s, 6H).

Example 68

(2R)-2-{[(2E)-3-(4-{[2-(4-Methylbenzoyl)-1H-pyrrol-1-yl]methyl-}phenyl)prop-2-en-1-yl]oxy}propionic acid Example 68-1

[1-(4-{(1E)-3-[(1R)-1-Methyl-2-morpholin-4-yl-2-oxoethoxy]prop-1-en-1-yl}benzyl)-1H-pyrrol-2-yl](4-methylphenyl)methanone

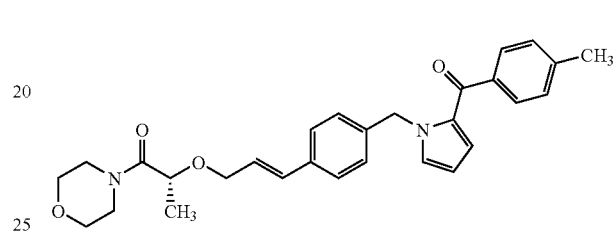

The compound of Reference example 63 (156 mg, 0.79 mmol), the compound of Reference example 59 (262 mg, 0.65 mmol), palladium acetate (15 mg, 0.07 mmol), tri n-butylphosphine (27 mg, 0.13 mmol) and potassium carbonate (118 mg, 0.85 mmol) were dissolved in DMF (3 ml) and the solution was stirred for 6 hours at 80° C. Thereto was added 10% aqueous thiosodium sulfate solution and the mixture was extracted with ethyl acetate. The organic layer was washed with 10% aqueous sodium thiosulfate solution and saturated brine, dried over anhydrous sodium sulfate and filtered. The solvent was removed in vacuo and the residue was purified by silica gel column chromatography to give the subject compound (139 mg, 45%).

$^1$H NMR (CDCl$_3$, 400 MHz) δ 7.69 (d, 2H, J=8.1 Hz), 7.31 (d, 2H, J=8.1 Hz), 7.23 (d, 2H, J=8.1 Hz), 7.13 (d, 2H, J=8.1 Hz), 7.00 (dd, 1H, J=2.4, 1.7 Hz), 6.77 (dd, 1H, J=4.0, 1.7 Hz), 6.55 (brd, 1H, J=15.9 Hz), 6.22 (ddd, 1H, J=15.9, 6.1, 6.1 Hz), 6.21 (dd, 1H, J=4.0, 2.4 Hz), 5.63 (s, 2H), 4.31 (q, 1H, J=6.8 Hz), 4.19 (ddd, 1H, J=12.5, 6.1, 1.4 Hz), 4.09 (ddd, 1H, J=12.5, 6.1, 1.4 Hz), 3.78-3.55 (m, 8H), 2.41 (s, 3H), 1.43 (d, 3H, J=6.8 Hz).

Example 68-2

(2R)-2-{[(2E)-3-(4-{[2-(4-Methylbenzoyl)-1H-pyrrol-1-yl]methyl}phenyl)prop-2-en-1-yl]oxy}propionic acid

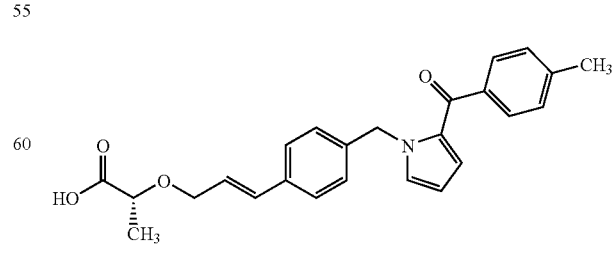

The compound of Example 68-1 (213 mg, 0.45 mmol) was dissolved in methanol (1 ml) and THF (1 ml) and thereto was added 2N aqueous lithium hydroxide (0.9 ml), followed by stirring under reflux for 7 hours. The reaction mixture was diluted with water and washed with diethyl water. The aqueous layer was adjusted to around pH4 with 5% aqueous potassium hydrogen sulfate solution and the solution was extracted with ethyl acetate. The organic layer was washed with saturated brine, dried over anhydrous sodium sulfate and filtered. The solvent was removed in vacuo to give the subject compound (155 mg, 85%).

$^1$H NMR (CDCl$_3$, 400 MHz) δ 7.69 (d, 2H, J=8.1 Hz), 7.31 (d, 2H, J=8.2 Hz), 7.23 (d, 2H, J=8.1 Hz), 7.13 (d, 2H, J=8.2 Hz), 7.00 (dd, 1H, J=2.3, 1.7 Hz), 6.77 (dd, 1H, J=4.0, 1.7 Hz), 6.57 (brd, 1H, J=16.0 Hz), 6.23 (ddd, 1H, J=16.0, 6.3, 6.3 Hz), 6.21 (dd, 1H, J=4.0, 2.3 Hz), 5.63 (s, 2H), 4.28 (ddd, 1H, J=12.3, 6.3, 1.3 Hz), 4.15 (ddd, 1H, J=12.3, 6.3, 1.3 Hz), 4.10 (q, 1H, J=6.9 Hz), 2.41 (s, 3H), 1.48 (d, 3H, J=6.9 Hz).

Example 69

(2R)-2-{[(2E)-3-(4-{[3-(4-Methylbenzoyl)-1H-pyrrol-1-yl]methyl}phenyl)prop-2-en-1-yl]oxy}propionic acid

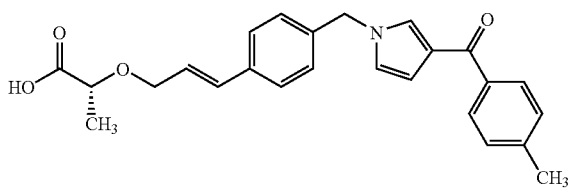

The subject compound was prepared in the same method as Example 68 by using the compounds of Reference example 63 and Reference example 60.

$^1$H NMR (CDCl$_3$, 400 MHz) δ 7.74 (d, 2H, J=8.1 Hz), 7.36 (d, 2H, J=8.2 Hz), 7.28 (dd, 1H, J=1.9, 1.9 Hz), 7.25 (d, 2H, J=8.1 Hz), 7.11 (d, 2H, J=8.2 Hz), 6.71 (dd, 1H, J=2.9, 1.9 Hz), 6.68 (dd, 1H, J=2.9, 1.9 Hz), 6.61 (brd, 1H, J=15.9 Hz), 6.28 (ddd, 1H, J=15.9, 6.2, 6.2 Hz), 5.07 (s, 2H), 4.31 (ddd, 1H, J=12.4, 6.2, 1.3 Hz), 4.19 (ddd, 1H, J=12.4, 6.2, 1.3 Hz), 4.12 (q, 1H, J=6.9 Hz), 2.41 (s, 3H), 1.49 (d, 3H, J=6.9 Hz).

Example 70

(2R)-2-{[(2E)-3-(4-{[3-(4-Methylbenzoyl)-1H-indol-1-yl]methyl-}phenyl)prop-2-en-1-yl]oxy}propionic acid

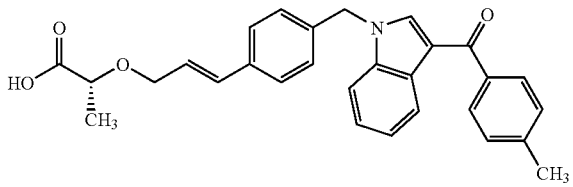

The subject compound was prepared in the same method as Example 68 by using the compounds of Reference example 63 and Reference example 61.

$^1$H NMR (CDCl$_3$, 400 MHz) δ 8.43 (dd, 1H, J=7.6, 1.1 Hz), 7.75 (d, 2H, J=8.1 Hz), 7.63 (s, 1H), 7.35-7.25 (m, 7H), 7.08 (d, 2H, J=8.2 Hz), 6.58 (brd, 1H, J=16.0 Hz), 6.28 (ddd, 1H, J=16.0, 6.2, 6.2 Hz), 5.35 (s, 2H), 4.28 (ddd, 1H, J=12.4, 6.2, 1.2 Hz), 4.18 (ddd, 1H, J=12.4, 6.2, 1.2 Hz), 4.10 (q, 1H, J=6.9 Hz), 2.43 (s, 3H), 1.48 (d, 3H, J=6.9 Hz).

Example 71

[1-(4-{(2E)-3-[1R)-1-Methyl-2-morpholin-4-yl-2-oxoethoxy]prop-2-en-1-yl}benzyl)-1H-indol-3-yl](4-methylphenyl)methanone

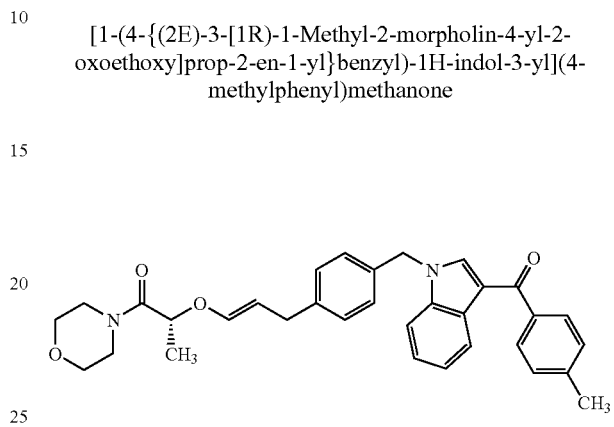

The subject compound was prepared in the same method as Example 68-1 by using the compounds of Reference example 63 and Reference example 61.

$^1$H NMR (CDCl$_3$, 400 MHz) δ 8.42 (dd, 1H, J=8.2, 1.6 Hz), 7.74 (d, 2H, J=8.1 Hz), 7.63 (s, 1H), 7.35-7.25 (m, 5H), 7.11 (d, 2H, J=8.2 Hz), 7.05 (d, 2H, J=8.2 Hz), 6.23 (d, 1H, J=12.5 Hz), 5.32 (s, 2H), 5.00 (dt, 1H, J=12.5, 7.4 Hz), 4.55 (q, 1H, J=6.8 Hz), 3.70-3.51 (m, 8H), 3.21 (d, 2H, J=7.4 Hz), 2.43 (s, 3H), 1.46 (d, 3H, J=6.8 Hz).

Example 72

[1-(4-{(2Z)-3-[(1R)-1-Methyl-2-morpholin-4-yl-2-oxoethoxy]prop-2-en-1-yl}benzyl)-1H-indol-3-yl](4-methylphenyl)methanone

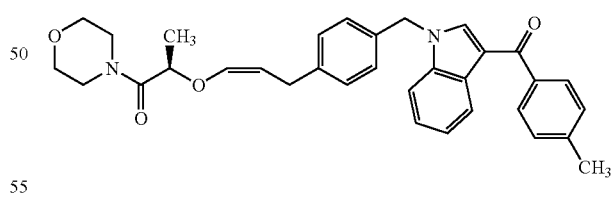

The subject compound was prepared in the same method as Example 68-1 by using the compounds of Reference example 63 and Reference example 61.

$^1$H NMR (CDCl$_3$, 400 MHz) δ 8.42 (dd, 1H, J=8.2, 1.4 Hz), 7.74 (d, 2H, J=8.1 Hz), 7.63 (s, 1H), 7.34-7.25 (m, 3H), 7.28 (d, 2H, J=8.1 Hz), 7.15 (d, 2H, J=8.1 Hz), 7.05 (d, 2H, J=8.1 Hz), 6.06 (ddd, 1H, J=6.2, 1.4, 1.4 Hz), 5.33 (s, 2H), 4.65 (ddd, 1H, J=7.5, 7.5, 6.2 Hz), 4.55 (q, 1H, J=6.8 Hz), 3.69-3.53 (m, 8H), 3.42 (brdd, 1H, J=15.6, 7.5 Hz), 3.36 (brdd, 1H, J=15.6, 7.5 Hz), 2.43 (s, 3H), 1.47 (d, 3H, J=6.8 Hz).

Example 73

(2R)-2-{[(2E)-3-(4-{[2,5-Dimethyl-3-(4-methylbenzoyl)-1H-indol-1-yl]methyl-}phenyl)prop-2-en-1-yl]oxy}propionic acid

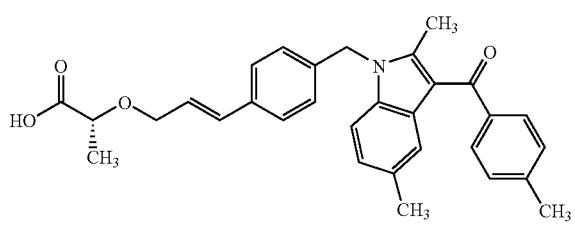

The subject compound was prepared in the same method as Example 68 by using the compounds of Reference example 63 and Reference example 62.

$^1$H NMR (CDCl$_3$, 400 MHz) δ 7.71 (d, 1H, J=8.1 Hz), 7.31 (d, 2H, J=8.1 Hz), 7.28 (brs, 1H), 7.25 (d, 2H, J=8.1 Hz), 7.13 (d, 1H, J=8.3 Hz), 6.99 (dd, 1H, J=8.3, 1.4 Hz), 6.97 (d, 2H, J=8.1 Hz), 6.58 (brd, 1H, J=15.9 Hz), 6.24 (ddd, 1H, J=15.9, 6.2, 6.2 Hz), 5.34 (s, 2H), 4.28 (ddd, 1H, J=12.4, 6.2, 1.2 Hz), 4.18 (ddd, 1H, J=12.4, 6.2, 1.2 Hz), 4.11 (q, 1H, J=6.9 Hz), 2.46 (s, 3H), 2.44 (s, 3H), 2.34 (s, 3H), 1.48 (d, 3H, J=6.9 Hz).

Example 74

(2R)-2-{[(2E)-3-(4-{[2-Methyl-3-(4-methylbenzoyl)-1H-pyrrolo[2,3-b]pyridin-1-yl]methyl-}phenyl)prop-2-en-1-yl]oxy}propionic acid

Example 74-1

[2-Methyl-1-(4-{(1E)-3-[(1R)-1-methyl-2-morpholin-4-yl-2-oxoethoxy]prop-1-en-1-yl}benzyl)-1H-pyrrolo[2,3-b]pyridin-3-yl] (4-methylphenyl)methanone

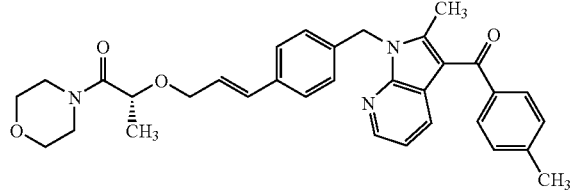

To the compound of Reference example 65 (51 mg, 0.17 mmol) in methylene chloride (1 ml) was added under ice cooling thionyl chloride (24 μl, 0.34 mmol) and the mixture was stirred for 1 hour. The solvent was removed in vacuo to give the residue.

To the compound of Reference example 20 (63 mg, 0.25 mmol) in DMF (2 ml) was added potassium carbonate (69 mg, 0.50 mmol) and the mixture was stirred for 30 minutes at room temperature. Thereto were added the above residue and tetra n-butylammonium iodide (6 mg, 0.02 mmol) and the mixture was stirred for 4 hours and 50 minutes at 80° C. After being cooled to room temperature, thereto was added 5% aqueous potassium hydrogen sulfate solution and the mixture was extracted with ethyl acetate. The organic layer was washed with water and saturated brine, dried over anhydrous sodium sulfate and filtered. The solvent was removed in vacuo and the residue was purified by silica gel column chromatography to give the subject compound (33 mg, 37%).

$^1$H NMR (CDCl$_3$, 400 MHz) δ 8.30 (dd, 1H, J=4.7, 1.5 Hz), 7.66 (d, 2H, J=8.1 Hz), 7.65 (dd, 1H, J=7.9, 1.5 Hz), 7.30 (d, 2H, J=8.1 Hz), 7.26 (d, 2H, J=8.1 Hz), 7.08 (d, 2H, J=8.1 Hz), 7.08 (dd, 1H, J=7.9, 4.7 Hz), 6.55 (brd, 1H, J=15.9 Hz), 6.22 (ddd, 1H, J=15.9, 6.0, 6.0 Hz), 5.59 (s, 2H), 4.31 (q, 1H, J=6.8 Hz), 4.18 (ddd, 1H, J=12.6, 6.0, 1.2 Hz), 4.09 (ddd, 1H, J=12.6, 6.0, 1.2 Hz), 3.77-3.59 (m, 8H), 2.54 (s, 3H), 2.44 (s, 3H), 1.43 (d, 3H, J=6.8 Hz).

Example 74-2

(2R)-2-{[(2E)-3-(4-{[2-Methyl-3-(4-methylbenzoyl)-1H-pyrrolo[2,3-b]pyridin-1-yl]methyl-}phenyl)prop-2-en-1-yl]oxy}propionic acid

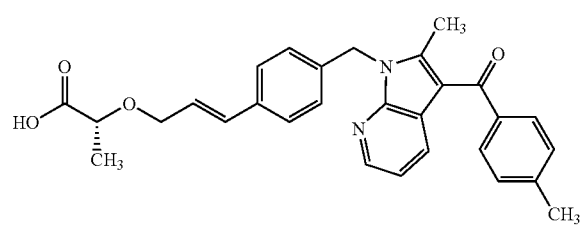

The compound of Example 74-1 (33 mg, 0.06 mmol) was dissolved in methanol (1 ml) and THF (1 ml) and thereto was added 2N aqueous lithium hydroxide solution (1 ml), followed by stirring under reflux for 8 hours. The mixture was diluted with water and washed with ethyl ether. The aqueous layer was adjusted to around pH 4 with 5% aqueous potassium hydrogen sulfate solution and the solution was extracted with ethyl acetate. The organic layer was washed with saturated brine, dried over anhydrous sodium sulfate and filtered. The solvent was removed in vacuo to give the subject compound (28 mg, 96%).

$^1$H NMR (CDCl$_3$, 400 MHz) δ 8.32 (dd, 1H, J=4.7, 1.5 Hz), 7.68 (dd, 1H, J=7.9, 1.5 Hz), 7.66 (d, 2H, J=8.1 Hz), 7.30 (d, 2H, J=8.1 Hz), 7.27 (d, 2H, J=8.1 Hz), 7.09 (dd, 1H, J=7.9, 4.7 Hz), 7.07 (d, 2H, J=8.1 Hz), 6.56 (brd, 1H, J=15.9 Hz), 6.21 (ddd, 1H, J=15.9, 6.3, 6.3 Hz), 5.61 (s, 2H), 4.23 (brdd, 1H, J=12.3, 6.3 Hz), 4.08 (brdd, 1H, J=12.3, 6.3 Hz), 4.08 (q, 1H, J=6.9 Hz), 2.54 (s, 3H), 2.45 (s, 3H), 1.47 (d, 3H, J=6.9 Hz).

Example 75

(2R)-2-{[(2E)-3-(4-{[2-(4-Methylbenzoyl)-1H-imidazol-1-yl]methyl}phenyl) prop-2-en-1-yl]oxy}propionic acid

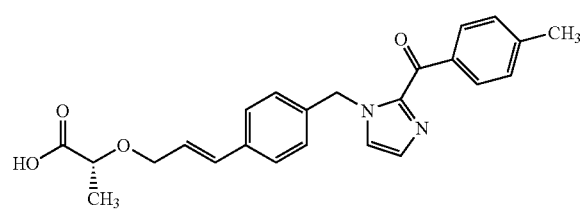

The subject compound was prepared in the same method as Example 74 by using the compounds of Reference example 65 and Reference example 67.

$^1$H NMR (CDCl$_3$, 400 MHz) δ 8.12 (d, 2H, J=8.2 Hz), 7.35 (d, 2H, J=8.2 Hz), 7.27 (d, 2H, J=8.2 Hz), 7.29-7.24 (m, 1H), 7.19 (d, 2H, J=8.2 Hz), 7.12 (d, 1H, J=0.9 Hz), 6.59 (brd, 1H, J=15.9 Hz), 6.26 (ddd, 1H, J=15.9, 6.2, 6.2 Hz), 5.64 (s, 2H), 4.28 (ddd, 1H, J=12.4, 6.2, 1.3 Hz), 4.16 (brdd, 1H, J=12.4, 6.2 Hz), 4.08 (q, 1H, J=6.9 Hz), 2.41 (s, 3H), 1.46 (d, 3H, J=6.9 Hz).

Example 76

(2R)-2-{[(2E)-3-(4-{[2-(4-Methylbenzoyl)-1H-benzimidazol-1-yl]methyl-}phenyl)prop-2-en-1-yl]oxy}propionic acid

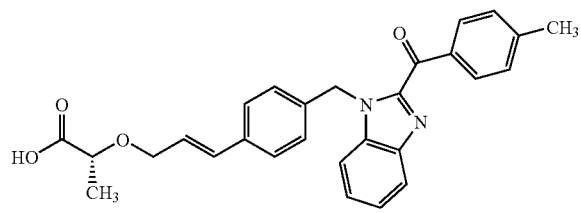

The subject compound was prepared in the same method as Example 74 by using the compounds of Reference example 65 and Reference example 68.

LC-MS: R.T. 4.23 min., m/z 455 (M+1)

Example 77

(2R)-2-{[(2E)-3-(4-{[3-(4-Methylbenzoyl)-1H-indazol-1-yl]methyl}phenyl)prop-2-en-1-yl]oxy}propionic acid

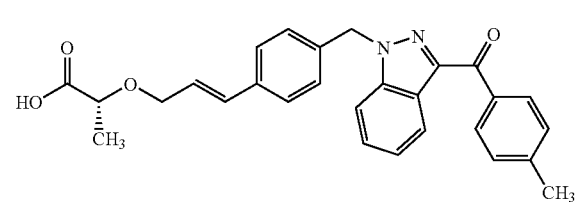

The subject compound was prepared in the same method as Example 74 by using the compounds of Reference example 65 and Reference example 46.

$^1$H NMR (CDCl$_3$, 400 MHz) δ 8.46 (d, 1H, J=8.0 Hz), 8.26 (d, 2H, J=8.2 Hz), 7.42-7.30 (m, 7H), 7.19 (d, 2H, J=8.1 Hz), 6.59 (brd, 1H, J=15.9 Hz), 6.25 (ddd, 1H, J=15.9, 6.2, 6.2 Hz), 5.69 (s, 2H), 4.28 (ddd, 1H, J=12.4, 6.2, 1.2 Hz), 4.18 (brdd, 1H, J=12.4, 6.2 Hz), 4.10 (q, 1H, J=6.9 Hz), 2.45 (s, 3H), 1.48 (d, 3H, J=6.9 Hz).

Example 78

(2R)-2-{[(2E)-3-(4-{[2-Methyl-3-(4-methylbenzoyl)-1H-indol-1-yl]methyl-}phenyl)prop-2-en-1-yl]oxy}propionic acid

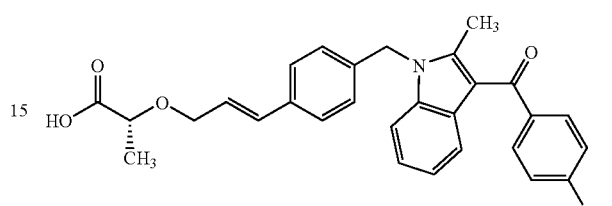

The subject compound was prepared in the same method as Example 74 by using the compounds of Reference example 65 and Reference example 23.

$^1$H NMR (CDCl$_3$, 400 MHz) δ 7.71 (d, 2H, J=8.1 Hz), 7.39 (brd, 1H, J=8.1 Hz), 7.31 (d, 2H, J=8.2 Hz), 7.25 (d, 2H, J=8.1 Hz), 7.28-7.23 (m, 1H), 7.16 (ddd, 1H, J=8.1, 7.1, 1.1 Hz), 7.08 (ddd, 1H, J=8.1, 7.1, 1.1 Hz), 6.98 (d, 2H, J=8.2 Hz), 6.58 (brd, 1H, J=15.9 Hz), 6.24 (ddd, 1H, J=15.9, 6.2, 6.2 Hz), 5.38 (s, 2H), 4.28 (ddd, 1H, J=12.4, 6.2, 1.2 Hz), 4.17 (brdd, 1H, J=12.4, 6.2 Hz), 4.10 (q, 1H, J=6.9 Hz), 2.53 (s, 3H), 2.44 (s, 3H), 1.48 (d, 3H, J=6.9 Hz).

Example 79

2-Methyl-2-{[(2E)-3-(4-{[2-methyl-3-(4-methylbenzoyl)-1H-indol-1-yl]methyl-}phenyl)prop-2-en-1-yl]oxy}propionic acid

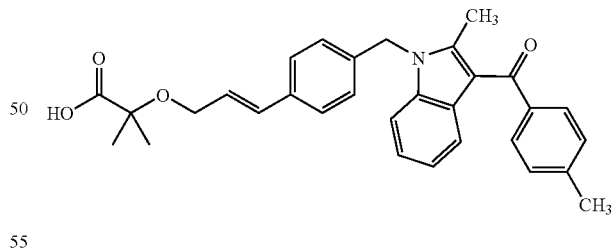

The subject compound was prepared in the same method as Example 74 by using the compounds of Reference example 66 and Reference example 23.

$^1$H NMR (CDCl$_3$, 400 MHz) δ 7.71 (d, 2H, J=8.1 Hz), 7.39 (brd, 1H, J=8.2 Hz), 7.31 (d, 2H, J=8.2 Hz), 7.26 (d, 2H, J=8.1 Hz), 7.28-7.23 (m, 1H), 7.16 (ddd, 1H, J=8.2, 7.1, 1.2 Hz), 7.08 (ddd, 1H, J=8.2, 7.1, 1.2 Hz), 6.98 (d, 2H, J=8.2 Hz), 6.58 (brd, 1H, J=15.9 Hz), 6.25 (ddt, 1H, J=15.9, 5.9 Hz), 5.38 (s, 2H), 4.16 (dd, 2H, J=5.9, 1.1 Hz), 2.52 (s, 3H), 2.44 (s, 3H), 1.52 (s, 6H).

Example 80

2-Methyl-2-{[(2E)-3-(4-{[2-methyl-3-(4-methylben-zoyl)-5-(trifluoromethoxy)-1H-indol-1-yl]methyl-}phenyl)prop-2-en-1-yl]oxy}propionic acid

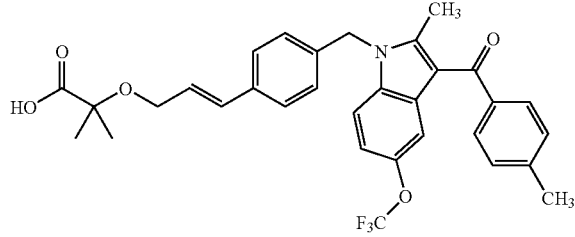

The subject compound was prepared in the same method as Example 74 by using the compounds of Reference example 66 and Reference example 24.

$^1$H NMR (CDCl$_3$, 400 MHz) δ 7.68 (d, 2H, J=8.1 Hz), 7.33 (d, 2H, J=8.1 Hz), 7.29 (brs, 1H), 7.27 (d, 2H, J=8.1 Hz), 7.21 (d, 1H, J=8.9 Hz), 7.02 (dd, 1H, J=8.9, 1.4 Hz), 7.06 (d, 2H, J=8.1 Hz), 6.58 (brd, 1H, J=15.9 Hz), 6.27 (dt, 1H, J=15.9, 6.0 Hz), 5.37 (s, 2H), 4.15 (brd, 2H, J=6.0 Hz), 2.51 (s, 3H), 2.44 (s, 3H), 1.52 (s, 6H).

Example 81

2-{[(2E)-3-(4-{[6-Methoxy-2-methyl-3-(4-methyl-benzoyl)-1H-indol-1-yl]methyl-}phenyl)prop-2-en-1-yl]oxy}-2-methylpropionic acid

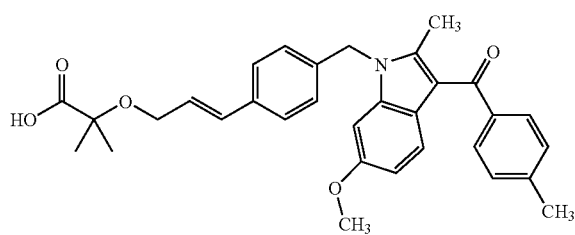

The subject compound was prepared in the same method as Example 74 by using the compounds of Reference example 66 and Reference example 12.

$^1$H NMR (CDCl$_3$, 400 MHz) δ 7.69 (d, 2H, J=8.1 Hz), 7.32 (d, 2H, J=8.2 Hz), 7.29 (d, 1H, J=8.7 Hz), 7.25 (d, 2H, J=8.1 Hz), 6.98 (d, 2H, J=8.2 Hz), 6.74 (dd, 1H, J=8.7, 2.3 Hz), 6.71 (d, 1H, J=2.3 Hz), 6.58 (brd, 1H, J=15.9 Hz), 6.26 (dt, 1H, J=15.9, 6.0 Hz), 5.30 (s, 2H), 4.15 (dd, 2H, J=6.0, 1.0 Hz), 3.77 (s, 3H), 2.48 (s, 3H), 2.43 (s, 3H), 1.52 (s, 6H).

Example 82

2-Methyl-2-{[(2E)-3-(4-{[2-methyl-3-(4-methylben-zoyl)-1H-pyrrolo[2,3-b]pyridin-1-yl]methyl}phenyl)prop-2-en-1-yl]oxy}propionic acid

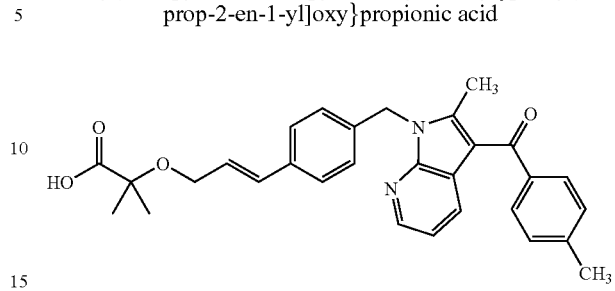

The subject compound was prepared in the same method as Example 74 by using the compounds of Reference example 66 and Reference example 20.

$^1$H NMR (CDCl$_3$, 400 MHz) δ 8.32 (dd, 1H, J=4.7, 1.6 Hz), 7.68 (dd, 1H, J=8.0, 1.6 Hz), 7.66 (d, 2H, J=8.2 Hz), 7.29 (d, 2H, J=8.2 Hz), 7.26 (d, 2H, J=8.2 Hz), 7.09 (dd, 1H, J=8.0, 4.7 Hz), 7.06 (d, 2H, J=8.2 Hz), 6.54 (brd, 1H, J=15.9 Hz), 6.21 (dt, 1H, J=15.9, 6.0 Hz), 5.60 (s, 2H), 4.08 (brd, 2H, J=6.0 Hz), 2.53 (s, 3H), 2.44 (s, 3H), 1.50 (s, 6H).

Example 83

2-Methyl-2-{[(2E)-3-(4-{[3-methyl-2-(4-methylben-zoyl)-6-(trifluoromethyl)-1H-indol-1-yl]methyl}phenyl)prop-2-en-1-yl]oxy}propionic acid

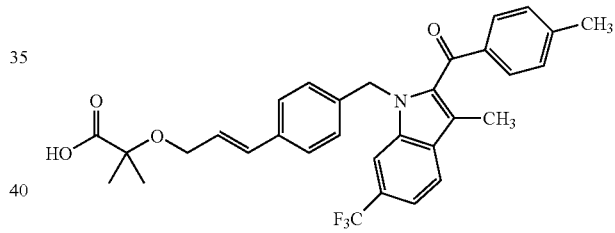

The subject compound was prepared in the same method as Example 74 by using the compounds of Reference example 66 and Reference example 18.

$^1$H NMR (CDCl$_3$, 400 MHz) δ 7.73 (d, 1H, J=8.4 Hz), 7.63 (d, 2H, J=8.1 Hz), 7.66-7.61 (m, 1H), 7.39 (dd, 1H, J=8.4, 1.1 Hz), 7.24 (d, 2H, J=8.1 Hz), 7.20 (d, 2H, J=8.2 Hz), 6.94 (d, 2H, J=8.2 Hz), 6.50 (brd, 1H, J=15.9 Hz), 6.18 (dt, 1H, J=15.9, 6.1 Hz), 5.54 (s, 2H), 4.11 (dd, 2H, J=6.1, 1.3 Hz), 2.42 (s, 3H), 2.12 (s, 3H), 1.49 (s, 6H).

Example 84

2-Methyl-2-{[(2E)-3-(4-{[3-(4-methylbenzoyl)-1H-indazol-1-yl]methyl-}phenyl)prop-2-en-1-yl]oxy}propanoic acid

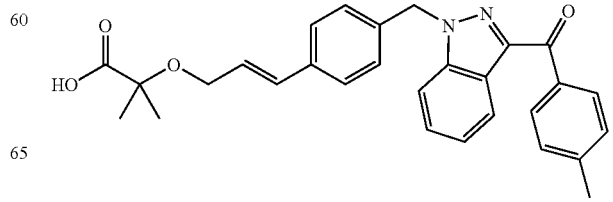

The subject compound was prepared in the same method as Example 74 by using the compounds of Reference example 66 and Reference example 46.

LC-MS R.T. 4.40 min., m/z 469 (M+1)

Example 85

2-Methyl-2-{[(2E)-3-(4-{[3-(4-methylbenzoyl)-6-(trifluoromethyl)-1H-indazol-1-yl]methyl}phenyl)prop-2-en-1-yl]oxy}propanoic acid

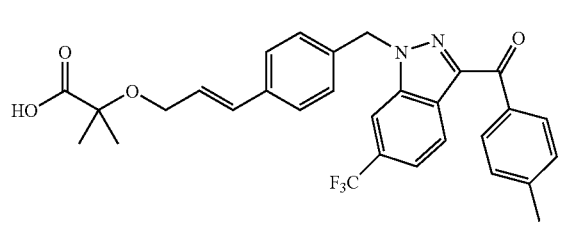

The subject compound was prepared in the same method as Example 74 by using the compounds of Reference example 66 and Reference example 47.

LC-MS R.T. 4.69 min., m/z 559 (M+Na)

Example 86

1-({4-[2-Methyl-3-(4-methylbenzoyl)-1H-indol-1-yl]benzyl}oxy)cyclobutane carboxylic acid

Example 86-1

Ethyl 1-({4-[2-methyl-3-(4-methylbenzoyl)-1H-indol-1-yl]benzyl}oxy)cyclobutanecarboxylate

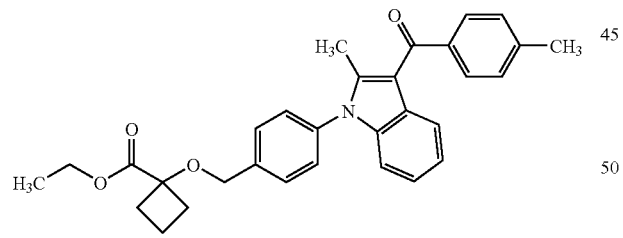

To the compound of Reference example 69-2 (100 mg, 0.28 mmol) in THF (2 ml) was added sodium hydride (55% in liquid paraffin) (15 mg, 0.34 mmol) and the mixture was stirred for 30 minutes at room temperature. Thereto was added ethyl 1-bromocyclobutanoate and the mixture was stirred for 6 hours at 60° C. After being cooled to room temperature, thereto was added 5% aqueous potassium hydrogen sulfate solution and the mixture was extracted with ethyl acetate. The organic layer was washed with saturated brine, dried over anhydrous sodium sulfate and filtered. The solvent was removed in vacuo and the residue was purified by silica gel column chromatography to give the subject compound (36 mg, 26%).

LC-MS: R.T. 4.83 min., m/z 482 (M+1)

Example 86-2

1-({4-[2-Methyl-3-(4-methylbenzoyl)-1H-indol-1-yl]benzyl}oxy)cyclobutanecarboxylic acid

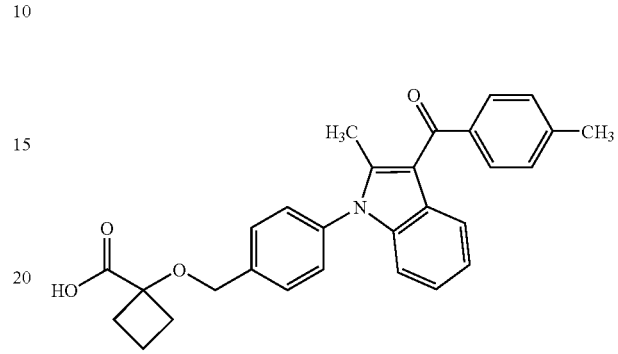

The compound of Example 86-1 (36 mg, 0.07 mmol) was dissolved in methanol (1 ml) and THF (1 ml) and thereto was added 1N aqueous sodium hydroxide solution (1 ml), followed by stirring under reflux for 20 hours. The mixture was diluted with water and washed with ethyl ether. The aqueous layer was adjusted to around pH 4 with 5% aqueous potassium hydrogen sulfate solution and the solution was extracted with ethyl acetate. The organic layer was washed with saturated brine, dried over anhydrous sodium sulfate and filtered. The solvent was removed in vacuo to give the subject compound (14 mg, 43%).

LC-MS: R.T. 4.27 min., m/z 454 (M+1)

Example 87

1-({4-[2-Methyl-3-(4-methylbenzoyl)-1H-indol-1-yl]benzyl}oxy)cyclohexanecarboxylic acid

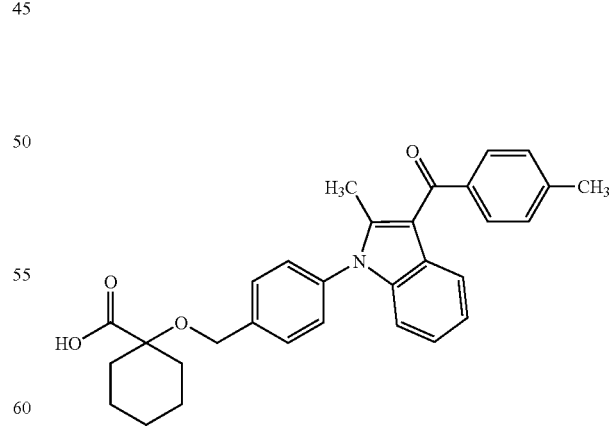

The subject compound was prepared in the same method as Example 86 by using the compound of Reference example 69-2 and methyl 1-bromocyclohexanoate.

LC-MS: R.T. 4.66 min., m/z 482 (M+1)

Example 88

({4-[2-Methyl-3-(4-methylbenzoyl)-1H-indol-1-yl]benzyl}oxy)acetic acid

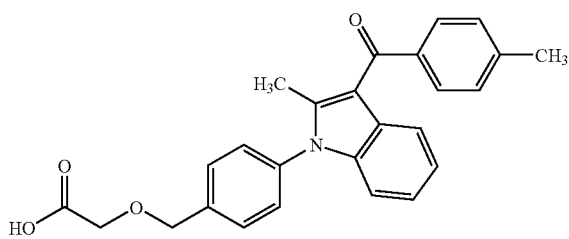

The subject compound was prepared in the same method as Example 86 by using the compound of Reference example 69-2 and t-butyl 2-bromoacetate.

$^1$H NMR (CDCl$_3$, 400 MHz) δ 7.76 (d, 2H, J=8.1 Hz), 7.61 (d, 2H, J=8.3 Hz), 7.41 (dd, 1H, J=7.0, 1.6 Hz), 7.39 (d, 2H, J=8.3 Hz), 7.28 (d, 2H, J=8.1 Hz), 7.13 (ddd, 1H, J=7.0, 7.0, 1.6 Hz), 7.10 (ddd, 1H, J=7.0, 7.0, 1.6 Hz), 7.04 (dd, 1H, J=7.0, 1.6 Hz), 4.77 (s, 2H), 4.28 (s, 2H), 2.45 (s, 3H), 2.40 (s, 3H).

Example 89

(2R)-2-({4-[2-Methyl-3-(4-methylbenzoyl)-1H-indol-1-yl]benzyl}oxy)propionic acid

Example 89-1

[2-Methyl-1-(4-{[(1R)-1-methyl-2-morphlin-4-yl-2-oxoethoxy]methyl}phenyl)-1H-indol-3-yl](4-methylphenyl)methanone

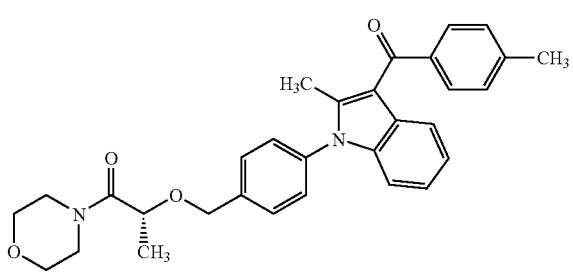

To the compound of Reference example 42-1 (25 mg, 0.16 mmol) in THF (1 ml) was added sodium hydride (55% in liquid paraffin) (7 mg, 0.16 mmol) and the mixture was stirred for 30 minutes at room temperature. Thereto was added the compound of Reference example 69-3 (50 mg, 0.12 mmol) and the mixture was stirred for 6 hours at 50° C. After being cooled to room temperature, thereto was added 5% aqueous potassium hydrogen sulfate solution and the mixture was extracted with ethyl acetate. The organic layer was washed with saturated brine, dried over anhydrous sodium sulfate and filtered. The solvent was removed in vacuo and the residue was purified by silica gel column chromatography to give the subject compound (51 mg, 86%).

$^1$H NMR (CDCl$_3$, 400 MHz) δ 7.76 (d, 2H, J=8.1 Hz), 7.57 (d, 2H, J=8.4 Hz), 7.42 (dd, 1H, J=7.1, 1.7 Hz), 7.37 (d, 2H, J=8.4 Hz), 7.28 (d, 2H, J=8.1 Hz), 7.13 (ddd, 1H, J=7.1, 7.1, 1.7 Hz), 7.10 (ddd, 1H, J=7.1, 7.1, 1.7 Hz), 7.04 (dd, 1H, J=7.1, 1.7 Hz), 4.72 (d, 1H, J=11.8 Hz), 4.57 (d, 1H, J=11.8 Hz), 4.45 (q, 1H, J=6.8 Hz), 3.80-3.63 (m, 8H), 2.45 (s, 3H), 2.40 (s, 3H), 1.53 (d, 3H, J=6.8 Hz).

Example 89-2

(2R)-2-({4-[2-Methyl-3-(4-methylbenzoyl)-1H-indol-1-yl]benzyl}oxy)propionic acid

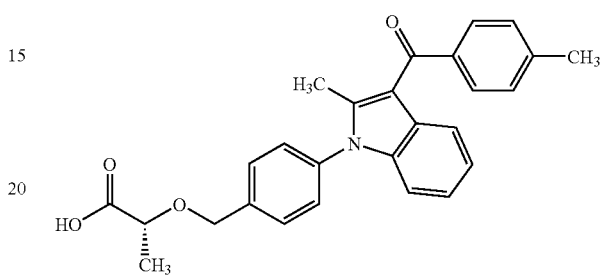

The compound of Example 89-1 (33 mg, 0.06 mmol) was dissolved in methanol (1 ml) and THF (1 ml) and thereto was added 2N aqueous lithium hydroxide solution (1 ml), followed by stirring under reflux for 10 hours. The mixture was diluted with water and washed with ethyl ether. The aqueous layer was adjusted to around pH 4 with 5% aqueous potassium hydrogen sulfate solution and the solution was extracted with ethyl acetate. The organic layer was washed with saturated brine, dried over anhydrous sodium sulfate and filtered. The solvent was removed in vacuo to give the subject compound (quant.).

$^1$H NMR (CDCl$_3$, 400 MHz) δ 7.76 (d, 2H, J=8.1 Hz), 7.60 (d, 2H, J=8.3 Hz), 7.41 (dd, 1H, J=7.0, 1.7 Hz), 7.38 (d, 2H, J=8.3 Hz), 7.27 (d, 2H, J=8.1 Hz), 7.13 (ddd, 1H, J=7.0, 7.0, 1.7 Hz), 7.10 (ddd, 1H, J=7.0, 7.0, 1.7 Hz), 7.04 (dd, 1H, J=7.0, 1.7 Hz), 4.82 (d, 1H, J=11.6 Hz), 4.65 (d, 1H, J=11.6 Hz), 4.23 (q, 1H, J=6.9 Hz), 2.45 (s, 3H), 2.40 (s, 3H), 1.58 (d, 3H, J=6.9 Hz).

Example 90

1-({4-[2-Methyl-3-(4-methylbenzoyl)-1H-indol-1-yl]benzyl}oxy)cyclopropanecarboxylic acid

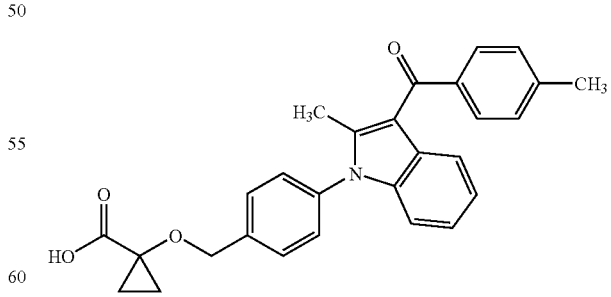

The subject compound was prepared in the same method as Example 89 by using the compound of Reference example 69-3 and ethyl 1-hydroxycyclopropanecarboxylate.

$^1$H NMR (CDCl$_3$, 400 MHz) δ 7.76 (d, 2H, J=8.1 Hz), 7.60 (d, 2H, J=8.3 Hz), 7.41 (dd, 1H, J=7.0, 1.9 Hz), 7.36 (d, 2H,

J=8.3 Hz), 7.27 (d, 2H, J=8.1 Hz), 7.12 (ddd, 1H, J=7.0, 7.0, 1.9 Hz), 7.09 (ddd, 1H, J=7.0, 7.0, 1.9 Hz), 7.03 (dd, 1H, J=7.0, 1.9 Hz), 4.81 (s, 2H), 2.45 (s, 3H), 2.39 (s, 3H), 1.55-1.49 (m, 2H), 1.43-1.38 (m, 2H).

Example 91

2-Methyl-2-({4-[2-methyl-3-(4-methylbenzoyl)-1H-indol-1-yl]benzyl}oxy)propionic acid

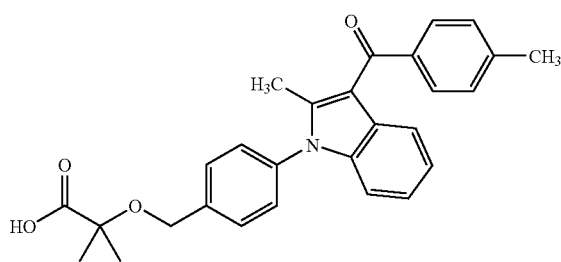

The subject compound was prepared in the same method as Example 89 by using the compound of Reference example 69-3 and ethyl 2-hydroxyisobutyrate.

$^1$H NMR (CDCl$_3$, 400 MHz) δ 7.76 (d, 2H, J=8.1 Hz), 7.61 (d, 2H, J=8.3 Hz), 7.41 (dd, 1H, J=7.1, 1.8 Hz), 7.37 (d, 2H, J=8.3 Hz), 7.27 (d, 2H, J=8.1 Hz), 7.12 (ddd, 1H, J=7.1, 7.1, 1.8 Hz), 7.09 (ddd, 1H, J=7.1, 7.1, 1.8 Hz), 7.04 (dd, 1H, J=7.1, 1.8 Hz), 4.66 (s, 2H), 2.45 (s, 3H), 2.40 (s, 3H), 1.64 (s, 6H).

Example 92

(2R)-2-({3-[3-(4-Methylbenzoyl)-1H-indazol-1-yl]benzyl}oxy)propanoic acid

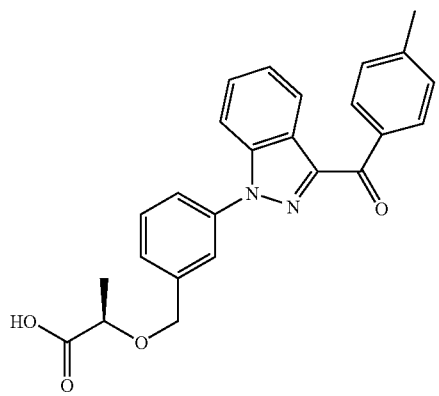

The subject compound was prepared in the same method as Example 89 by using the compounds of Reference example 42 and Reference example 46.

LC-MS R.T. 4.26 min., m/z 415 (M+1)

Example 93

(2R)-2-({3-[3-(4-Methylbenzoyl)-6-(trifluoromethyl)-1H-indazol-1-yl]benzyl}oxy)propanoic acid

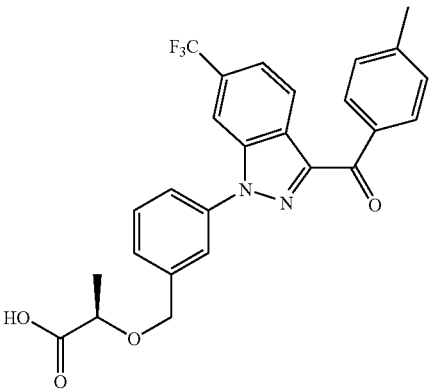

The subject compound was prepared in the same method as Example 89 by using the compounds of Reference example 42 and Reference example 47.

LC-MS R.T. 4.74 min., m/z 483 (M+1)

Example 94

2-methyl-2-({4-[3-(4-methyl-benzoyl)-1H-indazol-1-yl]benzyl}oxy)propanoic acid

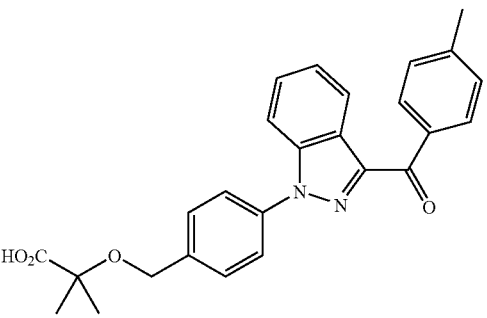

The subject compound was prepared in the same method as Example 89 by using the compounds of Reference example 40 and Reference example 46.

LC-MS R.T. 3.73 min., m/z 429 (M+1)

Example 95

2-Methyl-2-({4-[3-(4-methylbenzoyl)-6-(trifluoromethyl)-1H-indazol-1-yl]benzyl}oxy)propanoic acid

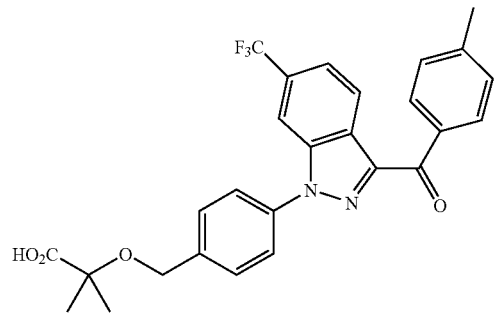

The subject compound was prepared in the same method as Example 89 by using the compounds of Reference example 40 and Reference example 47.

LC-MS R.T. 3.93 min., m/z 497 (M+1)

Test 1

Evaluation of PPAR α or γ Agonistic Activity

Construction of Reporter Plasmid

By inserting a gene fragment encoding the ligand binding domain of human PPARα (including amino acid residues 167-468) or a gene fragment encoding the ligand binding domain of human PPARγ (including amino acids residue 204-505) into a multicloning site of expressing vector pM containing DNA binding domain of yeast GAL4 protein (Clonetech), a vector plasmid for expressing a fused protein of GAL4 protein DNA binding domain and human PPARα or γ ligand binding domain was obtained.

As a reporter plasmid, pGL3-Basic Vector containing firefly luciferase gene (Promega Corporation) was used wherein Gal 4-responsive sequence UAS and rabbit β-globin promoter were inserted.

For the correction of transformation efficiency, a plasmid pβgal control (Clonetech) containing lacZ gene, was used.

Luciferase Assay

COS-1 cells were cultured in the phenol red free Dulbecco's Modified Eagles Medium (DMEM) (Gibco) supplemented with 5% activated charcoal/dextran stripped fetal bovine serum at 37° C. with 5% carbon dioxide. The COS-1 cells were plated at a concentration of $5 \times 10^4$ cells/well into a 24-well plate, and were incubated overnight. The medium was replaced with a fresh medium supplemented without 5% activated charcoal/dextran treated fetal bovine serum. Further, the cells were transfected using Lipofectamine plus reagent (Gibco) with plasmids GAL4-PPARα- or γ-expressing plasmid (5 ng), the reporter plasmid (50 ng), and pβgal control (350 ng) per well. After incubation for 4 hours, the medium was changed with a fresh medium supplemented with 5% activated charcoal/dextran treated fetal bovine serum. Then, the compound of the present invention was added thereto in such an amount that the final concentration thereof is 0.1 μM, 0.3 μM, 1 μM, 3 μM or 10 μM. After the cultivation for 24 hours, the cells were lysed with a solution for cell lysis accompanied to the Luciferase Assay System (Promega Corporation). The luciferase activity therein was measured by a luminometer using the reagent for measuring luciferase which was also accompanied to said System.

The PPARα- or γ-agonistic activity was expressed as a relative activity where the luciferase activity in the well to which the vehicle (DMSO) was added as control was regarded as 1. The PPARα-agonistic activity and the PPARγ-agonistic activity at each 10 μM, and the maximum PPARγ-agonistic activity (%) of the compound of the present invention per the maximum PPARγ-agonistic activity (100%) of pioglitazone are shown in the following Table 1.

TABLE 1

| Test Comp. (Example No.) | PPARα- agonistic activity (10 μM) | PPARγ- agonistic activity (10 μM) | PPARγ maximum activity (%) |
|---|---|---|---|
| 1 | 9.9 | 5.3 | 51 |
| 20 | 9.7 | 3.9 | 68 |
| 21 | 10.7 | 6.8 | 71 |
| 35 | 13.8 | 3.8 | 57 |
| 46 | 8.0 | 2.5 | 26 |
| 54 | 10.2 | 3.6 | 39 |

TABLE 1-continued

| Test Comp. (Example No.) | PPARα- agonistic activity (10 μM) | PPARγ- agonistic activity (10 μM) | PPARγ maximum activity (%) |
|---|---|---|---|
| 59 | 6.2 | 4.2 | 41 |
| 68 | 15.9 | 6.1 | 71 |
| 79 | 10.8 | 2.4 | 35 |
| 81 | 7.4 | 2.3 | 42 |
| 83 | 5.7 | 1.4 | 13 |
| 86 | 1.3 | 2.8 | 20 |

Test 2

The test compounds as disclosed in Examples were dissolved or suspended in a 0.5% carbomethyl cellulose solution, and orally administered to male db/db mice (7 to 8 weeks old) at a final dose of 30 mg/kg once a day for 2 weeks. On the last day, the blood was taken at the tail vein, and immediately thereafter, perchloric acid was added for removing proteins, and the blood glucose level was measured by Glucolse CII Test Wako (Wako Pure Industries, Ltd.). The results are shown in the following Table 2.

The hypoglycemic activity was calculated by the following equation.

$$\text{Hypoglycemic Activity}(\%) = \frac{\text{Blood Glucose Level in Vehicle (on Last day)} - \text{Blood Glucose Level in test compound-treated group(on Last day)}}{\text{Blood Glucose Level in Vehicle (on Last Day)}} \times 100$$

TABLE 2

| Test Comp. (Example No.) | Hypoglycemic Activity (%) |
|---|---|
| Example 20 | 50.4 |
| Example 34 | 47.4 |
| Example 35 | 27.3 |
| Example 54 | 47.7 |

INDUSTRIAL APPLICABILITY

The compound of the present invention can be used as an agent for treatment or prophylaxis of diabetic mellitus, a blood glucose regulator or an agent for treating hyperlipidema.

The invention claimed is:

1. A compound of the formula (I):

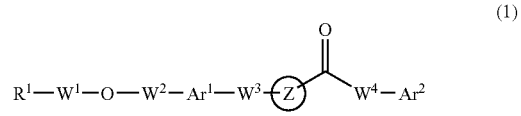

wherein Ring Z is the following formula (3):

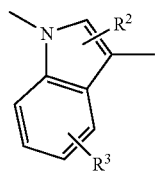

(3)

wherein the number of R² may be zero or one, and R² is a halogen atom, an optionally substituted alkyl group, an optionally substituted aryl group, an optionally substituted heteroaryl group, or an optionally substituted thiol group, the number of R³ may be zero, one or more, and R³ is independently, a halogen atom, an optionally substituted alkyl group, an optionally substituted thiol group, a methoxy group, an ethoxy group, a 2-propoxy group, an optionally substituted amino group, hydroxy group, cyano group, nitro group, carboxyl group, an optionally substituted acyl group, an optionally substituted saturated heterocyclic group, or an optionally substituted carbamoyl group, W⁴ is a single bond,
Ar² is an optionally substituted phenyl group,
W³ is a lower alkylene group or a lower alkenylene group,
Ar¹ is an optionally substituted phenylene group;
W¹ and W² are independently an optionally substituted lower alkylene group or an optionally substituted lower alkenylene group;
R¹ is a carboxyl group, an alkoxycarbonyl group, an optionally substituted carbamoyl group, an optionally substituted cyclic aminocarbonyl group, an optionally substituted alkylsulfonylcarbamoyl group, an optionally substituted arylsulfonylcarbamoyl group, or a tetrazolyl group, or a pharmaceutically acceptable salt thereof.

2. The compound according to claim 1,
wherein W³ is a methylene, ethylene, vinylene, or propenylene group, W¹ is a methylene group optionally substituted by a C₁-C₃ alkyl group, W² is a methylene or propenylene group, and Ar¹ is a phenylene group, or a pharmaceutically acceptable salt thereof.

3. The compound according to claim 2, wherein W³ is a methylene or propenylene group, Ar² is a phenyl group optionally substituted by a lower alkyl group or alkoxy group, and R¹ is a carboxy group, or a pharmaceutically acceptable salt thereof.

4. The compound according to claim 1, wherein W¹ or W² is a lower alkenylene group,
or a pharmaceutically acceptable salt thereof.

5. The compound according to claim 1, wherein W³ is a C₁-C₃ alkylene group, or a C₂-C₃ alkenylene group, and Ar¹ is a phenylene group, or a pharmaceutically acceptable salt thereof.

6. The compound according to claim 5, wherein W¹ or W² is a propenylene group, W³ is a methylene, ethylene, vinylene, or propenylene group, Ar¹ is a phenylene group, and Ar² is a phenyl group optionally substituted by a lower alkyl group or an alkoxy group,
or a pharmaceutically acceptable salt thereof.

7. The compound according to claim 6, wherein W³ is a methylene or propenylene group, and R¹ is a carboxyl group,
or a pharmaceutically acceptable salt thereof.

8. A pharmaceutical composition comprising the compound according to claim 1,
or a pharmaceutically acceptable salt thereof as an active ingredient.

9. A method for treating diabetes mellitus or hyperlipidemia by administering to a patient who needs treatment of diabetes mellitus or hyperlidemia an effective amount of the compound according to claim 1 or a pharmaceutically acceptable salt thereof.

10. A compound of the structure

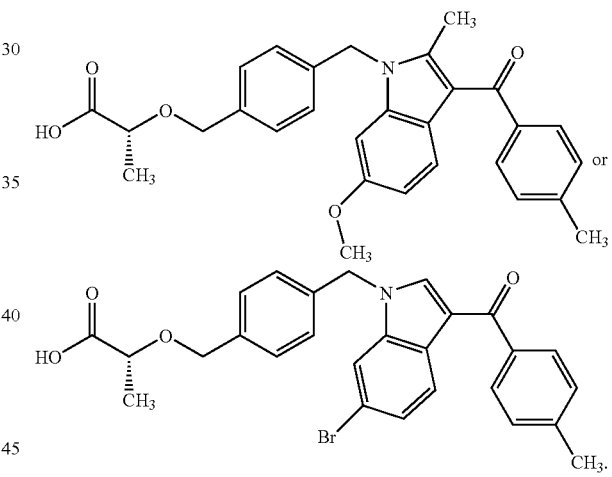

* * * * *